United States Patent [19]
Bischofberger et al.

[11] Patent Number: 5,811,450
[45] Date of Patent: Sep. 22, 1998

[54] THIEPANE COMPOUNDS

[75] Inventors: Norbert W. Bischofberger; Choung U. Kim; Steven H. Krawczyk, all of San Carlos; Lawrence R. McGee, Pacifica; Michael J. Postich, San Mateo; Wenjin Yang, Foster City, all of Calif.

[73] Assignee: Gilead Sciences, Inc., Foster City, Calif.

[21] Appl. No.: 740,568

[22] Filed: Oct. 31, 1996

Related U.S. Application Data

[60] Provisional application No. 60/007,216, Nov. 3, 1995.

[51] Int. Cl.$^6$ .......................... A61K 31/38; C07D 337/00
[52] U.S. Cl. ................................................ 514/431; 549/9
[58] Field of Search ................................ 549/9; 514/431

[56] References Cited

U.S. PATENT DOCUMENTS

| | | | |
|---|---|---|---|
| 4,959,385 | 9/1990 | Cook et al. | 514/431 |
| 5,158,943 | 10/1992 | Sohda et al. | 514/96 |
| 5,525,736 | 6/1996 | Nystrom et al. | 549/5 |
| 5,705,524 | 1/1998 | McGee et al. | 514/431 |

FOREIGN PATENT DOCUMENTS

WO 94/19329  9/1994  WIPO .

OTHER PUBLICATIONS

Billich et al., "Review: Antiviral Assays, No. 1—Assay systems for HIV–1 proteinase and their use for evaluation of inhibitors," Antiviral Chem & Chemo 2(2):65–73 (1991).

Matayoshi et al., "Novel Fluorogenic Substrates for Assaying Retroviral Proteases by Resonance Energy Transfer," Science 247:954–958 (Feb. 23, 1990).

Wang et al., "Design and Synthesis of New Fluorogenic HIV Protease Substrates Based on Resonance Energy Transfer," TET LETT 31(45):6493–6496 (1990).

Wong et al., "A Pharmacokinetic Evaluation of HIV Protease Inhibitors, Cyclic Ureas, in Rats and Dogs," Biochem Pharm 15:535–544 (1994).

*Primary Examiner*—Deborah C. Lambkin
*Attorney, Agent, or Firm*—Mark L. Bosse

[57] ABSTRACT

Tri- and tetra substituted thiepane compositions having use as immunogens, therapeutics, diagnostics and for other industrial purposes are disclosed. The compositions inhibit proteolytic activity of viral enzymes and are useful for the inhibition of such enzymes as well as in assays for the detection of such enzymes. Embodiments in which antigenic polypeptides are bonded to the compositions are useful in raising antibodies against the thiepane haptens or the polypeptide. Labeled thiepanes of this invention are useful as diagnostic reagents.

29 Claims, No Drawings

THIEPANE COMPOUNDS

This application claims priority from United States Provisional patent application Ser. No. 60/007,216 filed Nov. 3, 1995. This application is related to U.S. patent application Ser. No. 08/552,429, filed Nov. 3, 1995, which was a continuation-in-part of Ser. No. 08/552,042, filed Nov. 2, 1995, which was a continuation-in-part of Ser. No. 08/473,876, filed Jun. 7, 1995, which was a continuation-in-part of Ser. No. 08/470,864, filed Jun. 6, 1995, which was a continuation-in-part of Ser. No. 08/334,471, filed Nov. 4, 1994; each of which is now pending, and all of which are incorporated by reference in their entirety herein.

BACKGROUND OF THE INVENTION

1. Field of the Invention

HIV infection and related disease is a major public health problem worldwide. A virally encoded protease (HIV protease) mediates specific protein cleavage reactions during the natural reproduction of the virus. Accordingly, inhibition of HIV protease is an important therapeutic target for treatment of HIV infection and related disease.

Assay methods capable of determining the presence, absence or amount of HIV protease are of practical utility in the search for inhibitors as well as for diagnosing the presence of HIV.

2. Brief Description of Related Disclosures

Lam, P.; Jadhav, P.; Eyermann, C.; Hodge, C.; De Lucca, G.; and Rodgers, J.; WO 94/19329, Sep. 1, 1994, discloses substituted cyclic carbonyls and derivatives thereof useful as retroviral protease inhibitors.

Billich, A.; Billich, S.; and Rosenwirth, B; Antiviral Chem. & Chemoth., 1991, 2(2), 65–73, discloses assays for HIV protease.

Matayoshi, E. D.; Wang, G. T.; Krafft, G. A.; and Erickson, J. W.; Science, 1990, 247, 954–958; and Wang, G. T.; Huffker, J. A.; Matayoshi, E.; and Krafft, G. A.; Tetrahedron Lett., 1990, 165, 6493–6496; disclose a fluorometric assay method for measurement of HIV-protease (HIV-PR) activity utilizing a synthetic peptide substrate for HIV-PR.

Wong, Y.; Burcham, D.; Saxton, P.; Erickson-Viitanen, S.; Grubb, M.; Quon, C.; and Huang, S.-M.; Biopharm. & Drug Disp., 1994, 15, 535–544, discloses pharmacokinetic evaluation of cyclic urea HIV protease inhibitors in rats and dogs.

Inhibition of HIV protease is an object of the invention. Inhibitors of HIV protease are useful to limit the establishment and progression of infection by HIV as well as in assays for HIV protease, both of which are further objects of the invention. Preparation of compositions capable of inhibiting HIV protease is also an object of the invention.

Thus, it is an object of this invention to provide HIV protease inhibitors having improved antiviral and pharmacokinetic properties, including enhanced activity against development of HIV resistance, improved oral bioavailability, greater potency and extended effective half-life in vivo. It is another object herein to provide compounds useful in diagnostic assays for HIV, for use in the preparation of polymers and for use as surfactants, and in other industrial utilities that will be readily apparent to the artisan.

SUMMARY OF THE INVENTION

Compositions of the invention comprise compounds of the formula:

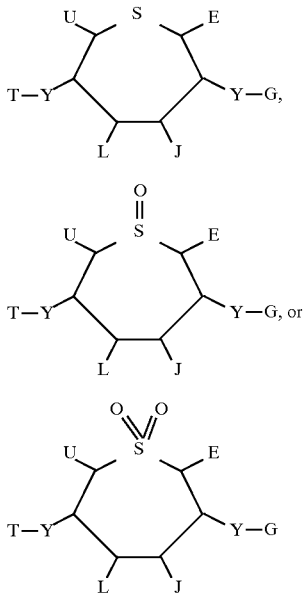

wherein:
Y is independently —O—, —S—, —SO—, —SO$_2$—, —N(R$_1$)—, —N(R$_1$)—SO$_2$—, —N(R$_1$)—CO—, or —O—SO$_2$—;

E and U are independently H, or —(CR$_1$R$_1$)$_{m1}$—W$_1$, with the proviso that at least one of E and U is —(CR$_1$R$_1$)$_{m1}$—W$_1$;

G and T are independently —(CR$_1$R$_1$)$_{m1}$—W$_1$, or —(CR$_1$R$_1$)$_{m1}$—C(R$_1$)(W$_1$)(W$_2$), with the provisos that:

when E is —(CR$_1$R$_1$)$_{m1}$—W$_1$, then G is —(CR$_1$R$_1$)$_{m1}$—W$_1$;

when U is —(CR$_1$R$_1$)$_{m1}$—W$_1$, then T is —(CR$_1$R$_1$)$_{m1}$—W$_1$; and G and T may be the same or different;

J and L are independently H, N$_3$, —OR$_2$, —N(R$_2$)(R$_2$), or —N(R$_2$)(R$_3$), wherein R$_2$ is H, or PRT, with the proviso that at least one of J and L is —OR$_2$, or J and L are taken together to form an epoxide or a cyclic protecting group;

W$_1$ is W$_2$ or W$_3$;

W$_2$ is carbocycle or heterocycle, with the proviso that each W$_2$ is independently substituted with 0 to 3 R$_5$ groups;

W$_3$ is alkyl, alkenyl, or alkynyl, with the proviso that each W$_3$ is independently substituted with 0 to 3 R$_6$ groups;

R$_1$ is R$_3$ or R$_6$;

R$_3$ is H or R$_4$;

R$_4$ is alkyl;

R$_5$ is R$_6$, or R$_7$, with the proviso that each R$_7$ is independently substituted with 0 to 3 R$_6$ groups;

R$_6$ is —O-(antigenic polypeptide), —N(R$_3$)-(antigenic polypeptide), —C(O)O-(antigenic polypeptide), —C(O)N(R$_3$)-(antigenic polypeptide), —S—(antigenic polypeptide), —S—S-(antigenic polypeptide), —O-(label), —N(R$_3$)-(label), —C(O)O-(label), —C(O)N(R$_3$)-(label), —S-(label), —S—S-(label), F, Cl, Br, I, —CN, N$_3$, —NO$_2$, —OR$_3$, —OPRT, —O—C(O)R$_4$, =O, —N(R$_3$)(R$_3$), —N(R$_3$)(PRT), —N(PRT)$_2$, —N(R$_3$)—C(O)R$_4$, =N(R$_3$), =N(PRT), —N(OR$_3$)(R$_3$), —N(OPRT)(R$_3$), —N(OR$_3$)(PRT), —N(OPRT)(R$_3$), —N(N(R$_3$)(R$_3$))

(R$_3$), —N(N(PRT)(R$_3$))(R$_3$), —N(N(R$_3$)(R$_3$))(PRT), —N(N(PRT)(PRT))(R$_3$), —N(N(PRT)(R$_3$))(PRT), —N(N(PRT)(PRT))(PRT), —N(R$_3$)—C(N(R$_3$))(N(R$_3$)$_2$), —N(PRT)—C(N(R$_3$))(N(R$_3$)$_2$), —N(R$_3$)—C(N(PRT))(N(R$_3$)$_2$), —N(R$_3$)—C(N(R$_3$))(N(R$_3$)(PRT)), —N(PRT)—C(N(PRT))(N(R$_3$)$_2$), —N(PRT)—C(N(R$_3$))(N(R$_3$)(PRT)), —N(R$_3$)—C(N(PRT))(N(R$_3$)(PRT)), —N(R$_3$)—C(N(R$_3$))(N(PRT)$_2$), —N(PRT)—C(N(PRT))(N(R$_3$)(PRT)), —N(PRT)—C(N(R$_3$))(N(PRT)$_2$), —N(R$_3$)—C(N(PRT))(N(PRT)$_2$), —N(PRT)—C(N(PRT))(N(PRT)$_2$), —C(NR$_3$)(N(R$_3$)$_2$), —C(N(R$_3$))(N(R$_3$)(PRT)), —C(NPRT)(N(R$_3$)$_2$), —C(N(PRT))(N(R$_3$)(PRT)), —C(N(R$_3$))(N(PRT)$_2$), —C(N(PRT))(N(PRT)$_2$), —SR$_3$, —S(PRT), =S, —S(O)—R$_3$, —S(O)—OR$_3$, —S(O)—OPRT, —O—S(O)—R$_3$, —S(O)$_2$—R$_3$, —S(O)$_2$—OR$_3$, —S(O)$_2$—OPRT, —O—S(O)$_2$—R$_3$, —C(O)OR$_3$, —C(O)OPRT, —C(O)N(R$_3$)$_2$, —C(O)N(R$_3$)(PRT), —C(O)N(PRT)$_2$, —C(S)N(R$_3$)$_2$, —C(S)N(R$_3$)(PRT), —C(S)N(PRT)$_2$, —N(R$_3$)—S(O)$_2$—R$_3$, —N(PRT)—S(O)$_2$—R$_3$, —S(O)$_2$—N(R$_3$)—R$_3$, —S(O)$_2$—N(PRT)—R$_3$, carbocycle, or heterocycle;

R$_7$ is alkyl, alkenyl, or alkynyl;

m1 is an integer from 0 to 3; and with the proviso that the compound, taken as a whole, contains 0 to 16 R$_6$ groups, and that each E, G, T, and U, taken individually, contain 0 to 8 R$_6$ groups.

The invention is also directed to methods of detecting the presence or amount of HIV protease comprising contacting a test sample with a composition of the invention comprising a detectable label.

The invention is also directed to methods of inhibiting the activity of HIV protease comprising contacting the protease with an inhibitory effective amount of a composition of the invention.

DETAILED DESCRIPTION

Compositions of the Invention

Compositions of the invention comprise compounds of the formulas:

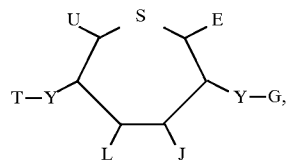

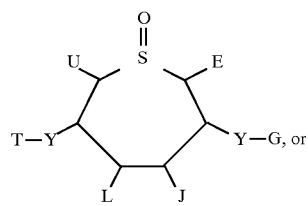

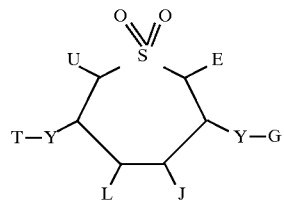

The E, G, T and U groups may be the same or different. Y is independently —O—, —S—, —SO—, —SO$_2$—, —N(R$_1$)—, —N(R$_1$)—SO$_2$—, —N(R$_1$)—CO—, or —O—SO$_2$—.

Typically the compositions of the invention comprise compounds of the formula:

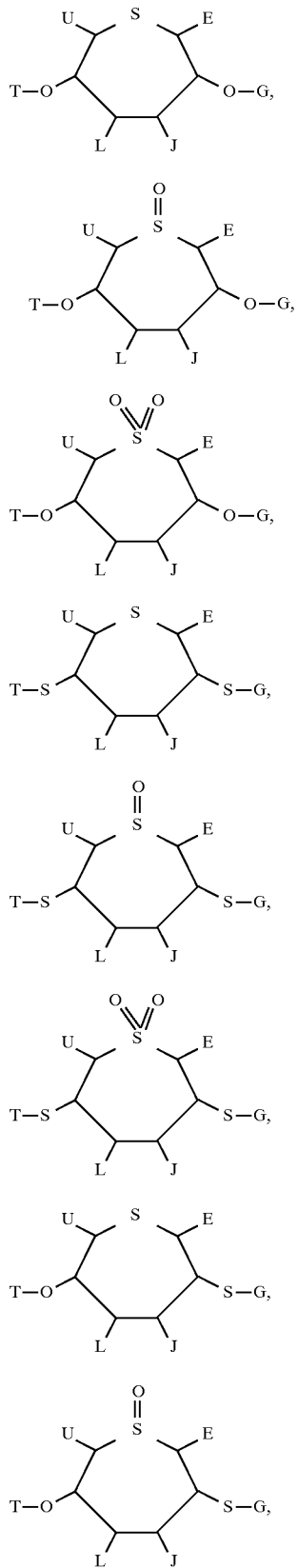

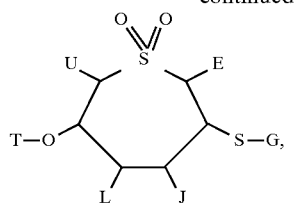
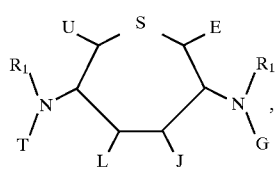
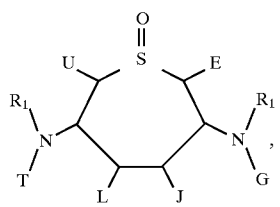
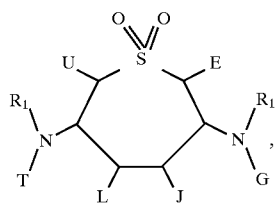
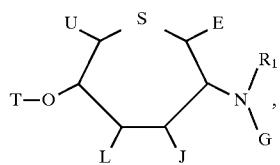
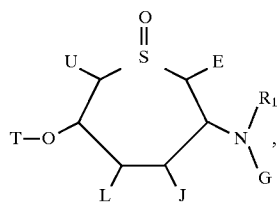
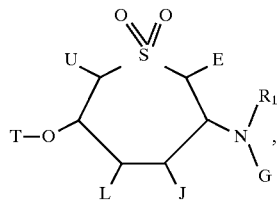
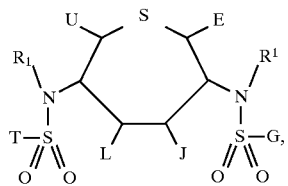
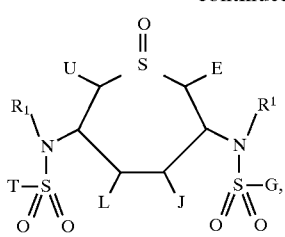
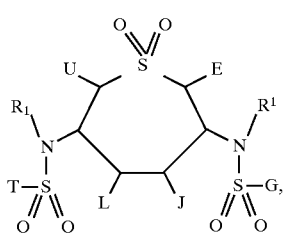
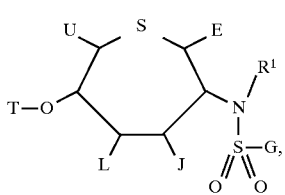
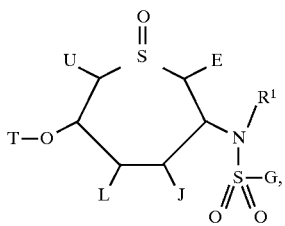
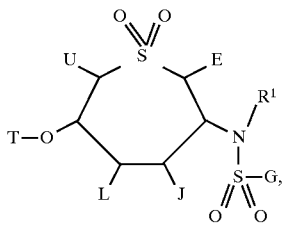
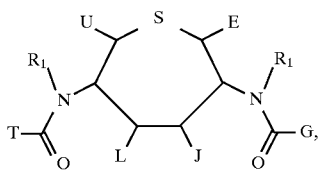
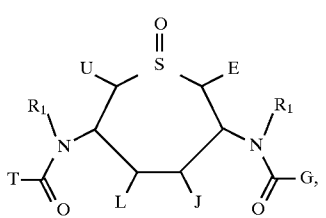

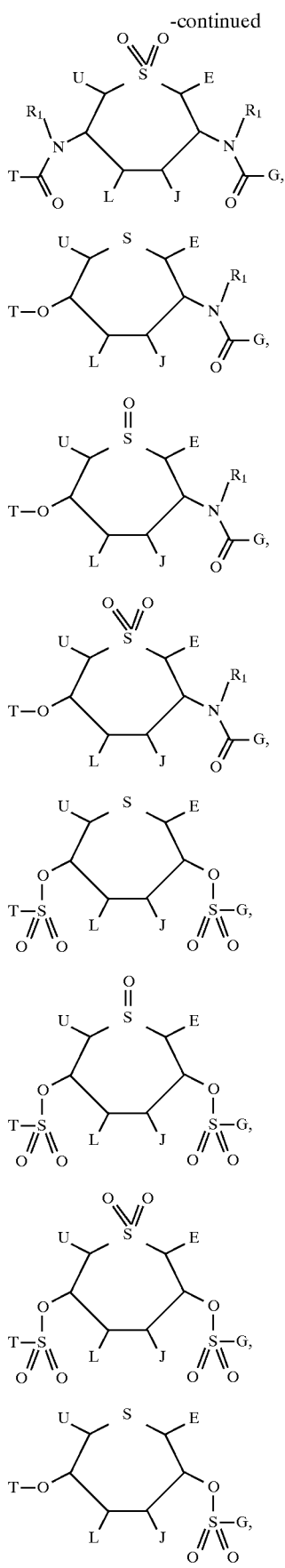

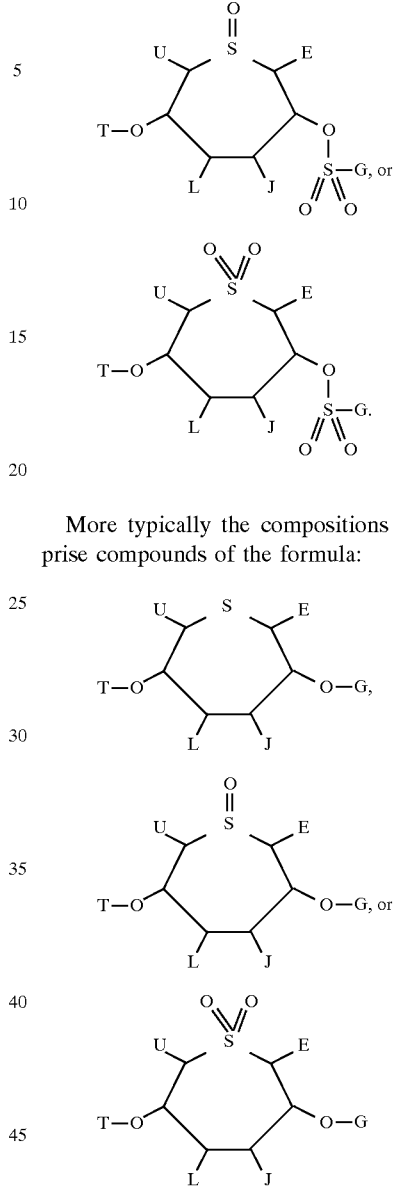

More typically the compositions of the invention comprise compounds of the formula:

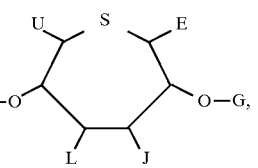

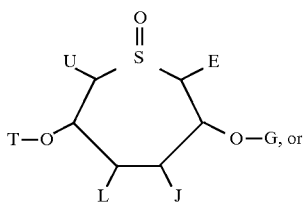

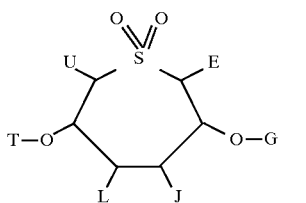

TABLE 1

| Intended Stereochemistries of Formulas I, II and III | |
|---|---|
| αE, αG, αJ, αL, αT, αU | αE, αG, αJ, αL, αT, βU |
| αE, αG, αJ, αL, βT, αU | αE, αG, αJ, αL, βT, βU |
| αE, αG, αJ, βL, αT, αU | αE, αG, αJ, βL, αT, βU |
| αE, αG, αJ, βL, βT, αU | αE, αG, αJ, βL, βT, βU |
| αE, αG, βJ, αL, αT, αU | αE, αG, βJ, αL, αT, βU |
| αE, αG, βJ, αL, βT, αU | αE, αG, βJ, αL, βT, βU |
| αE, αG, βJ, βL, αT, αU | αE, αG, βJ, βL, αT, βU |
| αE, αG, βJ, βL, βT, αU | αE, αG, βJ, βL, βT, βU |
| αE, βG, αJ, αL, αT, αU | αE, βG, αJ, αL, αT, βU |
| αE, βG, αJ, αL, βT, αU | αE, βG, αJ, αL, βT, βU |
| αE, βG, αJ, βL, αT, αU | αE, βG, αJ, βL, αT, βU |
| αE, βG, αJ, βL, βT, αU | αE, βG, αJ, βL, βT, βU |
| αE, βG, βJ, αL, αT, αU | αE, βG, βJ, αL, αT, βU |
| αE, βG, βJ, αL, βT, αU | αE, βG, βJ, αL, βT, βU |
| αE, βG, βJ, βL, αT, αU | αE, βG, βJ, βL, αT, βU |
| αE, βG, βJ, βL, βT, αU | αE, βG, βJ, βL, βT, βU |
| βE, αG, αJ, αL, αT, αU | βE, αG, αJ, αL, αT, βU |
| βE, αG, αJ, αL, βT, αU | βE, αG, αJ, αL, βT, βU |

TABLE 1-continued

Intended Stereochemistries of Formulas I, II and III

| | |
|---|---|
| βE, αG, αJ, βL, αT, αU | βE, αG, αJ, βL, αT, βU |
| βE, αG, αJ, βL, βT, αU | βE, αG, αJ, βL, βT, βU |
| βE, αG, βJ, αL, αT, αU | βE, αG, βJ, αL, αT, βU |
| βE, αG, βJ, αL, βT, αU | βE, αG, βJ, αL, βT, βU |
| βE, αG, βJ, βL, αT, αU | βE, αG, βJ, βL, αT, βU |
| βE, αG, βJ, βL, βT, αU | βE, αG, βJ, βL, βT, βU |
| βE, βG, αJ, αL, αT, αU | βE, βG, αJ, αL, αT, βU |
| βE, βG, αJ, αL, βT, αU | βE, βG, αJ, αL, βT, βU |
| βE, βG, αJ, βL, αT, αU | βE, βG, αJ, βL, αT, βU |
| βE, βG, αJ, βL, βT, αU | βE, βG, αJ, βL, βT, βU |
| βE, βG, βJ, αL, αT, αU | βE, βG, βJ, αL, αT, βU |
| βE, βG, βJ, αL, βT, αU | βE, βG, βJ, αL, βT, βU |
| βE, βG, βJ, βL, αT, αU | βE, βG, βJ, βL, αT, βU |
| βE, βG, βJ, βL, βT, αU | βE, βG, βJ, βL, βT, βU |

E, G, T, and U

In all embodiments, E and U are independently H, or —$(CR_1R_1)_{m1}$—$W_1$, provided that at least one of E and U is —$(CR_1R_1)_{m1}$—$W_1$. Typically E and U are independently groups of the formula —$(CR_1R_1)_{m1}$—$W_2$, more typically, —$(CR_3R_3)_{m1}$—$W_2$. Preferably, E and U are not H.

G and T are independently —$(CR_1R_1)_{m1}$—$W_1$, or —$(CR_1R_1)_{m1}$—$C(R_1)(W_1)(W_2)$, provided that when E is —$(CR_1R_1)_{m1}$—$W_1$, G is —$(CR_1R_1)_{m1}$—$W_1$, and when U is —$(CR_1R_1)_{m1}$—$W_1$, T is —$(CR_1R_1)_{m1}$—$W_1$. Typically, G and T are independently groups of the formula —$(CR_1R_1)_{m1}$—$W_2$, more typically, —$(CR_3R_3)_{m1}$—$W_2$.

In another embodiment, E, G, T and U are all —$(CR_1R_1)_{m1}$—$W_1$. Typically, E, G, T and U are —$(CR_3R_3)_{m1}$—$W_1$. More typically, E, G, T and U are —$(CR_1R_1)_{m1}$—$W_2$. Still more typically, E, G, T and U are —$(CR_3R_3)_{m1}$—$W_2$.

In another embodiment one of E and U is H and the other is —$(CR_1R_1)_{m1}$—$W_1$; and T and G are —$(CR_1R_1)_{m1}$—$W_1$. Typically, one of E and U is H and the other is —$(CR_3R_3)_{m1}$—$W_1$; and T and G are —$(CR_3R_3)_{m1}$—$W_1$. More typically, one of E and U is H and the other is —$(CR_1R_1)_{m1}$—$W_2$; and T and G are —$(CR_1R_1)_{m1}$—$W_2$. Still more typically, one of E and U is H and the other is —$(CR_3R_3)_{m1}$—$W_2$; and T and G are —$(CR_3R_3)_{m1}$—$W_2$.

In another embodiment one of E and U is H and the other is —$(CR_1R_1)_{m1}$—$W_1$, provided that when E is H, then G is —$(CR_1R_1)_{m1}$—$C(R_1)(W_1)(W_2)$, when E is —$(CR_1R_1)_{m1}$—$W_1$, then G is —$(CR_1R_1)_{m1}$—$W_1$, when U is H, then T is —$(CR_1R_1)_{m1}$—$C(R_1)(W_1)(W_2)$, and when U is —$(CR_1R_1)_{m1}$—$W_1$, then T is —$(CR_1R_1)_{m1}$—$W_1$. Typically, one of E and U is H and the other is —$(CR_3R_3)_{m1}$—$W_1$, provided that when E is H, then G is —$(CR_1R_1)_{m1}$—$C(R_1)(W_1)(W_2)$, when E is —$(CR_3R_3)_{m1}$—$W_1$, then G is —$(CR_1R_1)_{m1}$—$W_1$, when U is H, then T is —$(CR_1R_1)_{m1}$—$C(R_1)(W_1)(W_2)$, and when U is —$(CR_3R_3)_{m1}$—$W_1$, then T is —$(CR_1R_1)_{m1}$—$W_1$. More typically, one of E and U is H and the other is —$(CR_1R_1)_{m1}$—$W_2$, provided that when E is H, then G is —$(CR_1R_1)_{m1}$—$C(R_1)(W_1)(W_2)$, when E is —$(CR_1R_1)_{m1}$—$W_2$, then G is —$(CR_1R_1)_{m1}$—$W_1$, when U is H, then T is —$(CR_1R_1)_{m1}$—$C(R_1)(W_1)(W_2)$, and when U is —$(CR_1R_1)_{m1}$—$W_2$, then T is —$(CR_1R_1)_{m1}$—$W_1$. Still more typically one of E and U is H and the other is —$(CR_3R_3)_{m1}$—$W_2$, provided that when E is H, then G is —$(CR_1R_1)_{m1}$—$C(R_1)(W_1)(W_2)$, when E is —$(CR_3R_3)_{m1}$—$W_2$, then G is —$(CR_1R_1)_{m1}$—$W_1$, when U is H, then T is —$(CR_1R_1)_{m1}$—$C(R_1)(W_1)(W_2)$, and when U is —$(CR_3R_3)_{m1}$—$W_2$, then T is —$(CR_1R_1)_{m1}$—$W_1$.

In another embodiment, E, G, T and U are independently —$CR_3R_3$—$W_2$ wherein $R_3$ is H or a 1 to 3 carbon alkyl group and $W_2$ is a monocyclic carbocycle (3 to 6 carbon atoms) or monocyclic heterocycle (3 to 6 ring members, 2 to 5 carbon atoms, and 1 to 2 heteroatoms selected from O, N, and S) provided that $W_2$ is substituted with 0 to 1 —OH, —OMe, —$NH_2$, —N(H)(Me), —N(H)(Et), —N(H)(i—Pr), —N(H)(n—Pr), —N(Me)$_2$, —$NO_2$, or —CN. Typically, in this embodiment $W_2$ is phenyl, pyridyl, tetrahydrothiophene, sulfur oxidized (sulfoxide or sulfone) tetrahydrothiophene, or thiazole.

In another embodiment, E, G, T and U are independently —$CR_3R_3$—$W_2$ wherein $W_2$ is phenyl or thiazole provided that each $W_2$ is independently substituted with 0, 1 or 2 $R_5$ groups as described above.

In another embodiment, E, G, T and U are independently —$CHR_3$—$W_2$ wherein $W_2$ is phenyl or thiazole provided that each $W_2$ is independently substituted with 0 to 1 $R_5$ groups as described above.

In another embodiment, E, G, T and U are independently —$CHR_3$—$W_2$ wherein $W_2$ is phenyl or thiazole provided that each $W_2$ is independently substituted with 0 to 1 $R_3$ groups as described above.

In another embodiment, E, G, T and U are benzyl.

Another embodiment is directed to compositions of the formula:

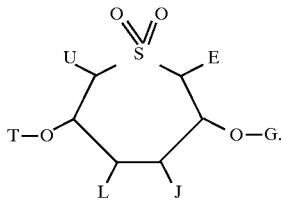

E, G, J, L, T, and U are as described above.

E, G, T, and U, when taken individually, are substituted with no more than 8 $R_6$ groups, typically, no more than 3 $R_4$ or $R_7$ and 6 $R_6$ groups. More typically, each is substituted with 1 or 2 $R_4$ or $R_7$ groups of 1 or 3, or 2 or 3 carbon atoms, respectively, and 0 to 4 $R_6$ groups selected from —$OR_3$, —$SR_3$, —$N(R_3)(R_3)$, F, CN, —$NO_2$, and heterocycle. Still more typically, each is substituted with 0 or 1 $R_4$ of 1 to 3 carbon atoms and 0 or 1 $R_6$ groups selected from —OH, —OMe, —OEt, —$NH_2$, —N(H)(Me) F, CN, —$NO_2$, 1-aziridyl, and 1-azetidyl.

Additional exemplary E, G, T, and U groups are described below in Table 12.

Additional exemplary compositions of the invention are described in Table 14.

$R_1$ is $R_3$ or $R_6$.

$R_3$ is H or $R_4$.

$R_4$ is alkyl. Typically, $R_4$ is an alkyl of 1 to 6 carbon atoms such as methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3- pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), or the like. More typically, R$_4$ is an alkyl of 1, 2, 3 or 4 carbon atoms. Still more typically, R$_4$ is an alkyl of 1, 2 or 3 carbon atoms selected from methyl, ethyl, n-propyl, and i-propyl.

R$_5$ is R$_6$ or R$_7$, provided that each R$_7$ is independently substituted with 0 to 3 R$_6$ atoms or groups. R$_6$ and R$_7$ are as defined below. Typically, R$_5$ is R$_6$, unsubstituted R$_7$ or mono-, di- and trihaloalkyls of 1 to 6 carbon atoms, more typically, mono- di-, and trifluoro-n-alkyls of 1, 2 or 3 carbon atoms, still more typically monofluoromethyl, difluoromethyl, or trifluoromethyl.

R$_6$ is —O-(antigenic polypeptide), —N(R$_3$)-(antigenic polypeptide), —C(O)O-(antigenic polypeptide), —C(O)N(R$_3$)-(antigenic polypeptide), —S—(antigenic polypeptide), —S—S-(antigenic polypeptide), —O-(label), —N(R$_3$)-(label), —C(O)O-(label), —C(O)N(R$_3$)-(label), —S-(label), —S—S-(label), F, Cl, Br, I, —CN, N$_3$, —NO$_2$, —OR$_3$, —OPRT, —O—C(O)R$_4$, =O, —N(R$_3$)(R$_3$), —N(R$_3$)(PRT), —N(PRT)$_2$, —N(R$_3$)—C(O)R$_4$, =N(R$_3$), =N(PRT), —N(OR$_3$)(R$_3$), —N(OPRT)(R$_3$), —N(OR$_3$)(PRT), —N(OPRT)(R$_3$), —N(N(R$_3$)(R$_3$))(R$_3$), —N(N(PRT)(R$_3$))(R$_3$), —N(N(R$_3$)(R$_3$))(PRT), —N(N(PRT)(PRT))(R$_3$), —N(N(PRT)(R$_3$))(PRT), —N(N(PRT)(PRT))(PRT), —N(R$_3$)—C(N(R$_3$))(N(R$_3$)$_2$), —N(PRT)—C(N(R$_3$))(N(R$_3$)$_2$), —N(R$_3$)—C(N(PRT))(N(R$_3$)$_2$), —N(R$_3$)—C(N(R$_3$)) (N(R$_3$)(PRT)), —N(PRT)—C(N(PRT))(N(R$_3$)$_2$), —N(PRT)—C(N(R$_3$))(N(R$_3$)(PRT)), —N(R$_3$)—C(N(PRT)) (N(R$_3$) (PRT)), —N(R$_3$)—C(N(R$_3$))(N(PRT)$_2$), —N(PRT)—C(N(PRT))(N(R$_3$)(PRT)), —N(PRT)—C(N(R$_3$))(N(PRT)$_2$), —N(R$_3$)—C(N(PRT))(N(PRT)$_2$), —N(PRT)—C(N(PRT))(N(PRT)$_2$), —C(NR$_3$)(N(R$_3$)$_2$), —C(N(R$_3$))(N(R$_3$)(PRT)), —C(NPRT)(N(R$_3$)$_2$), —C(N(PRT))(N(R$_3$)(PRT)), —C(N(R$_3$))(N(PRT)$_2$), —C(N(PRT))(N(PRT)$_2$), —SR$_3$, —S(PRT), =S, —S(O)—R$_3$, —S(O)—OR$_3$, —S(O)—OPRT, —O—S(O)—R$_3$, —S(O)$_2$—R$_3$, —S(O)$_2$—OR$_3$, —S(O)$_2$—OPRT, —O—S(O)$_2$—R$_3$, —C(O)OR$_3$, —C(O)OPRT, —C(O)N(R$_3$)$_2$, —C(O)N(R$_3$)(PRT), —C(O)N(PRT)2, —C(S)N(R$_3$)$_2$, —C(S)N(R$_3$)(PRT), —C(S)N(PRT)$_2$, —N(R$_3$)—S(O)$_2$—R$_3$, —N(PRT)—S(O)$_2$—R$_3$, —S(O)$_2$—N(R$_3$)—R$_3$, —S(O)$_2$—N(PRT)—R$_3$, carbocycle, or hetercycle. Ordinarily R$_6$ is —O—(antigenic polypeptide), —N(R$_3$)-(antigenic polypeptide), —C(O)O—(antigenic polypeptide), —C(O)N(R$_3$)-(antigenic polypeptide), F, Cl, Br, I, —CN, N$_3$, —NO$_2$, —OR$_3$, —N(R$_3$)(R$_3$), —SR$_3$, —O—C(O)R$_4$, —N(R$_3$)—C(O)R$_4$, —C(O)N(R$_3$)(PRT), —C(O)N(PRT)$_2$, —C(O)N(R$_3$)$_2$, —C(O)OR$_3$, —OPRT, —N(PRT)$_2$, —C(NR$_3$)(N(R$_3$)$_2$), —C(N(PRT))(N(R$_3$)(PRT)), —C(N(R$_3$))(N(R$_3$)(PRT)), —C(N(R$_3$))(N(PRT)$_2$), —C(N(PRT))(N(PRT)$_2$), —N(R$_3$) (PRT), —S(PRT), carbocycle or heterocycle. Typically, R$_6$ groups are selected from —OR$_3$, —SR$_3$, —N(R$_3$)(R$_3$), F, CN, —NO$_2$, and heterocycle. More typically, R$_6$ groups are selected from —OH, —OMe, —OEt, —O—i—Pr, —NH$_2$, —N(H)(Me), F, CN, —NO$_2$, 1-aziridyl, and 1-azetidyl.

When R$_6$ is carbocycle or heterocycle, it is typically a monocycle having 3 or 4 ring atoms, more typically, it is a heterocycle having 2 to 3 carbon atoms and 1 heteroatom selected from O, S, and N, still more typically, it is aziridyl, or azetidyl, more typically yet, it is 1-aziridyl, or 1-azetidyl. Other heterocycles or carbocycles suitable for R$_6$, and their substitution sites, are described below under W$_2$.

W$_1$ is W$_2$ or W$_3$.

W$_2$ is carbocycle or heterocycle. Carbocycles and heterocycles within the context of W$_2$ are stable chemical structures. Such structures are isolatable in measurable yield, with measurable purity, from reaction mixtures at temperatures from −78° C. to 200° C. Each W$_2$ is independently substituted with 0 to 3 R$_6$ groups. Typically, W$_2$ is a saturated, unsaturated or aromatic ring comprising a mono- or bicyclic carbocycle or heterocycle. More typically, W$_2$ has 3 to 10 ring atoms, still more typically, 3 to 7 ring atoms.

Typically, W$_2$ is a carbocyclic or heterocyclic monocycle with 3 to 6 ring atoms. The carbocycles or heterocycles are typically saturated if they have 3 ring atoms, saturated or monounsaturated if they have 4 ring atoms, saturated, or mono- or diunsaturated if they have 5 ring atoms, and saturated, mono- or diunsaturated, or aromatic if they have 6 or more ring atoms.

When W$_2$ is carbocyclic, it is typically a 3 to 7 carbon monocycle or a 7 to 10 carbon atom bicycle. More typically, W$_2$ monocyclic carbocycles have 3 to 6 ring atoms, still more typically 5 or 6 ring atoms. More typically, W$_2$ bicyclic carbocycles have 7 to 10 ring atoms arranged as a bicyclo [4,5], [5,5], [5,6] or [6,6] system, still more typically, 9 or 10 ring atoms arranged as a bicyclo [5,6] or [6,6] system. Examples include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, and naphthyl.

When W$_2$ is a heterocycle, it is typically a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). More typically, W$_2$ heterocyclic monocycles have 3 to 6 ring atoms (2 to 5 carbon atoms and 1 to 2 heteroatoms selected from N, O, and S), still more typically, 5 or 6 ring atoms (3 to 5 carbon atoms and 1 to 2 heteroatoms selected from N and S). More typically, W$_2$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system, still more typically, 9 to 10 ring atoms (8 to 9 carbon atoms and 1 to 2 hetero atoms selected from N and S) arranged as a bicyclo [5,6] or [6,6] system.

Heterocycles include by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82, 5566; each of which is incorporated herein by reference.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H, 6H-1,5 2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Typically $W_2$ heterocycles are selected from pyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, or pyrrolyl.

In general the $W_2$ heterocycle is bonded to $-(CR_1 R_1)_{m1}-$ through a ring carbon or heteroatom and, where the heterocycle is polycyclic, through a nonbridging hetero or carbon atom. Aromatic heterocycles are bonded typically through a nonbridging carbon or heteroatom. Usually, the $W_2$ heterocycle is bonded through a carbon atom. For example, $W_2$ is bonded at position 2, 3, 4, 5, or 6 of a pyridine, position 3, 4, 5, or 6 of a pyridazine, position 2, 4, 5, or 6 of a pyrimidine, positon 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, the heterocycle of $W_2$ is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

Ordinary and typical $W_2$'s are selected from those shown in Table 2. More typically, $W_2$ is phenyl, thiazole, tetrahydrothiophene, and sulfur oxidized tetrahydrothiophene structures.

TABLE 2

Ordinary $W_2$s

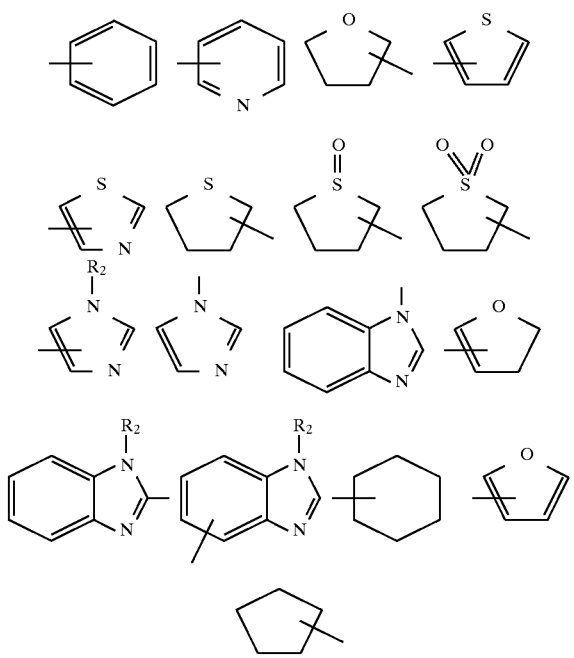

TABLE 2-continued

Typical $W_2$s

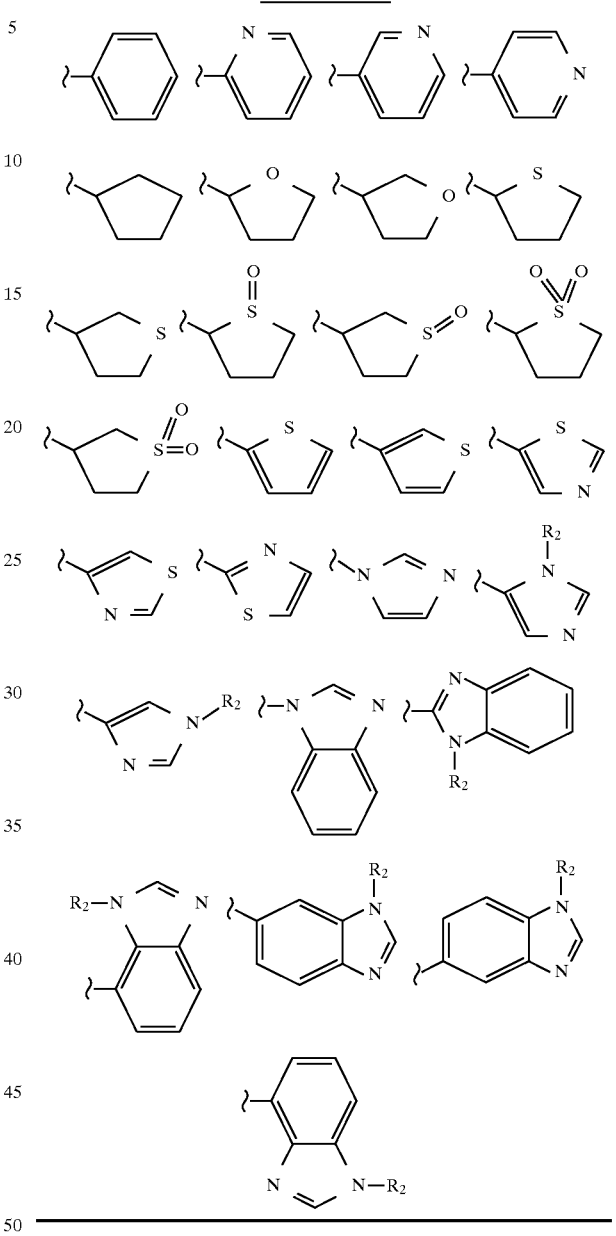

$R_7$ is alkyl, alkenyl, or alkynyl. Typically, $R_7$ is a group of 1 to 8 carbon atoms. When $R_7$ is alkyl it is typically selected from those described above with respect to $R_4$ and the corresponding 7 and 8 carbon homologs. When $R_7$ is alkenyl it is a group of 2 to 8 carbons, typically ethenyl ($-CH=CH_2$), 1-prop-1-enyl ($-CH=CHCH_3$), 1-prop-2-enyl ($-CH_2CH=CH_2$), 2-prop-1-enyl ($-C(=CH_2)(CH_3)$), 1-but-1-enyl ($-CH=CHCH_2CH_3$), 1-but-2-enyl ($-CH_2CH=CHCH_3$), 1-but-3-enyl ($-CH_2CH_2CH=CH_2$), 2-methyl-1-prop-1-enyl ($-CH=C(CH_3)_2$), 2-methyl-1-prop-2-enyl ($-CH_2C(=CH_2)(CH_3)$), 2-but-1-enyl ($-C(=CH_2)CH_2CH_3$), 2-but-2-enyl ($-C(CH_3)=CHCH_3$), 2-but-3-enyl ($-CH(CH_3)CH=CH_2$), 1-pent-1-enyl ($-C=CHCH_2CH_2CH_3$), 1-pent-2-enyl ($-CHCH=CHCH_2CH_3$), 1-pent-3-enyl ($-CHCH_2CH=CHCH_3$), 1-pent-4enyl ($-CHCH_2CH_2CH=CH_2$), 2-pent-1-enyl ($-C(=CH_2)$ CH₂CH₂CH₃), 2-pent-2-enyl (—C(CH₃)=CH₂CH₂CH₃), 2-pent-3-enyl (—CH(CH₃)CH=CHCH₃), 2-pent-4-enyl (—CH(CH₃)CH₂CH=CH₂), 3-methyl-1-but-2-enyl (-CH₂CH=C(CH₃)2), or the like. More typically, R₇ alkenyl groups are of 2 to 6 carbon atoms, still more typically, 2, 3 or 4 carbon atoms. When R₇ is alkynyl it is a group of 2 to 8 carbon atoms, typically ethynyl (—CCH), 1-prop-1-ynyl (—CCCH₃), 1-prop-2-ynyl (—CH₂CCH), 1-but-1-ynyl (—CCCH₂CH₃), 1-but-2-ynyl (—CH₂CCCH₃), 1-but-3-ynyl (—CH₂CH₂CCH), 2-but-3-ynyl (CH(CH₃)CCH), 1-pent-1-ynyl (—CCCH₂CH₂CH₃), 1-pent-2-ynyl (—CH₂CCCH₂CH₃), 1-pent-3-ynyl (—CH₂CH₂CCCH₃), 1-pent-4-ynyl (—CH₂CH₂CH₂CCH), or the like. More typically, R₇ alkynyl groups are of 2 to 6 carbon atoms. Still more typically, 2, 3 or 4 carbon atoms.

W₃ is alkyl, alkenyl, or alkynyl provided that each W₃ is independently substituted with 0 to 2 R₆ groups. Typically, W₃ is an alkyl of 1 to 8 carbon atoms, alkenyl of 2 to 8 carbon atoms, or alkynyl of 2 to 8 carbon atoms. Such groups are described above with respect to R₇. More typically, W₃ is an alkyl of 1 to 6 carbon atoms, alkenyl of 2 to 6 carbon atoms, or alkynyl of 2 to 6 carbon atoms. Still more typically, W₃ is an alkyl of 1 to 3 carbon atoms, alkenyl of 2 to 3 carbon atoms, or alkynyl of 2 to 3 carbon atoms.

Each m1 is an integer from 0 to 3, typically 0 to 2, and more typically 0 or 1. When E, G, T, or U, contains a W₂ heterocycle group and m1 is 0, then W₂ is typically bonded through a carbon atom of W₂ as described above.

In one embodiment of the invention, Y is —O—, and both G and T are hydroxy protecting groups as described below. In another embodiment of the invention, Y is —O—, and one or both of G and T are not a hydroxy protecting group. For example, in the latter case when Y is —O— and one or both of G and T are benzyl, then one or both of the benzyls is substituted in such a way as to render it not useful as a hydroxy protecting group, e.g. not useful in the method described in Greene (cited below). Such substitutions include by way of example and not limitation, incorporation of a protonatable group in the meta position of the benzene ring of a benzyl group to render the group non-removable by conventional debenzylation methods or to render the group cleavable, but only under conditions that do not result in cleavage of conventional benzyl protecting groups. Such groups include R₆ groups containing sulfur, nitrogen or oxygen. Typical benzyls of this type include meta amino, sulfhydryl, and hydroxyl substituted benzyls. G and T optionally are selected to be stable in acid or base deprotecting conditions used heretofore to remove OH protecting groups.

I and L

J and L are independently H, N₃, —OR₂, —N(R₂)(R₂), or —N(R₂)(R₃) provided that at least one of J and L is —OR₂. Alternatively, J and L are taken together to form an epoxide, or a cyclic protecting group.

Typically, one of J and L is —OH. In this embodiment, the other of J and L is typically, —OH, —NH₂, —N(R₃)(H) or H. More typically, the other of J and L is —OH. In another typical embodiment, one of J and L is —OR₈ and the other is H, —OR₂, —N(R₂)(R₂), or —N(R₂)(R₃). In this embodiment, R₈ is —(CR₃R₃)ₘ₂—C (O)(Rg), —(CR₃ R₃)ₘ₂- P(O)(R₉)(R₉), or —(CR₃R₃)ₘ₂-S(O)₂(R₉), Rg is W₁, —OW₁, —N(R₃)(W₁), —N(W₁)(W₁), or —SW₁, and ₘ₂ is an integer from 0 to 2, typically 0 to 1. Other ordinary and typical embodiments of J and L are depicted in Table 3.

In each of the embodiments of J and L, R₃ is typically H or an alkyl group of 1, 2 or 3 carbon atoms as described above with respect to R₄.

TABLE 3

Ordinary Epoxide and Cyclic Protecting Groups of J and L

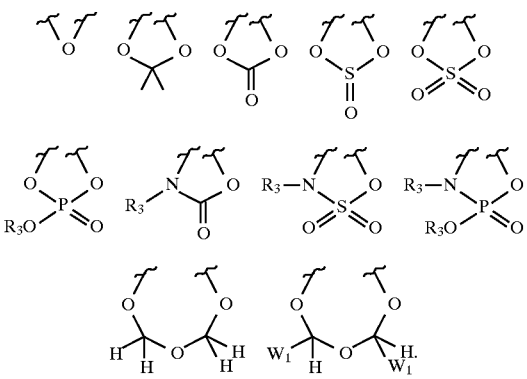

Typical Epoxide and Cyclic Protecting Groups of J and L

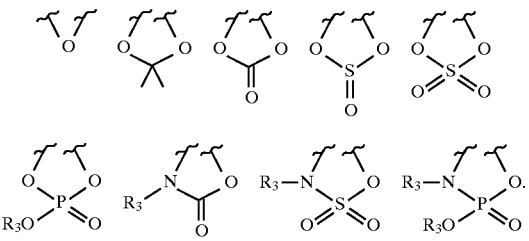

R₂ is H. or a cyclic protecting group. When J or L is —OR₂, —N(R₂)(R₂), or —N(R₂)(R₃), R₂ is H, or PRT.

PRT

A very large number of protecting groups (PRT) and cyclic protecting groups and corresponding cleavage reactions are described in "Protective Groups in Organic Chemistry", Theodora W. Greene (John Wiley & Sons, Inc., New York, 1991, ISBN 0-471-62301-6)(Greene) and will not be detailed here. In the context of the present invention, these protecting groups are groups that can be removed from the molecule of the invention without irreversibly changing the covalent bond structure or oxidation/reduction state of the remainder of the molecule. For example, PRT of a —OPRT or —N(R₃)(PRT) group can be removed to form a —OH or —N(R₃)(H) group, respectively, without affecting other covalent bonds in the molecule. At times, when desired, more than one PRT group can be removed at a time, or they can be removed sequentially. In compounds of the invention containing more than one PRT, the PRT are the same or different.

Determination of whether a group is a protecting group is made in the conventional manner, illustrated by the work of Kocienski, Section 1.1, page 2, and Greene Chapter 1, pages 1–9, both cited herein. In particular, a group is a protecting group if when, based on mole ratio, 90% of that protecting group has been removed by a deprotection reaction, no more than 50%, preferably 25%, more preferably 10%, of the deprotected product molecules of the invention have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment of the invention, a group is a protecting group if when, based on mole ratio determined by conventional techniques, 90% of that protecting group has been removed by a conventional deprotection reaction, no more than 50%, preferably 25%, more preferably 10%, of the deprotected product molecules of the invention have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected molecule of the invention.

Protecting groups are also described in detail together with general concepts and specific strategies for their use in Kocienski, Philip J.; "Protecting Groups" (Georg Thieme Verlag Stuttgart, New York, 1994)(Philip), which is incorporated by reference in its entirety herein. In particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184, Chapter 6, Amino Protecting Groups, pages 185–243, Chapter 7, Epilogue, pages 244–252, and Index, pages 253–260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Typical hydroxy protecting groups are described in Greene at pages 14–118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, , p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p, p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4', 4"-Tris(4,5-dichlorophthalimidophenyl)methyl, 4,4', 4"-Tris(levulinoyloxyphenyl)methyl, 4,4', 4"-Tris(benzoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3-tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N', N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically hydroxy protecting groups include substituted methyl ethers, substituted benzyl ethers, silyl ethers, and esters including sulfonic acid esters, still more typically, trialkylsilyl ethers, tosylates and acetates.

Typical 1,2- and 1,3-diol protecting groups are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); and Silyl Derivatives (Di-t-butylsilylene Group, 1,3-(1,1,3,3-Tetraisopropyldisiloxanylidene) Derivative, Tetra-t-butoxydisiloxane-1,3-diylidene Derivative, Cyclic Carbonates, Cyclic Boronates, Ethyl Boronate, Phenyl Boronate).

More typically, 1,2- and 1,3-diol protecting groups include those shown in Table 3, still more typically, epoxides and acetonides.

Typical amino protecting groups are described in Greene at pages 315–385 and include Carbamates (Methyl and Ethyl, 9-Fluorenylmethyl, 9(2-Sulfo)fluoroenylmethyl, 9-(2, 7-Dibromo)fluorenylmethyl, 2,7-Di-t-buthyl-[9-(10,10-dioxo-10,10,10,10-tetrahydrothioxanthyl)]methyl, 4-Methoxyphenacyl); Substituted Ethyl (2,2,2-Trichoroethyl, 2-Trimethylsilylethyl, 2-Phenylethyl, 1-(1-Adamantyl)-1-methylethyl, 1,1-Dimethyl-2-haloethyl, 1,1-Dimethyl-2,2-dibromoethyl, 1,1-Dimethyl-2,2,2-trichloroethyl, 1-Methyl-1-(4-biphenylyl)ethyl, 1-(3,5-Di-t-butylphenyl)-1-methylethyl, 2-(2'- and 4'-Pyridyl)ethyl, 2-(N,N-Dicyclohexylcarboxamido)ethyl, t-Butyl, 1-Adamantyl, Vinyl, Allyl, 1-Isopropylallyl, Cinnamyl, 4-Nitrocinnamyl, 8-Quinolyl, N-Hydroxypiperidinyl, Alkyldithio, Benzyl, p-Methoxybenzyl, p-Nitrobenzyl, p-Bromobenzyl, p-Chorobenzyl, 2,4-Dichlorobenzyl, 4-Methylsulfinylbenzyl, 9-Anthrylmethyl, Diphenylmethyl); Groups With Assisted Cleavage (2-Methylthioethyl, 2-Methylsulfonylethyl, 2-(p-Toluenesulfonyl)ethyl, [2-(1,3-Dithianyl)]methyl, 4-Methylthiophenyl, 2,4-Dimethylthiophenyl, 2-Phosphonioethyl, 2-Triphenylphosphonioisopropyl, 1,1-Dimethyl-2-cyanoethyl, m-Choro-p-acyloxybenzyl, p-(Dihydroxyboryl)benzyl, 5-Benzisoxazolylmethyl, 2-(Trifluoromethyl)-6-chromonylmethyl); Groups Capable of Photolytic Cleavage (m-Nitrophenyl, 3,5-Dimethoxybenzyl, o-Nitrobenzyl, 3,4-Dimethoxy-6-nitrobenzyl, Phenyl(o-nitrophenyl)methyl); Urea-Type Derivatives (Phenothiazinyl-(10)-carbonyl Derivative, N'-p-Toluenesulfonylaminocarbonyl, N'-Phenylaminothiocarbonyl); Miscellaneous Carbamates (t-Amyl, S-Benzyl Thiocarbamate, p-Cyanobenzyl, Cyclobutyl, Cyclohexyl, Cyclopentyl, Cyclopropylmethyl, p-Decyloxybenzyl, Diisopropylmethyl, 2,2-Dimethoxycarbonylvinyl, o-(N,N-Dimethylcarboxamido) benzyl, 1,1-Dimethyl-3-(N,N-dimethylcarboxamido)propyl, 1,1-Dimethylpropynyl, Di(2-pyridyl)methyl, 2-Furanylmethyl, 2-Iodoethyl, Isobornyl, Isobutyl, Isonicotinyl, p-(p'-Methoxyphenylazo)benzyl, 1-Methylcyclobutyl, 1-Methylcyclohexyl, 1-Methyl-1-cyclopropylmethyl, 1-Methyl-1-(3,5-dimethoxyphenyl) ethyl, 1-Methyl-1-(p-phenylazophenyl)ethyl, 1-Methyl-1-phenylethyl, 1-Methyl-1-(4-pyridyl)ethyl, Phenyl, p-(Phenylazo)benzyl, 2,4,6-Tri-t-butylphenyl, 4-(Trimethylammonium)benzyl, 2,4,6-Trimethylbenzyl); Amides (N-Formyl, N-Acetyl, N-Choroacetyl, N-Trichoroacetyl, N-Trifluoroacetyl, N-Phenylacetyl, N-3-Phenylpropionyl, N-Picolinoyl, N-3-Pyridylcarboxamide, N-Benzoylphenylalanyl Derivative, N-Benzoyl, N-p-Phenylbenzoyl); Amides With Assisted Cleavage (N-o-Nitrophenylacetyl, N-o-Nitrophenoxyacetyl, N-Acetoacetyl, (N'-Dithiobenzyloxycarbonylamino)acetyl, N-3-(p-Hydroxyphenyl)propionyl, N-3-(o-Nitrophenyl) propionyl, N-2-Methyl-2-(o-nitrophenoxy)propionyl, N-2-Methyl-2-(o-phenylazophenoxy)propionyl, N-4-Chlorobutyryl, N-3-Methyl-3-nitrobutyryl, N-o-Nitrocinnamoyl, N-Acetylmethionine Derivative, N-o-Nitrobenzoyl, N-o-(Benzoyloxymethyl)benzoyl, 4,5-Diphenyl-3-oxazolin-2-one); Cyclic Imide Derivatives (N-Phthalimide, N-Dithiasuccinoyl, N-2,3-Diphenylmaleoyl, N-2,5-Dimethylpyrrolyl, N-1,1,4,4-Tetramethyldisilylazacyclopentane Adduct, 5-Substituted 1,3-Dimethyl-1,3,5-triazacyclohexan-2-one, 5-Substituted 1,3-Dibenzyl-1,3,5-triazacyclohexan-2-one, 1-Substituted 3,5-Dinitro-4-pyridonyl); N-Alkyl and N-Aryl Amines (N-Methyl, N-Allyl, N-[2-(Trimethylsilyl)ethoxy]methyl, N-3-Acetoxypropyl, N-(1-Isopropyl-4-nitro-2-oxo-3-pyrrolin-3-yl), Quaternary Ammonium Salts, N-Benzyl, N-Di(4-methoxyphenyl)methyl, N-5-Dibenzosuberyl, N-Triphenylmethyl, N-(4-Methoxyphenyl)diphenylmethyl, N-9-Phenylfluorenyl, N-2,7-Dichloro-9-fluorenylmethylene, N-Ferrocenylmethyl, N-2-Picolylamine N'-Oxide); Imine Derivatives (N-1,1-Dimethylthiomethylene, N-Benzylidene, N-p-methoxybenylidene, N-Diphenylmethylene, N-[(2-Pyridyl) mesityl]methylene, N,(N',N'-Dimethylaminomethylene, N,N'-Isopropylidene, N-p-Nitrobenzylidene, N-Salicylidene, N-5-Chlorosalicylidene, N-(5-Chloro-2-hydroxyphenyl)phenylmethylene, N-Cyclohexylidene); Enamine Derivative (N-(5,5-Dimethyl-3-oxo-1-cyclohexenyl)); N-Metal Derivatives (N-Borane Derivatives, N-Diphenylborinic Acid Derivative, N-[Phenyl (pentacarbonylchromium- or -tungsten)]carbenyl, N-Copper or N-Zinc Chelate); N-N Derivatives (N-Nitro, N-Nitroso, N-Oxide); N-P Derivatives (N-Diphenylphosphinyl, N-Dimethylthiophosphinyl, N-Diphenylthiophosphinyl, N-Dialkyl Phosphoryl, N-Dibenzyl Phosphoryl, N-Diphenyl Phosphoryl); N-Si Derivatives; N-S Derivatives; N-Sulfenyl Derivatives (N-Benzenesulfenyl, N-o-Nitrobenzenesulfenyl, N-2,4-Dinitrobenzenesulfenyl, N-Pentachlorobenzenesulfenyl, N-2-nitro-4-methoxybenzenesulfenyl, N-Triphenylmethylsulfenyl, N-3-Nitropyridinesulfenyl); andN-Sulfonyl Derivatives (N-p-Toluenesulfonyl, N-Benzenesulfonyl, N-2,3,6-Trimethyl-4-methoxybenzenesulfonyl, N-2,4,6-Trimethoxybenzenesulfonyl, N-2,6-Dimethyl-4-methoxybenzenesulfonyl, N-Pentamethylbenzenesulfonyl, N-2,3,5,6,-Tetramethyl-4-methoxybenzenesulfonyl, N-4-methoxybenzenesulfonyl, N-2,4,6-Trimethylbenzenesulfonyl, N-2,6-Dimethoxy-4-methylbenzenesulfonyl, N-2,2,5,7,8-Pentamethylchroman-6-sulfonyl, N-Methanesulfonyl, N-β-Trimethylsilyethanesulfonyl, N-9-Anthracenesulfonyl, N-4-(4', 8'-Dimethoxynaphthylmethyl)benzenesulfonyl, N-Benzylsulfonyl, N-Trifluoromethylsulfonyl, N-Phenacylsulfonyl).

More typically, amino protecting groups include carbamates and amides, still more typically, N-acetyl groups.

Groups capable of biological cleavage typically include common prodrugs. A large number of such groups are described in "Design of Prodrugs", Hans Bundgaard (Elsevier, N.Y., 1985, ISBN 0-444-80675-X) (Bundgaard) and will not be detailed here. In particular, Bundgaard, pages 1 to 92 describe prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs, as for example when J and L are taken together, at pages 62 to 70.

Additional exemplary J and L groups are described below in Table 13.

The compounds of this invention contains 0 to 6 $R_6$ groups, typically 0 to 3 $R_6$ groups.

Another embodiment of the invention is directed to compositions comprising compounds of the formula:

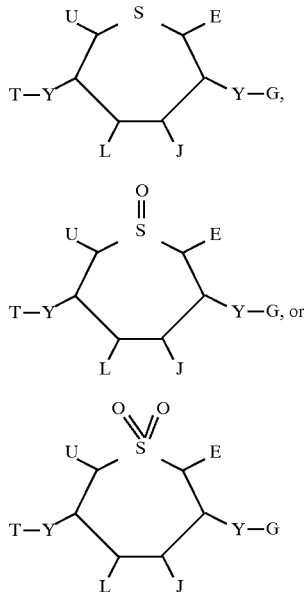

wherein:

Y is independently —$N(R_1)$—, —$N(R_1)$—$SO_2$—, or —$N(R_1)$—CO—;

E and U are independently H, or —$(CR_1R_1)_{m1}$—$W_1$, with the proviso that at least one of E and U is —$(CR_1R_1)_{m1}$—$W_1$;

G and T are independently —$(CR_1R_1)_{m1}$—$W_1$, or —$(CR_1R_1)_{m1}$—$C(R_1)(W_1)(W_2)$, with the proviso that: when E is —$(CR_1R_1)_{m1}$—$W_1$, then G is —$(CR_1R_1)_{m1}$—$W_1$, and when U is —$(CR_1R_1)_{m1}$—$W_1$, then T is —$(CR_1R_1)_{m1}$—$W_1$ and G and T may be the same or different;

J and L are independently H, $N_3$, —$OR_2$, —$N(R_2)(R_2)$, or —$N(R_2)(R_3)$, wherein $R_2$ is H, or PRT with the proviso that at least one of J and L is —$OR_2$; or J and L are taken together to form an epoxide, or a cyclic protecting group;

$W_1$ is $W_2$ or $W_3$;

$W_2$ is carbocycle or heterocycle, with the proviso that each $W_2$ is independently substituted with 0 to 3 $R_5$ groups;

$W_3$ is alkyl, alkenyl, or alkynyl, with the proviso that each $W_3$ is independently substituted with 0 to 3 $R_6$ groups;

$R_1$ is $R_3$ or $R_6$;

$R_3$ is H or $R_4$;

$R_4$ is alkyl;

$R_5$ is $R_6$, or $R_7$, with the proviso that each $R_7$ is independently substituted with 0 to 3 $R_6$ groups;

$R_6$ is —O—(antigenic polypeptide), —$N(R_3)$-(antigenic polypeptide), —C(O)O—(antigenic polypeptide), —C(O)$N(R_3)$-(antigenic polypeptide), F, Cl, Br, I, —CN, $N_3$, —$NO_2$, —$OR_3$, —$N(R_3)(R_3)$, —$SR_3$, —O—$C(O)R_4$, —$N(R_3)$—$C(O)R_4$, —$C(O)N(R_3)$(PRT), —$C(O)N(PRT)_2$, —$C(O)N(R_3)_2$, —$C(O)OR_3$, —OPRT, —$N(PRT)_2$, —$C(NR_3)(N(R_3)_2)$, —$C(N(PRT))(N(R_3)(PRT))$, —$C(N(R_3))(N(R_3)(PRT))$, —$C(N(R_3))(N(PRT)_2)$, —$C(N(PRT))(N(PRT)_2)$, —$N(R_3)(PRT)$, —S(PRT), carbocycle or heterocycle;

$R_7$ is alkyl, alkenyl, or alkynyl;

Each $m_1$ is independently an integer from 0 to 3; and with the proviso that the compound, taken as a whole, contains 0 to 16 $R_6$ groups, and that each E, G, T, and U, taken individually, contain 0 to 8 $R_6$ groups.

Typically, in this embodiment Y is —$N(R_3)$—, more typically, Y is —N(H)—. The preferred embodiments of E, G, J, L, T, discussed above, are also preferred in each of these embodiments.

Stereochemistry

Formulas herein that do not depict stereochemistry are intended to include all possible stereochemistries. For example, formulas I, II, and III do not depict stereochemistry for the sulfoxide or groups E, G, J, L, T, and U. All possible stereochemistries of these groups are intended. Table 1 lists specifically each of these intended stereochemistries for groups E, G, J, L, T and V. Depending on the choice of substituents, certain of the individual compounds of Table 1 may be redundant, being identical to one another by symmetry options.

The designation α indicates that the group is projected behind the plane of the page and the designation, β indicates that the group projects above the plane of the page. For example, structure "a" in Table 10 is $\alpha Q_b$, $\alpha O$—$Q_c$, $\alpha Q_d$, $\alpha Q_e$, $\beta O$—$Q_f$, $\alpha Q_g$, structure "k" is $\alpha Q_b$, $\alpha O$—$Q_c$, $\alpha Q_d$, $\beta Q_e$, $\beta O$—$Q_f$, $\beta Q_g$, and structure "q" is $\beta Q_b$, $\beta O$—$Q_c$, $\beta Q_d$, $\alpha O$—$Q_e$, $\alpha O$—$Q_f$, $\alpha Q$.

If each of the substituents E, G, T and U are independently selected from the structures of Table 12; and if each of the substituents J and L are independently selected from the structures of Table 13, then the 36 structures of Table 10 each represent a typical stereochemistry.

One typical group of stereochemistries is represented by structures "a"–"k" in Table 10. These structures are available, inter alia from L-mannitol as described by Schemes 1–3, and 5–6 below.

Another typical group of stereochemistries is represented by structures "l"–"v" in Table 10. These structures are available, inter alia, from D-mannitol as described by Schemes 1–3, and 5–6 below.

Another typical group of stereochemistries is represented by structures "w"–"B" in Table 10. These structures are available, inter alia, from L- or D-mannitol as described by Scheme 4 below.

Another typical group of stereochemistries is represented by structures "C"–"J" in Table 10. These structures are available, inter alia from inostitol derivatives known in the art as described by Scheme 7 below.

One preferred stereochemistry is that shown in structure "k" of Table 10, $\alpha Q_b$, $\alpha O$-$Q_c$, $\alpha Q_d$, $\beta Q_e$, $\beta O$-$Q_f$, $\beta Q_g$ or $\alpha E$, $\alpha O$-G, $\alpha J$, $\beta L$, $\beta O$-T, $\beta U$.

When group $Q_a$ is —S(O)— (structure "b" from Table 11) then, depending on the choice of the remaining substituents and the ring substituent stereochemistries, an additional stereocenter is introduced. Each of the two possible sulfoxide diastereomers is intended, neither being uniquely preferred.

The compounds of the invention can exist as optical isomers at any asymmetric atoms. For example, the chiral centers designated by "*" in the depictions can exist as stereoisomers. Both racemic and diasteromeric mixtures of these isomers which may exist for certain compounds, as well as the individual optical isomers isolated or synthesized, being resolved or substantially (>90%) free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. A large number of such techniques are described in "Enantiomers, Racemates, and resolutions", Jean Jacques, Andre Collet, and Samuel H. Wilen (Krieger Publishing Company, Malabar, Fla., 1991, ISBN 0-89464-618-4). In particular, Part 2, Resolution of Enantiomer Mixture, pages 217–435; more particularly, section 4, Resolution by Direct Crystallization, pages 217–251, section 5, Formation and Separation of Diastereomers, pages 251–369, section 6, Crystallization-Induced Asymmetric Transformations, pages 369–378, and section 7, Experimental Aspects and Art of Resolutions, pages 378–435; still more particularly, section 5.1.4, Resolution of Alcohols. Transformation of Alcohols into Salt-Forming Derivatives, pages 263–266, section 5.2.3 Covalent Derivatives of Alcohols, Thiols, and Phenols, pages 332–335, and section 5.2.7, Chromatographic Behavior of Covalent Diastereomers, pages 348–354, are cited as examples of the skill of the art. In most instances, the desired optical isomer is synthesized by means of stereoselective reactions, beginning with the appropriate stereoisomer of the desired starting material.

The compounds of the invention can also exist as tautomeric isomers in certain cases. For example, ene-amine tautomers can exist for imidazole, guanine, amidine, and tetrazole systems and all the possible tautomeric forms of either are within the scope of the invention.

The compositions of this invention optionally comprise pharmaceutically acceptable non-toxic salts of the compounds herein, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety, typically a carboxylic acid, phenol, or the like.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$ amino acids such as glutamic acid or aspartic acid, lysine, hydroxylysine, arginine or histidine, or organic sulfonic acids, with basic centers, typically amines, pyridine, or the like. Finally, it is to be understood that the compositions herein comprise compounds of the invention in their un-ionized, as well as zwitterionic form, as appropriate.

Oxidation and alkylation of amine groups of the compositions of the invention to form N-oxides and quaternary ammonium salts, respectively, is also contemplated within the scope of the invention.

Exemplary Enumerated Compounds.

By way of example and not limitation, a number of exemplary specifically enumerated compounds of the invention are listed below in Table 14. Generally, the compositions of the invention are depicted by the structures of formulas I, II, and III.

The compounds in the Table 14 exemplary list are designated by an alphanumerical format in which the first field is the seven membered ring structure of formulas I, II or III as numbered in Table 10. The second field represents $Q_a$, the third field represents $Q_b$, the fourth field represents $Q_c$, the fifth field represents $Q_d$, the sixth field represents $Q_e$, the seventh field represents $Q_f$, and the eight field represents $Q_g$, each attached by a covalent bond to the ring system as depicted in Table 10. Fields are separated by periods.

The ring structures of Table 10 have labels $Q_a$, $Q_b$, $Q_c$, $Q_d$, $Q_e$, $Q_f$, and $Q_g$ as shown. The groups shown in Table 11 are $Q_a$ groups. The groups shown in Table 12 are the Qb, Qc, Qf and Qg groups. The groups shown in Table 13 are the Qd and Qe groups.

The following process is followed to determine the identity of a Table 14 compound.

1. The first letter from left to right is one of the ring systems shown in Table 10, designated a-z and A-Y. This is the cyclic structure which is substituted by the 7 substituents specified by the remaining 7 designation codes.

2. The second letter encodes the Qa group of the Table 10 structures specified in the first code letter. The Qa groups are listed in Table 11, where they are shown with flanking Qi sites. The Qi sites are located at the ring carbon atoms occupied by the $Q_g$ and $Q_b$ substituents. $Q_1$ is not a depiction of a group or bond but is only intended to show orientation of $Q_a$.

3. The third letter (or combination of letters not separated by a period) encodes the $Q_b$ group of the Table 10 ring structure specified by the first letter in the compound code. Refer to Table 12 and select the encoded $Q_b$ group. The "$Q_2$" designation in the Table 12 groups depicts the site at which the $Q_b$ group is bonded to the ring carbon atom; $Q_2$ does not stand for any group or bond, but instead (like $Q_1$) is only intended to aid in determining the substitution site.

4. The fourth letter (or combination of letters not separated by a period) encodes the Qc group of the designated ring structure. Again, refer to Table 12 to select the encoded group. $Q_2$ has the same meaning as with $Q_b$ except that the bonding site is the oxygen atom shown in the Table 10 structure encoded by the first letter.

5. The fifth letter encodes $Q_d$. It is determined by reference to Table 13 in the same general fashion as was done for $Q_a$, $Q_b$ and $Q_c$. $Q_3$ in Table 13 similarly is the designation of ring carbon atom site, but does not represent a bond or group in its own right.

6. The sixth letter encodes $Q_e$. It is decoded from Table 13 in the same was as $Q_d$.

7. The seventh and eight letters (or combinations of letters) encode $Q_f$ and $Q_g$, respectively. They are decoded from Table 12 in the same fashion as $Q_b$ and $Q_c$.

By way of example, three compounds having the designation k.c.a.a.b.b.a.a, k.b.a.a.c.c.a.a, and q.a.aN.J.b.c.a.aA are shown below.

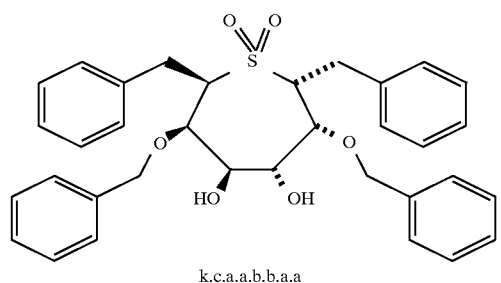

k.c.a.a.b.b.a.a

-continued
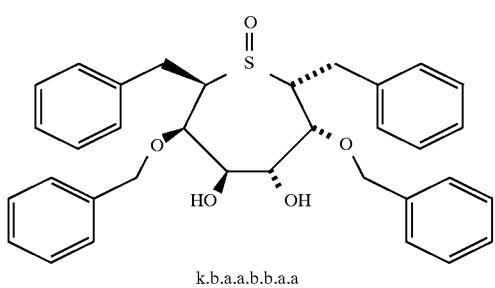
k.b.a.a.b.b.a.a
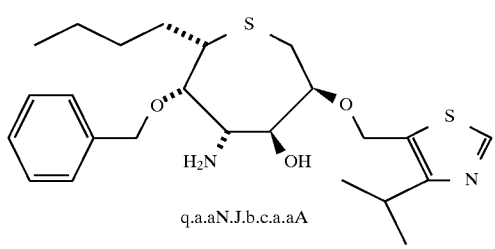
q.a.aN.J.b.c.a.aA
TABLE 10
Seven Membered Heterocycles
| | |
|---|---|
| 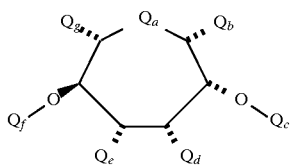 | a |
| 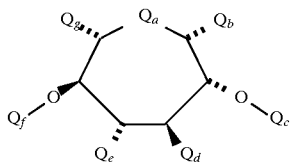 | b |
| 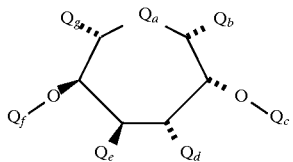 | c |
| 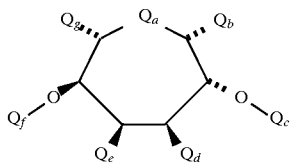 | d |
| 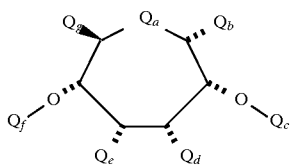 | e |
TABLE 10-continued
Seven Membered Heterocycles
| | |
|---|---|
| 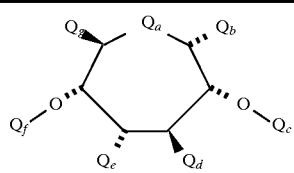 | f |
| 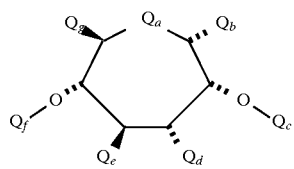 | g |
| 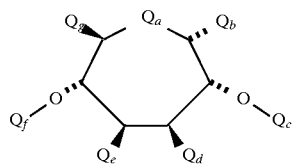 | h |
| 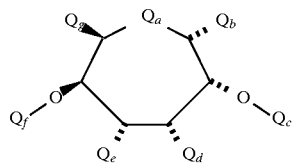 | i |
| 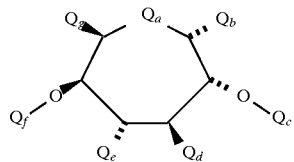 | j |
| 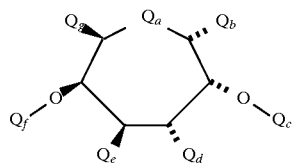 | k |
| 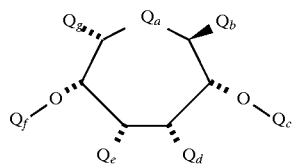 | l |
| 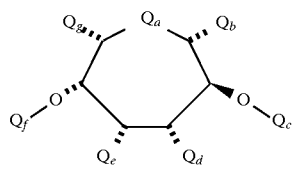 | m |
| 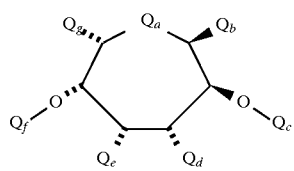 | n |

TABLE 10-continued

Seven Membered Heterocycles o p q r s t u v w x y z

A

B

C

D

E

F

TABLE 10-continued

Seven Membered Heterocycles

TABLE 10-continued
Seven Membered Heterocycles
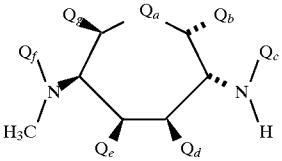
TABLE 11
Qa groups
TABLE 12
Qb, Qc, Qf and Qg groups

TABLE 12-continued
$Q_b$, $Q_c$, $Q_f$ and $Q_g$ groups
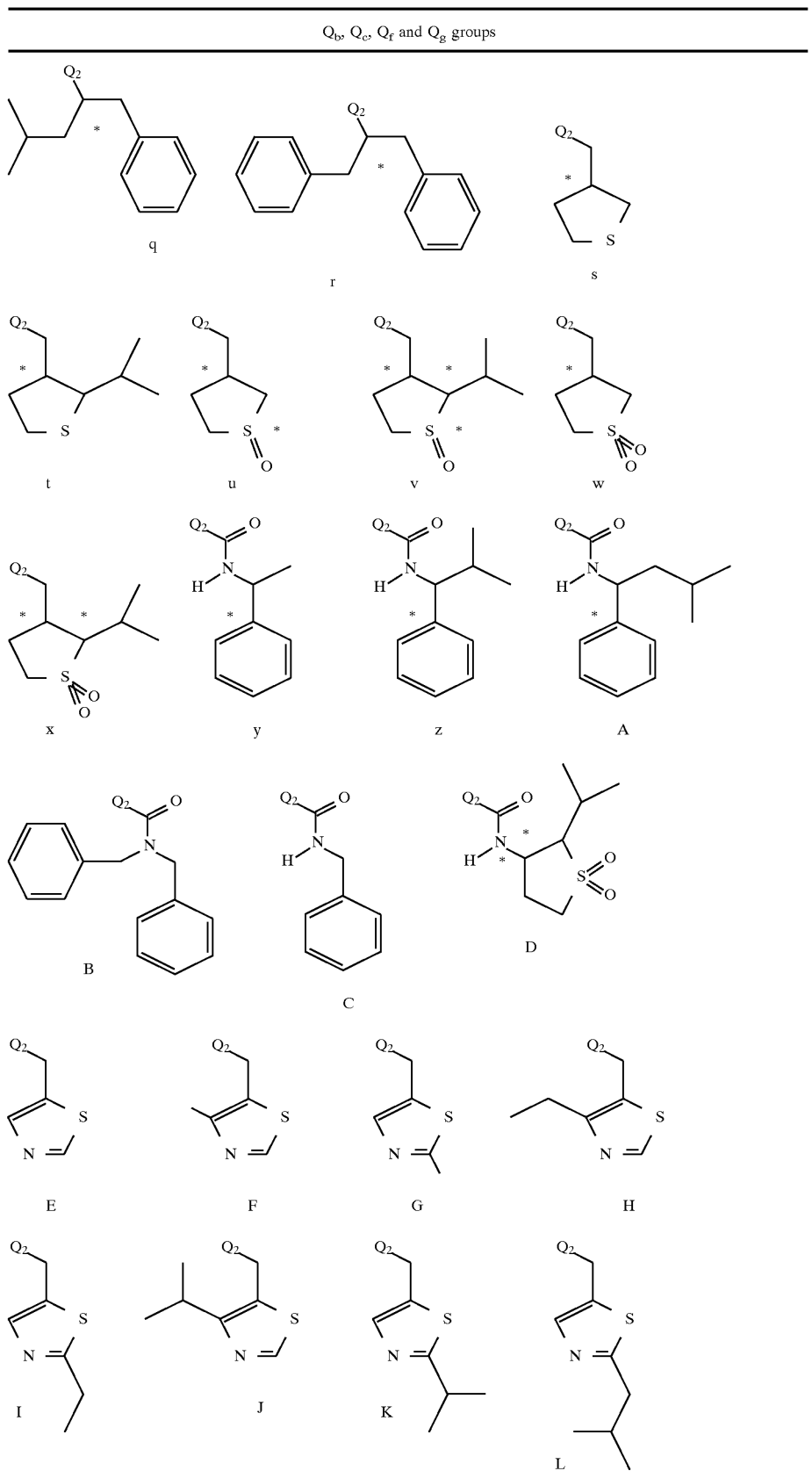

TABLE 12-continued
Q$_b$, Q$_c$, Q$_f$ and Q$_g$ groups
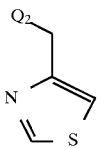 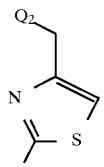 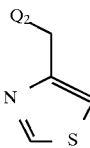 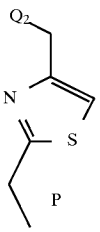
M　　　　　　N　　　　　　O　　　　　　P
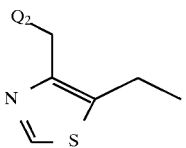 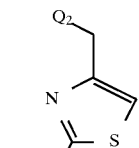 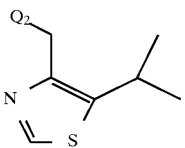 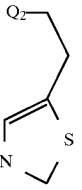
Q　　　　　　R　　　　　　S　　　　　　T
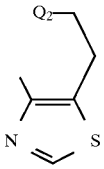 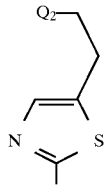 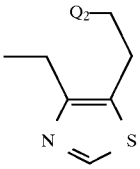 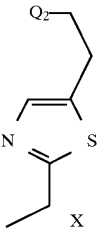
U　　　　　　V　　　　　　W　　　　　　X
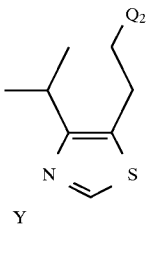 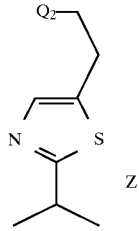 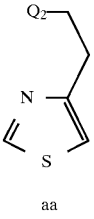 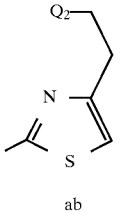
Y　　　　　　Z　　　　　　aa　　　　　　ab
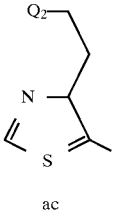 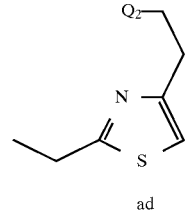 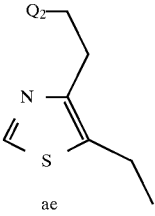 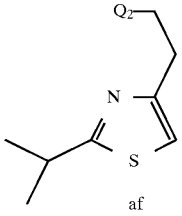
ac　　　　　　ad　　　　　　ae　　　　　　af
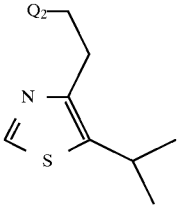 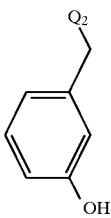 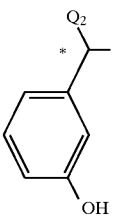 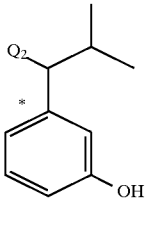
ag　　　　　　ah　　　　　　ai　　　　　　aj TABLE 12-continued Q_b, Q_c, Q_f and Q_g groups TABLE 12-continued
$Q_b$, $Q_c$, $Q_f$ and $Q_g$ groups
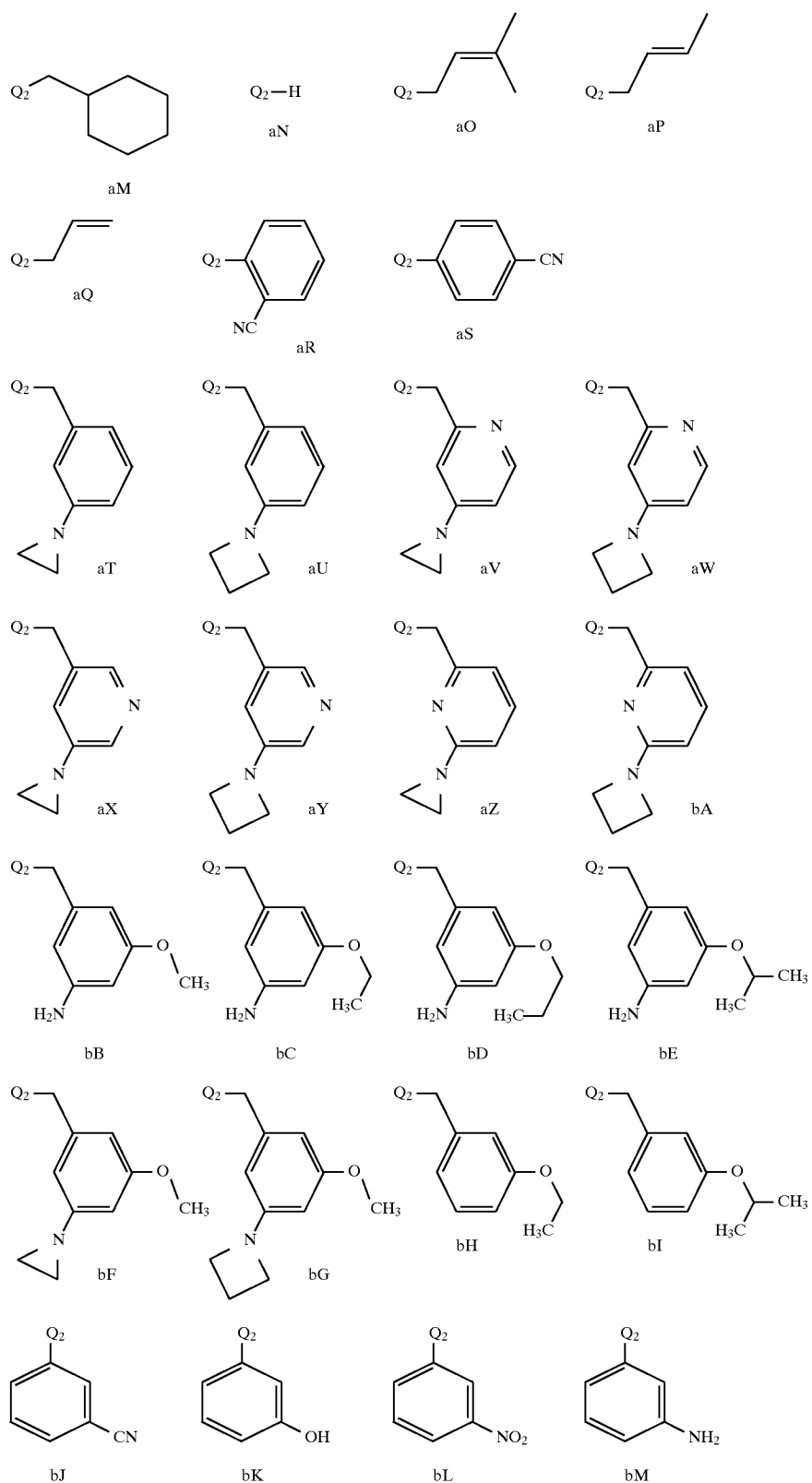

TABLE 12-continued
$Q_b$, $Q_c$, $Q_f$ and $Q_g$ groups
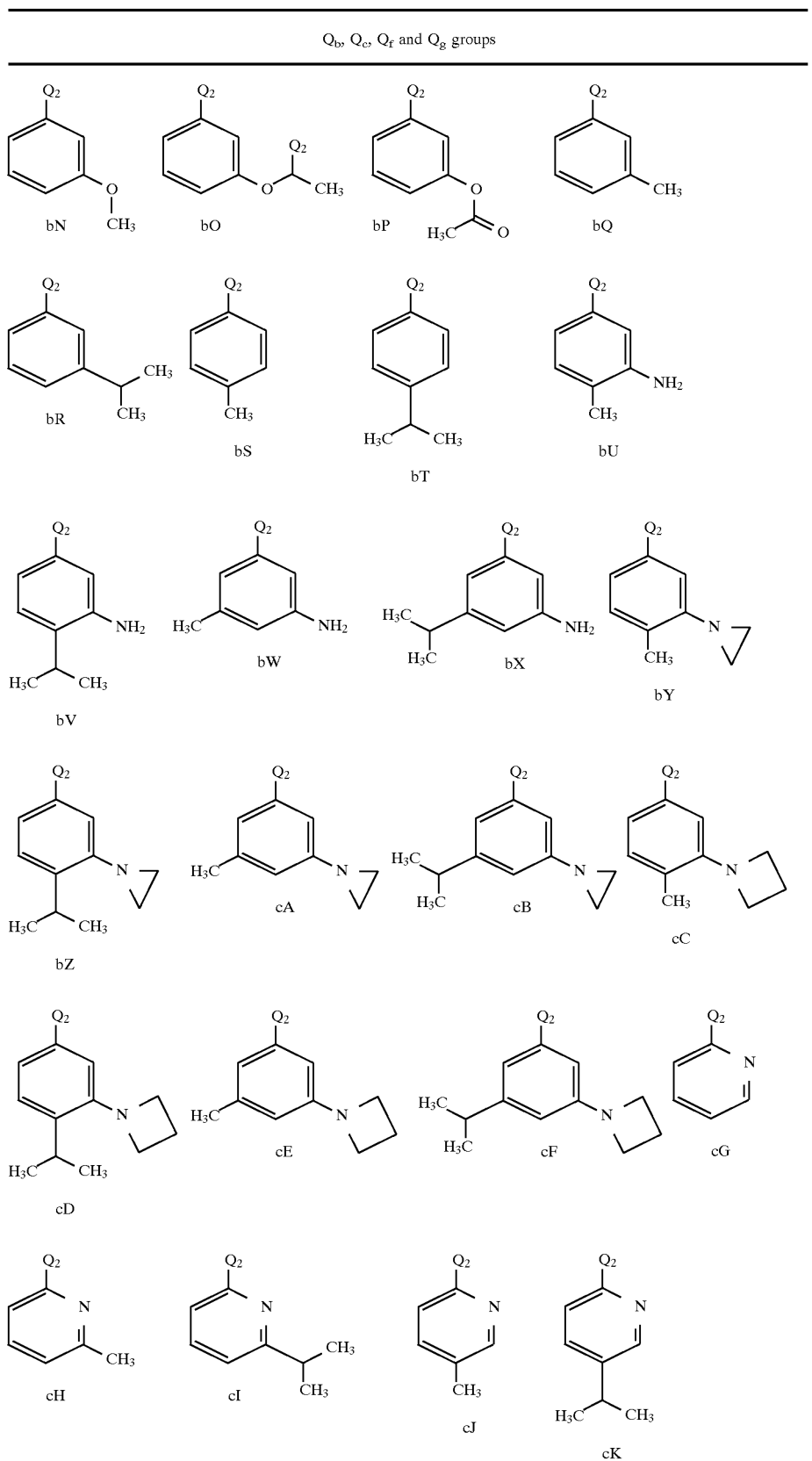

5,811,450
TABLE 12-continued
Q_b, Q_c, Q_f and Q_g groups
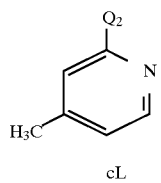 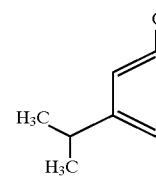 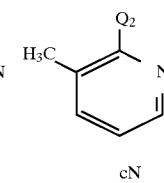 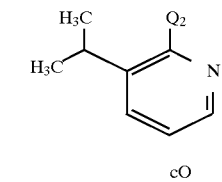
cL cM cN cO
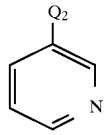 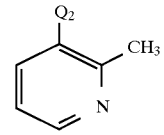 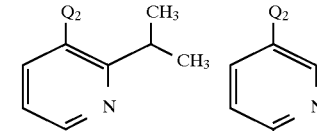 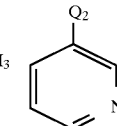
cP cQ cR cS
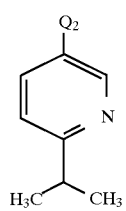 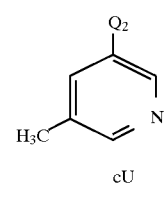 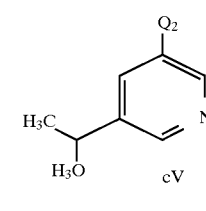 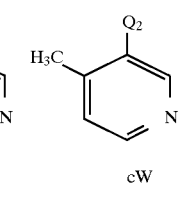
cT cU cV cW
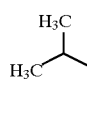 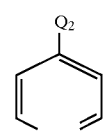 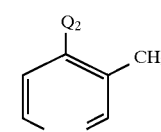 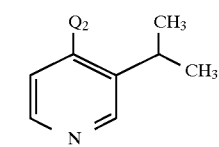
cX cY cZ dA
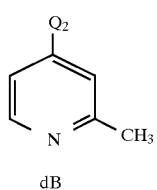 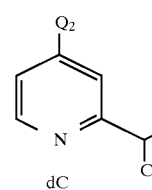 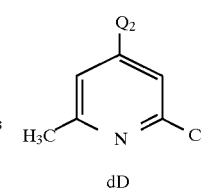 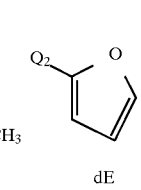
dB dC dD dE
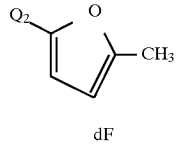 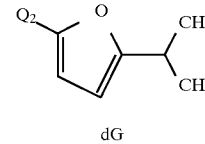 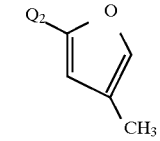 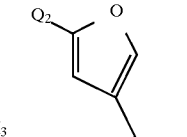
dF dG dH dI
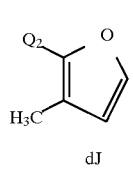 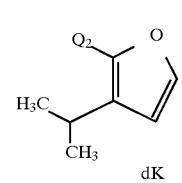 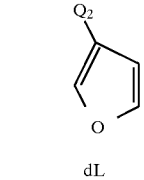 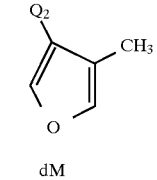
dJ dK dL dM TABLE 12-continued
Q_b, Q_c, Q_f and Q_g groups
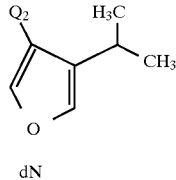 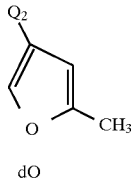 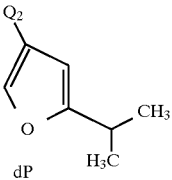 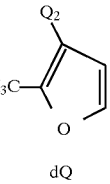
dN dO dP dQ
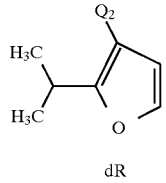 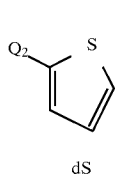 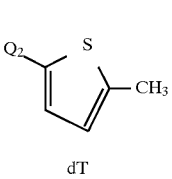 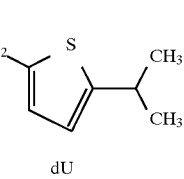
dR dS dT dU
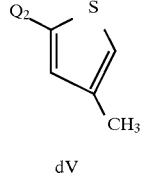 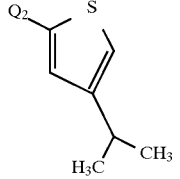 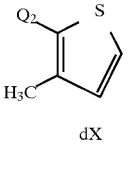 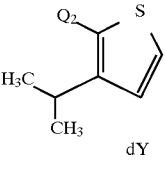
dV dW dX dY
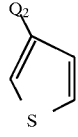 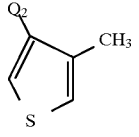 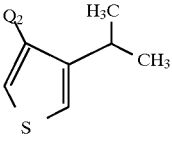 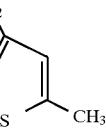
dZ eA eB eC
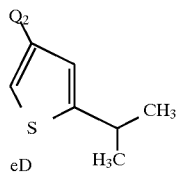 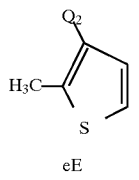 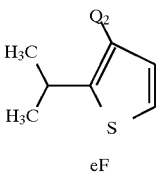 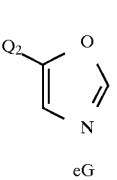
eD eE eF eG
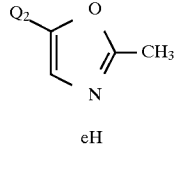 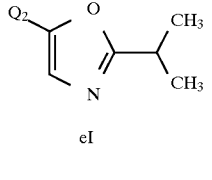 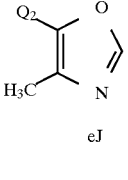 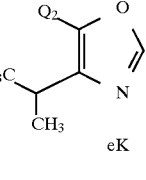
eH eI eJ eK
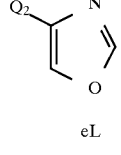 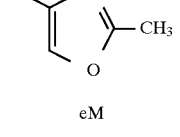 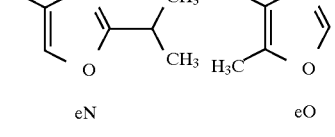 
eL eM eN eO
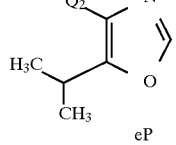 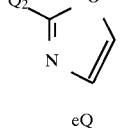 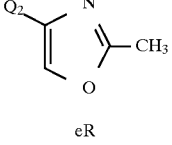 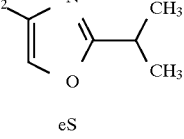
eP eQ eR eS TABLE 12-continued
Q$_b$, Q$_c$, Q$_f$ and Q$_g$ groups
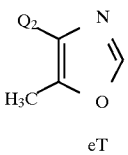
eT
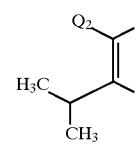
eU
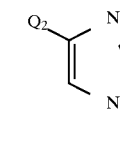
eV
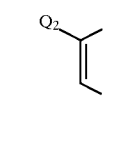
eW
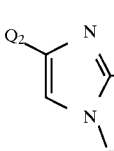
eX
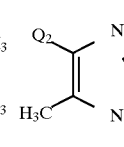
eY
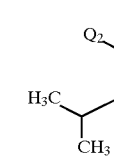
eZ
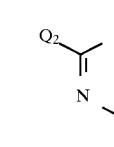
fA
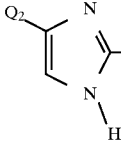
fB
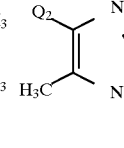
fC
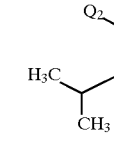
fD
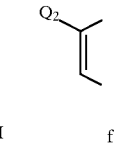
fE
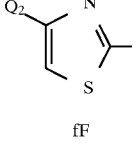
fF
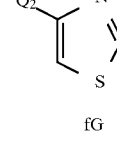
fG
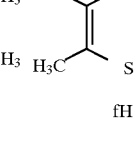
fH
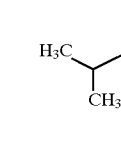
fI
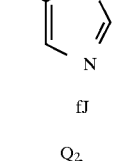
fJ
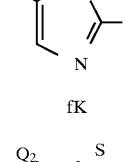
fK
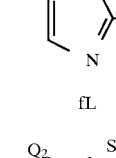
fL
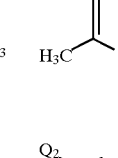
fM
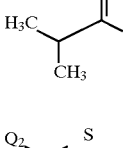
fN
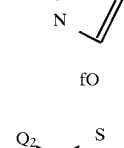
fO
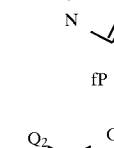
fP
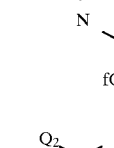
fQ
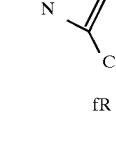
fR
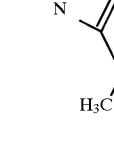
fS
fT
fU
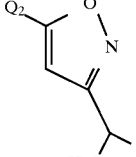
fV
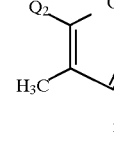
fW
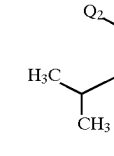
fX
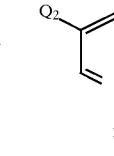
fY TABLE 12-continued
Q_b, Q_c, Q_f and Q_g groups
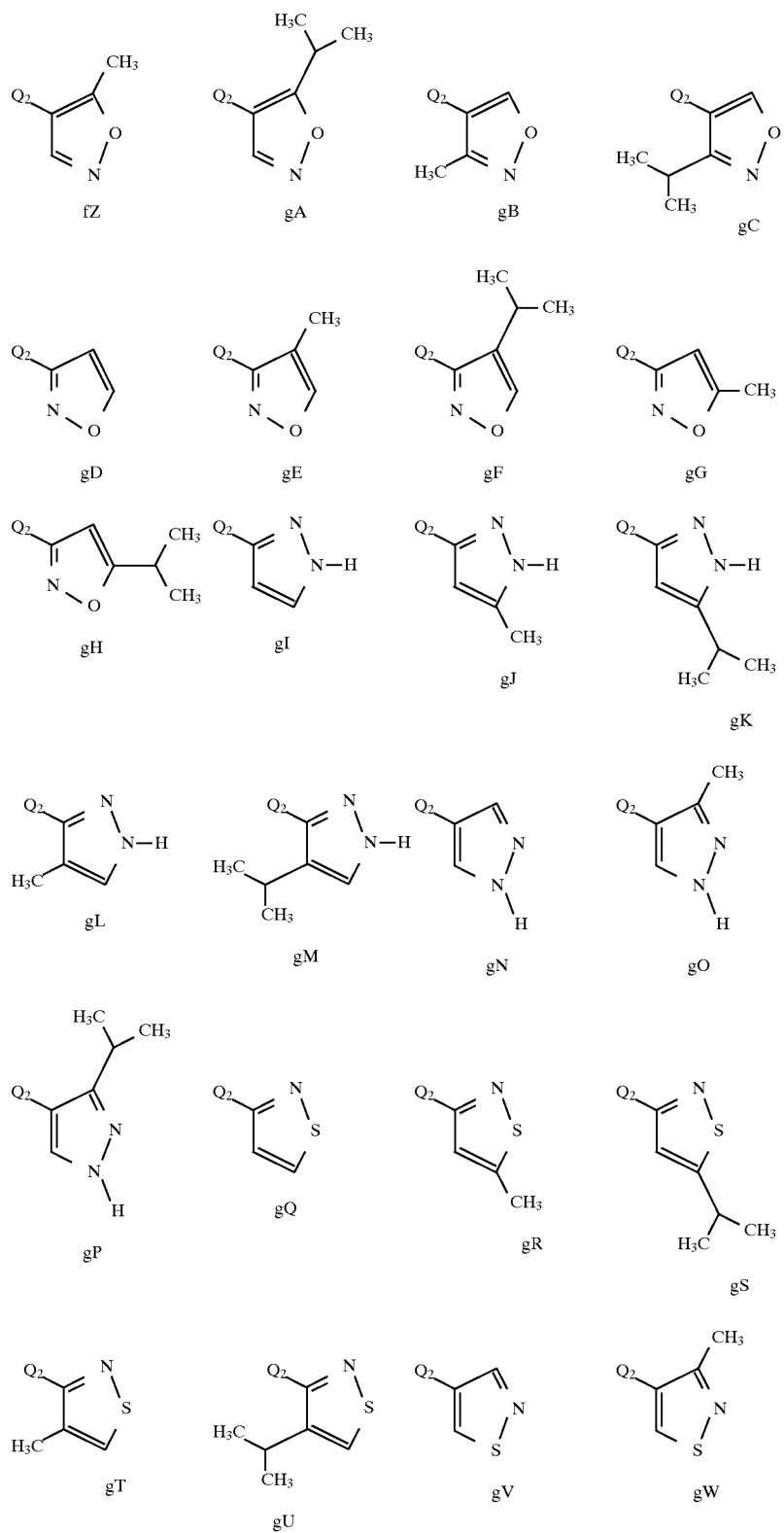

TABLE 12-continued
$Q_b$, $Q_e$, $Q_f$ and $Q_g$ groups
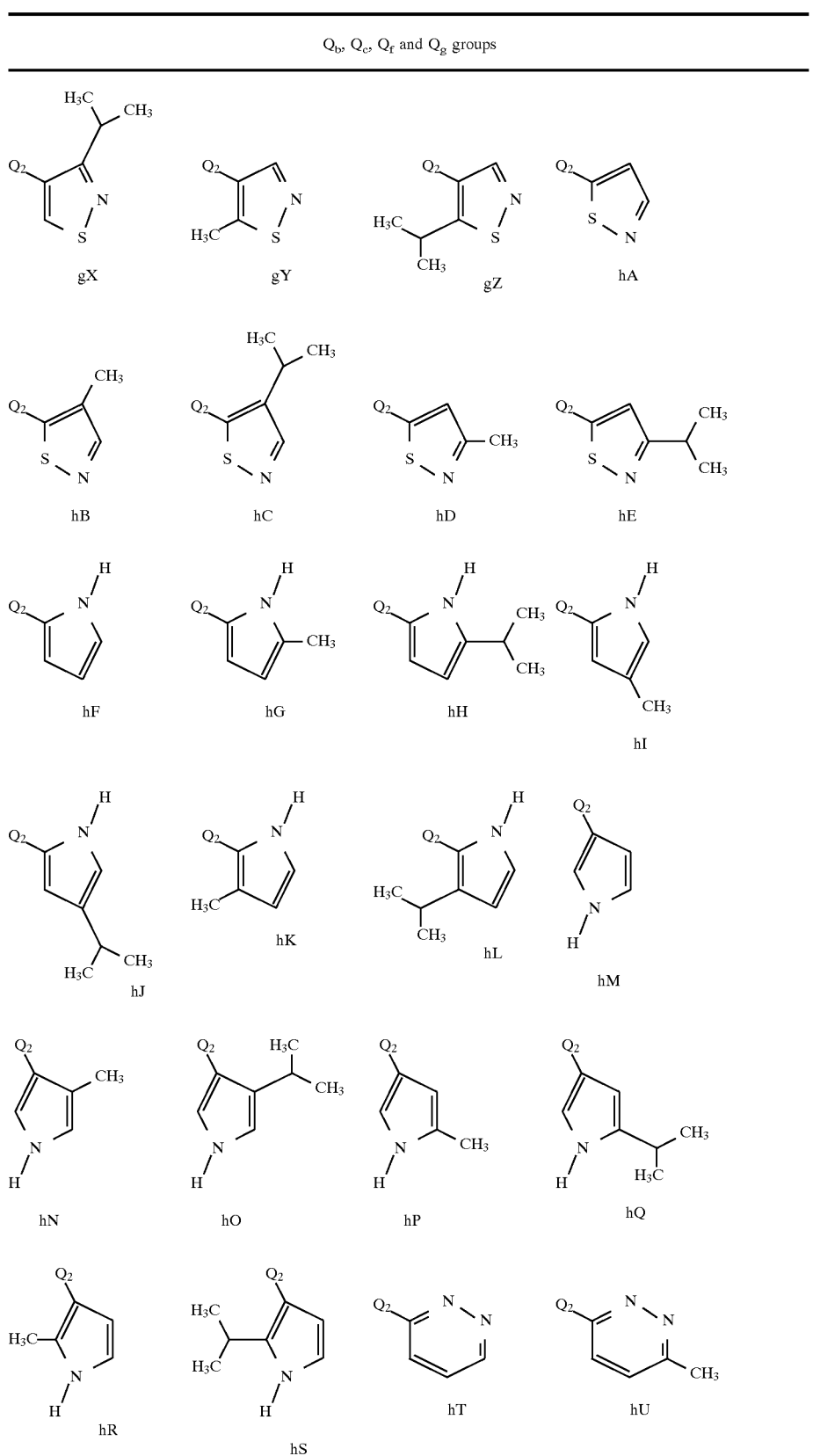

TABLE 12-continued $Q_b$, $Q_c$, $Q_f$ and $Q_g$ groups

TABLE 12-continued $Q_b$, $Q_e$, $Q_f$ and $Q_g$ groups

TABLE 12-continued $Q_b$, $Q_c$, $Q_f$ and $Q_g$ groups

TABLE 12-continued
$Q_b$, $Q_c$, $Q_f$ and $Q_g$ groups
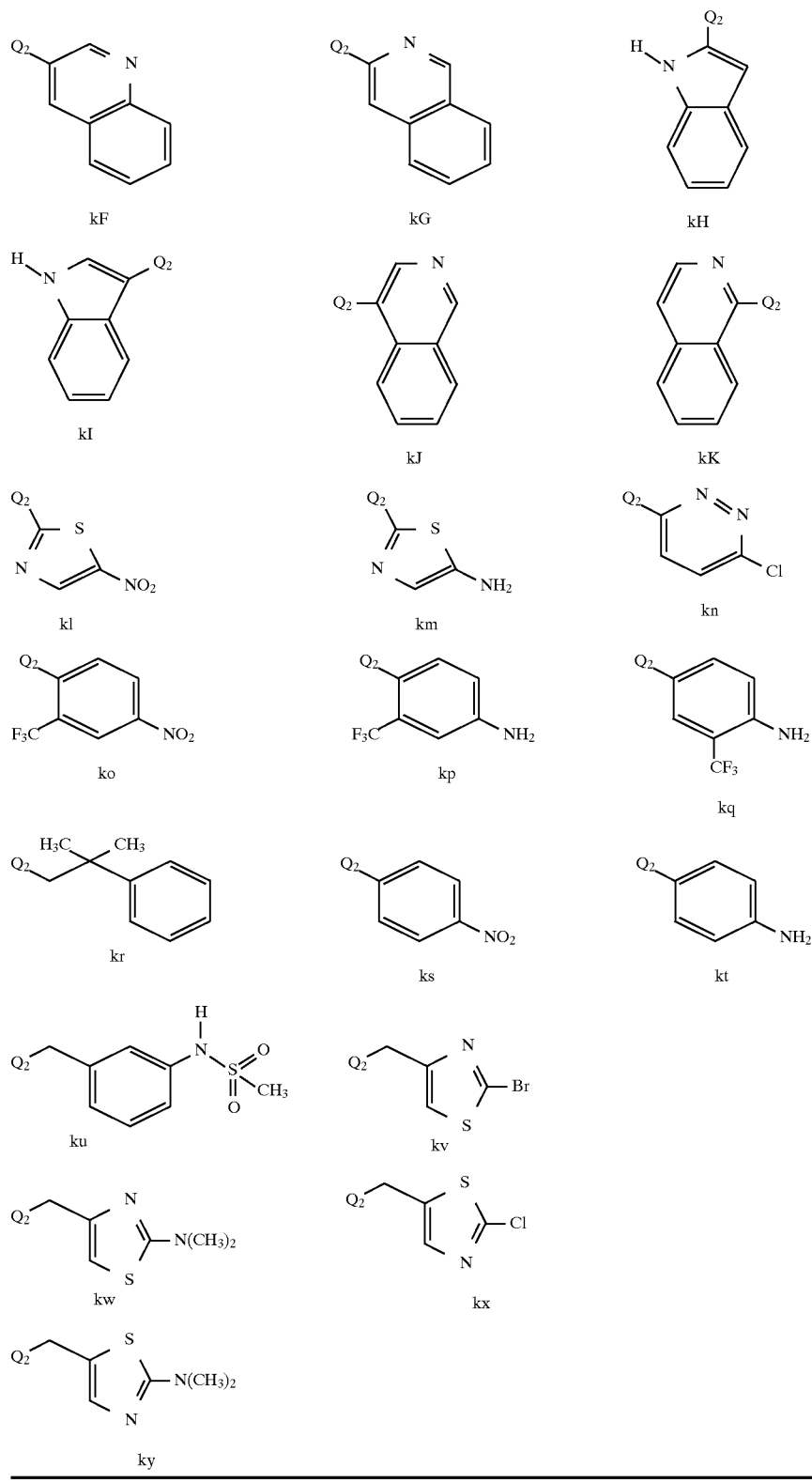

TABLE 13

$Q_d$ and $Q_e$ groups

| $Q_3$—H | $Q_3$—OH | $Q_3$—NH$_2$ | $Q_3$—N$_3$ | $Q_3$—O—C(=O)CH$_3$ |
|---|---|---|---|---|
| a | b | c | d | e |

TABLE 13-continued

$Q_d$ and $Q_e$ groups $Q_3$—O—S(=O)$_2$—C$_6$H$_4$—CH$_3$ f

TABLE 14

Exemplary Compounds of the Invention

| | | | |
|---|---|---|---|
| k.c.a.a.a.b.a.a | k.c.a.a.a.b.a.aA | k.c.a.a.a.b.a.aG | k.c.a.a.a.b.e.a |
| k.c.a.a.a.b.e.aA | k.c.a.a.a.b.e.aG | k.c.a.a.a.b.m.a | k.c.a.a.a.b.m.aA |
| k.c.a.a.a.b.m.aG | k.c.a.a.a.b.ao.a | k.c.a.a.a.b.o.aA | k.c.a.a.a.b.o.aG |
| k.c.a.a.a.b.E.a | k.c.a.a.a.b.E.aA | k.c.a.a.a.b.E.aG | k.c.a.a.a.b.R.a |
| k.c.a.a.a.b.R.aA | k.c.a.a.a.b.R.aG | k.c.a.a.a.b.aw.a | k.c.a.a.a.b.aw.aA |
| k.c.a.a.a.b.aw.aG | k.c.a.a.a.b.aA.a | k.c.a.a.a.b.aA.aA | k.c.a.a.a.b.aA.aG |
| k.c.a.a.a.b.aG.a | k.c.a.a.a.b.aG.aA | k.c.a.a.a.b.aG.aG | k.c.a.a.b.a.a.a |
| k.c.a.a.b.a.a.aA | k.c.a.a.b.a.a.aG | k.c.a.a.b.a.e.a | k.c.a.a.b.a.e.aA |
| k.c.a.a.b.a.e.aG | k.c.a.a.b.a.m.a | k.c.a.a.b.a.m.aA | k.c.a.a.b.a.m.aG |
| k.c.a.a.b.a.ao.a | k.c.a.a.b.a.o.aA | k.c.a.a.b.a.o.aG | k.c.a.a.b.a.E.a |
| k.c.a.a.b.a.E.aA | k.c.a.a.b.a.E.aG | k.c.a.a.b.a.R.a | k.c.a.a.b.a.R.aA |
| k.c.a.a.b.a.R.aG | k.c.a.a.b.a.aw.a | k.c.a.a.b.a.aw.aA | k.c.a.a.b.a.aw.aG |
| k.c.a.a.b.a.aA.a | k.c.a.a.b.a.aA.aA | k.c.a.a.b.a.aA.aG | k.c.a.a.b.a.aG.a |
| k.c.a.a.b.a.aG.aA | k.c.a.a.b.a.aG.aG | k.c.a.a.b.b.a.a | k.c.a.a.b.b.a.aA |
| k.c.a.a.b.b.a.aG | k.c.a.a.b.b.e.a | k.c.a.a.b.b.e.aA | k.c.a.a.b.b.e.aG |
| k.c.a.a.b.b.m.a | k.c.a.a.b.b.m.aA | k.c.a.a.b.b.m.aG | k.c.a.a.b.b.ao.a |
| k.c.a.a.b.b.o.aA | k.c.a.a.b.b.o.aG | k.c.a.a.b.b.E.a | k.c.a.a.b.b.E.aA |
| k.c.a.a.b.b.E.aG | k.c.a.a.b.b.R.a | k.c.a.a.b.b.R.aA | k.c.a.a.b.b.R.aG |
| k.c.a.a.b.b.aw.a | k.c.a.a.b.b.aw.aA | k.c.a.a.b.b.aw.aG | k.c.a.a.b.b.aA.a |
| k.c.a.a.b.b.aA.aA | k.c.a.a.b.b.aA.aG | k.c.a.a.b.b.aG.a | k.c.a.a.b.b.aG.aA |
| k.c.a.a.b.b.aG.aG | k.c.a.e.a.b.a.a | k.c.a.e.a.b.a.aA | k.c.a.e.a.b.a.aG |
| k.c.a.e.a.b.e.a | k.c.a.e.a.b.e.aA | k.c.a.e.a.b.e.aG | k.c.a.e.a.b.m.a |
| k.c.a.e.a.b.m.aA | k.c.a.e.a.b.m.aG | k.c.a.e.a.b.ao.a | k.c.a.e.a.b.o.aA |
| k.c.a.e.a.b.o.aG | k.c.a.e.a.b.E.a | k.c.a.e.a.b.E.aA | k.c.a.e.a.b.E.aG |
| k.c.a.e.a.b.R.a | k.c.a.e.a.b.R.aA | k.c.a.e.a.b.R.aG | k.c.a.e.a.b.aw.a |
| k.c.a.e.a.b.aw.aA | k.c.a.e.a.b.aw.aG | k.c.a.e.a.b.aA.a | k.c.a.e.a.b.aA.aA |
| k.c.a.e.a.b.aA.aG | k.c.a.e.a.h.aG.a | k.c.a.e.a.b.aG.aA | k.c.a.e.a.b.aG.aG |
| k.c.a.e.b.a.a.a | k.c.a.e.b.a.a.aA | k.c.a.e.b.a.a.aG | k.c.a.e.b.a.e.a |
| k.c.a.e.b.a.e.aA | k.c.a.e.b.a.e.aG | k.c.a.e.b.a.m.a | k.c.a.e.b.a.m.aA |
| k.c.a.e.b.a.m.aG | k.c.a.e.b.a.ao.a | k.c.a.e.b.a.o.aA | k.c.a.e.b.a.o.aG |
| k.c.a.e.b.a.E.a | k.c.a.e.b.a.E.aA | k.c.a.e.b.a.E.aG | k.c.a.e.b.a.R.a |
| k.c.a.e.b.a.R.aA | k.c.a.e.b.a.R.aG | k.c.a.e.b.a.aw.a | k.c.a.e.b.a.aw.aA |
| k.c.a.e.b.a.aw.aG | k.c.a.e.b.a.aA.a | k.c.a.e.b.a.aA.aA | k.c.a.e.b.a.aA.aG |
| k.c.a.e.b.a.aG.a | k.c.a.e.b.a.aG.aA | k.c.a.e.b.a.aG.aG | k.c.a.e.b.b.a.a |
| k.c.a.e.b.b.a.aA | k.c.a.e.b.b.a.aG | k.c.a;e.b.b.e.a | k.c.a.e.b.b.e.aA |
| k.c.a.e.b.b.e.aG | k.c.a.e.b.b.m.a | k.c.a.e.b.b.m.aA | k.c.a.e.b.b.m.aG |
| k.c.a.e.b.b.aG.a | k.c.a.e.b.b.o.aA | k.c.a.e.b.b.o.aG | k.c.a.e.b.b.E.a |
| k.c.a.e.b.b.E.aA | k.c.a.e.b.b.E.aG | k.c.a.e.b.b.R.a | k.c.a.e.b.b.R.aA |
| k.c.a.e.b.b.R.aG | k.c.a.e.b.b.aw.a | k.c.a.e.b.b.aw.aA | k.c.a.e.b.b.aw.aG |
| k.c.a.e.b.b.aA.a | k.c.a.e.b.b.aA.aA | k.c.a.e.b.b.aA.aG | k.c.a.e.b.b.aG.a |
| k.c.a.e.b.b.aG.aA | k.c.a.e.b.b.aG.aG | k.c.a.m.a.b.a.a | k.c.a.m.a.b.a.aA |
| k.c.a.m.a.b.a.aG | k.c.a.m.a.b.e.a | k.c.a.m.a.b.e.aA | k.c.a.m.a.b.e.aG |
| k.c.a.m.a.b.m.a | k.c.a.m.a.b.m.aA | k.c.a.m.a.b.m.aG | k.c.a.m.a.b.ao.a |
| k.c.a.m.a.b.o.aA | k.c.a.m.a.b.o.aG | k.c.a.m.a.b.E.a | k.c.a.m.a.b.E.aA |
| k.c.a.m.a.b.E.aG | k.c.a.m.a.b.R.a | k.c.a.m.a.b.R.aA | k.c.a.m.a.b.R.aG |
| k.c.a.m.a.b.aw.a | k.c.a.m.a.b.aw.aA | k.c.a.m.a.b.aw.aG | k.c.a.m.a.b.aA.a |
| k.c.a.m.a.b.aA.aA | k.c.a.m.a.b.aA.aG | k.c.a.m.a.b.aG.a | k.c.a.m.a.b.aG.aA |
| k.c.a.m.b.a.aG.aG | k.c.a.m.b.a.a.a | k.c.a.m.b.a.a.aA | k.c.a.m.b.a.a.aG |
| k.c.a.m.b.a.e.a | k.c.a.m.b.a.e.aA | k.c.a.m.b.a.e.aG | k.c.a.m.b.a.m.a |
| k.c.a.m.b.a.m.aA | k.c.a.m.b.a.m.aG | k.c.a.m.b.a.ao.a | k.c.a.m.b.a.o.aA |
| k.c.a.m.b.a.o.aG | k.c.a.m.b.a.E.a | k.c.a.m.b.a.E.aA | k.c.a.m.b.a.E.aG |
| k.c.a.m.b.a.R.a | k.c.a.m.b.a.R.aA | k.c.a.m.b.a.R.aG | k.c.a.m.b.a.aw.a |
| k.c.a.m.b.a.aw.aA | k.c.a.m.b.a.aw.aG | k.c.a.m.h.a.aA.a | k.c.a.m.b.a.aA.aA |
| k.c.a.m.b.a.aA.aG | k.c.a.m.b.a.aG.a | k.c.a.m.b.a.aG.aA | k.c.a.m.b.a.aG.aG |
| k.c.a.m.b.b.a.a | k.c.a.m.b.b.a.aA | k.c.a.m.b.b.a.aG | k.c.a.m.b.b.e.a |
| k.c.a.m.b.b.e.aA | k.c.a.m.b.b.e.aG | k.c.a.m.b.b.m.a | k.c.a.m.b.b.m.aA |
| k.c.a.m.b.b.m.aG | k.c.a.m.b.b.ao.a | k.c.a.m.b.b.o.aA | k.c.a.m.b.b.o.aG |
| k.c.a.m.b.b.E.a | k.c.a.m.b.b.E.aA | k.c.a.m.b.b.E.aG | k.c.a.m.b.b.R.a |
| k.c.a.m.b.b.R.aA | k.c.a.m.b.b.R.aG | k.c.a.m.b.b.aw.a | k.c.a.m.b.b.aw.aA |

TABLE 14-continued

Exemplary Compounds of the Invention

| | | | |
|---|---|---|---|
| k.c.a.m.b.b.aw.aG | k.c.a.m.b.b.aA.a | k.c.a.m.b.b.aA.aA | k.c.a.m.b.b.aA.aG |
| k.c.a.m.b.b.aG.a | k.c.a.m.b.b.aG.aA | k.c.a.m.b.b.aG.aG | k.c.a.o.a.b.a.a |
| k.c.a.o.a.b.a.aA | k.c.a.o.a.b.a.aG | k.c.a.o.a.b.e.a | k.c.a.d.a.b.e.aA |
| k.c.a.o.a.b.e.aG | k.c.a.o.a.b.m.a | k.c.a.o.a.b.m.aA | k.c.a.o.a.b.m.aG |
| k.c.a.o.a.b.ao.a | k.c.a.o.a.b.o.aA | k.c.a.o.a.b.o.aG | k.c.a.o.a.b.E.a |
| k.c.a.o.a.b.E.aA | k.c.a.o.a.b.E.aG | k.c.a.o.a.b.R.a | k.c.a.o.a.b.R.aA |
| k.c.a.o.a.b.R.aG | k.c.a.o.a.b.aw.a | k.c.a.o.a.b.aw.aA | k.c.a.o.a.b.aw.aG |
| k.c.a.o.a.b.aA.a | k.c.a.o.a.b.aA.aA | k.c.a.o.a.b.aA.aG | k.c.a.o.a.b.aG.a |
| k.c.a.o.a.b.aG.aA | k.c.a.o.a.b.aG.aG | k.c.a.o.b.a.a.a | k.c.a.o.b.a.a.aA |
| k.c.a.o.b.a.a.aG | k.c.a.o.b.a.e.a | k.c.a.o.b.a.e.aA | k.c.a.o.b.a.e.aG |
| k.c.a.o.b.a.m.a | k.c.a.o.b.a.m.aA | k.c.a.o.b.a.m.aG | k.c.a.o.b.a.ao.a |
| k.c.a.o.b.a.o.aA | k.c.a.o.b.a.o.aG | k.c.a.o.b.a.E.a | k.c.a.o.b.a.E.aA |
| k.c.a.o.b.a.E.aG | k.c.a.o.b.a.R.a | k.c.a.o.b.a.R.aA | k.c.a.o.b.a.R.aG |
| k.c.a.o.b.a.aw.a | k.c.a.o.b.a.aw.aA | k.c.a.o.b.a.aw.aG | k.c.a.o.b.a.aA.a |
| k.c.a.o.b.a.aA.aA | k.c.a.o.b.a.aA.aG | k.c.a.o.b.a.aG.a | k.c.a.o.b.a.aG.aA |
| k.c.a.o.b.a.aG.aG | k.c.a.o.b.b.a.a | k.c.a.o.b.b.a.aA | k.c.a.o.b.b.a.aG |
| k.c.a.o.b.b.e.a | k.c.a.o.b.b.e.aA | k.c.a.o.b.b.e.aG | k.c.a.o.b.b.m.a |
| k.c.a.o.b.b.m.aA | k.c.a.o.b.b.m.aG | k.c.a.o.b.b.ao.a | k.c.a.o.b.b.o.aA |
| k.c.a.o.b.b.o.aG | k.c.a.o.b.b.E.a | k.c.a.o.b.b.E.aA | k.c.a.o.b.b.E.aG |
| k.c.a.o.b.b.R.a | k.c.a.o.b.b.R.aA | k.c.a.o.b.b.R.aG | k.c.a.o.b.b.aw.a |
| k.c.a.o.b.b.aw.aA | k.c.a.o.b.b.aw.aG | k.c.a.o.b.b.aA.a | k.c.a.o.b.b.aA.aA |
| k.c.a.o.b.b.aA.aG | k.c.a.o.b.b.aG.a | k.c.a.o.b.b.aG.aA | k.c.a.o.b.b.aG.aG |
| k.c.a.E.a.b.a.a | k.c.a.E.a.b.a.aA | k.c.a.E.a.b.a.aG | k.c.a.E.a.b.e.a |
| k.c.a.E.a.b.e.aA | k.c.a.E.a.b.e.aG | k.c.a.E.a.b.m.a | k.c.a.E.a.b.m.aA |
| k.c.a.E.a.b.m.aG | k.c.a.E.a.b.ao.a | k.c.a.E.a.b.o.aA | k.c.a.E.a.b.o.aG |
| k.c.a.E.a.b.E.a | k.c.a.E.a.b.E.aA | k.c.a.E.a.b.E.aG | k.c.a.E.a.b.R.a |
| k.c.a.E.a.b.R.aA | k.c.a.E.a.b.R.aG | k.c.a.E.a.b.aw.a | k.c.a.E.a.b.aw.aA |
| k.c.a.E.a.b.aw.aG | k.c.a.E.a.b.aA.a | k.c.a.E.a.b.aA.aA | k.c.a.E.a.b.aA.aG |
| k.c.a.E.a.b.aG.a | k.c.a.E.a.b.aG.aA | k.c.a.E.a.b.aG.aG | k.c.a.E.b.a.a.a |
| k.c.a.E.b.a.a.aA | k.c.a.E.b.a.a.aG | k.c.a.E.b.a.e.a | k.c.a.E.b.a.e.aA |
| k.c.a.E.b.a.e.aG | k.c.a.E.b.a.m.a | k.c.a.E.b.a.m.aA | k.c.a.E.b.a.m.aG |
| k.c.a.E.b.a.ao.a | k.c.a.F.b.a.o.aA | k.c.a.E.b.a.o.aG | k.c.a.E.b.a.E.a |
| k.c.a.E.b.a.E.aA | k.c.a.E.b.a.E.aG | k.c.a.E.b.a.R.a | k.c.a.E.b.a.R:aA |
| k.c.a.E.b.a.R.aG | k.c.a.E.b.a.aw.a | k.c.a.E.b.a.aw.aA | k.c.a.E.b.a.aw.aG |
| k.c.a.E.b.a.aA.a | k.c.a.E.b.a.aA.aA | k.c.a.E.b.a.aA.aG | k.c.a.E.b.a.aG.a |
| k.c.a.E.b.a.aG.aA | k.c.a.E.b.a.aG.aG | k.c.a.E.b.b.a.a | k.c.a.E.b.b.a.aA |
| k.c.a.E.b.b.a.aG | k.c.a.E.b.b.e.a | k.c.a.E.b.b.e.aA | k.c.a.E.b.b.e.aG |
| k.c.a.E.b.b.m.a | k.c.a.E.b.b.m.aA | k.c.a.E.b.b.m.aG | k.c.a.E.b.b.ao.a |
| k.c.a.E.b.b.o.aA | k.c.a.E.b.b.o.aG | k.c.a.E.b.b.E.a | k.c.a.E.b.b.E.aA |
| k.c.a.E.b.b.E.aG | k.c.a.E.b.b.R.a | k.c.a.E.b.b.R.aA | k.c.a.E.b.b.R.aG |
| k.c.a.E.b.b.aw.a | k.c.a.E.b.b.aw.aA | k.c.a.E.b.b.aw.aG | k.c.a.E.b.b.aA.a |
| k.c.a.E.b.b.aA.aA | k.c.a.E.b.b.aA.aG | k.c.a.E.b.b.aG.a | k.c.a.E.b.b.aG.aA |
| k.c.a.E.b.b.aG.aG | k.c.a.R.a.b.a.a | k.c.a.R.a.b.a.aA | k.c.a.R.a.b.a.aG |
| k.c.a.R.a.b.e.a | k.c.a.R.a.b.e.aA | k.c.a.R.a.b.e.aG | k.c.a.R.a.b.m.a |
| k.c.a.R.a.b.m.aA | k.c.a.R.a.b.m.aG | k.c.a.R.a.b.ao.a | k.c.a.R.a.b.o.aA |
| k.c.a.R.a.b.o.aG | k.c.a.R.a.b.E.a | k.c.a.R.a.b.E.aA | k.c.a.R.a.b.E.aG |
| k.c.a.R.a.b.R.a | k.c.a.R.a.b.R.aA | k.c.a.R.a.b.R.aG | k.c.a.R.a.b.aw.a |
| k.c.a.R.a.b.aw.aA | k.c.a.R.a.b.aw.aG | k.c.a.R.a.b.aA.a | k.c.a.R.a.b.aA.aA |
| k.c.a.R.a.b.aA.aG | k.c.a.R.a.b.aG.a | k.c.a.R.a.b.aG.aA | k.c.a.R.a.b.aG.aG |
| k.c.a.R.b.a.a.a | k.c.a.R.b.a.a.aA | k.c.a.R.b.a.a.aG | k.c.a.R.b.a.e.a |
| k.c.a.R.b.a.e.aA | k.c.a.R.b.a.e.aG | k.c.a.R.b.a.m.a | k.c.a.R.b.a.m.aA |
| k.c.a.R.b.a.m.aG | k.c.a.R.b.a.ao.a | k.c.a.R.b.a.o.aA | k.c.a.R.b.a.o.aG |
| k.c.a.R.b.a.E.a | k.c.a.R.b.a.E.aA | k.c.a.R.b.a.E.aG | k.c.a.R.b.a.R.a |
| k.c.a.R.b.a.R.aA | k.c.a.R.b.a.R.aG | k.c.a.R.b.a.aw.a | k.c.a.R.b.a.aw.aA |
| k.c.a.R.b.a.aw.aG | k.c.a.R.b.a.aA.a | k.c.a.R.b.a.aA.aA | k.c.a.R.b.a.aA.aG |
| k.c.a.R.b.a.aG.a | k.c.a.R.b.a.aG.aA | k.c.a.R.b.a.aG.aG | k.c.a.R.b.b.a.a |
| k.c.a.R.b.b.a.aA | k.c.a.R.b.b.a.aG | k.c.a.R.b.b.e.a | k.c.a.R.b.b.e.aA |
| k.c.a.R.b.b.e.aG | k.c.a.R.b.b.m.a | k.c.a.R.b.b.m.aA | k.c.a.R.b.b.m.aG |
| k.c.a.R.b.b.ao.a | k.c.a.R.b.b.o.aA | k.c.a.R.b.b.o.aG | k.c.a.R.b.b.E.a |
| k.c.a.R.b.b.E.aA | k.c.a.R.b.b.F.aG | k.c.a.R.b.b.R.a | k.c.a.R.b.b.R.aA |
| k.c.a.R.b.b.R.aG | k.c.a.R.b.b.aw.a | k.c.a.R.b.b.aw.aA | k.c.a.R.b.b.aw.aG |
| k.c.a.R.b.b.aA.a | k.c.a.R.b.b.aA.aA | k.c.a.R.b.b.aA.aG | k.c.a.R.b.b.aG.a |
| k.c.a.R.b.b.aG.aA | k.c.a.R.b.b.aG.aG | k.c.a.aw.a.b.a.a | k.c.a.aw.a.b.a.aA |
| k.c.a.aw.a.b.a.aG | k.c.a.aw.a.b.e.a | k.c.a.aw.a.b.e.aA | k.c.a.aw.a.b.e.aG |
| k.c.a.aw.a.b.m.a | k.c.a.aw.a.b.m.aA | k.c.a.aw.a.b.m.aG | k.c.a.aw.a.b.ao.a |
| k.c.a.aw.a.b.o.aA | k.c.a.aw.a.b.o.aG | k.c.a.aw.a.b.E.a | k.c.a.aw.a.b.E.aA |
| k.c.a.aw.a.b.E.aG | k.c.a.aw.a.b.R.a | k.c.a.aw.a.b.R.aA | k.c.a.aw.a.b.R.aG |
| k.c.a.aw.a.b.aw.a | k.c.a.aw.a.b.aw.aA | k.c.a.aw.a.b.aw.aG | k.c.a.aw.a.b.aA.a |
| k.c.a.aw.a.b.aA.aA | k.c.a.aw.a.b.aA.aG | k.c.a.aw.a.b.aG.a | |
| k.c.a.aw.a.b.aG.aA | k.c.a.aw.a.b.aG.aG | k.c.a.aw.b.a.a.a | k.c.a.aw.b.a.a.aA |
| k.c.a.aw.b.a.a.aG | k.c.a.aw.b.a.e.a | k.c.a.aw.b.a.e.aA | k.c.a.aw.b.a.e.aG |
| k.c.a.aw.b.a.m.a | k.c.a.aw.b.a.m.aA | k.c.a.aw.b.a.m.aG | k.c.a.aw.b.a.a.aG |
| k.c.a.aw.b.a.o.aA | k.c.a.aw.b.a.o.aG | k.c.a.aw.h.a.E.a | k.c.a.aw.b.a.E.aA |
| k.c.a.aw.b.a.E.aG | k.c.a.aw.b.a.R.a | k.c.a.aw.b.a.R.aA | k.c.a.aw.b.a.R.aG |
| k.c.a.aw.b.a.aw.a | k.c.a.aw.b.a.aw.aA | k.c.a.aw.b.a.aw.aG | k.c.a.aw.b.a.aA.a |
| k.c.a.aw.b.a.aA.aA | k.c.a.aw.b.a.aA.aG | k.c.a.aw.b.a.aG.a | |
| k.c.a.aw.b.a.aG.aA | k.c.a.aw.b.a.aG.aG | k.c.a.aw.b.b.a.a | k.c.a.aw.b.b.a.aA |

TABLE 14-continued

Exemplary Compounds of the Invention

| | | | |
|---|---|---|---|
| k.c.a.aw.b.b.a.aG | k.c.a.aw.b.b.e.a | k.c.a.aw.b.b.e.aA | k.c.a.aw.b.b.e.aG |
| k.c.a.aw.b.b.m.a | k.c.a.aw.b.b.m.aA | k.c.a.aw.b.b.m.aG | k.c.a.aw.b.b.ao.a |
| k.c.a.aw.b.b.o.aA | k.c.a.aw.b.b.o.aG | k.c.a.aw.b.b.E.a | k.c.a.aw.b.b.E.aA |
| k.c.a.aw.b.b.E.aG | k.c.a.aw.b.b.R.a | k.c.a.aw.b.b.R.aA | k.c.a.aw.b.b.R.aG |
| k.c.a.aw.b.b.aw.a | k.c.a.aw.b.b.aw.aA | k.c.a.aw.b.b.aw.aG | k.c.a.aw.b.b.aA.a |
| k.c.a.aw.b.b.aA.aA | k.c.a.aw.b.b.aA.aG | k.c.a.aw.b.b.aG.a | |
| k.c.a.aw.b.b.aG.aA | k.c.a.aw.b.b.aG.aG | k.c.a.aA.a.b.a.a | k.c.a.aA.a.b.a.aA |
| k.c.a.aA.a.b.a.aG | k.c.a.aA.a.b.e.a | k.c.a.aA.a.b.e.aA | k.c.a.aA.a.b.e.aG |
| k.c.a.aA.a.b.m.a | k.c.a.aA.a.b.m.aA | k.c.a.aA.a.b.m.aG | k.c.a.aA.a.b.ao.a |
| k.c.a.aA.a.b.o.aA | k.c.a.aA.a.b.o.aG | k.c.a.aA.a.b.E.a | k.c.a.aA.a.b.E.aA |
| k.c.a.aA.a.b.E.aG | k.c.a.aA.a.b.R.a | k.c.a.aA.a.b.R.aA | k.c.a.aA.a.b.R.aG |
| k.c.a.aA.a.b.aw.a | k.c.a.aA.a.b.aw.aA | k.c.a.aA.a.b.aw.aG | k.c.a.aA.a.b.aA.a |
| k.c.a.aA.a.b.aA.aA | k.c.a.aA.a.b.aA.aG | k.c.a.aA.a.b.aG.a | |
| k.c.a.aA.a.b.aG.aA | k.c.a.aA.a.b.aG.aG | k.c.a.aA.b.a.a.a | k.c.a.aA.b.a.a.aA |
| k.c.a.aA.b.a.a.aG | k.c.a.aA.b.a.e.a | k.c.a.aA.b.a.e.aA | k.c.a.aA.b.a.e.aG |
| k.c.a.aA.b.a.m.a | k.c.a.aA.b.a.m.aA | k.c.a.aA.b.a.m.aG | k.c.a.aA.b.a.ao.a |
| k.c.a.aA.b.a.o.aA | k.c.a.aA.b.a.o.aG | k.c.a.aA.b.a.E.a | k.c.a.aA.b.a.E.aA |
| k.c.a.aA.b.a.E.aG | k.c.a.aA.b.a.R.a | k.c.a.aA.b.a.R.aA | k.c.a.aA.b.a.R.aG |
| k.c.a.aA.b.a.aw.a | k.c.a.aA.b.a.aw.aA | k.c.a.aA.b.a.aw.aG | k.c.a.aA.b.a.aA.a |
| k.c.a.aA.b.a.aA.aA | k.c.a.aA.b.a.aA.aG | k.c.a.aA.b.a.aG.a | |
| k.c.a.aA.b.a.aG.aA | k.c.a.aA.b.a.aG.aG | k.c.a.aA.b.b.a.a | k.c.a.aA.b.b.a.aA |
| k.c.a.aA.b.b.a.aG | k.c.a.aA.b.b.e.a | k.c.a.aA.b.b.e.aA | k.c.a.aA.b.b.e.aG |
| k.c.a.aA.b.b.m.a | k.c.a.aA.b.b.m.aA | k.c.a.aA.b.b.m.aG | k.c.a.aA.b.b.ao.a |
| k.c.a.aA.b.b.o.aA | k.c.a.aA.b.b.o.aG | k.c.a.aA.b.b.E.a | k.c.a.aA.b.b.E.aA |
| k.c.a.aA.b.b.E.aG | k.c.a.aA.b.b.R.a | k.c.a.aA.b.b.R.aA | k.c.a.aA.b.b.R.aG |
| k.c.a.aA.b.b.aw.a | k.c.a.aA.b.b.aw.aA | k.c.a.aA.b.b.aw.aG | k.c.a.aA.b.b.aA.a |
| k.c.a.aA.b.b.aA.aA | k.c.a.aA.b.b.aA.aG | k.c.a.aA.b.b.aG.a | |
| k.c.a.aA.b.b.aG.aA | k.c.a.aA.b.b.aG.aG | | |
| k.c.a.aG.a.b.a.a | k.c.a.aG.a.b.a.aA | k.c.a.aG.a.b.a.aG | k.c.a.aG.a.b.e.a |
| k.c.a.aG.a.b.e.aA | k.c.a.aG.a.b.e.aG | k.c.a.aG.a.b.m.a | k.c.a.aG.a.b.m.aA |
| k.c.a.aG.a.b.m.aG | k.c.a.aG.a.b.ao.a | k.c.a.aG.a.b.o.aA | k.c.a.aG.a.b.o.aG |
| k.c.a.aG.a.b.E.a | k.c.a.aG.a.b.E.aA | k.c.a.aG.a.b.E.aG | k.c.a.aG.a.b:R.a |
| k.c.a.aG.a.b.R.aA | k.c.a.aG.a.b.R.aG | k.c.a.aG.a.b.aw.a | |
| k.c.a.aG.a.b.aw.aA | k.c.a.aG.a.b.aw.aG | k.c.a.aG.a.b.aA.a | |
| k.c.a.aG.a.b.aA.aA | k.c.a.aG.a.b.aA.aG | k.c.a.aG.a.b.aG.a | |
| k.c.a.aG.a.b.aG.aA | k.c.a.aG.a.b.aG.aG | k.c.a.aG.b.a.a.a | k.c.a.aG.b.a.a.aA |
| k.c.a.aG.b.a.a.aG | k.c.a.aG.b.a.e.a | k.c.a.aG.b.a.e.aA | k.c.a.aG.b.a.e.aG |
| k.c.a.aG.b.a.m.a | k.c.a.aG.b.a.m.aA | k.c.a.aG.b.a.m.aG | k.c.a.aG.b.a.ao.a |
| k.c.a.aG.b.a.o.aA | k.c.a.aG.b.a.o.aG | k.c.a.aG.b.a.E.a | k.c.a.aG.b.a.E.aA |
| k.c.a.aG.b.a.E.aG | k.c.a.aG.b.a.R.a | k.c.a.aG.b.a.R.aA | k.c.a.aG.b.a.R.aG |
| k.c.a.aG.b.a.aw.a | k.c.a.aG.b.a.aw.aA | k.c.a.aG.b.a.aw.aG | k.c.a.aG.b.a.aA.a |
| k.c.a.aG.b.a.aA.aA | k.c.a.aG.b.a.aA.aG | k.c.a.aG.b.a.aG.a | |
| k.c.a.aG.b.a.aG.aA | k.c.a.aG.b.a.aG.aG | k.c.a.aG.b.b.a.a | k.c.a.aG.b.b.a.aA |
| k.c.a.aG.b.b.a.aG | k.c.a.aG.b.b.e.a | k.c.a.aG.b.b.e.aA | k.c.a.aG.b.b.e.aG |
| k.c.a.aG.b.b.m.a | k.c.a.aG.b.b.m.aA | k.c.a.aG.b.b.m.aG | k.c.a.aG.b.b.ao.a |
| k.c.a.aG.b.b.d.aA | k.c.a.a.G.b.b.o.aG | k.c.a.aG.b.b.E.a | k.c.a.aG.b.b.E.aA |
| k.c.a.aG.b.b.E.aG | k.c.a.aG.b.b.R.a | k.c.a.aG.b.b.R.aA | k.c.a.aG.b.b.R.aG |
| k.c.a.aG.b.b.aw.a | k.c.a.aG.b.b.aw.aA | k.c.a.aG.b.b.aw.aG | k.c.a.aG.b.b.aA.a |
| k.c.a.aG.b.b.aA.aA | k.c.a.aG.b.b.aA.aG | k.c.a.aG.b.b.aG.a | |
| k.c.a.aG.b.b.aG.aA | k.c.a.aG.b.b.aG.aG | k.c.aA.a.a.b.a.a | k.c.aA.a.a.b.a.aA |
| k.c.aA.a.a.b.a.aG | k.c.aA.a.a.b.e.a | k.c.aA.a.a.b.e.aA | k.c.aA.a.a.b.e.aG |
| k.c.aA.a.a.b.m.a | k.c.aA.a.a.b.m.aA | k.c.aA.a.a.b.m.aG | k.c.aA.a.a.b.ao.a |
| k.c.aA.a.a.b.o.aA | k.c.aA.a.a.b.o.aG | k.c.aA.a.a.b.E.a | k.c.aA.a.a.b.E.aA |
| k.c.aA.a.a.b.E.aG | k.c.aA.a.a.b.R.a | k.c.aA.a.a.b.R.aA | k.c.aA.a.a.b.R.aG |
| k.c.aA.a.a.b.aw.a | k.c.aA.a.a.b.aw.aA | k.c.aA.a.a.b.aw.aG | k.c.aA.a.a.b.aA.a |
| k.c.aA.a.a.b.aA.aA | k.c.aA.a.a.b.aA.aG | k.c.aA.a.a.b.aG.a | |
| k.c.aA.a.a.b.aG.aA | k.c.aA.a.a.b.aG.aG | k.c.aA.a.b.a.a.a | k.c.aA.a.b.a.a.aA |
| k.c.aA.a.b.a.a.aG | k.c.aA.a.b.a.e.a | k.c.aA.a.b.a.e.aA | k.c.aA.a.b.a.e.aG |
| k.c.aA.a.b.a.m.a | k.c.aA.a.b.a.m.aA | k.c.aA.a.b.a.m.aG | k.c.aA.a.b.a.ao.a |
| k.c.aA.a.b.a.o.aA | k.c.aA.a.b.a.o.aG | k.c.aA.a.b.a.F.a | k.c.aA.a.b.a.E.aA |
| k.c.aA.a.b.a.E.aG | k.c.aA.a.b.a.R.a | k.c.aA.a.b.a.R.aA | k.c.aA.a.b.a.R.aG |
| k.c.aA.a.b.a.aw.a | k.c.aA.a.b.a.aw.aA | k.c.aA.a.b.a.aw.aG | k.c.aA.a.b.a.aA.a |
| k.c.aA.a.b.a.a.aA | k.c.a.A.a.b.a.aA.aG | k.c.aA.a.b.a.aG.a | |
| k.c.aA.a.b.a.aG.aA | k.c.aA.a.b.a.aG.aG | k.c.aA.a.b.b.a.a | k.c.aA.a.b.b.a.aA |
| k.c.aA.a.b.b.a.aG | k.c.aA.a.b.b.e.a | k.c.aA.a.b.b.e.aA | k.c.aA.a.b.b.e.aG |
| k.c.aA.a.b.b.m.a | k.c.aA.a.b.b.m.aA | k.c.aA.a.b.b.m.aG | k.c.aA.a.b.b.ao.a |
| k.c.aA.a.b.b.o.aA | k.c.aA.a.b.b.o.aG | k.c.aA.a.b.b.E.a | k.c.aA.a.b.b.E.aA |
| k.c.aA.a.b.b.E.aG | k.c.aA.a.b.b.R.a | k.c.aA.a.b.b.R.aA | k.c.aA.a.b.b.R.aG |
| k.c.aA.a.b.b.aw.a | k.c.aA.a.b.b.aw.aA | k.c.aA.a.b.b.aw.aG | k.c.aA.a.b.b.aA.a |
| k.c.aA.a.b.b.aA.aA | k.c.aA.a.b.b.aA.aG | k.c.aA.a.b.b.aG.a | |
| k.c.aA.a.b.b.aG.aA | k.c.aA.a.b.b.aG.aG | k.c.aA.e.a.b.a.a | k.c.aA.e.a.b.a.aA |
| k.c.aA.e.a.b.a.aG | k.c.aA.e.a.b.e.a | k.c.aA.e.a.b.e.aA | k.c.aA.e.a.b.e.aG |
| k.c.aA.e.a.b.m.a | k.c.aA.e.a.b.m.aA | k.c.aA.e.a.b.m.aG | k.c.aA.e.a.b.ao.a |
| k.c.aA.e.a.b.o.aA | k.c.aA.e.a.b.o.aG | k.c.aA.e.a.b.E.a | k.c.aA.e.a.b.E.aA |
| k.c.aA.e.a.b.E.aG | k.c.aA.e.a.b.R.a | k.c.aA.e.a.b.R.aA | k.c.aA.e.a.b.R.aG |
| k.c.aA.e.a.b.aw.a | k.c.aA.e.a.b.aw.aA | k.c.aA.e.a.b.aw.aG | k.c.aA.e.a.b.aA.a |
| k.c.aA.e.a.b.aA.aA | k.c.aA.e.a.b.aA.aG | k.c.aA.e.a.b.aG.a | |

TABLE 14-continued

Exemplary Compounds of the Invention

| | | | |
|---|---|---|---|
| k.c.aA.e.a.b.aG.aA | k.c.aA.e.a.b.aG.aG | k.c.aA.e.b.a.a.a | k.c.aA.e.b.a.a.a.A |
| k.c.aA.e.b.a.a.aG | k.c.aA.e.b.a.e.a | k.c.aA.e.b.a.e.aA | k.c.aA.e.b.a.e.aG |
| k.c.aA.et.a.m.a | k.c.aA.e.b.a.m.aA | k.c.aA.e.b.a.m.aG | k.c.aA.e.b.a.ao.a |
| k.c.aA.e.b.a.o.aA | k.c.aA.e.b.a.o.aG | k.c.aA.e.b.a.E.a | k.c.aA.e.b.a.E.aA |
| k.c.aA.e.b.a.E.aG | k.c.aA.e.b.a.R.a | k.c.aA.e.b.a.R.aA | k.c.aA.e.b.a.R.aG |
| k.c.aA.e.b.a.aw.a | k.c.aA.e.b.a.aw.aA | k.c.aA.e.b.a.aw.aG | k.c.aA.e.b.a.aA.a |
| k.c.aA.e.b.a.aA.aA | k.c.aA.e.b.a.aA.aG | k.c.aA.e.b.a.aG.a | |
| k.c.aA.e.b.a.aG.aA | k.c.aA.e.b.a.aG.aG | k.c.aA.e.b.b.a.a | k.c.aA.e.b.b.a.aA |
| k.c.aA.e.b.b.a.aG | k.c.aA.e.b.b.e.a | k.c.aA.e.b.b.e.aA | k.c.aA.e.b.b.e.aG |
| k.c.aA.e.b.b.m.a | k.c.aA.e.b.b.m.aA | k.c.aA.e.b.b.m.aG | k.c.aA.e.b.b.ao.a |
| k.c.aA.e.b.b.o.aA | k.c.aA.e.b.b.o.aG | k.c.aA.e.b.b.E.a | k.c.aA.e.b.b.E.aA |
| k.c.aA.e.b.b.E.aG | k.c.aA.e.b.k.R.a | k.c.aA.e.b.b.R.aA | k.c.aA.e.b.b.R.aG |
| k.c.aA.e.b.b.aw.a | k.c.aA.e.b.b.aw.aA | k.c.aA.e.b.b.aw.aG | k.c.aA.e.b.b.aA.a |
| k.c.aA.e.b.b.aA.aA | k.c.aA.e.b.b.aA.aG | k.c.aA.e.b.b.aG.a | |
| k.c.aA.e.b.b.aG.aA | k.c.aA.e.b.b.aG.aG | k.c.aA.m.a.b.a.a | k.c.aA.m.a.b.a.aA |
| k.c.aA.m.a.b.a.aG | k.c.aA.m.a.b.e.a | k.c.aA.m.a.b.e.aA | k.c.aA.m.a.b.e.aG |
| k.c.aA.m.a.b.m.a | k.c.aA.m.a.b.m.aA | k.c.aA.m.a.b.m.aG | k.c.aA.m.a.b.ao.a |
| k.c.aA.m.a.b.o.aA | k.c.aA.m.a.b.o.aG | k.c.aA.m.a.b.E.a | k.c.aA.m.a.b.E.aA |
| k.c.aA.m.a.b.E.aG | k.c.aA.m.a.b.R.a | k.c.aA.m.a.b.R.aA | |
| k.c.aA.m.a.b.R.aG | k.c.aA.m.a.b.aw.a | k.c.aA.m.a.b.aw.aA | |
| k.c.aA.m.a.h.aw.aG | | k.c.aA.m.a.b.aA.a | |
| k.c.aA.m.a.b.aA.aA | | k.c.aA.m.a.b.aA.aG | |
| k.c.aA.m.a.b.aG.a | k.c.aA.m.a.b.aG.aA | | |
| k.c.aA.m.a.b.aG.aG | k.c.aA.m.b.a.a.a | k.c.aA.m.b.a.a.aA | k.c.aA.m.b.a.a.aG |
| k.c.aA.m.b.a.e.a | k.c.aA.m.b.a.e.aA | k.c.aA.m.b.a.e.aG | k.c.aA.m.b.a.m.a |
| k.c.aA.m.b.a.m.aA | k.c.aA.m.b.a.m.aG | k.c.aA.m.b.a.ao.a | k.c.aA.m.b.a.ao.aA |
| k.c.aA.m.b.a.o.aG | k.c.aA.m.b.a.E.a | k.c.aA.m.b.a.E.aA | k.c.aA.m.h.a.E.aG |
| k.c.aA.m.b.a.R.a | k.c.aA.m.b.a.R.aA | k.c.aA.m.b.a.R.aG | k.c.aA.m.b.a.aw.a |
| k.c.aA.m.b.a.aw.aA | | k.c.aA.m.b.a.aw.aG | |
| k.c.aA.m.b.a.aA.a | k.c.aA.m.b.a.aA.aA | | |
| k.c.aA.m.b.a.aA.aG | | k.c.aA.m.b.a.aG.a | |
| k.c.aA.m.b.a.aG.aA | | k.c.aA.m.b.a.aG.aG | k.c.aA.m.b.b.a.a |
| k.c.aA.m.b.b.a.aA | k.c.aA.m.b.b.a.aG | k.c.aA.m.b.b.e.a | k.c.aA.m.b.b.e.aA |
| k.c.aA.m.b.b.e.aG | k.c.aA.m.b.b.m.a | k.c.aA.m.b.b.m.aA | |
| k.c.aA.m.b.b.m.aG | k.c.aA.m.b.b.ao.a | k.c.aA.m.b.b.o.aA | k.c.aA.m.b.b.6.aG |
| k.c.aA.m.b.b.E.a | k.c.aA.m.b.b.E.aA | k.c.aA.m.b.b.E.aG | k.c.aA.m.b.b.R.a |
| k.c.aA.m.b.b.R.aA | k.c.aA.m.b.b.R.aG | k.c.aA.m.b.b.aw.a | |
| k.c.aA.m.b.b.aw.aA | | k.c.aA.m.b.b.aw.aG | |
| k.c.aA.m.b.b.aA.a | k.c.aA.m.b.b.aA.aA | | |
| k.c.aA.m.b.b.aA.aG | | k.c.aA.m.b.b.aG.a | |
| k.c.aA.m.b.b.aG.aA | | k.c.aA.m.b.b.aG.aG | k.c.aA.9.a.b.a.a |
| k.c.aA.o.a.b.a.aA | k.c.aA.o.a.b.e.a | k.c.aA.o.a.b.e.aA | k.c.aA.o.a.b.e.aA |
| k.c.aA.o.a.b.e.aG | k.c.aA.o.a.b.m.a | k.c.aA.o.a.b.m.aA | k.c.aA.o.a.b.m.aG |
| k.c.aA.o.a.b.ao.a | k.c.aA.o.a.b.o.aA | k.c.aA.o.a.b.o.aG | k.c.aA.o.a.b.E.a |
| k.c.aA.o.a.b.E.aA | k.c.aA.o.a.b.E.aG | k.c.aA.o.a.b.R.a | k.c.aA.o.a.b.R.aA |
| k.c.aA.o.a.b.R.aG | k.c.aA.o.a.b.aw.a | k.c.aA.o.a.b.aw.aA | |
| k.c.aA.o.a.b.aw.aA | k.c.aA.o.a.b.aA.aA | k.c.aA.o.a.b.aA.aA | |
| k.c.aA.o.a.b.aA.aG | k.c.aA.o.a.b.aG.a | k.c.aA.o.a.b.aG.aA | |
| k.c.aA.o.a.b.aG.aG | k.c.aA.o.b.a.a.a | k.c.aA.o.b.a.a.aA | k.c.aA.o.b.a.a.aG |
| k.c.aA.o.b.a.e.a | k.c.aA.o.b.a.e.aA | k.c.aA.o.b.a.e.aG | k.c.aA.o.b.a.m.a |
| k.c.aA.o.b.a.m.aA | k.c.aA.o.b.a.m.aG | k.c.aA.o.b.a.ao.a | k.c.aA.o.b.a.ao.aA |
| k.c.aA.o.b.a.o.aG | k.c.aA.o.b.a.E.a | k.c.aA.o.b.a.E.aA | k.c.aA.o.b.a.E.aG |
| k.c.aA.o.b.a.R.a | k.c.aA.o.b.a.R.aA | k.c.aA.o.b.a.R.aG | k.c.aA.o.b.a.aw.a |
| k.c.aA.o.b.a.aw.aA | k.c.aA.o.b.a.aw.aG | k.c.aA.o.b.a.aA.a | |
| k.c.aA.o.b.a.aA.aA | k.c.aA.o.b.a.aA.aG | Lc.aA.o.b.a.aG.a | |
| k.c.aA.o.b.a.aG.aA | k.c.aA.o.b.a.aG.aG | k.c.aA.o.b.b.a.a | k.c.aA.o.b.b.a.aA |
| k.c.aA.o.b.b.a.aG | k.c.a.A.o.b.b.e.a | k.c.aA.o.b.b.e.aA | k.c.aA.o.b.b.e.aG |
| k.c.aA.o.b.b.m.a | k.c.aA.o.b.b.m.aA | k.c.aA.o.b.b.m.aG | k.c.aA.o.b.b.ao.a |
| k.c.aA.o.b.b.o.aA | k.c.aA.o.b.b.o.aG | k.c.aA.o.b.b.E.a | k.c.aA.o.b.b.E.aA |
| k.c.aA.o.b.b.E.aG | k.c.aA.o.b.b.R.a | k.c.aA.o.b.b.R.aA | k.c.aA.o.b.b.R.aG |
| k.c.aA.o.b.b.aw.a | k.c.aA.o.b.b.aw.aA | k.c.aA.o.b.b.aw.aG | k.c.aA.o.b.b.aA.a |
| k.c.aA.o.b.b.aA.aA | k.c.aA.o.b.b.aA.aG | k.c.aA.o.b.b.aG.a | |
| k.c.aA.o.b.b.aG.aA | k.c.aA.o.b.b.aG.aG | k.c.aA.E.a.b.a.a | k.c.aA.E.a.b.a.aA |
| k.c.aA.E.a.b.a.aG | k.c.aA.E.a.b.e.a | k.c.aA.E.a.b.e.aA | k.c.aA.E.a.b.e.aG |
| k.c.aA.E.a.b.m.a | k.c.aA.E.a.b.m.aA | k.c.aA.E.a.b.m.aG | k.c.aA.E.a.b.ao.a |
| k.c.aA.E.a.b.o.aA | k.c.aA.E.a.b.o.aG | k.c.aA.E.a.b.E.a | k.c.aA.E.a.b.E.aA |
| k.c.aA.E.a.b.E.aG | k.c.aA.E.a.b.R.a | k.c.aA.E.a.b.R.aA | k.c.aA.E.a.b.R.aG |
| k.c.aA.E.a.b.aw.a | k.c.aA.E.a.b.aw.aA | k.c.aA.E.a.b.aw.aG | k.c.aA.E.a.b.aA.a |
| k.c.aA.E.a.b.aA.aA | k.c.aA.E.a.b.aA.aG | k.c.aA.E.a.b.aG.a | |
| k.c.aA.E.a.b.aG.aA | k.c.aA.E.a.b.aG.aG | k.c.aA.E.b.a.a.a | k.c.aA.E.b.a.a.aA |
| k.c.aA.E.b.a.a.aG | k.c.aA.E.b.a.e.a | k.c.aA.E.b.a.e.aA | k.c.aA.E.b.a.e.aG |
| k.c.aA.E.b.a.m.a | k.c.aA.E.b.a.m.aA | k.c.aA.E.b.a.m.aG | k.c.aA.E.b.a.ao.a |
| k.c.aA.E.b.a.o.aA | k.c.aA.E.b.a.o.aG | k.c.aA.E.b.a.E.a | k.c.aA.E.b.a.E.aA |
| k.c.aA.E.b.a.E.aG | k.c.aA.E.b.a.R.a | k.c.aA.E.b.a.R.aA | k.c.aA.E.b.a.R.aG |
| k.c.aA.E.b.a.aw.a | k.c.aA.E.b.a.aw.aA | k.c.aA.E.b.a.aw.aG | k.c.aA.E.b.a.aA.a |
| k.c.aA.E.b.a.aA.aA | k.c.aA.E.b.a.aA.aG | k.c.aA.E.b.a.aG.a | |
| k.c.aA.E.b.a.aG.aA | k.c.aA.E.b.a.aG.aG | k.c.aA.E.b.b.a.a | 'k.c.aA.E.b.b.a.aA |

TABLE 14-continued

Exemplary Compounds of the Invention

| | | | |
|---|---|---|---|
| k.c.aA.E.b.b.a.aG | k.c.aA.E.b.b.e.a | k.c.aA.E.b.b.e.aA | k.c.aA.E.b.b.e.aG |
| k.c.aA.E.b.b.m.a | k.c.aA.E.b.b.m.aA | k.c.aA.E.b.b.m.aG | k.c.aA.E.b.b.ao.a |
| k.c.aA.E.b.b.o.aA | k.c.aA.E.b.b.o.aG | k.c.aA.E.b.b.E.a | k.c.aA.E.b.b.E.aA |
| k.c.aA.E.b.b.E.aG | k.c.aA.E.b.b.R.a | k.c.aA.E.b.b.R.aA | k.c.aA.E.b.b.R.aG |
| k.c.aA.E.b.b.aw.a | k.c.aA.E.b.b.aw.aA | k.c.aA.E.b.b.aw.aG | k.c.aA.E.b.b.aA.a |
| k.c.aA.E.b.b.aA.aA | k.c.aA.E.b.b.aA.aG | k.c.aA.E.b.b.aG.a | |
| k.c.aA.E.b.b.a.G.aA | k.c.aA.E.b.b.aG.aG | k.c.aA.R.a.b.a.a | k.c.aA.R.a.b.a.aA |
| k.c.aA.R.a.b.a.aG | k.c.aA.R.a.b.e.a | k.c.aA.R.a.b.e.aA | k.c.aA.R.a.b.e.aG |
| k.c.aA.R.a.b.m.a | k.c.aA.R.a.b.m.aA | k.c.aA.R.a.b.m.aG | k.c.aA.R.a.b.ao.a |
| k.c.aA.R.a.b.o.aA | k.c.aA R.a.b.o.aG | k.c.aA.R.a.b.E.a | k.c.aA.R.a.b.E.aA |
| k.c.aA.R.a.b.E.aG | k.c.aA.R.a.b.R.a | k.c aA.R a.b.R.aA | k.c aA.R.a.b.R.aG |
| k.c.aA.R.a.b.aw.a | k.c.aA.R.a.b.aw.aA | k.c.aA.R.a.b.aw.aG | k.c.aA.R.a.b.aA.a |
| k.c.aA.R.a.b.aA.aA | k.c.aA.R.a.b.aA.aG | k.c.aA.R.a.b.aG.a | |
| k.c.aA.R.a.b.aG.aA | k.c.aA.R.a.b.aG.aG | k.c.aA.R.b.a.a.a | k.c.aA.R.b.a.a.aA |
| k.c.aA.R.b.a.a.aG | k.c.aA.R.b.a.e.a | k.c.aA.R.b.a.e.aA | k.c.aA.R.b.a.e.aG |
| k.c.aA.R.b.a.m.a | k.c.aA.R.b.a.m.aA | k.c.aA.R.b.a.m.aG | k.c.aA.R.b.a.ao.a |
| k.c.aA.R.b.a.o.aA | k.c.aA.R.b.a.o.aG | k.c.aA.R.b.a.E.a | k.c.aA.R.b.a.E.aA |
| k.c.aA.R.b.a.E.aG | k.c.aA.R.b.a.R.a | k.c.aA.R.b.a.R.aA | k.c.aA.R.b.a.R.aG |
| k.c.aA.R.b.a.aw.a | k.c.aA.R.b.a.aw.aA | k.c.aA.R.b.a.aw.aG | k.c.aA.R.b.a.aA.a |
| k.c.aA.R.b.a.aA.aA | k.c.aA.R.b.a.aA.aG | k.c.aA.R.b.a.aG.a | |
| k.c.aA.R.b.a.aG.aA | k.c.aA.R.b.a.aG.aG | k.c.aA.R.b.b.a.a | k.c.aA.R.b.b.a.aA |
| k.c.aA.R.b.b.a.aG | k.c.aA.R.b.b.e.a | k.c.aA.R.b.b.e.aA | k.c.aA.R.b.b.e.aG |
| k.c.aA.R.b.b.m.a | k.c.aA.R.b.b.m.aA | k.c.aA.R.b.b.m.aG | k.c.aA.R.b.b.ao.a |
| k.c.aA.R.b.b.o.aA | k.c.aA.R.b.b.o.aG | k.c.aA.R.b.b.E.a | k.c.aA.R.b.b.E.aA |
| k.c.aA.R.b.b.E.aG | k.c.aA.R.b.b.R.a | k.c.aA.R.b.b.R.aA | k.c.aA.R.b.b.R.aG |
| k.c.aA.R.b.b.aw.a | k.c.aA.R.b.b.aw.aA | k.c.aA.R.b.b.aw.aG | k.c.aA.R.b.b.aA.a |
| k.c.aA.R.b.b.aA.aA | k.c.aA.R.b.b.aA.aG | k.c.aA.R.b.b.aG.a | |
| k.c.aA.R.b.b.aG.aA | k.c.aA.R.b.b.aG.aG | k.c.aA.aw.a.b.a.a | |
| k.c.aA.aw.a.b.a.aA | k.c.aA.aw.a.b.a.aG | k.c.aA.aw.a.b.e.a | |
| k.c.aA.aw.a.b.e.aA | k.c.aA.aw.a.b.e.aG | k.c.aA.aw.a.b.m.a | |
| k.c.aA.aw.a.b.m.aA | | k.c.aA.aw.a.b.m.aG | |
| k.c.aA.aw.a.b.ao.a | k.c.aA.aw.a.b.o.aA | k.c.aA.aw.a.b.o.aG | k.c.aA.aw.a.b.E.a |
| k.c.aA.aw.a.b.E.aA | k.c.aA.aw.a.b.E.aG | k.c.aA.aw.a.b.R.a | |
| k.c.aA.aw.a.b.R.aA | k.c.aA.aw.a.b.R.aG | k.c.aA.aw.a.b.aw.a | |
| k.c.aA.aw.a.b.aw.aA | | k.c.aA.aw.a.b.aw.aG | |
| k.c.aA.aw.a.b.aA.a | k.c.aA.aw.a.b.aA.aA | | |
| k.c.aA.aw.a.b.aA.aG | | k.c.aA.aw.a.b.aG.a | |
| k.c.aA.aw.a.b.aG.aA | | k.c.aA.aw.a.b.aG.aG | |
| k.c.aA.aw.b.a.a.a | k.c.aA.aw.b.a.a.aA | k.c.aA.aw.b.a.a.aG | k.c.aA.aw.b.a.e.a |
| k.c.aA.aw.b.a.e.aA | k.c.aA.aw.b.a.e.aG | k.c.aA.aw.b.a.m.a | |
| k.c.aA.aw.b.a.m.aA | | k.c.aA.aw.b.a.m.aG | |
| k.c.aA.aw.b.a.ao.a | | k.c.aA.aw.b.a.o.aG | k.c.aA.aw.b.a.E.a |
| k.c.aA.aw.b.a.E.aA | k.c.aA.aw.b.a.E.aG | k.c.aA.aw.b.a.R.a | |
| k.c.aA.aw.b.a.R.aA | k.c.aA.aw.b.a.R.aG | k.c.aA.aw.b.a.aw.a | |
| k.c.aA.aw.b.a.aw.aA | | k.c.aA.aw.b.a.aw.aG | |
| k.c.aA.aw.b.a.aA.a | k.c.aA.aw.b.a.aA.aA | | |
| k.c.aA.aw.b.a.aA.aG | | k.c.aA.aw.b.a.aG.a | |
| k.c.aA.aw.b.a.aG.aA | | k.c.aA.aw.b.a.aG.aG | |
| k.c.aA.aw.b.b.a.a | k.c.aA.aw.b.b.a.aA | k.c.aA.aw.b.b.a.aG | k.c.aA.aw.b.b.e.a |
| k.c.aA.aw.b.b.e.aA | k.c.aA.aw.b.b.e.aG | k.c.aA.aw.b.b.m.a | |
| k.c.aA.aw.b.b.m.aA | | k.c.aA.aw.b.b.m.aG | |
| k.c.aA.aw.b.b.ao.a | k.c.aA.aw.b.b.o.aA | k.c.aA.aw.b.b.o.aG | k.c.aA.aw.b.b.E.a |
| k.c.aA.aw.b.b.E.aA | k.c.aA.aw.b.b.E.aG | k.c.aA.aw.b.b.R.a | |
| k.c.aA.aw.b.b.R.aA | k.c.aA.aw.b.b.R.aG | k.c.aA.aw.b.b.aw.a | |
| k.c.aA.aw.b.b.aw.aA | | k.c.aA.aw.b.b.aw.aG | |
| k.c.aA.aw.b.b.aA.a | k.c.aA.aw.b.b.aA.aA | | |
| k.c.aA.aw.b.b.aA.aG | | k.c.aA.aw.b.b.aG.a | |
| k.c.aA.aw.b.b.aG.aA | | k.c.aA.aw.b.b.aG.aG | |
| k.c.aA.aA.a.b.a.a | k.c.aA.aA.a.b.a.aA | k.c.aA.aA.a.b.a.aG | k.c.aA.aA.a.b.e.a |
| k.c.aA.aA.a.b.e.aA | k.c.aA.aA.a.b.e.aG | k.c.aA.aA.a.b.m.a | |
| k.c.aA.aA.a.b.m.aA | | k.c.aA.aA.a.b.m.aG | |
| k.c.aA.aA.a.b.ao.a | k.c.aA.aA.a.b.o.aA | k.c.aA.aA.a.b.o.aG | k.c.aA.aA.a.b.E.a |
| k.c.aA.aA.a.b.E.aA | k.c.aA.aA.a.b.E.aG | k.c.aA.aA.a.b.R.a | |
| k.c.aA.aA.a.b.R.aA | k.c.aA.aA.a.b.R.aG | k.c.aA.aA.a.b.aw.a | |
| k.c.aA.aA.a.b.aw.aA | | k.c.aA.aA.a.b.aw.aG | |
| k.c.aA.aA.a.b.aA.a | k.c.aA.aA.a.b.aA.aA | | |
| k.c.aA.aA.a.b.aA.aG | | k.c.aA.aA.a.b.aG.a | |
| k.c.aA.aA.a.b.aG.aA | | k.c.aA.aA.a.b.aG.aG | |
| k.c.aA.aA.b.a.a.a | k.c.aA.aA.b.a.a.aA | k.c.aA.aA.b.a.a.aG | k.c.aA.aA.b.a.e.a |
| k.c.aA.aA.b.a.e.aA | k.c.aA.aA.b.a.e.aG | k.c.aA.aA.b.a.m.a | |
| k.c.aA.aA.b.a.m.aA | | k.c.aA.aA.b.a.m.aG | |
| k.c.aA.aA.b.a.ao.a | k.c.aA.aA.b.a.o.aA | k.c.aA.aA.b.a.o.aG | k.c.aA.aA.b.a.E.a |
| k.c.aA.aA.b.a.E.aA | k.c.aA.aA.b.a.E.aG | k.c.aA.aA.b.a.R.a | |
| k.c.aA.aA.b.a.R.aA | k.c.aA.aA.b.a.R.aG | k.c.aA.aA.b.a.aw.a | |
| k.c.aA.aA.b.a.aw.aA | | k.c.aA.aA.b.a.aw.aG | |
| k.c.aA.aA.b.a.aA.a | k.c.aA.aA.b.a.aA.aA | | |
| k.c.aA.aA.b.a.aA.aG | | k.c.aA.aA.b.a.aG.a | |

TABLE 14-continued

Exemplary Compounds of the Invention

| | | | |
|---|---|---|---|
| k.c.aA.aA.b.a.aG.aA | | k.c.aA.aA.b.a.aG.aG | |
| k.c.aA.aA.b.b.a.a | k.c.aA.aA.b.b.a.aA | k.c.aA.aA.b.b.a.aG | k.c.aA.aA.b.b.e.a |
| k.c.aA.aA.b.b.e.aA | k.c.aA.aA.b.h.e.aG | k.c.aA.aA.b.b.m.a | |
| k.c.aA.aA.b.b.m.aA | | k.c.aA.aA.b.b.m.aG | |
| k.c.aA.aA.b.b.ao.a | | k.c.aA.aA.b.b.ao.aG | k.c.aA.aA.b.b.E.a |
| k.c.aA.aA.b.b.E.aA | k.c.aA.aA.b.b.E.aG | k.c.aA.aA.b.b.R.a | |
| k.c.aA.aA.b.b.R.aA | k.c.aA.aA.b.b.R.aG | k.c.aA.aA.b.b.aw.a | |
| k.c.aA.aA.b.b.aw.aA | | k.c.aA.aA.b.b.aw.aG | |
| k.c.aA.aA.b.b.aA.a | k.c.aA.aA.b.b.aA.aA | | |
| k.c.aA.aA.b.b.aA.aG | | k.c.aA.aA.b.b.aG.a | |
| k.c.aA.aA.b.b.aG.aA | | k.c.aA.aA.b.b.aG.aG | |
| k.c.aA.aG.a.b.a.a | k.c.aA.aG.a.b.a.aA | k.c.aA.aG.a.b.a.aG | k.c.aA.aG.a.b.e.a |
| k.c.aA.aG.a.b.e.aA | k.c.aA.aG.a.b.e.aG | k.c.aA.aG.a.b.m.a | |
| k.c.aA.aG.a.b.m.aA | | k.c.aA.aG.a.b.m.aG | k.c.aA.aG.a.b.ao.a |
| k.c.aA.aG.a.b.o.aA | k.c.aA.aG.a.b.d.aG | k.c.aA.aG.a.b.E.a | |
| k.c.aA.aG.a.b.E.aA | k.c.aA.aG.a.b.E.aG | k.c.aA.aG.a.b.R.a | |
| k.c.aA.aG.a.b.R.aA | k.c.aA.aG.a.b.R.aG | k.c.aA.aG.a.b.aw.a | |
| k.c.aA.aG.a.b.aw.aA | | k.c.aA.aG.a.b.aw.aG | |
| k.c.aA.aG.a.b.aA.a | k.c.aA.aG.a.b.aA.aA | | |
| k.c.aA.aG.a.b.aA.aG | | k.c.aA.aG.a.b.aG.a | |
| k.c.aA.aG.a.b.aG.aA | | k.c.aA.aG.a.b.aG.aG | |
| k.c.aA.aG.b.a.a.a | k.c.aA.aG.b.a.a.aA | k.c.aA.aG.b.a.a.aG | k.c.aA.aG.b.a.e.a |
| k.c.aA.aG.b.a.e.aA | k.c.aA.aG.b.a.e.aG | k.c.aA.aG.b.a.m.a | |
| k.c.aA.aG.b.a.m.aA | | k.c.aA.aG.b.a.m.aG | k.c.aA.aG.b.a.ao.a |
| k.c.aA.aG.b.a.o.aA | k.c.aA.aG.b.a.o.aG | k.c.aA.aG.b.a.E.a | |
| k.c.aA.aG.b.a.E.aA | k.c.aA.aG.b.a.E.aG | k.c.aA.aG.b.a.R.a | |
| k.c.aA.aG.b.a.R.aA | k.c.aA.aG.b.a.R.aG | k.c.aA.aG.b.a.aw.a | |
| k.c.aA.aG.b.a.aw.aA | | k.c.aA.aG.k.a.aw.aG | |
| k.c.aA.aG.b.a.aA.a | k.c.aA.aG.b.a.aA.aA | | |
| k.c.aA.aG.b.a.aA.aG | | k.c.aA.aG.b.a.aG.a | |
| k.c.aA.aG.b.a.aw.aA | | k.c.aA.aG.b.a.aG.aG | |
| k.c.aA.aG.b.b.a.a | k.c.aA.aG.b.b.a.aA | k.c.aA.aG.b.b.a.amG | k.c.aA.aG.b.b.e.a |
| k.c.aA.aG.b.b.e.aA | k.c.aA.aG.b.b.e.aG | k.c.aA.aG.b.b.m.a | |
| k.c.aA.aG.b.b.m.aA | | k.c.aA.aG.b.b.m.aG | k.c.aA.aG.b.b.ao.a |
| k.c.aA.aG.b.b.o.aA | k.c.aA.aG.b.b.o.aG | k.c.aA.aG.b.b.E.a | |
| k.c.aA.aG.b.b.E.aG | k.c.aA.aG.b.b.E.aG | k.c.aA.mG.b.b.R.a | |
| k.c.aA.aG.b.b.R.aA | k.c.aA.aG.b.b.R.aG | k.c.aA.aG.b.b.aw.a | |
| k.c.aA.aG.b.b.aw.aA | | k.c.aA.aG.b.b.aw.aG | |
| k.c.aA.aG.b.b.aA.a | k.c.aA.aG.b.b.aA.aA | | |
| k.c.aA.aG.b.b.aA.aG | | k.c.aA.aG.b.b.aG.a | |
| k.c.aA.aG.b.b.aG.aA | | k.c.aA.aG.b.b.aG.aG | k.c.aG.a.a.b.a.a |
| k.c.aG.a.a.b.a.aA | k.c.aG.a.a.b.a.aG | k.c.aG.a.a.b.e.a | k.c.aG.a.a.b.e.aA |
| k.c.aG.a.a.b.e.aG | k.c.aG.a.a.b.m.a | k.c.aG.a.a.b.m.aA | k.c.aG.a.a.b.m.aG |
| k.c.aG.a.a.b.ao.a | k.c.aG.a.a.b.o.aA | k.c.aG.a.a.b.o.aG | k.c.aG.a.a.b.E.a |
| k.c.aG.a.a.b.E.aA | k.c.aG.a.a.b.E.aG | k.c.aG.a.a.b.R.a | k.c.aG.a.a.b.R.aA |
| k.c.aG.a.a.b.R.aG | k.c.aG.a.a.b.aw.a | k.c.aG.a.a.b.aw.aA | |
| k.c.aG.a.a.b.aw.aG | k.c.aG.a.amb.aA.a | k.c.aG.a.a.b.aA.aA | |
| k.c.aG.a.a.b.aA.aG | k.c.aG.a.a.b.aG.a | k.c.aG.a.a.b.aG.aA | k.c.aG.a.a.b.aG.aG |
| k.c.aG.a.b.a.a.a | k.c.aG.a.b.a.a.aA | k.c.aG.a.b.a.a.aG | k.c.aG.a.b.a.e.a |
| k.c.aG.a.b.a.e.aA | k.c.aG.a.b.a.e.aG | k.c.aG.a.b.a.m.a | k.c.aG.a.b.a.m.aA |
| k.c.aG.a.b.a.m.aG | k.c.aG.a.b.a.ao.a | k.c.aG.a.b.a.o.aA | k.c.aG.a.b.a.o.aG |
| k.c.aG.a.b.a.E.a | k.c.aG.a.b.a.E.aA | k.c.aG.a.b.a.E.aG | k.c.aG.a.b.a.R.a |
| k.c.aG.a.b.a.R.aA | k.c.aG.a.b.a.R.aG | k.c.aG.a.b.a.aw.a | |
| k.c.aG.a.b.a.aw.aA | k.c.aG.a.b.aJaw.aG | k.c.aG.a.b.a.aA.a | |
| k.c.aG.a.b.a.aA.aA | k.c.aG.a.b.a.aA.aG | k.c.aG.a.b.a.aG.a | |
| k.c.aG.a.b.a.aG.aA | k.c.aG.a.b.a.aG.aG | k.c.aG.a.b.b.a.a | k.c.aG.a.b.b.a.aA |
| k.c.aG.a.b.b.a.aG | k.c.aG.a.b.b.e.a | k.c.aG.a.b.b.e.aA | k.c.aG.a.b.b.e.aG |
| k.c.aG.a.b.b.m.a | k.c.aG.a.b.b.m.aA | k.c.aG.a.b.b.m.aG | k.c.aG.a.b.b.ao.a |
| k.c.aG.a.b.b.o.aA | k.c.aG.a.b.b.o.aG | k.c.aG.a.b.b.E.a | k.c.aG.a.b.b.E.aA |
| k.c.aG.a.b.b.E.aG | k.c.aG.a.b.b.R.a | k.c.aG.a.b.b.R.aA | k.c.aG.a.b.b.R.aG |
| k.c.aG.a.b.b.aw.a | k.c.aG.a.b.b.aw.aA | k.c.aG.a.b.b.aw.aG | k.c.aG.a.b.b.aA.a |
| k.c.aG.a.b.b.aA.aA | k.c.aG.a.b.b.aA.aG | k.c.aG.a.b.b.aG.a | |
| k.c.aG.a.b.b.aG.aA | k.c.aG.a.b.b.aG.aG | k.c.aG.e.a.b.a.a | k.c.aG.e.a.b.a.aA |
| k.c.aG.e.a.b.a.aG | k.c.aG.e.a.b.e.a | k.c.aG.e.a.b.e.aA | k.c.aG.e.a.b.e.aG |
| k.c.aG.e.a.b.m.a | k.c.aG.e.a.b.m.aA | k.c.aG.e.a.b.m.aG | k.c.aG.e.a.b.ao.a |
| k.c.aG.e.a.b.o.aA | k.c.aG.e.a.b.o.aG | k.c.aG.e.a.b.E.a | k.c.aG.e.a.b.E.aA |
| k.c.aG.e.a.b.F.aG | k.c.aG.e.a.b.R.a | k.c.aG.e.a.b.R.aA | k.c.aG.e.a.b.R.aG |
| k.c.aG.e.a.b.aw.a | k.c.aG.e.a.b.aw.aA | k.c.aG.e.a.b.aw.aG | k.c.aG.e.a.b.aA.a |
| k.c.aG.e.a.b.aA.aA | k.c.aG.e.a.b.aA.aG | k.c.aG.e.a.b.aG.a | |
| k.c.aG.e.a.b.aG.aA | k.c.aG.e.a.b.aG.aG | k.c.aG.e.b.a.a.a | k.c.aG.e.b.a.a.aA |
| k.c.aG.e.b.a.a.aG | k.c.aG.e.b.a.e.a | k.c.aG.e.b.a.e.aA | k.c.aG.e.b.a.e.aG |
| k.c.aG.e.b.a.m.a | k.c.aG.e.b.a.m.aA | k.c.aG.e.b.a.m.aG | k.c.aG.e.b.a.ao.a |
| k.c.aG.e.b.a.o.aA | k.c.aG.e.b.a.o.aG | k.c.aG.e.b.a.E.a | k.c.aG.e.b.a.E.aA |
| k.c.aG.e.b.a.E.aG | k.c.aG.e.b.a.R.a | k.c.aG.e.b.a.R.aA | k.c.aG.e.b.a.R.aG |
| k.c.aG.e.b.a.aw.a | k.c.aG.e.b.a.aw.aA | k.c.aG.e.b.a.aw.aG | k.c.aG.e.b.a.aA.a |
| k.c.aG.e.b.a.aA.aA | k.c.aG.e.b.a.aA.aG | k.c.aG.e.b.a.aG.a | |
| k.c.aG.e.b.a.aG.aA | k.c.aG.e.b.a.aG.aG | k.c.aG.e.b.b.a.a | k.c.aG.e.b.b.a.aA |

TABLE 14-continued

Exemplary Compounds of the Invention

| | | | |
|---|---|---|---|
| k.c.aG.e.b.b.a.aG | k.c.aG.e.b.b.e.a | k.c.aG.e.b.b.e.aA | k.c.aG.e.b.b.e.aG |
| k.c.aG.e.b.b.m.a | k.c.aG.e.b.b.m.aA | k.c.aG.e.b.b.m.aG | k.c.aG.e.b.b.ao.a |
| k.c.aG.e.b.b.o.aA | k.c.aG.e.b.b.o.aG | k.c.aG.e.b.b.E.a | k.c.aG.e.b.b.E.aA |
| k.c.aG.e.b.b.E.aG | k.c.aG.e.b.b.R.a | k.c.aG.e.b.b.R.aA | k.c.aG.e.b.b.R.aG |
| k.c.aG.e.b.b.aw.a | k.c.aG.e.b.b.aw.aA | k.c.aG.e.b.b.aw.aG | k.cmaG.e.b.b.aA.a |
| k.c.aG.e.b.b.aA.aA | k.c.aG.e.b.b.aw.aG | k.c.aG.e.b.b.aG.a | |
| k.c.aG.e.b.b.aG.aA | k.c.aG.e.b.b.aG.aG | k.c.aG.m.a.b.a.a | k.c.aG.m.a.b.a.aA |
| k.c.aG.m.a.b.a.aG | k.c.aG.m.a.b.e.a | k.c.aG.m.a.b.e.aA | k.c.aG.m.a.b.e.aG |
| k.c.aG.m.a.b.m.a | k.c.aG.m.a.b.m.aA | k.c.aG.m.a.b.m.aG | k.c.aG.m.a.b.ao.a |
| k.c.aG.m.a.b.o.aA | k.c.aG.m.a.b.o.aG | k.c.aG.m.a.b.E.a | k.c.aG.m.a.b.E.aA |
| k.c.aG.m.a.b.E.aG | k.c.aG.m.a.b.R.a | k.c.aG.m.a.b.R.aA | k.c.aG.m.a.b.R.aG |
| k.c.aG.m.a.b.aw.a | k.c.aG.m.a.b.aw.aA | | |
| k.c.aG.m.a.b.aG.aG | k.c.aG.m.b.a.a.a | k.c.aG.m.b.a.a.aA | k.c.aG.m.b.a.a.aG |
| k.c.aG.m.b.a.e.a | k.c.aG.m.b.a.e.aA | k.c.aG.m.b.a.e.aG | k.c.aG.m.b.a.m.a |
| k.c.aG.m.b.a.m.aA | k.c.aG.m.b.a.m.aG | k.c.aG.m.b.a.ao.a | k.c.aG.m.b.a.ao.aA |
| k.c.aG.m.b.a.o.aG | k.c.aG.m.b.a.E.a | k.c.aG.m.b.a.E.aA | k.c.aG.m.b.a.E.aG |
| k.c.aG.m.b.a.R.a | k.c.aG.m.b.a.R.aA | k.c.aG.m.b.a.R.aG | k.c.aG.m.b.a.aw.a |
| k.c.aG.m.b.a.aw.aA | | k.c.aG.m.b.a.aw.aG | k.c.aG.m.b.a.aA.a |
| k.c.a.G.m.b.a.aA.aA | | k.c.aG.m.b.a.aA.aG | k.c.aG.m.b.a.aG.a |
| k.c.aG.m.b.a.aG.aA | k.c.aG.m.b.a.aG.aG | k.c.aG.m.b.b.a.a | k.c.aG.m.b.b.a.aA |
| k.c.aG.m.b.b.a.aG | k.c.aG.m.b.b.e.a | k.c.aG.m.b.b.e.aA | k.c.aG.m.b.b.e.aG |
| k.c.aG.m.b.b.m.a | k.c.aG.m.b.b.m.aA | k.c.aG.m.b.b.m.aG | k.c.aG.m.b.b.ao.a |
| k.c.aG.m.b.b.o.aA | k.c.aG.m.b.b.o.aG | k.c.aG.m.b.b.E.a | k.c.aG.m.b.b.E.aA |
| k.c.aG.m.b.b.E.aG | k.c.aG.m.b.b.R.a | k.c.aG.m.b.b.R.aA | k.c.aG.m.b.b.R.aG |
| k.c.aG.m.b.b.aw.a | k.c.aG.m.b.b.aw.aA | | |
| k.c.aG.m.b.b.aw.aG | k.c.aG.m.b.b.aA.a | k.c.aG.m.b.b.aA.aA | |
| k.c.aG.m.b.b.aA.aG | k.c.aG.m.b.b.aG.a | k.c.aG.rh.b.b.aG.aA | |
| k.c.aG.m.b.b.aG.aG | k.c.aG.o.a.b.a.a | k.c.aG.o.a.b.a.aA | k.c.aG.o.a.b.a.aG |
| k.c.aG.o.a.b.e.a | k.c.aG.o.a.b.e.aA | k.c.aG.o.a.b.e.aG | k.c.aG.o.a.b.m.a |
| k.c.aG.o.a.b.m.aA | k.c.aG.o.a.b.m.aG | k.c.aG.o.a.b.ao.a | k.c.aG.o.a.b.o.aA |
| k.c.aG.o.a.b.o.aG | k.c.aG.o.a.b.E.a | k.c.aG.o.a.b.E.aA | k.c.aG.o.a.b.E.aG |
| k.c.aG.o.a.b.R.a | k.c.aG.o.a.b.R.aA | k.c.aG.o.a.b.R.aG | k.c.aG.o.a.b.aw.a |
| k.c.aG.o.a.b.aw.aA | k.c.amG.o.a.b.a.w.aG | k.c.aG.o.a.b.aA.a | |
| k.c.aG.o.a.b.aA.aA | k.c.aG.o.a.b.aA.aG | k.c.aG.o.a.b.aG.a | |
| k.c.aG.o.a.b.aG.aA | k.c.aG.o.a.b.aG.aG | k.c.aG.o.b.a.a.a | k.c.aG.o.b.a.a.aA |
| k.c.aG.o.b.a.a.aG | k.c.aG.G.b.a.e.a | k.c.aG.o.b.a.e.aA | k.c.aG.o.b.a.e.aG |
| k.c.aG.o.b.a.m.a | k.c.aG.o.b.a.m.aA | k.c.aG.o.b.a.m.aG | k.c.aG.o.b.a.ao.a |
| k.c.aG.o.b.a.o.aA | k.c.aG.o.b.a.o.aG | k.c.a.G.o.b.a.E.a | k.c.aG.o.b.a.E.aA |
| k.c.aG.o.b.a.E.aG | k.c.aG.o.b.a.R.a | k.c.aG.o.b.a.R.aA | k.c.aG.o.b.a.R.aG |
| k.c.aG.o.b.a.aw.a | k.c.aG.o.b.a.aw.aA | k.c.aG.o.b.a.aw.aG | k.c.aG.o.b.a.aA.a |
| k.c.aG.o.b.a.aA.aA | k.c.aG.o.b.a.aA.aG | k.c.aG.o.b.a.aG.a | |
| k.c.aG.o.b.a.aG.aA | k.c.aG.o.b.a.aG.aG | k.c.aG.o.b.b.a.a | k.c.aG.o.b.b.a.aA |
| k.c.aG.o.b.b.a.aG | k.c.aG.o.b.b.e.a | k.c.aG.o.b.b.e.aA. | k.c.aG.d.b.b.e.aG |
| k.c.aG.o.b.b.m.a | k.c.aG.o.b.b.m.aA | k.c.aG.o.b.b.m.aG | k.c.aG.o.b.b.ao.a |
| k.c.aG.o.b.b.o.aA | k.c.aG.o.b.b.o.aG | k.c.aG.o.b.b.E.a | k.c.aG.o.b.b.E.aA |
| k.c.aG.o.b.b.E.aG | k.c.aG.o.b.b.R.a | k.c.aG.o.b.b.R.aA | k.c.aG.o.b.b.R.aG |
| k.c.aG.o.b.b.aw.a | k.c.aG.o.b.b.aw.aA | k.c.aG.o.b.b.aw.aG | k.c.aG.o.b.b.aA.a |
| k.c.aG.o.b.b.aA.aA | k.c.aG.o.b.b.aA.aG | k.c.aG.o.b.b.aG.a | |
| k.c.aG.o.b.b.aG.aA | k.c.aG.o.b.b.aG.aG | k.c.aG.E.a.b.a.a | k.c.aG.E.a.b.a.aA |
| k.c.aG.E.a.b.a.aG | k.c.aG.E.a.b.e.a | k.c.aG.E.a.b.e.aA | k.c.aG.E.a.b.e.aG |
| k.c.aG.E.a.b.m.a | k.c.aG.E.a.b.m.aA | k.c.aG.E.a.b.m.aG | k.c.aG.E.a.b.ao.a |
| k.c.aG.E.a.b.o.aA | k.c.aG.E.a.b.o.aG | k.c.aG.E.a.b.E.a | k.c.aG.E.a.b.E.aA |
| k.c.aG.E.a.b.E.aG | k.c.aG.E.a.b.R.a | k.c.aG.E.a.b.R.aA | k.c.aG.E.a.b.R.aG |
| k.c.aG.E.a.b.aw.a | k.c.aG.E.a.b.aw.aA | k.c.aG.E.a.b.aw.aG | k.c.aG.E.a.b.aA.a |
| k.c.aG.E.a.b.aA.aA | k.c.aG.E.a.b.aA.aG | k.c.aG.E.a.b.aG.a | |
| k.c.aG.E.a.b.aG.aA | k.c.aG.E.a.b.aG.aG | k.c.aG.E.b.a.a.a | k.c.aG.E.b.a.a.aA |
| k.c.aG.E.b.a.a.aG | k.c.aG.E.b.a.e.a | k.c.aG.E.b.a.e.aA | k.c.aG.E.b.a.e.aG |
| k.c.aG.E.b.a.m.a | k.c.aG.E.b.a.m.aA | k.c.aG.E.b.a.m.aG | k.c.aG.E.b.a.ao.a |
| k.c.aG.E.b.a.o.aA | k.c.aG.E.b.a.G.aG | k.c.aG.E.b.a.E.a | k.c.aG.E.b.a.E |
| k.c.aG.E.b.a.E.a.G | k.c.aG.E.b.a.R.a | k.c.aG.E.b.a.R.aA | k.c.aG.E.b.a.R.aG |
| k.c.aG.E.b.a.aw.a | k.c.aG.E.b.a.aw.aA | k.c.aG.E.b.a.aw.aG | k.c.aG.E.b.a.aA.a |
| k.c.aG.E.b.a.aA.aA | k.c.aG.E.b.a.aA.aG | k.c.aG.E.b.a.aG.a | |
| k.c.aG.E.b.a.aG.aA | k.c.aG.E.b.a.aG.aG | k.c.aG.E.b.b.a.a | k.c.aG.E.b.b.a.aA |
| k.c.aG.E.b.b.a.aG | k.c.aG.E.b.b.e.a | k.c.aG.E.b.b.e.aA | k.c.aG.E.b.b.e.aG |
| k.c.aG.E.b.b.m.a | k.c.aG.E.b.b.m.aA | k.c.aG.E.b.b.m.aG | k.c.aG.E.b.b.ao.a |
| k.c.aG.E.b.b.o.aA | k.c.aG.E.b.b.o.aG | k.c.aG.E.b.b.E.a | k.c.aG.E.b.b.E.aA |
| k.c.aG.E.b.b.E.aG | k.c.aG.E.b.b.R.a | k.c.aG.E.b.b.R.aA | k.c.aG.E.b.b.R.aG |
| k.c.aG.E.b.b.aw.a | k.c.aG.E.b.b.aw.aA | k.c.aG.E.b.b.aw.aG | k.c.aG.E.b.b.aA.a |
| k.c.aG.E.b.b.aA.aA | k.c.aG.E.b.b.aA.aG | k.c.aG.E.b.b.aG.a | |
| k.c.aG.E.b.b.aG.aA | k.c.aG.E.b.b.aG.aG | k.c.aG.R.a.b.a.a | k.c.aG.R.a.b.a.aA |
| k.c.aG.R.a.b.a.aG | k.c.aG.R.a.b.e.a | k.c.aG.R.a.b.e.aA | k.c.aG.R.a.b.e.aG |
| k.c.aG.R.a.b.m.a | k.c.aG.R.a.b.m.aA | k.c.aG.R.a.b.m.aG | k.c.aG.R.a.b.ao.a |
| k.c.aG.R.a.b.o.aA | k.c.aG.R.a.b.o.aG | k.c.aG.R.a.b.E.a | k.c.aG.R.a.b.E.aA |
| k.c.aG.R.a.b.E.a.G | k.c.aG.R.a.b.R.a | k.c.aG.R.a.b.R.aA | k.c.aG.R.a.b.R.aG |
| k.c.aG.R.a.b.aw.a | k.c.aG.R.a.b.aw.aA | k.c.aG.R.a.b.aw.aG | k.c.aG.R.a.b.aA.a |
| k.c.aqR.a.b.aA.aA | k.c.aG.R.a.b.aA.aG | k.c.aG.R.a.b.aG.a | |
| k.c.aG.R.a.b.aG.aA | k.c.aG.R.a.b.aG.aG | k.c.aG.R.b.a.a.a | k.c.aG.R.b.a.a.aA |

TABLE 14-continued

Exemplary Compounds of the Invention

| | | | |
|---|---|---|---|
| k.c.aG.R.b.a.a.aG | k.c.aG.R.b.a.e.a | k.c.aG.R.b.a.e.aA | k.c.aG.R.b.a.e.aG |
| k.c.aG.R.b.a.m.a | k.c.aG.R.b.a.m.aA | k.c.aG.R.b.a.m.aG | k.c.aG.R.b.a.ao.a |
| k.c.aG.R.b.a.o.aA | k.c.aG.R.b.a.o.aG | k.c.aG.R.b.a.E.a | k.c.aG.R.b.a.E.aA |
| k.c.aG.R.b.a.E.aG | k.c.aG.R.b.a.R.a | k.c.aG.R.b.a.R.aA | k.c.aG.R.b.a.R.aG |
| k.c.aG.R.b.a.aw.a | k.c.aG.R.b.a.aw.aA | k.c.aG.R.b.a.aw.aG | k.c.aG.R.b.a.aA.a |
| k.c.aG.R.b.a.aA.aA | k.c.aG.R.b.a.aA.aG | k.c.aG.R.b.a.aG.a | |
| k.c.aG.R.b.a.aG.aA | k.c.aG.R.b.a.aG.aG | k.c.aG.R.b.b.a.a | k.c.aG.R.b.b.a.aA |
| k.c.aG.R.b.b.a.aG | k.c.aG.R.b.b.e.a | k.c.aG.R.b.b.e.aA | k.c.aG.R.b.b.e.aG |
| k.c.aG.R.b.b.m.a | k.c.aG.R.b.b.m.aA | k.c.aG.R.b.b.m.aG | k.c.aG.R.b.b.ao.a |
| k.c.aG.R.b.b.o.aA | k.c.aG.R.b.b.o.aG | k.c.aG.R.b.b.E.a | k.c.aG.R.b.b.E.aA |
| k.c.aG.R.b.b.E.aG | k.c.aG.R.b.b.R.a | k.c.aG.R.b.b.R.aA | k.c.aG.R.b.b.R.aG |
| k.c.aG.R.b.b.aw.a | k.c.aG.R.b.b.aw.aA | k.c.aG.R.b.b.aw.aG | k.c.aG.R.b.b.aA.a |
| k.c.aG.R.b.b.aA.aA | k.c.aG.R.b.b.aA.aG | k.c.aG.R.b.b.aG.a | |
| k.c.aG.R.b.b.aG.aA | k.c.aG.R.b.t.aG.aG | k.c.aG.aw.a.b.a.a | |
| k.c.aG.aw.a.b.a.aA | k.c.aG.aw.a.b.a.aG | k.c.aG.aw.a.b.e.a | |
| k.c.aG.aw.a.b.e.aA | k.c.aG.aw.a.b.e.aG | k.c.aG.aw.a.b.m.a | |
| k.c.aG.aw.a.b.m.aA | | k.c.aG.aw.a.b.m.aG | k.c.aG.aw.a.b.ao.a |
| k.c.aG.aw.a.b.o.aA | k.c.aG.aw.a.b.o.aG | k.c.aG.aw.a.b.E.a | |
| k.c.aG.aw.a.b.E.aA | k.c.aG.aw.a.b.E.aG | k.c.aG.aw.a.b.R.a | |
| k.c.aG.aw.a.b.R.aA | k.c.aG.aw.a.b.R.aG | k.c.aG.aw.a.b.aw.a | |
| k.c.aG.aw.a.b.aw.aA | | k.c.aG.aw.a.b.aw.aG | |
| k.c.aG.aw.a.b.aA.a | k.c.aG.aw.a.b.aA.aA | | |
| k.c.aG.aw.a.b.aA.aG | | k.c.aG.aw.a.b.aG.a | |
| k.c.aG.aw.a.b.aG.aA | | k.c.aG.aw.a.b.aG.aG | |
| k.c.aG.aw.h.a.a.a | k.c.aG.aw.b.a.a.aA | k.c.aG.aw.b.a.a.aG | k.c.aG.aw.b.a.e.a |
| k.c.aG.aw.b.a.e.aA | k.c.aG.aw.b.a.e.aG | k.c.aG.aw.b.a.m.a | |
| k.c.aG.aw.b.a.m.aA | | k.c.aG.aw.b.a.m.aG | k.c.aG.aw.b.a.ao.a |
| k.c.aG.aw.b.a.o.aA | k.c.aG.aw.b.a.o.aG | k.c.aG.aw.b.a.E.a | |
| k.c.aG.aw.b.a.E.aA | k.c.aG.aw.h.a.aG | k.c.aG.aw.b.a.R.a | |
| k.c.aG.aw.b.a.R.aA | k.c.aG.aw.b.a.R.aG | k.c.aG.aw.b.a.aw.a | |
| k.c.aG.aw.b.a.aw.aA | | k.c.aG.aw.b.a.aw.aG | |
| k.c.aG.aw.b.a.aA.a | k.c.aG.aw.b.a.aA.aA | | |
| k.c.aG.aw.b.a.aA.aG | | k.c.aG.aw.b.a.aG.a | |
| k.c.aG.aw.b.a.aG.aA | | k.c.aG.aw.b.a.aG.aG | |
| k.c.aG.aw.b.b.a.a | k.c.aG.aw.b.b.a.aA | k.c.aG.aw.b.b.a.aG | k.c.aG.aw.b.b.e.a |
| k.c.aG.aw.b.b.e.aA | k.c.aG.aw.b.b.e.aG | k.c.aG.aw.b.b.m.a | |
| k.c.aG.aw.b.b.m.aA | | k.c.aG.aw.b.b.m.aG | k.c.aG.aw.b.b.ao.a |
| k.c.aG.aw.b.b.o.aA | k.c.aG.aw.b.b.o.aG | k.c.aG.aw.b.b.F.a | |
| k.c.aG.aw.b.b.E.aA | k.c.aG.aw.b.b.E.aG | k.c.aG.aw.b.b.R.a | |
| k.c.aG.aw.b.b.R.aA | k.c.aG.aw.b.b.R.aG | k.c.aG.aw.b.b.aw.a | |
| k.c.aG.aw.b.b.aw.aA | | k.c.aG.aw.b.b.aw.aG | |
| k.c.aG.aw.b.b.aA.a | k.c.aG.aw.b.b.aA.aA | | |
| k.c.aG.aw.b.b.aA.aG | | k.c.aG.aw.b.b.aG.a | |
| k.c.aG.aw.b.b.aG.aA | | k.c.aG.aw.b.b.aG.aG | |
| k.c.aG.aA.a.b.a.a | k.c.aG.aA.a.b.a.aA | k.c.aG.aA.a.b.a.aG | k.c.aG.aA.a.b.e.a |
| k.c.aG.aA.a.b.e.aA | k.c.aG.aA.a.b.e.aG | k.c.aG.aA.a.b.m.a | |
| k.c.aG.aA.a.b.m.aA | | k.c.aG.aA.a.b.m.aG | k.c.aG.aA.a.b.ao.a |
| k.c.aG.aA.a.b.o.aA | k.c.aG.aA.a.b.o.aG | k.c.aG.aA.a.b.E.a | |
| k.c.aG.aA.a.b.E.aA | k.c.aG.aA.a.b.E.aG | k.c.aG.aA.a.b.R.a | |
| k.c.aG.aA.a.b.R.aA | k.c.aG.aA.a.b.R.aG | k.c.aG.aA.a.b.aw.a | |
| k.c.aG.aA.a.b.aw.aA | | k.c.aG.aA.a.b.aw.aG | |
| k.c.aG.aA.a.b.aA.a | k.c.aG.aA.a.b.aA.aA | | |
| k.c.aG.aA.a.b.aA.aG | | k.c.aG.aA.a.b.aG.a | |
| k.c.aG.aA.a.b.aG.aA | | k.c.aG.aA.a.b.aG.aG | |
| k.c.aG.aA.b.a.a.a | k.c.aG.aA.b.a.a.aA | k.c.aG.aA.b.a.a.aG | k.c.aG.aA.b.a.e.a |
| k.c.aG.aA.b.a.e.aA | k.c.aG.aA.b.a.e.aG | k.c.aG.aA.b.a.m.a | |
| k.c.aG.aA.b.a.m.aA | | k.c.aG.aA.b.a.m.aG | k.c.aG.aA.b.a.ao.a |
| k.c.aG.aA.b.a.o.aA | k.c.aG.aA.b.a.o.aG | k.c.aG.aA.b.a.E.a | |
| k.c.aG.aA.b.a.E.aA | k.c.aG.aA.b.a.E.aG | k.c.aG.aA.b.a.R.a | |
| k.c.aG.aA.b.a.R.aA | k.c.aG.aA.b.a.R.aG | k.c.aG.aA.b.a.aw.a | |
| k.c.aG.aA.b.a.aw.aA | | k.c.aG.aA.b.a.aw.aG | |
| k.c.aG.aA.b.a.aA.a | k.c.aG.aA.b.a.aA.aA | | |
| k.c.aG.aA.b.a.aA.aG | | k.c.aG.aA.b.a.aG.a | |
| k.c.aG.aA.b.a.aG.aA | | k.c.aG.aA.b.a.aG.aG | |
| k.c.aG.aA.b.b.a.a | k.c.aG.aA.b.b.a.aA | k.c.aG.aA.b.b.a.aG | k.c.aG.aA.b.b.e.a |
| k.c.aG.aA.b.b.e.aA | k.c.aG.aA.b.b.e.aG | k.c.aG.aA.b.b.m.a | |
| k.c.aG.aA.b.b.m.aA | | k.c.aG.aA.b.b.m.aG | k.c.aG.aA.b.b.ao.a |
| k.c.aG.aA.b.b.o.aA | k.c.aG.aA.b.b.o.aG | k.c.aG.aA.b.b.E.a | |
| k.c.aG.aA.b.b.E.aA | k.c.aG.aA.b.b.E.aG | k.c.aG.aA.b.b.R.a | |
| k.c.aG.aA.b.b.R.aA | k.c.aG.aA.b.b.R.aG | k.c.aG.aA.b.b.aw.a | |
| k.c.aG.aA.b.b.aw.aA | | k.c.aG.aA.b.b.aw.aG | |
| k.c.aG.aA.b.b.aA.a | k.c.aG.aA.b.b.aA.aA | | |
| k.c.aG.aA.b.b.aA.aG | | k.c.aG.aA.b.b.aG.a | |
| k.c.aG.aA.b.b.aG.aA | | k.c.aG.aA.b.b.aG.aG | |
| k.c.aG.aG.a.b.a.a | k.c.aG.aG.a.b.a.aA | k.c.aG.aG.a.b.a.aG | k.c.aG.aG.a.b.e.a |
| k.c.aG.aG.a.b.e.aA | k.c.aG.aG.a.b.e.aG | k.c.aG.aG.a.b.m.a | |
| k.c.aG.aG.a.b.m.aA | k.c.aG.aG.a.b.m.aG | k.c.aG.aG.a.b.ao.a | |

TABLE 14-continued

Exemplary Compounds of the Invention

| | | | |
|---|---|---|---|
| k.c.aG.aG.a.b.o.aA | k.c.aG.aG.a.b.o.aG | k.c.aG.aG.a.b.E.a | |
| k.c.aG.aG.a.b.E.aA | k.c.aG.aG.a.b.E.aG | k.c.aG.aG.a.b.R.a | |
| k.c.aG.aG.a.b.R.aA | k.c.aG.aG.a.b.R.aG | k.c.aG.aG.a.b.aw.a | |
| k.c.aG.aG.a.b.aw.aA | | k.c.aG.aG.a.b.aw.aG | |
| k.c.aG.aG.a.b.aA.a | k.c.aG.aG.a.b.aA.aA | | |
| k.c.aG.aG.a.b.aA.aG | | k.c.aG.aG.a.b.aG.a | |
| k.c.aG.aG.a.b.aG.aA | | k.c.aG.aG.a.b.aG.aG | k.c.aG.aG.b.a.a.a |
| k.c.aG.aG.b.a.a.aA | k.c.aG.aG.b.a.a.aG | k.c.aG.aG.b.a.e.a | |
| k.c.aG.aG.b.a.e.aA | k.c.aG.aG.b.a.e.aG | k.c.aG.aG.bta.m.a | |
| k.c.aG.aG.b.a.m.aA | k.c.aG.aG.b.a.m.aG | k.c.aG.aG.b.a.ao.a | |
| k.c.aG.aG.b.a.o.aA | k.c.aG.aG.b.a.o.aG | k.c.aG.aG.b.a.E.a | |
| k.c.aG.aG.b.a.E.aA | k.c.a.G.aG.b.a.E.aG | k.c.aG.aG.b.a.R.a | |
| k.c.aG.aG.b.a.R.aA | k.c.aG.aG.b.a.R.aG | k.c.aG.aG.b.a.aw.a | |
| k.c.aG.aG.b.a.aw.aA | | k.c.aG.aG.b.a.aw.aG | |
| k.c.aG.aG.b.a.aA.a | k.c.aG.aG.b.a.aA.aA | | |
| k.c.aG.aG.b.a.aA.aG | | k.c.aG.aG.b.a.aG.a | |
| k.c.aG.aG.b.a.aG.aA | | k.c.aG.aG.b.a.aG.aG | k.c.aG.aG.b.b.a.a |
| k.c.aG.aG.b.b.a.aA | k.c.aG.aG.b.b.a.aG | k.c.aG.a.G.b.b.e.a | |
| k.c.aG.aG.b.b.e.aA | k.c.aG.aG.b.b.e.aG | k.c.aG.aG.b.b.m.a | |
| k.c.aG.aG.b.b.m.aA | k.c.aG.aG.b.b.m.aG | k.c.aG.aG.b.b.ao.a | |
| k.c.aG.aG.b.b.o.aA | k.c.aG.aG.b.b.o.aG | k.c.aG.aG.b.b.E.a | |
| k.c.aG.aG.b.b.E.aA | k.c.aG.aG.b.b.E.aG | k.c.aG.aG.b.b.R.a | |
| k.c.aG.aG.b.b.R.aA | k.c.aG.aG.b.b.R.aG | k.c.aG.aG.b.b.aw.a | |
| k.c.aG.aG.b.b.aw.aA | | k.c.aG.aG.b.b.aw.aG | |
| k.c.aG.aG.b.b.aA.a | k.c.aG.aG.b.b.aA.aA | | |
| k.c.aG.aG.b.b.aA.aG | | k.c.aG.aG.b.b.aG.a | |
| k.c.aG.aG.b.b.aG.aA | | k.c.aG.aG.b.b.aG.aG | q.c.a.a.a.b.a.a |
| q.c.a.a.a.b.a.aA | q.c.a.a.a.b.a.aG | q.c.a.a.a.b.e.a | q.c.a.a.a.b.e.aA |
| q.c.a.a.a.b.e.aG | q.c.a.a.a.b.m.a | q.c.a.a.a.b.m.aA | q.c.a.a.a.b.m.aG |
| q.c.a.a.a.b.ao.a | q.c.a.a.a.b.o.aA | q.c.a.a.a.b.o.aG | q.c.a.a.a.b.E.a |
| q.c.a.a.a.b.E.aA | q.c.a.a.a.b.E.aG | q.c.a.a.a.b.R.a | q.c.a.a.a.b.R.aA |
| q.c.a.a.a.b.R.aG | q.c.a.a.a.b.aw.a | q.c.a.a.a.b.aw.aA | q.c.a.a.a.b.aw.aG |
| q.c.a.a.a.b.aA.a | q.c.a.a.a.b.aA.aA | q.c.a.a.a.b.aA.aG | q.c.a.a.a.b.aG.a |
| q.c.a.a.a.b.aG.aA | q.c.a.a.a.b.aG.aG | q.c.a.a.b.a.a.a | q.c.a.a.b.a.a.aA |
| q.c.a.a.b.a.a.aG | q.c.a.a.b.a.e.a | q.c.a.a.b.a.e.aA | q.c.a.a.b.a.e.aG |
| q.c.a.a.b.a.m.a | q.c.a.a.b.a.m.aA | q.c.a.a.b.a.m.aG | q.c.a.a.b.a.ao.a |
| q.c.a.a.b.a.o.aA | q.c.a.a.b.a.o.aG | q.c.a.a.b.a.E.a | q.c.a.a.b.a.E.aA |
| q.c.a.a.b.a.E.aG | q.c.a.a.b.a.R.a | q.c.a.a.b.a.R.aA | q.c.a.a.b.a.R.aG |
| q.c.a.a.b.a.aw.a | q.c.a.a.b.a.aw.a | q.c.a.a.b.a.aw.aG | q.c.a.a.b.a.aA.a |
| q.c.a.a.b.a.aA.aA | q.c.a.a.b.a.aA.aG | q.c.a.a.b.a.aG.a | q.c.a.a.b.a.aG.aA |
| q.c.a.a.b.a.aG.aG | q.c.a.a.b.b.a.a. | q.c.a.a.b.b.a.a | q.c.a.a.b.b.a.aG |
| q.c.a.a.b.b.e.a | q.c.a.a.b.b.e.aA | q.c.a.a.b.b.e.aG | q.c.a.a.b.b.m.a |
| q.c.a.a.b.b.m.aA | q.c.a.a.b.b.m.a.G | q.c.a.a.b.b.ao.a | q.c.a.a.b.b.o.aA |
| q.c.a.a.b.b.o.aG | q.c.a.a.b.b.E.a | q.c.a.a.b.b.E.aA | q.c.a.a.b.b.E.aG |
| q.c.a.a.b.b.R.a | q.c.a.a.b.b.R.aA | q.c.a.a.b.b.R.aG | q.c.a.a.b.b.aw.a |
| q.c.a.a.b.b.aw.aA | q.c.a.a.b.b.aw.aG | q.c.a.a.b.b.aA.a | q.c.a.a.b.b.aA.aA |
| q.c.a.a.b.b.aA.aG | q.c.a.a.b.b.aG.a | q.c.a.a.b.b.aG.aA | q.c.a.a.b.b.aG.aG |
| q.c.a.e.a.b.a.a | q.c.a.e.a.b.a.aA | q.c.a.e.a.b.a.aG | q.c.a.e.a.b.e.a |
| q.c.a.e.a.b.e.aA | q.c.a.e.a.b.e.aG | q.c.a.e.a.b.m.a | q.c.a.e.a.b.m.aA |
| q.c.a.e.a.b.m.aG | q.c.a.e.a.b.ao.a | q.c.a.e.a.b.o.aA | q.c.a.e.a.b.o.aG |
| q.c.a.e.a.b.E.a | q.c.a.e.a.b.E.aA | q.c.a.e.a.b.E.aG | q.c.a.e.a.b.R.a |
| q.c.a.e.a.b.R.aA | q.c.a.a.b.R.aG | q.c.a.e.a.b.aw.a | q.c.a.e.a.b.aw.aA |
| q.c.a.e.a.b.aw.aG | q.c.a.e.a.b.aA.a | q.c.a.e.a.b.aA.aA | q.c.a.e.a.b.aA.aG |
| q.c.a.e.a.b.aG.a | q.c.a.e.a.b.aG.aA | q.c.a.e.a.b.aG.aG | q.c.a.e.b.a.a.a |
| q.c.a.e.b.a.a.aA | q.c.a.e.b.a.a.aG | q.c.a.e.b.a.e.a | q.c.a.e.b.a.e.aA |
| q.c.a.e.b.a.e.aG | q.c.a.e.b.a.m.a | q.c.a.e.b.a.m.aA | q.c.a.e.b.a.m.aG |
| q.c.a.e.b.a.ao.a | q.c.a.e.b.a.o.aA | q.c.a.e.b.a.o.aG | q.c.a.e.b.a.E.a |
| q.c.a.e.b.a.E.aA | q.c.a.e.b.a.E.aG | q.c.a.e.b.a.R.a | q.c.a.e.b.a.R.aA |
| q.c.a.e.b.a.R.aG | q.c.a.e.b.a.aw.a | q.c.a.e.b.a.aw.aA | q.c.a.e.b.a.aw.aG |
| q.c.a.e.b.a.aA.a | q.c.a.e.b.a.aA.aA | q.c.a.e.b.a.aA.aG | q.c.a.e.b.a.aG.a |
| q.c.a.e.b.a.aG.aA | q.c.a.e.b.a.aG.aG | q.c.a.e.b.b.a.a | q.c.a.e.b.b.a.aA |
| q.c.a.e.b.b.a.aG | q.c.a.e.b.b.e.a | q.c.a.e.b.b.e.aA | q.c.a.e.b.b.e.aG |
| q.c.a.e.b.b.m.a | q.c.a.e.b.b.m.aA | q.c.a.e.b.b.m.aG | q.c.a.e.b.b.ao.a |
| q.c.a.e.b.b.o.aA | q.c.a.e.b.b.o.aG | q.c.a.e.b.b.E.a | q.c.a.e.b.b.E.aA |
| q.c.a.e.b.b.E.aG | q.c.a.e.b.b.R.a | q.c.a.e.b.b.R.aA | q.c.a.e.b.b.R.aG |
| q.c.a.e.b.b.aw.a | q.c.a.e.b.b.aw.aA | q.c.a.e.b.b.aw.aG | q.c.a.e.b.b.aA.a |
| q.c.a.e.b.b.aA.aA | q.c.a.e.b.b.aA.aG | q.c.a.e.b.b.aG.a | q.c.a.e.b.b.aG.aA |
| q.c.a.e.b.b.aG.aG | q.c.a.m.a.b.a.a | q.c.a.m.a.b.a.aA | q.c.a.m.a.b.a.aG |
| q.c.a.m.a.b.e.a | q.c.a.m.a.b.e.aA | q.c.a.m.a.b.e.aG | q.c.a.m.a.b.m.a |
| q.c.a.m.a.b.m.aA | q.c.a.m.a.b.m.aG | q.c.a.m.a.b.ao.a | q.c.a.m.a.b.o.aA |
| q.c.a.m.a.b.o.aG | q.c.a.m.a.b.E.a | q.c.a.m.a.b.E.aA | q.c.a.m.a.b.E.aG |
| q.c.a.m.a.b.R.a | q.c.a.m.a.b.R.aA | q.c.a.m.a.b.R.aG | q.c.a.m.a.b.aw.a |
| q.c.a.m.a.b.aw.aA | q.c.a.m.a.b.aw.aG | q.c.a.m.a.b.aA.a | q.c.a.m.a.b.aA.aA |
| q.c.a.m.a.b.aA.aG | q.c.a.m.a.b.aG.a | q.c.a.m.a.b.aG.aA | q.c.a.m.a.b.aG.aG |
| q.c.a.m.b.a.a.a | q.c.a.m.b.a.a.aA | q.c.a.m.b.a.a.aG | q.c.a.m.b.a.e.a |
| q.c.a.m.b.a.e.aA | q.c.a.m.b.a.e.aG | q.c.a.m.b.a.m.a | q.c.a.m.b.a.m.aA |
| q.c.a.m.b.a.m.aG | q.c.a.m.b.a.ao.a | q.c.a.m.b.a.o.a.A | q.c.a.m.b.a.o.aG |

TABLE 14-continued

Exemplary Compounds of the Invention

| | | | |
|---|---|---|---|
| q.c.a.m.b.a.E.a | q.c.a.m.b.a.E.aA | q.c.a.m.b.a.E.aG | q.c.a.m.b.a.R.a |
| q.c.a.m.b.a.R.aA | q.c.a.m.b.a.R.aG | q.c.a.m.b.a.aw.a | q.c.a.m.b.a.aw.aA |
| q.c.a.m.b.a.aw.aG | q.c.a.m.b.a.aA.a | q.c.a.m.b.a.aA.aA | q.c.a.m.b.a.aA.aG |
| q.c.a.m.b.a.aG.a | q.c.a.m.b.a.aG.aA | q.c.atm.b.a.aG.aG | q.c.a.m.b.b.a.a |
| q.c.a.m.b.b.a.aA | q.c.a.m.b.b.a.aG | q.c.a.m.b.b.e.a | q.c.a.m.b.b.e.aA |
| q.c.a.m.b.b.e.aG | q.c.a.m.b.b.m.a | q.c.a.m.b.b.m.aA | q.c.a.m.b.b.m.aG |
| q.c.a.m.b.b.ao.a | q.c.a.m.b.b.o.aA | q.c.a.m.b.b.o.aG | q.c.a.m.b.b.E.a |
| q.c.a.m.b.b.E.aA | q.c.a.m.b.b.E.aG | q.c.a.m.b.b.R.a | q.c.a.m.b.b.R.aA |
| q.c.a.m.b.b.R.aG | q.c.a.m.b.b.aw.a | q.c.a.m.b.b.aw.aA | q.c.a.m.b.b.aw.aG |
| q.c.a.m.b.b.aA.a | q.c.a.m.b.b.aA.aA | q.c.a.m.b.b.aA aG | q.c.a.m.b.b.aG.a |
| q.c.a.m.b.aG.aA | q.c.a.m.b.b.aG.aG | q.c.a.o.a.b.a.a | q c.a.o.a.b.a.aA |
| q.c.a.o.a.b.a.aG | q.c.a.o.a.b.e.a | q.c.a.o.a.b.e.aA | q c.a.o.a.b.e.aG |
| q.c.a.o.a.b.m.a | q.c.a.o.a.b.m.aA | q.c.a.o.a.b.m.aG | q.c.a.o.a.b.ao.a |
| q.c.a.o.a.b.o.aA | q.c.a.o.a.b.o.aG | q.c.a.o.a.b.E.a | q.c.a.o.a.b.E.aA |
| q.c.a.o.a.b.E.aG | q.c.a.o.a.b.R.a | q.c.a.o.a.b.R.aA | q.c.a.o.a.b.R.aG |
| q.c.a.o.a.b.aw.a | q.c.a.o.a.b.aw.aA | q.c.a.o.a.b.aw.aG | q.c.a.o.a.b.aA.a |
| q.c.a.o.a.b.aA.aA | q.c.a.d.a.b.aA.aG | q.c.a.o.b.a.aG.a | q.c.a.o.a.b.aG.aA |
| q.c.a.o.a.b.aG.aG | q.c.a.o.b.a.a.a | q.c.a.o.b.a.a.aN | q.c.a.o.b.a.a.aG |
| q.c.a.o.b.a.e.a | q.c.a.o.b.a.e.aA | q.c.a.o.b.a.e.aG | q.c.a.o.b.a.m.a |
| q.c.a.o.b.a.m.aA | q.c.a.o.b.a.m.aG | q.c.a.o.b.a.ao.a | q.c.a.o.b.a.o.aA |
| q.c.a.o.b.a.o.aG | q.c.a.o.b.a.E.a | q.c.a.d.b.a.E.aA | q.c.a.o.b.a.E.a.G |
| q.c.a.o.b.a.R.a | q.c.a.o.b.a.R.aA | q.c.a.d.b.a.R.aG | q.c.a.o.b.a.aw.a |
| q.c.a.p.b.a.aw.aA | q.c.a.o.b.a.aw.aG | q.c.a.d.b.a.aA.a | q.c.a.o.b.a.aA.aA |
| q.c.a.o.b.a.aA.aG | q.c.a.o.b.a.aG.a | q.c.a.o.b.a.aG.aA | q.c.a.o.b.a.aG.aG |
| q.c.a.o.b.b.a.a | q.c.a.o.b.b.a.aA | q.c.a.o.b.b.a.aG | q.c.a.o.b.b.e.a |
| q.c.a.o.b.b.e.aA | q.c.a.o.b.b.e.aG | q.c.a.o.b.b.m.a | q.c.a.o.b.b.m.aA |
| q.c.a.o.b.b.m.aG | q.c.a.o.b.b.ao.a | q.c.a.o.b.b.o.aA | q.c.a.o.b.b.o.aG |
| q.c.a.o.b.b.E.a | q.c.a.o.b.b.E.aA | q.c.a.o.b.b.E.aG | q.c.a.o.b.b.R.a |
| q.c.a.o.b.b.R.aA | q.c.a.o.b.b.R.aG | q.c.a.o.b.b.aw.a | q.c.a.o.b.b.aw.aA |
| q.c.a.o.b.b.aw.aG | q.c.a.o.b.b.aA.a | q.c.a.o.b.b.aA.aA | q.c.a.o.b.b.aA.aG |
| q.c.a.o.b.b.aG.a | q.c.a.o.b.b.aG.aA | q.c.a.o.b.b.aG.aG | q.c.a.E.a.b.a.a |
| q.c.a.E.a.b.a.aA | q.c.a.E.a.b.a.aG | q.c.a.E.a.b.e.a | q.c.a.E.a.b.e.aA |
| q.c.a.E.a.b.e.aG | q.c.a.E.a.b.m.a | q.c.a.E.a.b.m.aA | q.c.a.E.a.b.m.aG |
| q.c.a.E.a.b.ao.a | q.c.a.E.a.b.o.aA | q.c.a.E.a.b.o.aG | q.c.a.E.a.b.E.a |
| q.c.a.E.a.b.E.aA | q.c.a.E.a.b.E.aG | q.c.a.E.a.b.R.a | q.c.a.E.a.b.R.aA |
| q.c.a.E.a.b.R.aG | q.c.a.E.a.b.aw.a | q.c.a.E.a.b.aw.aA | q.c.a.E.a.b.aw.aG |
| q.c.a.E.a.b.a.A.a | q.c.a.E.a.b.aA.aA | q.c.a.E.a.b.aA.aG | q.c.a.E.a.b.aG.a |
| q.c.a.E.a.b.aG.aA | q.c.a.E.a.b.aG.aG | q.c.a.E.h.a.a.a | q.c.a.E.b.a.a.aA |
| q.c.a.E.b.a.a.aG | q.c.a.b.a.e.a | q.c.a.E.b.a.e.aA | q.c.a.E.b.a.e.aG |
| q.c.a.E.b.a.m.a | q.c.a.E.b.a.m.aA | q.c.a.E.b.a.m.aG | q.c.a.E.b.a.ao.a |
| q.c.a.E.b.a.o.aA | q.c.a.E.b.a.o.aG | q.c.a.E.b.a.E.a | q.c.a.E.b.a.E.aA |
| q.c.a.E.b.a.E.aG | q.c.a.E.b.a.R.a | q.c.a.E.b.a.R.aA | q.c.a.E.b.a.R.aG |
| q.c.a.E.b.a.aw.a | q.c.a.E.b.a.aw.aA | q.c.a.E.b.a.aw.aG | q.c.a.E.b.a.R.a |
| q.c.a.E.b.a.aA.aA | q.c.a.E.b.a.aA.aG | q.c.a.E.b.a.aG.a | q.c.a.E.b.a.aG.aA |
| q.c.a.E.b.a.aG.aG | q.c.a.E.b.b.a.a | q.c.a.E.b.b.a.aA | q.c.a.E.b.b.a.aG |
| q.c.a.E.b.b.e.a | q.c.a.E.b.b.e.aA | q.c.a.E.b.b.e.aG | q.c.a.E.b.b.m.a |
| q.c.a.E.b.b.m.aA | q.c.a.E.b.b.m.aG | q.c.a.E.b.b.ao.a | q.c.a.E.b.b.o.aA |
| q.c.a.E.b.b.o.aG | q.c.a.E.b.b.E.a | q.c.a.E.b.b.E.aA | q.c.a.E.b.b.E.aG |
| q.c.a.E.b.b.R.a | q.c.a.E.b.b.R.aA | q.c.a.E.b.b.R.aG | q.c.a.E.b.b.aw.a |
| q.c.a.E.b.b.aw.aA | q.c.a.E.b.b.aw.aG | q.c.a.E.b.b.aA.a | q.c.a.E.b.b.aA.aA |
| q.c.a.E.b.b.aA.aG | q.c.a.E.b.b.aG.a | q.c.a.E.b.b.aG.aA | q.c.a.E.b.b.aG.aG |
| q.c.a.R.a.b.a.a | q.c.a.R.a.b.a.aA | q.c.a.R.a.b.a.aG | q.c.a.R.a.b.e.a |
| q.c.a.R.a.b.e.aA | q.c.a.R.a.b.e.aG | q.c.a.R.a.b.m.a | q.c.a.R.a.b.m.aA |
| q.c.a.R.a.b.m.aG | q.c.a.R.a.b.ao.a | q.c.a.R.a.b.o.aA | q.c.a.R.a.b.o.aG |
| q.c.a.R.a.b.E.a | q.c.a.R.a.b.E.aA | q.c.a.R.a.b.E.aG | q.c.a.R.a.b.R.a |
| q.c.a.R.a.b.R.aA | q.c.a.R.a.b.R.aG | q.c.a.R.a.b.aw.a | q.c.a.R.a.b.aw.aA |
| q.c.a.R.a.b.aw.aG | q.c.a.R.a.b.aA.a | q.c.a.R.a.b.aA.aA | q.c.a.R.a.b.aA.aG |
| q.c.a.R.a.b.aG.a | q.c.a.R.a.b.aG.aA | q.c.a.R.a.b.aG.aG | q.c.a.R.b.a.a.a |
| q.c.a.R.b.a.a.aA | q.c.a.R.b.a.a.aG | q.c.a.R.b.a.e.a | q.c.a.R.b.a.e.aA |
| q.c.a.R.b.a.e.aG | q.c.a.R.b.a.m.a | q.c.a.R.b.a.m.aA | q.c.a.R.b.a.m.aG |
| q.c.a.R.b.a.ao.a | q.c.a.R.b.a.o.aA | q.c.a.R.b.a.o.aG | q.c.a.R.b.a.E.a |
| q.c.a.R.b.a.E.aA | q.c.a.R.b.a.E.aG | q.c.a.R.b.a.R.a | q.c.a.R.b.a.R.aA |
| q.c.a.R.b.a.R.aG | q.c.a.R.b.a.aw.a | q.c.a.R.b.a.aw.aA | q.c.a.R.b.a.aw.aG |
| q.c.a.R.b.a.aA.a | q.c.a.R.b.a.aA.aA | q.c.a.R.b.a.aA.aG | q.c.a.R.b.a.aG.a |
| q.c.a.R.b.a.aG.aA | q.c.a.R.b.a.aG.aG | q.c.a.R.b.b.a.a | q.c.a.R.b.b.a.aA |
| q.c.a.R.b.b.a.aG | q.c.a.R.b.b.e.a | q.c.a.R.b.b.e.aA | q.c.a.R.b.b.e.aG |
| q.c.a.R.b.b.m.a | q.c.a.R.b.b.m.aA | q.c.a.R.b.b.m.aG | q.c.a.R.b.b.ao.a |
| q.c.a.R.b.b.o.aA | q.c.a.R.b.b.o.aG | q.c.a.R.b.b.E.a | q.c.a.R.b.b.E.aA |
| q.c.a.R.b.b.E.aG | q.c.a.R.b.b.R.a | q.c.a.R.b.b.R.aA | q.c.a.R.b.b.R.aG |
| q.c.a.R.b.b.aw.a | q.c.a.R.b.b.aw.aA | q.c.a.R.b.b.aw.aG | q.c.a.R.b.b.aA.a |
| q.c.a.R.b.b.aA.aA | q.c.a.R.b.b.aA.aG | q.c.a.R.b.b.aG.a | q.c.a.R.b.b.aG.aA |
| q.c.a.R.b.b.aG.aG | q.c.a.aw.a.b.a.a | q.c.a.aw.a.b.a.aA | q.c.a.aw.a.b.a.aG |
| q.c.a.aw.a.b.e.a | q.c.a.aw.a.b.e.aA | q.c.a.aw.a.b.e.aG | q.c.a.aw.a.b.m.a |
| q.c.a.aw.a.b.m.aA | q.c.a.aw.a.b.m.aG | q.c.a.aw.a.b.ao.a | q.c.a.aw.a.b.o.aA |
| q.c.a.aw.a.b.o.aG | q.c.a.aw.a.b.E.a | q.c.a.aw.a.b.E.aA | q.c.a.aw.a.b.E.aG |
| q.c.a.aw.a.b.R.a | q.c.a.aw.a.b.R.aA | q.c.a.aw.a.b.R.aG | q.c.a.aw.a.b.aw.a |
| q.c.a.aw.a.b.aw.aA | q.c.a.aw.a.b.aw.aG | q.c.a.aw.a.b.aA.a | |

TABLE 14-continued

Exemplary Compounds of the Invention

| | | | |
|---|---|---|---|
| q.c.a.aw.a.b.aA.aA | q.c.a.aw.a.b.aA.aG | q.c.a.aw.a.b.aG.a | |
| q.c.a.aw.a.b.aG.aA | q.c.a.aw.a.b.aG.aG | q.c.a.aw.b.a.a.a | q.c.a.aw.b.a.a.aA |
| q.c.a.aw.b.a.a.aG | q.c.a.aw.b.a.e.a | q.c.a.aw.b.a.e.aA | q.c.a.aw.b.a.e.aG |
| q.c.a.aw.b.a.m.a | q.c.a.aw.b.a.m.aA | q.c.a.aw.b.a.m.aG | q.c.a.aw.b.a.ao.a |
| q.c.a.aw.b.a.o.aA | q.c.a.aw.b.a.o.aG | q.c.a.aw.b.a.E.a | q.c.a.aw.b.a.E.aA |
| q.c.a.aw.b.a.E.aG | q.c.a.aw.b.a.R.a | q.c.a.aw.b.a.R.aA | q.c.a.aw.b.a.R.aG |
| q.c.a.aw.b.a.aw.a | q.c.a.aw.b.a.aw.aA | q.c.a.aw.b.a.aw.aG | q.c.a.aw.b.a.aA.a |
| q.c.a.aw.b.a.aA.aA | q.c.a.aw.b.a.aA.aG | q.c.a.aw.b.a.aG.a | |
| q.c.a.aw.b.a.aG.aA | q.c.a.aw.b.a.aG.aG | q.c.a.aw.b.b.a.a | q.c.a.aw.b.b.a.aA |
| q.c.a.aw.b.b.a.aG | q.c.a.aw.b.b.e.a | q.c.a.aw.b.b.e.aA | q.c.a.aw.b.b.e.aG |
| q.c.a.aw.b.b.m.a | q.c.a.aw.b.b.m.aA | q.c.a.aw.b.b.m.aG | q.c.a.aw.b.b.ao.a |
| q.c.a.aw.b.b.o.aA | q.c.a.aw.b.b.o.aG | q.c.a.aw.b.b.E.a | q.c.a.aw.b.b.E.aA |
| q.c.a.aw.b.b.E.aG | q.c.a.aw.b.b.R.a | q.c.a.aw.b.b.R.aA | q.c.a.aw.b.b.R.aG |
| q.c.a.aw.b.b.aw.a | q.c.a.aw.b.b.aw.aA | q.c.a.aw.b.b.aw.aG | q.c.a.aw.b.b.aA.a |
| q.c.a.aw.b.b.aA.aA | q.c.a.aw.b.b.aA.aG | q.c.a.aw.b.b.aG.a | |
| q.c.a.aw.b.b.aG.aA | q.c.a.aw.b.b.aG.aG | q.c.a.aA.a.b.a.a | q.c.a.aA.a.b.a.aA |
| q.c.a.aA.a.b.a.aG | q.c.a.aA.a.b.e.a | q.c.a.aA.a.b.e.aA | q.c.a.aA.a.b.e.aG |
| q.c.a.aA.a.b.m.a | q.c.a.aA.a.b.m.aA | q.c.a.aA.a.b.m.aG | q.c.a.aA.a.b.ao.a |
| q.c.a.aA.a.b.o.aA | q.c.a.aA.a.b.o.aG | q.c.a.aA.a.b.E.a | q.c.a.aA.a.b.E.aA |
| q.c.a.aA.a.b.E.aG | q.c.a.aA.a.b.R.a | q.c.a.aA.a.b.R.aA | q.c.a.aA.a.b.R.aG |
| q.c.a.aA.a.b.aw.a | q.c.a.aA.a.b.aw.aA | q.c.a.aA.a.b.aw.aG | q.c.a.aA.a.b.aA.a |
| q.c.a.aA.a.b.aA.aA | q.c.a.aA.a.b.aA.aG | q.c.a.aA.a.b.aG.a | |
| q.c.a.aA.a.b.aG.aA | q.c.a.aA.a.b.aG.aG | q.c.a.aA.b.a.a.a | q.c.a.aA.b.a.a.aA |
| q.c.a.aA.b.a.a.aG | q.c.a.aA.b.a.e.a | q.c.a.aA.b.a.e.aA | q.c.a.aA.b.a.e.aG |
| q.c.a.aA.b.a.m.a | q.c.a.aA.b.a.m.aA | q.c.a.aA.b.a.m.aG | q.c.a.aA.b.a.ao.a |
| q.c.a.aA.b.a.o.aA | q.c.a.aA.b.a.o.aG | q.c.a.aA.b.a.E.a | q.c.a.aA.b.a.E.aA |
| q.c.a.aA.b.a.E.aG | q.c.a.aA.b.a.R.a | q.c.a.aA.b.a.R.aA | q.c.a.aA.b.a.R.aG |
| q.c.a.aA.b.a.aw.a | q.c.a.aA.b.a.aw.aA | q.c.a.aA.b.a.aw.aG | q.c.a.aA.b.a.aA.a |
| q.c.a.aA.b.a.aA.aA | q.c.a.aA.b.a.aA.aG | q.c.a.aA.b.a.aG.a | |
| q.c.a.aA.b.a.aG.aA | q.c.a.aA.b.a.aG.aG | q.c.a.aA.b.b.a.a | q.c.a.aA.b.b.a.aA |
| q.c.a.aA.b.b.a.aG | q.c.a.aA.b.b.e.a | q.c.a.aA.b.b.e.aA | q.c.a.aA.b.b.e.aG |
| q.c.a.aA.b.b.m.a | q.c.a.aA.b.b.m.aA | q.c.a.aA.b.b.m.aG | q.c.a.aA.b.b.ao.a |
| q.c.a.aA.b.b.o.aA | q.c.a.aA.b.b.o.aG | q.c.a.aA.b.b.E.a | q.c.a.aA.b.b.E.aA |
| q.c.a.aA.b.b.E.aG | q.c.a.aA.b.b.R.a | q.c.a.aA.b.b.R.aA | q.c.a.aA.b.b.R.aG |
| q.c.a.aA.b.b.aw.a | q.c.a.aA.b.b.aw.aA | q.c.a.aA.b.b.aw.aG | q.c.a.aA.b.b.aA.a |
| q.c.a.aA.b.b.aA.aA | q.c.a.aA.b.b.aA.aG | q.c.a.aA.b.b.aG.a | |
| q.c.a.aA.b.b.aG.aA | q.c.a.aA.b.b.aG.aG | | |
| q.c.a.aG.a.b.a.a | q.c.a.aG.a.b.a.aA | q.c.a.aG.a.b.a.aG | q.c.a.aG.a.b.e.a |
| q.c.a.aG.a.b.e.aA | q.c.a.aG.a.b.e.aG | q.c.a.aG.a.b.m.a | q.c.a.aG.a.b.m.aA |
| q.c.a.aG.a.b.m.aG | q.c.a.aG.a.b.ao.a | q.c.a.aG.a.b.o.aA | q.c.a.aG.a.b.o.aG |
| q.c.a.aG.a.b.E.a | q.c.a.aG.a.b.E.aA | q.c.a.aG.a.b.E.aG | q.c.a.aG.a.b.R.a |
| q.c.a.aG.a.b.R.aA | q.c.a.aG.a.b.R.aG | q.c.a.aG.a.b.aw.a | |
| q.c.a.aG.a.b.aw.aA | q.c.a.aG.a.b.aw.aG | q.c.a.aG.a.b.aA.a | |
| q.c.a.aG.a.b.aA.aA | q.c.a.aG.a.b.aA.aG | q.c.a.aG.a.b.aG.a | q.c.a.aG.a.b.aG.aA |
| q.c.a.aG.a.b.aG.aG | q.c.a.aG.b.a.a.a | q.c.a.aG.b.a.a.aA | q.c.a.aG.b.a.a.aG |
| q.c.a.aG.b.a.e.a | q.c.a.aG.b.a.e.aA | q.c.a.aG.b.a.e.aG | q.c.a.aG.b.a.m.a |
| q.c.a.aG.b.a.m.aA | q.c.a.aG.b.a.m.aG | q.c.a.aG.b.a.ao.a | q.c.a.aG.b.a.o.aA |
| q.c.a.aG.b.a.o.aG | q.c.a.aG.b.a.E.a | q.c.a.aG.b.a.E.aA | q.c.a.aG.b.a.E.aG |
| q.c.a.aG.b.a.R.a | q.c.a.aG.b.a.R.aA | q.c.a.aG.b.a.R.aG | q.c.a.aG.b.a.aw.a |
| q.c.a.aG.b.a.aw.aA | q.c.a.aG.b.a.aw.aG | q.c.a.aG.b.a.aA.a | |
| q.c.a.aG.b.a.aA.aA | q.c.a.aG.b.a.aA.aG | q.c.a.aG.b.a.aG.a | q.c.a.aG.b.a.aG.aA |
| q.c.a.aG.b.a.aG.aG | q.c.a.aG.b.b.a.a | q.c.a.aG.b.b.a.aA | q.c.a.aG.b.b.a.aG |
| q.c.a.aG.b.b.e.a | q.c.a.aG.b.b.e.aA | q.c.a.aG.b.b.e.aG | q.c.a.aG.b.b.m.a |
| q.c.a.aG.b.b.m.aA | q.c.a.aG.b.b.m.aG | q.c.a.aG.b.b.ao.a | q.c.a.aG.b.b.o.aA |
| q.c.a.aG.b.b.o.aG | q.c.a.aG.b.b.E.a | q.c.a.aG.b.b.E.aA | q.c.a.aG.b.b.E.aG |
| q.c.a.aG.b.b.R.a | q.c.a.aG.b.b.R.aA | q.c.a.aG.b.b.R.aG | q.c.a.aG.b.b.aw.a |
| q.c.a.aG.b.b.aw.aA | q.c.a.aG.b.b.aw.aG | q.c.a.aG.b.b.aA.a | |
| q.c.a.aG.b.b.aA.aA | q.c.a.aG.b.b.aA.aG | q.c.a.aG.b.b.aG.a | q.c.a.aG.b.b.aG.aA |
| q.c.a.aG.b.b.aG.aG | q.c.aA.a.a.b.a.a | q.c.aA.a.a.b.a.aA | q.c.aA.a.a.b.a.aG |
| q.c.aA.a.a.b.e.a | q.c.aA.a.a.b.e.aA | q.c.aA.a.a.b.e.aG | q.c.aA.a.a.b.m.a |
| q.c.aA.a.a.b.m.aA | q.c.aA.a.a.b.m.aG | q.c.aA.a.a.b.ao.a | q.c.aA.a.a.b.o.aA |
| q.c.aA.a.a.b.o.aG | q.c.aA.a.a.b.E.a | q.c.aA.a.a.b.E.aA | q.c.aA.a.a.b.E.aG |
| q.c.aA.a.a.b.R.a | q.c.aA.a.a.b.R.aA | q.c.aA.a.a.b.R.aG | q.c.aA.a.a.b.aw.a |
| q.c.aA.a.a.b.aw.aA | q.c.aA.a.a.b.aw.aG | q.c.aA.a.a.b.aA.a | |
| q.c.aA.a.a.b.aA.aA | q.c.aA.a.a.b.aA.aG | q.c.aA.a.a.b.aG.a | |
| q.c.aA.a.a.b.aG.aA | q.c.aA.a.a.b.aG.aG | q.c.aA.a.b.a.a.a | q.c.aA.a.b.a.a.aA |
| q.c.aA.a.b.a.a.aG | q.c.aA.a.b.a.e.a | q.c.aA.a.b.a.e.aA | q.c.aA.a.b.a.e.aG |
| q.c.aA.a.b.a.m.a | q.c.aA.a.b.a.m.aA | q.c.aA.a.b.a.m.aG | q.c.aA.a.b.a.ao.a |
| q.c.aA.a.b.a.o.aA | q.c.aA.a.b.a.o.aG | q.c.aA.a.b.a.E.a | q.c.aA.a.b.a.E.aA |
| q.c.aA.a.b.a.E.aG | q.c.aA.a.b.a.R.a | q.c.aA.a.b.a.R.aA | q.c.aA.a.b.a.R.aG |
| q.c.aA.a.b.a.aw.a | q.c.aA.a.b.a.aw.aA | q.c.aA.a.b.a.aw.aG | q.c.aA.a.b.a.aA.a |
| q.c.aA.a.b.a.aA.aA | q.c.aA.a.b.a.aA.aG | q.c.aA.a.b.a.aG.a | |
| q.c.aA.a.b.a.aG.aA | q.c.aA.a.b.a.aG.aG | q.c.aA.a.b.b.a.a | q.c.aA.a.b.b.a.aA |
| q.c.aA.a.b.b.a.aG | q.c.aA.a.b.b.e.a | q.c.aA.a.b.b.e.aA | q.c.aA.a.b.b.e.aG |
| q.c.aA.a.b.b.m.a | q.c.aA.a.b.b.m.aA | q.c.aA.a.b.b.m.aG | q.c.aA.a.b.b.ao.a |
| q.c.aA.a.b.b.o.aA | q.c.aA.a.b.b.o.aG | q.c.aA.a.b.b.E.a | q.c.aA.a.b.b.E.aA |
| q.c.aA.a.b.b.E.aG | q.c.aA.a.b.b.R.a | q.c.aA.a.b.b.R.aA | q.c.aA.a.b.b.R.aG |

TABLE 14-continued

Exemplary Compounds of the Invention

| | | | |
|---|---|---|---|
| q.c.aA.a.b.b.aw.a | q.c.aA.a.b.b.aw.aA | q.c.aA.a.b.b.aw.aG | q.c.aA.a.b.b.aA.a |
| q.c.aA.a.b.b.aA.aA | q.c.aA.a.b.b.aA.aG | q.c.aA.a.b.b.aG.a | |
| q.c.aA.a.b.b.aG.aA | q.c.aA.a.b.b.aG.aG | q.c.aA.e.a.b.a.a | q.c.aA.e.a.b.a.aA |
| q.c.aA.e.a.b.a.aG | q.c.aA.e.a.b.e.a | q.c.aA.e.a.b.e.aA | q.c.aA.e.a.b.e.aG |
| q.c.aA.e.a.b.m.a | q.c.aA.e.a.b.m.aA | q.c.aA.e.a.b.m.aG | q.c.aA.e.a.b.ao.a |
| q.c.aA.e.a.b.o.aA | q.c.aA.e.a.b.o.aG | q.c.aA.e.a.b.E.a | q.c.aA.e.a.b.E.aA |
| q.c.aA.e.a.b.E.aG | q.c.aA.e.a.b.R.a | q.c.aA.e.a.b.R.aA | q.c.aA.e.a.b.R.aG |
| q.c.aA.e.a.b.aw.a | q.c.aA.e.a.b.aw.aA | q.c.aA.e.a.b.aw.aG | q.c.aA.e.a.b.aA.a |
| q.c.aA.e.a.b.aA.aA | q.c.aA.e.a.b.aA.aG | q.c.aA.e.a.b.aG.a | |
| q.c.aA.e.a.b.aG.aA | q.c.aA.e.a.b.aG.aG | q.c.aA.e.b.a.a.a | q.c.aA.e.b.a.a.aA |
| q.c.aA.e.b.a.a.aG | q.c.aA.e.b.a.e.a | q.c.aA.e.b.a.e.aA | q.c.aA.e.b.a.e.aG |
| q.c.aA.e.b.a.m.a | q.c.aA.e.b.a.m.aA | q.c.aA.e.b.a.m.aG | q.c.aA.e.b.a.ao.a |
| q.c.aA.e.b.a.o.aA | q.c.aA.e.b.a.o.aG | q.c.aA.e.b.a.E.a | q.c.aA.e.b.a.E.aA |
| q.c.aA.e.b.a.E.aG | q.c.aA.e.b.a.R.a | q.c.aA.e.b.a.R.aA | q.c.aA.e.b.a.R.aG |
| q.c.aA.e.b.a.aw.a | q.c.aA.e.b.a.aw.aA | q.c.aA.e.b.a.aw.aG | q.c.aA.e.b.a.aA.a |
| q.c.aA.e.b.a.aA.aA | q.c.aA.e.b.a.aA.aG | q.c.aA.e.b.a.aG.a | |
| q.c.aA.e.b.a.aG.aA | q.c.aA.e.b.a.aG.aG | q.c.aA.e.b.b.a.a | q.c.aA.e.b.b.a.aA |
| q.c.aA.e.b.b.a.aG | q.c.aA.e.b.b.e.a | q.c.aA.e.b.b.e.aA | q.c.aA.e.b.b.e.aG |
| q.c.aA.e.b.b.m.a | q.c.aA.e.b.b.m.aA | q.c.aA.e.b.b.m.aG | q.c.aA.e.b.b.ao.a |
| q.c.aA.e.b.b.o.aA | q.c.aA.e.b.b.o.aG | q.c.aA.e.b.b.E.a | q.c.aA.e.b.b.E.aA |
| q.c.aA.e.b.b.E.aG | q.c.aA.e.b.b.R.a | q.c.aA.e.b.b.R.aA | q.c.aA.e.b.b.R.aG |
| q.c.aA.e.b.b.aw.a | q.c.aA.e.b.b.aw.aA | q.c.aA.e.b.b.aw.aG | q.c.aA.e.b.b.aA.a |
| q.c.aA.e.b.b.aA.aA | q.c.aA.e.b.b.aA.aG | q.c.aA.e.b.b.aG.a | |
| q.c.aA.e.b.b.aG.aA | q.c.aA.e.b.b.aG.aG | q.c.aA.m.a.b.a.a | q.c.aA.m.a.b.a.aA |
| q.c.aA.m.a.b.a.aG | q.c.aA.m.a.b.e.a | q.c.aA.m.a.b.e.aA | q.c.aA.m.a.b.e.aG |
| q.c.aA.m.a.b.m.a | q.c.aA.m.a.b.m.aA | q.c.aA.m.a.b.m.aG | q.c.aA.m.a.b.ao.a |
| q.c.aA.m.a.b.o.aA | q.c.aA.m.a.b.o.aG | q.c.aA.m.a.b.E.a | q.c.aA.m.a.b.E.aA |
| q.c.aA.m.a.b.E.aG | q.c.aA.m.a.b.R.a | q.c.aA.m.a.b.R.aA | q.c.aA.m.a.b.R.aG |
| q.c.aA.m.a.b.aw.a | q.c.aA.m.a.b.aw.aA | | |
| q.c.aA.m.a.b.aw.aG | q.c.aA.m.a.b.aA.a | q.c.aA.m.a.b.aA.aA | |
| q.c.aA.m.a.b.aA.aG | q.c.aA.m.a.b.aG.a | q.c.aA.m.a.b.aG.aA | |
| q.c.aA.m.a.b.aG.aG | q.c.aA.m.b.a.a.a | q.c.aA.m.b.a.a.aA | q.c.aA.m.b.a.a.aG |
| q.c.aA.m.b.a.e.a | q.c.aA.m.b.a.e.aA | q.c.aA.m.b.a.e.aG | q.c.aA.m.b.a.m.a |
| q.c.aA.m.b.a.m.aA | q.c.aA.m.b.a.m.aG | q.c.aA.m.b.a.ao.a | q.c.aA.m.b.a.o.aA |
| q.c.aA.m.b.a.o.aG | q.c.aA.m.b.a.E.a | q.c.aA.m.b.a.E.aA | q.c.aA.m.b.a.E.aG |
| q.c.aA.m.b.a.R.a | q.c.aA.m.b.a.R.aA | q.c.aA.m.b.a.R.aG | q.c.aA.m.b.a.aw.a |
| q.c.aA.m.b.a.aw.aA | | q.c.aA.m.b.a.aw.aG | q.c.aA.m.b.a.aA.a |
| q.c.aA.m.b.a.aA.aA | | q.c.aA.m.b.a.aA.aG | q.c.aA.m.b.a.aG.a |
| q.c.aA.m.b.a.aG.aA | q.c.aA.m.b.a.aG.aG | q.c.aA.m.b.b.a.a | q.c.aA.m.b.b.a.aA |
| q.c.aA.m.b.b.a.aG | q.c.aA.m.b.b.e.a | q.c.aA.m.b.b.e.aA | q.c.aA.m.b.b.e.aG |
| q.c.aA.m.b.b.m.a | q.c.aA.m.b.b.m.aA | q.c.aA.m.b.b.m.aG | q.c.aA.m.b.b.ao.a |
| q.c.aA.m.b.b.o.aA | q.c.aA.m.b.b.o.aG | q.c.aA.m.b.b.E.a | q.c.aA.m.b.b.E.aA |
| q.c.aA.m.b.b.E.aG | q.c.aA.m.b.b.R.a | q.c.aA.m.b.b.R.aA | q.c.aA.m.b.b.R.aG |
| q.c.aA.m.b.b.aw.a | q.c.aA.m.b.b.aw.aA | | |
| q.c.aA.m.b.b.aw.aG | q.c.aA.m.b.b.aA.a | q.c.aA.m.b.b.aA.aA | |
| q.c.aA.m.b.b.aA.aG | q.c.aA.m.b.b.aG.a | q.c.aA.m.b.b.aG.aA | |
| q.c.aA.m.b.b.aG.aG | q.c.aA.o.a.b.a.a | q.c.aA.o.a.b.a.aA | q.c.aA.o.a.b.a.aG |
| q.c.aA.o.a.b.e.a | q.c.aA.o.a.b.e.aA | q.c.aA.o.a.b.e.aG | q.c.aA.o.a.b.m.a |
| q.c.aA.o.a.b.m.aA | q.c.aA.o.a.b.m.aG | q.c.aA.o.a.b.ao.a | q.c.aA.o.a.b.o.aA |
| q.c.aA.o.a.b.o.aG | q.c.aA.o.a.b.E.a | q.c.aA.o.a.b.E.aA | q.c.aA.o.a.b.E.aG |
| q.c.aA.o.a.b.R.a | q.c.aA.o.a.b.R.aA | q.c.aA.o.a.b.R.aG | q.c.aA.o.a.b.aw.a |
| q.c.aA.o.a.b.aw.aA | q.c.aA.o.a.b.aw.aG | q.c.aA.o.a.b.aA.a | |
| q.c.aA.o.a.b.aA.aA | q.c.aA.o.a.b.aA.aG | q.c.aA.o.a.b.aG.a | |
| q.c.aA.o.a.b.aG.aA | q.c.aA.o.a.b.aG.aG | q.c.aA.o.b.a.a.a | q.c.aA.o.b.a.a.aA |
| q.c.aA.o.b.a.a.aG | q.c.aA.o.b.a.e.a | q.c.aA.o.b.a.e.aA | q.c.aA.o.b.a.e.aG |
| q.c.aA.o.b.a.m.a | q.c.aA.o.b.a.m.aA | q.c.aA.o.b.a.m.aG | q.c.aA.o.b.a.ao.a |
| q.c.aA.o.b.a.o.aA | q.c.aA.o.b.a.o.aG | q.c.aA.o.b.a.E.a | q.c.aA.o.b.a.E.aA |
| q.c.aA.o.b.a.E.aG | q.c.aA.o.b.a.R.a | q.c.aA.o.b.a.R.aA | q.c.aA.o.b.a.R.aG |
| q.c.aA.o.b.a.aw.a | q.c.aA.o.b.a.aw.aA | q.c.aA.o.b.a.aw.aG | q.c.aA.o.b.a.aA.a |
| q.c.aA.o.b.a.aA.aA | q.c.aA.o.b.a.aA.aG | q.c.aA.o.b.a.aG.a | |
| q.c.aA.o.b.a.aG.aA | q.c.aA.o.b.a.aG.aG | q.c.aA.o.b.b.a.a | q.c.aA.o.b.b.a.aA |
| q.c.aA.o.b.b.a.aG | q.c.aA.o.b.b.e.a | q.c.aA.o.b.b.e.aA | q.c.aA.o.b.b.e.aG |
| q.c.aA.o.b.b.m.a | q.c.aA.o.b.b.m.aA | q.c.aA.o.b.b.m.aG | q.c.aA.o.b.b.ao.a |
| q.c.aA.o.b.b.o.aA | q.c.aA.o.b.b.o.aG | q.c.aA.o.b.b.E.a | q.c.aA.o.b.b.E.aA |
| q.c.aA.o.b.b.E.aG | q.c.aA.o.b.b.R.a | q.c.aA.o.b.b.R.aA | q.c.aA.o.b.b.R.aG |
| q.c.aA.o.b.b.aw.a | q.c.aA.o.b.b.aw.aA | q.c.aA.o.b.b.aw.aG | q.c.aA.o.b.b.aA.a |
| q.c.aA.o.b.b.aA.aA | q.c.aA.o.b.b.aA.aG | q.c.aA.o.b.b.aG.a | |
| q.c.aA.o.b.b.aG.aA | q.c.aA.o.b.b.aG.aG | q.c.aA.E.a.b.a.a | q.c.aA.E.a.b.a.aA |
| q.c.aA.E.a.b.a.aG | q.c.aA.E.a.b.e.a | q.c.aA.E.a.b.e.aA | q.c.aA.E.a.b.e.aG |
| q.c.aA.E.a.b.m.a | q.c.aA.E.a.b.m.aA | q.c.aA.E.a.b.m.aG | q.c.aA.E.a.b.ao.a |
| q.c.aA.E.a.b.o.aA | q.c.aA.E.a.b.o.aG | q.c.aA.E.a.b.E.a | q.c.aA.E.a.b.E.aA |
| q.c.aA.E.a.b.E.aG | q.c.aA.E.a.b.R.a | q.c.aA.E.a.b.R.aA | q.c.aA.E.a.b.R.aG |
| q.c.aA.E.a.b.aw.a | q.c.aA.E.a.b.aw.aA | q.c.aA.E.a.b.aw.aG | q.c.aA.E.a.b.aA.a |
| q.c.aA.E.a.b.aA.aA | q.c.aA.E.a.b.aA.aG | q.c.aA.E.a.b.aG.a | |
| q.c.aA.E.a.b.aG.aA | q.c.aA.E.a.b.aG.aG | q.c.aA.E.b.a.a.a | q.c.aA.E.b.a.a.aA |
| q.c.aA.E.b.a.a.aG | q.c.aA.E.b.a.e.a | q.c.aA.E.b.a.e.aA | q.c.aA.E.b.a.e.aG |
| q.c.aA.E.b.a.m.a | q.c.aA.E.b.a.m.aA | q.c.aA.E.b.a.m.aG | q.c.aA.E.b.a.ao.a |

TABLE 14-continued

Exemplary Compounds of the Invention

| | | | |
|---|---|---|---|
| q.c.aA.E.b.a.o.aA | q.c.aA.E.b.a.o.aG | q.c.aA.E.b.a.E.a | q.c.aA.E.b.a.E.aA |
| q.c.aA.E.b.a.E.aG | q.c.aA.E.b.a.R.a | q.c.aA.E.b.a.R.aA | q.c.aA.E.b.a.R.aG |
| q.c.aA.E.b.a.aw.a | q.c.aA.E.b.a.aw.aA | q.c.aA.E.b.a.aw.aG | q.c.aA.E.b.a.aA.a |
| q.c.aA.E.b.a.aA.aA | q.c.aA.E.b.a.aA.aG | q.c.aA.E.b.a.aG.a | |
| q.c.aA.E.b.a.aG.aA | q.c.aA.E.b.a.aG.aG | q.c.aA.E.b.b.a.a | q.c.aA.E.b.b.a.aA |
| q.c.aA.E.b.b.a.aG | q.c.aA.E.b.b.e.a | q.c.aA.E.b.b.e.aA | q.c.aA.E.b.b.e.aG |
| q.c.aA.E.b.b.m.a | q.c.aA.E.b.b.m.aA | q.c.aA.E.b.b.m.aG | q.c.aA.E.b.b.ao.a |
| q.c.aA.E.b.b.o.aA | q.c.aA.E.b.b.o.aG | q.c.aA.E.b.b.E.a | q.c.aA.E.b.b.E.aA |
| q.c.aA.E.b.b.E.aG | q.c.aA.E.b.b.R.a | q.c.aA.E.b.b.R.aA | q.c.aA.E.b.b.R.aG |
| q.c.aA.E.b.b.aw.a | q.c.aA.E.b.b.aw.aA | q.c.aA.E.b.b.aw.aG | q.c.aA.E.b.b.aA.a |
| q.c.aA.E.b.b.aA.aA | q.c.aA.E.b.b.aA.aG | q.c.aA.E.b.b.aG.a | |
| q.c.aA.E.b.b.aG.aA | q.c.aA.E.b.b.aG.aG | q.c.aA.R.a.b.a.a | q.c.aA.R.a.b.a.aA |
| q.c.aA.R.a.b.a.aG | q.c.aA.R.a.b.e.a | q.c.aA.R.a.b.e.aA | q.c.aA.R.a.b.e.aG |
| q.c.aA.R.a.b.m.a | q.c.aA.R.a.b.m.aA | q.c.aA.R.a.b.m.aG | q.c.aA.R.a.b.ao.a |
| q.c.aA.R.a.b.o.aA | q.c.aA.R.a.b.o.aG | q.c.aA.R.a.b.E.a | q.c.aA.R.a.b.E.aA |
| q.c.aA.R.a.b.E.aG | q.c.aA.R.a.b.R.a | q.c.aA.R.a.b.R.aA | q.c.aA.R.a.b.R.aG |
| q.c.aA.R.a.b.aw.a | q.c.aA.R.a.b.aw.aA | q.c.aA.R.a.b.aw.aG | q.c.aA.R.a.b.aA.a |
| q.c.aA.R.a.b.aA.aA | q.c.aA.R.a.b.aA.aG | q.c.aA.R.a.b.aG.a | |
| q.c.aA.R.a.b.aG.aA | q.c.aA.R.a.b.aG.aG | q.c.aA.R.b.a.a.a | q.c.aA.R.b.a.a.aA |
| q.c.aA.R.b.a.a.aG | q.c.aA.R.b.a.e.a | q.c.aA.R.b.a.e.aA | q.c.aA.R.b.a.e.aG |
| q.c.aA.R.b.a.m.a | q.c.aA.R.b.a.m.aA | q.c.aA.R.b.a.m.aG | q.c.aA.R.b.a.ao.a |
| q.c.aA.R.b.a.o.aA | q.c.aA.R.b.a.o.aG | q.c.aA.R.b.a.E.a | q.c.aA.R.b.a.E.aA |
| q.c.aA.R.b.a.E.aG | q.c.aA.R.b.a.R.a | q.c.aA.R.b.a.R.aA | q.c.aA.R.b.a.R.aG |
| q.c.aA.R.b.a.aw.a | q.c.aA.R.b.a.aw.aA | q.c.aA.R.b.a.aw.aG | q.c.aA.R.b.a.aA.a |
| q.c.aA.R.b.a.aA.aA | q.c.aA.R.b.a.aA.aG | q.c.aA.R.b.a.aG.a | |
| q.c.aA.R.b.a.aG.aA | q.c.aA.R.b.a.aG.aG | q.c.aA.R.b.b.a.a | q.c.aA.R.b.b.a.aA |
| q.c.aA.R.b.b.a.aG | q.c.aA.R.b.b.e.a | q.c.aA.R.b.b.e.aA | q.c.aA.R.b.b.e.aG |
| q.c.aA.R.b.b.m.a | q.c.aA.R.b.b.m.aA | q.c.aA.R.b.b.m.aG | q.c.aA.R.b.b.ao.a |
| q.c.aA.R.b.b.o.aA | q.c.aA.R.b.b.o.aG | q.c.aA.R.b.b.E.a | q.c.aA.R.b.b.E.aA |
| q.c.aA.R.b.b.E.aG | q.c.aA.R.b.b.R.a | q.c.aA.R.b.b.R.aA | q.c.aA.R.b.b.R.aG |
| q.c.aA.R.b.b.aw.a | q.c.aA.R.b.b.aw.aA | q.c.aA.R.b.b.aw.aG | q.c.aA.R.b.b.aA.a |
| q.c.aA.R.b.b.aA.aA | q.c.aA.R.b.b.aA.aG | q.c.aA.R.b.b.aG.a | |
| q.c.aA.R.b.b.aG.aA | q.c.aA.R.b.b.aG.aG | q.c.aA.aw.a.b.a.a | q.c.aA.aw.a.b.a.aA |
| q.c.aA.aw.a.b.a.aG | q.c.aA.aw.a.b.e.a | q.c.aA.aw.a.b.e.aA | q.c.aA.aw.a.b.e.aG |
| q.c.aA.aw.a.b.m.a | q.c.aA.aw.a.b.m.aA | q.c.aA.aw.a.b.m.aG | q.c.aA.aw.a.b.ao.a |
| q.c.aA.aw.a.b.o.aA | q.c.aA.aw.a.b.o.aG | q.c.aA.aw.a.b.E.a | |
| q.c.aA.aw.a.b.E.aA | q.c.aA.aw.a.b.E.aG | q.c.aA.aw.a.b.R.a | |
| q.c.aA.aw.a.b.R.aA | q.c.aA.aw.a.b.R.aG | q.c.aA.aw.a.b.aw.a | |
| q.c.aA.aw.a.b.aw.aA | | q.c.aA.aw.a.b.aw.aG | |
| q.c.aA.aw.a.b.aA.a | q.c.aA.aw.a.b.aA.aA | | |
| q.c.aA.aw.a.b.aA.aG | | q.c.aA.aw.a.b.aG.a | |
| q.c.aA.aw.a.b.aG.aA | | q.c.aA.aw.a.b.aG.aG | |
| q.c.aA.aw.b.a.a.a | q.c.aA.aw.b.a.a.aA | q.c.aA.aw.b.a.a.aG | q.c.aA.aw.b.a.e.a |
| q.c.aA.aw.b.a.e.aA | q.c.aA.aw.b.a.e.aG | q.c.aA.aw.b.a.m.a | |
| q.c.aA.aw.b.a.m.aA | | q.c.aA.aw.b.a.m.aG | q.c.aA.aw.b.a.ao.a |
| q.c.aA.aw.b.a.o.aA | q.c.aA.aw.b.a.o.aG | q.c.aA.aw.b.a.E.a | |
| q.c.aA.aw.b.a.E.aA | q.c.aA.aw.b.a.E.aG | q.c.aA.aw.b.a.R.a | |
| q.c.aA.aw.b.a.R.aA | q.c.aA.aw.b.a.R.aG | q.c.aA.aw.b.a.aw.a | |
| q.c.aA.aw.b.a.aw.aA | | q.c.aA.aw.b.a.aw.aG | |
| q.c.aA.aw.b.a.aA.a | q.c.aA.aw.b.a.aA.aA | | |
| q.c.aA.aw.b.a.aA.aG | | q.c.aA.aw.b.a.aG.a | |
| q.c.aA.aw.b.a.aG.aA | | q.c.aA.aw.b.a.aG.aG | |
| q.c.aA.aw.b.b.a.a | q.c.aA.aw.b.b.a.aA | q.c.aA.aw.b.b.a.aG | q.c.aA.aw.b.b.e.a |
| q.c.aA.aw.b.b.e.aA | q.c.aA.aw.b.b.e.aG | q.c.aA.aw.b.b.m.a | |
| q.c.aA.aw.b.b.m.aA | | q.c.aA.aw.b.b.m.aG | q.c.aA.aw.b.b.ao.a |
| q.c.aA.aw.b.b.o.aA | q.c.aA.aw.b.b.o.aG | q.c.aA.aw.b.b.E.a | |
| q.c.aA.aw.b.b.E.aA | q.c.aA.aw.b.b.E.aG | q.c.aA.aw.b.b.R.a | |
| q.c.aA.aw.b.b.R.aA | q.c.aA.aw.b.b.R.aG | q.c.aA.aw.b.b.aw.a | |
| q.c.aA.aw.b.b.aw.aA | | q.c.aA.aw.b.b.aw.aG | |
| q.c.aA.aw.b.b.aA.a | q.c.aA.aw.b.b.aA.aA | | |
| q.c.aA.aw.b.b.aA.aG | | q.c.aA.aw.b.b.aG.a | |
| q.c.aA.aw.b.b.aG.aA | | q.c.aA.aw.b.b.aG.aG | |
| q.c.aA.aA.a.b.a.a | q.c.aA.aA.a.b.a.aA | q.c.aA.aA.a.b.a.aG | q.c.aA.aA.a.b.e.a |
| q.c.aA.aA.a.b.e.aA | q.c.aA.aA.a.b.e.aG | q.c.aA.aA.a.b.m.a | |
| q.c.aA.aA.a.b.m.aA | | q.c.aA.aA.a.b.m.aG | q.c.aA.aA.a.b.ao.a |
| q.c.aA.aA.a.b.o.aA | q.c.aA.aA.a.b.o.aG | q.c.aA.aA.a.b.E.a | |
| q.c.aA.aA.a.b.E.aA | q.c.aA.aA.a.b.E.aG | q.c.aA.aA.a.b.R.a | |
| q.c.aA.aA.a.b.R.aA | q.c.aA.aA.a.b.R.aG | q.c.aA.aA.a.b.aw.a | |
| q.c.aA.aA.a.b.aw.aA | | q.c.aA.aA.a.b.aw.aG | |
| q.c.aA.aA.a.b.aA.a | q.c.aA.aA.a.b.aA.aA | | |
| q.c.aA.aA.a.b.aA.aG | | q.c.aA.aA.a.b.aG.a | |
| q.c.aA.aA.a.b.aG.aA | | q.c.aA.aA.a.b.aG.aG | |
| q.c.aA.aA.b.a.a.a | q.c.aA.aA.b.a.a.aA | q.c.aA.aA.b.a.a.aG | q.c.aA.aA.b.a.e.a |
| q.c.aA.aA.b.a.e.aA | q.c.aA.aA.b.a.e.aG | q.c.aA.aA.b.a.m.a | |
| q.c.aA.aA.b.a.m.aA | | q.c.aA.aA.b.a.m.aG | q.c.aA.aA.b.a.ao.a |
| q.c.aA.aA.b.a.o.aA | q.c.aA.aA.b.a.o.aG | q.c.aA.aA.b.a.E.a | |
| q.c.aA.aA.b.a.E.aA | q.c.aA.aA.b.a.E.aG | q.c.aA.aA.b.a.R.a | |

TABLE 14-continued

Exemplary Compounds of the Invention

| | | | |
|---|---|---|---|
| q.c.aA.aA.b.a.R.aA | q.c.aA.aA.b.a.R.aG | q.c.aA.aA.b.a.aw.a | |
| q.c.aA.aA.b.a.aw.aA | | q.c.aA.aA.b.a.aw.aG | |
| q.c.aA.aA.b.a.aA.a | q.c.aA.aA.b.a.aA.aA | | |
| q.c.aA.aA.b.a.aA.aG | | q.c.aA.aA.b.a.aG.a | |
| q.c.aA.aA.b.a.aG.aA | | q.c.aA.aA.b.a.aG.aG | |
| q.c.aA.aA.b.b.a.a | q.c.aA.aA.b.b.a.aA | q.c.aA.aA.b.b.a.aG | q.c.aA.aA.b.b.e.a |
| q.c.aA.aA.b.b.e.aA | q.c.aA.aA.b.b.e.aG | q.c.aA.aA.b.b.m.a | |
| q.c.aA.aA.b.b.m.aA | | q.c.aA.aA.b.b.m.aG | q.c.aA.aA.b.b.ao.a |
| q.c.aA.aA.b.b.o.aA | q.c.aA.aA.b.b.o.aG | q.c.aA.aA.b.b.E.a | |
| q.c.aA.aA.b.b.E.aA | q.c.aA.aA.b.b.E.aG | q.c.aA.aA.b.b.R.a | |
| q.c.aA.aA.b.b.R.aA | q.c.aA.aA.b.b.R.aG | q.c.aA.aA.b.b.aw.a | |
| q.c.aA.aA.b.b.aw.aA | | q.c.aA.aA.b.b.aw.aG | |
| q.c.aA.aA.b.b.aA.a | q.c.aA.aA.b.b.aA.aA | | |
| q.c.aA.aA.b.b.aA.aG | | q.c.aA.aA.b.b.aG.a | |
| q.c.aA.aA.b.b.aG.aA | | q.c.aA.aA.b.b.aG.aG | |
| q.c.aA.aG.a.b.a.a | q.c.aA.aG.a.b.a.aA | q.c.aA.aG.a.b.a.aG | q.c.aA.aG.a.b.e.a |
| q.c.aA.aG.a.b.e.aA | q.c.aA.aG.a.b.e.aG | q.c.aA.aG.a.b.m.a | |
| q.c.aA.aG.a.b.m.aA | | q.c.aA.aG.a.b.m.aG | q.c.aA.aG.a.b.ao.a |
| q.c.aA.aG.a.b.o.aA | q.c.aA.aG.a.b.o.aG | q.c.aA.aG.a.b.E.a | |
| q.c.aA.aG.a.b.E.aA | q.c.aA.aG.a.b.E.aG | q.c.aA.aG.a.b.R.a | |
| q.c.aA.aG.a.b.R.aA | q.c.aA.aG.a.b.R.aG | q.c.aA.aG.a.b.aw.a | |
| q.c.aA.aG.a.b.aw.aA | | q.c.aA.aG.a.b.aw.aG | |
| q.c.aA.aG.a.b.aA.a | q.c.aA.aG.a.b.aA.aA | | |
| q.c.aA.aG.a.b.aA.aG | | q.c.aA.aG.a.b.aG.a | |
| q.c.aA.aG.a.b.aG.aA | | q.c.aA.aG.a.b.aG.aG | |
| q.c.aA.aG.b.a.a.a | q.c.aA.aG.b.a.a.aA | q.c.aA.aG.b.a.a.aG | q.c.aA.aG.b.a.e.a |
| q.c.aA.aG.b.a.e.aA | q.c.aA.aG.b.a.e.aG | q.c.aA.aG.b.a.m.a | |
| q.c.aA.aG.b.a.m.aA | | q.c.aA.aG.b.a.m.aG | q.c.aA.aG.b.a.ao.a |
| q.c.aA.aG.b.a.o.aA | q.c.aA.aG.b.a.o.aG | q.c.aA.aG.b.a.E.a | |
| q.c.aA.aG.b.a.E.aA | q.c.aA.aG.b.a.E.aG | q.c.aA.aG.b.a.R.a | |
| q.c.aA.aG.b.a.R.aA | q.c.aA.aG.b.a.R.aG | q.c.aA.aG.b.a.aw.a | |
| q.c.aA.aG.b.a.aw.aA | | q.c.aA.aG.b.a.aw.aG | |
| q.c.aA.aG.b.a.aA.a | q.c.aA.aG.b.a.aA.aA | | |
| q.c.aA.aG.b.a.aA.aG | | q.c.aA.aG.b.a.aG.a | |
| q.c.aA.aG.b.a.aG.aA | | q.c.aA.aG.b.a.aG.aG | |
| q.c.aA.aG.b.b.a.a | q.c.aA.aG.b.b.a.aA | q.c.aA.aG.b.b.a.aG | q.c.aA.aG.b.b.e.a |
| q.c.aA.aG.b.b.e.aA | q.c.aA.aG.b.b.e.aG | q.c.aA.aG.b.b.m.a | |
| q.c.aA.aG.b.b.m.aA | | q.c.aA.aG.b.b.m.aG | q.c.aA.aG.b.b.ao.a |
| q.c.aA.aG.b.b.o.aA | q.c.aA.aG.b.b.o.aG | q.c.aA.aG.b.b.E.a | |
| q.c.aA.aG.b.b.E.aA | q.c.aA.aG.b.b.E.aG | q.c.aA.aG.b.b.R.a | |
| q.c.aA.aG.b.b.R.aA | q.c.aA.aG.b.b.R.aG | q.c.aA.aG.b.b.aw.a | |
| q.c.aA.aG.b.b.aw.aA | | q.c.aA.aG.b.b.aw.aG | |
| q.c.aA.aG.b.b.aA.a | q.c.aA.aG.b.b.aA.aA | | |
| q.c.aA.aG.b.b.aA.aG | | q.c.aA.aG.b.b.aG.a | |
| q.c.aA.aG.b.b.aG.aA | | q.c.aA.aG.b.b.aG.aG | q.c.aG.a.a.b.a.a |
| q.c.aG.a.a.b.a.aA | q.c.aG.a.a.b.a.aG | q.c.aG.a.a.b.e.a | q.c.aG.a.a.b.e.aA |
| q.c.aG.a.a.b.e.aG | q.c.aG.a.a.b.m.a | q.c.aG.a.a.b.m.aA | q.c.aG.a.a.b.m.aG |
| q.c.aG.a.a.b.ao.a | q.c.aG.a.a.b.o.aA | q.c.aG.a.a.b.o.aG | q.c.aG.a.a.b.E.a |
| q.c.aG.a.a.b.E.aA | q.c.aG.a.a.b.E.aG | q.c.aG.a.a.b.R.a | q.c.aG.a.a.b.R.aA |
| q.c.aG.a.a.b.R.aG | q.c.aG.a.a.b.aw.a | q.c.aG.a.a.b.aw.aA | q.c.aG.a.a.b.aw.aG |
| q.c.aG.a.a.b.aA.a | q.c.aG.a.a.b.aA.aA | q.c.aG.a.a.b.aA.aG | q.c.aG.a.a.b.aG.a |
| q.c.aG.a.a.b.aG.aA | q.c.aG.a.a.b.aG.aG | q.c.aG.a.b.a.a.a | q.c.aG.a.b.a.a.aA |
| q.c.aG.a.b.a.a.aG | q.c.aG.a.b.a.e.a | q.c.aG.a.b.a.e.aA | q.c.aG.a.b.a.e.aG |
| q.c.aG.a.b.a.m.a | q.c.aG.a.b.a.m.aA | q.c.aG.a.b.a.m.aG | q.c.aG.a.b.a.ao.a |
| q.c.aG.a.b.a.o.aA | q.c.aG.a.b.a.o.aG | q.c.aG.a.b.a.E.a | q.c.aG.a.b.a.E.aA |
| q.c.aG.a.b.a.E.aG | q.c.aG.a.b.a.R.a | q.c.aG.a.b.a.R.aA | q.c.aG.a.b.a.R.aG |
| q.c.aG.a.b.a.aw.a | q.c.aG.a.b.a.aw.aA | q.c.aG.a.b.a.aw.aG | q.c.aG.a.b.a.aA.a |
| q.c.aG.a.b.a.aA.aA | q.c.aG.a.b.a.aA.aG | q.c.aG.a.b.a.aG.a | q.c.aG.a.b.a.aG.aA |
| q.c.aG.a.b.a.aG.aG | q.c.aG.a.b.b.a.a | q.c.aG.a.b.b.a.aA | q.c.aG.a.b.b.a.aG |
| q.c.aG.a.b.b.e.a | q.c.aG.a.b.b.e.aA | q.c.aG.a.b.b.e.aG | q.c.aG.a.b.b.m.a |
| q.c.aG.a.b.b.m.aA | q.c.aG.a.b.b.m.aG | q.c.aG.a.b.b.ao.a | q.c.aG.a.b.b.o.aA |
| q.c.aG.a.b.b.o.aG | q.c.aG.a.b.b.E.a | q.c.aG.a.b.b.E.aA | q.c.aG.a.b.b.E.aG |
| q.c.aG.a.b.b.R.a | q.c.aG.a.b.b.R.aA | q.c.aG.a.b.b.R.aG | q.c.aG.a.b.b.aw.a |
| q.c.aG.a.b.b.aw.aA | q.c.aG.a.b.b.aw.aG | q.c.aG.a.b.b.aA.a | |
| q.c.aG.a.b.b.aA.aA | q.c.aG.a.b.b.aA.aG | q.c.aG.a.b.b.aG.a | q.c.aG.a.b.b.aG.aA |
| q.c.aG.a.b.b.aG.aG | q.c.aG.e.a.b.a.a | q.c.aG.e.a.b.a.aA | q.c.aG.e.a.b.a.aG |
| q.c.aG.e.a.b.e.a | q.c.aG.e.a.b.e.aA | q.c.aG.e.a.b.e.aG | q.c.aG.e.a.b.m.a |
| q.c.aG.e.a.b.m.aA | q.c.aG.e.a.b.m.aG | q.c.aG.e.a.b.ao.a | q.c.aG.e.a.b.o.aA |
| q.c.aG.e.a.b.o.aG | q.c.aG.e.a.b.E.a | q.c.aG.e.a.b.E.aA | q.c.aG.e.a.b.E.aG |
| q.c.aG.e.a.b.R.a | q.c.aG.e.a.b.R.aA | q.c.aG.e.a.b.R.aG | q.c.aG.e.a.b.aw.a |
| q.c.aG.e.a.b.aw.aA | q.c.aG.e.a.b.aw.aG | q.c.aG.e.a.b.aA.a | |
| q.c.aG.e.a.b.aA.aA | q.c.aG.e.a.b.aA.aG | q.c.aG.e.a.b.aG.a | q.c.aG.e.a.b.aG.aA |
| q.c.aG.e.a.b.aG.aG | q.c.aG.e.b.a.a.a | q.c.aG.e.b.a.a.aA | q.c.aG.e.b.a.a.aG |
| q.c.aG.e.b.a.e.a | q.c.aG.e.b.a.e.aA | q.c.aG.e.b.a.e.aG | q.c.aG.e.b.a.m.a |
| q.c.aG.e.b.a.m.aA | q.c.aG.e.b.a.m.aG | q.c.aG.e.b.a.ao.a | q.c.aG.e.b.a.o.aA |
| q.c.aG.e.b.a.o.aG | q.c.aG.e.b.a.E.a | q.c.aG.e.b.a.E.aA | q.c.aG.e.b.a.E.aG |
| q.c.aG.e.b.a.R.a | q.c.aG.e.b.a.R.aA | q.c.aG.e.b.a.R.aG | q.c.aG.e.b.a.aw.a |

TABLE 14-continued

Exemplary Compounds of the Invention

| | | | |
|---|---|---|---|
| q.c.aG.e.b.a.aw.aA | q.c.aG.e.b.a.aw.aG | q.c.aG.e.b.a.aA.a | |
| q.c.aG.e.b.a.aA.aA | q.c.aG.e.b.a.aA.aG | q.c.aG.e.b.a.aG.a | q.c.aG.e.b.a.aG.aA |
| q.c.aG.e.b.a.aG.aG | q.c.aG.e.b.b.a.a | q.c.aG.e.b.b.a.aA | q.c.aG.e.b.b.a.aG |
| q.c.aG.e.b.b.e.a | q.c.aG.e.b.b.e.aA | q.c.aG.e.b.b.e.aG | q.c.aG.e.b.b.m.a |
| q.c.aG.e.b.b.m.aA | q.c.aG.e.b.b.m.aG | q.c.aG.e.b.b.ao.a | q.c.aG.e.b.b.o.aA |
| q.c.aG.e.b.b.o.aG | q.c.aG.e.b.b.E.a | q.c.aG.e.b.b.E.aA | q.c.aG.e.b.b.E.aG |
| q.c.aG.e.b.b.R.a | q.c.aG.e.b.b.R.aA | q.c.aG.e.b.b.R.aG | q.c.aG.e.b.b.aw.a |
| q.c.aG.e.b.b.aw.aA | q.c.aG.e.b.b.aw.aG | q.c.aG.e.b.b.aA.a | |
| q.c.aG.e.b.b.aA.aA | q.c.aG.e.b.b.aA.aG | q.c.aG.e.b.b.aG.a | q.c.aG.e.b.b.aG.aA |
| q.c.aG.e.b.b.aG.aG | q.c.aG.m.a.b.a.a | q.c.aG.m.a.b.a.aA | q.c.aG.m.a.b.a.aG |
| q.c.aG.m.a.b.e.a | q.c.aG.m.a.b.e.aA | q.c.aG.m.a.b.e.aG | q.c.aG.m.a.b.m.a |
| q.c.aG.m.a.b.m.aA | q.c.aG.m.a.b.m.aG | q.c.aG.m.a.b.ao.a | q.c.aG.m.a.b.o.aA |
| q.c.aG.m.a.b.o.aG | q.c.aG.m.a.b.E.a | q.c.aG.m.a.b.E.aA | q.c.aG.m.a.b.E.aG |
| q.c.aG.m.a.b.R.a | q.c.aG.m.a.b.R.aA | q.c.aG.m.a.b.R.aG | q.c.aG.m.a.b.aw.a |
| q.c.aG.m.a.b.aw.aA | q.c.aG.m.a.b.aw.aG | q.c.aG.m.a.b.aA.a | |
| q.c.aG.m.a.b.aA.aA | q.c.aG.m.a.b.aA.aG | q.c.aG.m.a.b.aG.a | |
| q.c.aG.m.a.b.aG.aA | q.c.aG.m.a.b.aG.aG | q.c.aG.m.b.a.a.a | q.c.aG.m.b.a.a.aA |
| q.c.aG.m.b.a.a.aG | q.c.aG.m.b.a.e.a | q.c.aG.m.b.a.e.aA | q.c.aG.m.b.a.e.aG |
| q.c.aG.m.b.a.m.a | q.c.aG.m.b.a.m.aA | q.c.aG.m.b.a.m.aG | q.c.aG.m.b.a.ao.a |
| q.c.aG.m.b.a.o.aA | q.c.aG.m.b.a.o.aG | q.c.aG.m.b.a.E.a | q.c.aG.m.b.a.E.aA |
| q.c.aG.m.b.a.E.aG | q.c.aG.m.b.a.R.a | q.c.aG.m.b.a.R.aA | q.c.aG.m.b.a.R.aG |
| q.c.aG.m.b.a.aw.a | q.c.aG.m.b.a.aw.aA | q.c.aG.m.b.a.aw.aG | q.c.aG.m.b.a.aA.a |
| q.c.aG.m.b.a.aA.aA | q.c.aG.m.b.a.aA.aG | q.c.aG.m.b.a.aG.a | |
| q.c.aG.m.b.a.aG.aA | q.c.aG.m.b.a.aG.aG | q.c.aG.m.b.b.a.a | q.c.aG.m.b.b.a.aA |
| q.c.aG.m.b.b.a.aG | q.c.aG.m.b.b.e.a | q.c.aG.m.b.b.e.aA | q.c.aG.m.b.b.e.aG |
| q.c.aG.m.b.b.m.a | q.c.aG.m.b.b.m.aA | q.c.aG.m.b.b.m.aG | q.c.aG.m.b.b.ao.a |
| q.c.aG.m.b.b.o.aA | q.c.aG.m.b.b.o.aG | q.c.aG.m.b.b.E.a | q.c.aG.m.b.b.E.aA |
| q.c.aG.m.b.b.E.aG | q.c.aG.m.b.b.R.a | q.c.aG.m.b.b.R.aA | q.c.aG.m.b.b.R.aG |
| q.c.aG.m.b.b.aw.a | q.c.aG.m.b.b.aw.aA | q.c.aG.m.b.b.aw.aG | q.c.aG.m.b.b.aA.a |
| q.c.aG.m.b.b.aA.aA | q.c.aG.m.b.b.aA.aG | q.c.aG.m.b.b.aG.a | |
| q.c.aG.m.b.b.aG.aA | q.c.aG.m.b.b.aG.aG | q.c.aG.o.a.b.a.a | q.c.aG.o.a.b.a.aA |
| q.c.aG.o.a.b.a.aG | q.c.aG.o.a.b.e.a | q.c.aG.o.a.b.e.aA | q.c.aG.o.a.b.e.aG |
| q.c.aG.o.a.b.m.a | q.c.aG.o.a.b.m.aA | q.c.aG.o.a.b.m.aG | q.c.aG.o.a.b.ao.a |
| q.c.aG.o.a.b.o.aA | q.c.aG.o.a.b.o.aG | q.c.aG.o.a.b.E.a | q.c.aG.o.a.b.E.aA |
| q.c.aG.o.a.b.E.aG | q.c.aG.o.a.b.R.a | q.c.aG.o.a.b.R.aA | q.c.aG.o.a.b.R.aG |
| q.c.aG.o.a.b.aw.a | q.c.aG.o.a.b.aw.aA | q.c.aG.o.a.b.aw.aG | q.c.aG.o.a.b.aA.a |
| q.c.aG.o.a.b.aA.aA | q.c.aG.o.a.b.aA.aG | q.c.aG.o.a.b.aG.a | |
| q.c.aG.o.a.b.aG.aA | q.c.aG.o.a.b.aG.aG | q.c.aG.o.b.a.a.a | q.c.aG.o.b.a.a.aA |
| q.c.aG.o.b.a.a.aG | q.c.aG.o.b.a.e.a | q.c.aG.o.b.a.e.aA | q.c.aG.o.b.a.e.aG |
| q.c.aG.o.b.a.m.a | q.c.aG.o.b.a.m.aA | q.c.aG.o.b.a.m.aG | q.c.aG.o.b.a.ao.a |
| q.c.aG.o.b.a.o.aA | q.c.aG.o.b.a.o.aG | q.c.aG.o.b.a.E.a | q.c.aG.o.b.a.E.aA |
| q.c.aG.o.b.a.E.aG | q.c.aG.o.b.a.R.a | q.c.aG.o.b.a.R.aA | q.c.aG.o.b.a.R.aG |
| q.c.aG.o.b.a.aw.a | q.c.aG.o.b.a.aw.aA | q.c.aG.o.b.a.aw.aG | q.c.aG.o.b.a.aA.a |
| q.c.aG.o.b.a.aA.aA | q.c.aG.o.b.a.aA.aG | q.c.aG.o.b.a.aG.a | |
| q.c.aG.o.b.a.aG.aA | q.c.aG.o.b.a.aG.aG | q.c.aG.o.b.b.a.a | q.c.aG.o.b.b.a.aA |
| q.c.aG.o.b.b.a.aG | q.c.aG.o.b.b.e.a | q.c.aG.o.b.b.e.aA | q.c.aG.o.b.b.e.aG |
| q.c.aG.o.b.b.m.a | q.c.aG.o.b.b.m.aA | q.c.aG.o.b.b.m.aG | q.c.aG.o.b.b.ao.a |
| q.c.aG.o.b.b.o.aA | q.c.aG.o.b.b.o.aG | q.c.aG.o.b.b.E.a | q.c.aG.o.b.b.E.aA |
| q.c.aG.o.b.b.E.aG | q.c.aG.o.b.b.R.a | q.c.aG.o.b.b.R.aA | q.c.aG.o.b.b.R.aG |
| q.c.aG.o.b.b.aw.a | q.c.aG.o.b.b.aw.aA | q.c.aG.o.b.b.aw.aG | q.c.aG.o.b.b.aA.a |
| q.c.aG.o.b.b.aA.aA | q.c.aG.o.b.b.aA.aG | q.c.aG.o.b.b.aG.a | |
| q.c.aG.o.b.b.aG.aA | q.c.aG.o.b.b.aG.aG | q.c.aG.E.a.b.a.a | q.c.aG.E.a.b.a.aA |
| q.c.aG.E.a.b.a.aG | q.c.aG.E.a.b.e.a | q.c.aG.E.a.b.e.aA | q.c.aG.E.a.b.e.aG |
| q.c.aG.E.a.b.m.a | q.c.aG.E.a.b.m.aA | q.c.aG.E.a.b.m.aG | q.c.aG.E.a.b.ao.a |
| q.c.aG.E.a.b.o.aA | q.c.aG.E.a.b.o.aG | q.c.aG.E.a.b.E.a | q.c.aG.E.a.b.E.aA |
| q.c.aG.E.a.b.E.aG | q.c.aG.E.a.b.R.a | q.c.aG.E.a.b.R.aA | q.c.aG.E.a.b.R.aG |
| q.c.aG.E.a.b.aw.a | q.c.aG.E.a.b.aw.aA | q.c.aG.E.a.b.aw.aG | q.c.aG.E.a.b.aA.a |
| q.c.aG.E.a.b.aA.aA | q.c.aG.E.a.b.aA.aG | q.c.aG.E.a.b.aG.a | |
| q.c.aG.E.a.b.aG.aA | q.c.aG.E.a.b.aG.aG | q.c.aG.E.b.a.a.a | q.c.aG.E.b.a.a.aA |
| q.c.aG.E.b.a.a.aG | q.c.aG.E.b.a.e.a | q.c.aG.E.b.a.e.aA | q.c.aG.E.b.a.e.aG |
| q.c.aG.E.b.a.m.a | q.c.aG.E.b.a.m.aA | q.c.aG.E.b.a.m.aG | q.c.aG.E.b.a.ao.a |
| q.c.aG.E.b.a.o.aA | q.c.aG.E.b.a.o.aG | q.c.aG.E.b.a.E.a | q.c.aG.E.b.a.E.aA |
| q.c.aG.E.b.a.E.aG | q.c.aG.E.b.a.R.a | q.c.aG.E.b.a.R.aA | q.c.aG.E.b.a.R.aG |
| q.c.aG.E.b.a.aw.a | q.c.aG.E.b.a.aw.aA | q.c.aG.E.b.a.aw.aG | q.c.aG.E.b.a.aA.a |
| q.c.aG.E.b.a.aA.aA | q.c.aG.E.b.a.aA.aG | q.c.aG.E.b.a.aG.a | |
| q.c.aG.E.b.a.aG.aA | q.c.aG.E.b.a.aG.aG | q.c.aG.E.b.b.a.a | q.c.aG.E.b.b.a.aA |
| q.c.aG.E.b.b.a.aG | q.c.aG.E.b.b.e.a | q.c.aG.E.b.b.e.aA | q.c.aG.E.b.b.e.aG |
| q.c.aG.E.b.b.m.a | q.c.aG.E.b.b.m.aA | q.c.aG.E.b.b.m.aG | q.c.aG.E.b.b.ao.a |
| q.c.aG.E.b.b.o.aA | q.c.aG.E.b.b.o.aG | q.c.aG.E.b.b.E.a | q.c.aG.E.b.b.E.aA |
| q.c.aG.E.b.b.E.aG | q.c.aG.E.b.b.R.a | q.c.aG.E.b.b.R.aA | q.c.aG.E.b.b.R.aG |
| q.c.aG.E.b.b.aw.a | q.c.aG.E.b.b.aw.aA | q.c.aG.E.b.b.aw.aG | q.c.aG.E.b.b.aA.a |
| q.c.aG.E.b.b.aA.aA | q.c.aG.E.b.b.aA.aG | q.c.aG.E.b.b.aG.a | |
| q.c.aG.E.b.b.aG.aA | q.c.aG.E.b.b.aG.aG | q.c.aG.R.a.b.a.a | q.c.aG.R.a.b.a.aA |
| q.c.aG.R.a.b.a.aG | q.c.aG.R.a.b.e.a | q.c.aG.R.a.b.e.aA | q.c.aG.R.a.b.e.aG |
| q.c.aG.R.a.b.m.a | q.c.aG.R.a.b.m.aA | q.c.aG.R.a.b.m.aG | q.c.aG.R.a.b.ao.a |
| q.c.aG.R.a.b.o.aA | q.c.aG.R.a.b.o.aG | q.c.aG.R.a.b.E.a | q.c.aG.R.a.b.E.aA |
| q.c.aG.R.a.b.E.aG | q.c.aG.R.a.b.R.a | q.c.aG.R.a.b.R.aA | q.c.aG.R.a.b.R.aG |

TABLE 14-continued

Exemplary Compounds of the Invention

| | | | |
|---|---|---|---|
| q.c.aG.R.a.b.aw.a | q.c.aG.R.a.b.aw.aA | q.c.aG.R.a.b.aw.aG | q.c.aG.R.a.b.aA.a |
| q.c.aG.R.a.b.aA.aA | q.c.aG.R.a.b.aA.aG | q.c.aG.R.a.b.aG.a | |
| q.c.aG.R.a.b.aG.aA | q.c.aG.R.a.b.aG.aG | q.c.aG.R.b.a.a.a | q.c.aG.R.b.a.a.aA |
| q.c.aG.R.b.a.a.aG | q.c.aG.R.b.a.e.a | q.c.aG.R.b.a.e.aA | q.c.aG.R.b.a.e.aG |
| q.c.aG.R.b.a.m.a | q.c.aG.R.b.a.m.aA | q.c.aG.R.b.a.m.aG | q.c.aG.R.b.a.ao.a |
| q.c.aG.R.b.a.o.aA | q.c.aG.R.b.a.o.aG | q.c.aG.R.b.a.E.a | q.c.aG.R.b.a.E.aA |
| q.c.aG.R.b.a.E.aG | q.c.aG.R.b.a.R.a | q.c.aG.R.b.a.R.aA | q.c.aG.R.b.a.R.aG |
| q.c.aG.R.b.a.aw.a | q.c.aG.R.b.a.aw.aA | q.c.aG.R.b.a.aw.aG | q.c.aG.R.b.a.aA.a |
| q.c.aG.R.b.a.aA.aA | q.c.aG.R.b.a.aA.aG | q.c.aG.R.b.a.aG.a | |
| q.c.aG.R.b.a.aG.aA | q.c.aG.R.b.a.aG.aG | q.c.aG.R.b.b.a.a | q.c.aG.R.b.b.a.aA |
| q.c.aG.R.b.b.a.aG | q.c.aG.R.b.b.e.a | q.c.aG.R.b.b.e.aA | q.c.aG.R.b.b.e.aG |
| q.c.aG.R.b.b.m.a | q.c.aG.R.b.b.m.aA | q.c.aG.R.b.b.m.aG | q.c.aG.R.b.b.ao.a |
| q.c.aG.R.b.b.o.aA | q.c.aG.R.b.b.o.aG | q.c.aG.R.b.b.E.a | q.c.aG.R.b.b.E.aA |
| q.c.aG.R.b.b.E.aG | q.c.aG.R.b.b.R.a | q.c.aG.R.b.b.R.aA | q.c.aG.R.b.b.R.aG |
| q.c.aG.R.b.b.aw.a | q.c.aG.R.b.b.aw.aA | q.c.aG.R.b.b.aw.aG | q.c.aG.R.b.b.aA.a |
| q.c.aG.R.b.b.aA.aA | q.c.aG.R.b.b.aA.aG | q.c.aG.R.b.b.aG.a | |
| q.c.aG.R.b.b.aG.aA | q.c.aG.R.b.b.aG.aG | q.c.aG.aw.a.b.a.a | |
| q.c.aG.aw.a.b.a.aA | q.c.aG.aw.a.b.a.aG | q.c.aG.aw.a.b.e.a | |
| q.c.aG.aw.a.b.e.aA | q.c.aG.aw.a.b.e.aG | q.c.aG.aw.a.b.m.a | |
| q.c.aG.aw.a.b.m.aA | q.c.aG.aw.a.b.m.aG | q.c.aG.aw.a.b.ao.a | |
| q.c.aG.aw.a.b.o.aA | q.c.aG.aw.a.b.o.aG | q.c.aG.aw.a.b.E.a | |
| q.c.aG.aw.a.b.E.aA | q.c.aG.aw.a.b.E.aG | q.c.aG.aw.a.b.R.a | |
| q.c.aG.aw.a.b.R.aA | q.c.aG.aw.a.b.R.aG | q.c.aG.aw.a.b.aw.a | |
| q.c.aG.aw.a.b.aw.aA | | q.c.aG.aw.a.b.aw.aG | |
| q.c.aG.aw.a.b.aA.a | q.c.aG.aw.a.b.aA.aA | | |
| q.c.aG.aw.a.b.aA.aG | | q.c.aG.aw.a.b.aG.a | |
| q.c.aG.aw.a.b.aG.aA | | q.c.aG.aw.a.b.aG.aG | q.c.aG.aw.b.a.a.a |
| q.c.aG.aw.b.a.a.aA | q.c.aG.aw.b.a.a.aG | q.c.aG.aw.b.a.e.a | |
| q.c.aG.aw.b.a.e.aA | q.c.aG.aw.b.a.e.aG | q.c.aG.aw.b.a.m.a | |
| q.c.aG.aw.b.a.m.aA | q.c.aG.aw.b.a.m.aG | q.c.aG.aw.b.a.ao.a | |
| q.c.aG.aw.b.a.o.aA | q.c.aG.aw.b.a.o.aG | q.c.aG.aw.b.a.E.a | |
| q.c.aG.aw.b.a.E.aA | q.c.aG.aw.b.a.E.aG | q.c.aG.aw.b.a.R.a | |
| q.c.aG.aw.b.a.R.aA | q.c.aG.aw.b.a.R.aG | q.c.aG.aw.b.a.aw.a | |
| q.c.aG.aw.b.a.aw.aA | | q.c.aG.aw.b.a.aw.aG | |
| q.c.aG.aw.b.a.aA.a | q.c.aG.aw.b.a.aA.aA | | |
| q.c.aG.aw.b.a.aA.aG | | q.c.aG.aw.b.a.aG.a | |
| q.c.aG.aw.b.a.aG.aA | | q.c.aG.aw.b.a.aG.aG | q.c.aG.aw.b.b.a.a |
| q.c.aG.aw.b.b.a.aA | q.c.aG.aw.b.b.a.aG | q.c.aG.aw.b.b.e.a | |
| q.c.aG.aw.b.b.e.aA | q.c.aG.aw.b.b.e.aG | q.c.aG.aw.b.b.m.a | |
| q.c.aG.aw.b.b.m.aA | q.c.aG.aw.b.b.m.aG | q.c.aG.aw.b.b.ao.a | |
| q.c.aG.aw.b.b.o.aA | q.c.aG.aw.b.b.o.aG | q.c.aG.aw.b.b.E.a | |
| q.c.aG.aw.b.b.E.aA | q.c.aG.aw.b.b.E.aG | q.c.aG.aw.b.b.R.a | |
| q.c.aG.aw.b.b.R.aA | q.c.aG.aw.b.b.R.aG | q.c.aG.aw.b.b.aw.a | |
| q.c.aG.aw.b.b.aw.aA | | q.c.aG.aw.b.b.aw.aG | |
| q.c.aG.aw.b.b.aA.a | q.c.aG.aw.b.b.aA.aA | | |
| q.c.aG.aw.b.b.aA.aG | | q.c.aG.aw.b.b.aG.a | |
| q.c.aG.aw.b.b.aG.aA | | q.c.aG.aw.b.b.aG.aG | q.c.aG.aA.a.b.a.a |
| q.c.aG.aA.a.b.a.aA | q.c.aG.aA.a.b.a.aG | q.c.aG.aA.a.b.e.a | |
| q.c.aG.aA.a.b.e.aA | q.c.aG.aA.a.b.e.aG | q.c.aG.aA.a.b.m.a | |
| q.c.aG.aA.a.b.m.aA | q.c.aG.aA.a.b.m.aG | q.c.aG.aA.a.b.ao.a | |
| q.c.aG.aA.a.b.o.aA | q.c.aG.aA.a.b.o.aG | q.c.aG.aA.a.b.E.a | |
| q.c.aG.aA.a.b.E.aA | q.c.aG.aA.a.b.E.aG | q.c.aG.aA.a.b.R.a | |
| q.c.aG.aA.a.b.R.aA | q.c.aG.aA.a.b.R.aG | q.c.aG.aA.a.b.aw.a | |
| q.c.aG.aA.a.b.aw.aA | | q.c.aG.aA.a.b.aw.aG | |
| q.c.aG.aA.a.b.aA.a | q.c.aG.aA.a.b.aA.aA | | |
| q.c.aG.aA.a.b.aA.aG | | q.c.aG.aA.a.b.aG.a | |
| q.c.aG.aA.a.b.aG.aA | | q.c.aG.aA.a.b.aG.aG | q.c.aG.aA.b.a.a.a |
| q.c.aG.aA.b.a.a.a | | | |
| q.c.aG.aA.b.a.a.aA | q.c.aG.aA.b.a.a.aG | q.c.aG.aA.a.b.e.a | |
| q.c.aG.aA.a.b.e.aA | q.c.aG.aA.a.b.e.aG | q.c.aG.aA.a.b.m.a | |
| q.c.aG.aA.a.b.m.aA | q.c.aG.aA.a.b.m.aG | q.c.aG.aA.a.b.ao.a | |
| q.c.aG.aA.a.b.o.aA | q.c.aG.aA.a.b.o.aG | q.c.aG.aA.a.b.E.a | |
| q.c.aG.aA.a.b.E.aA | q.c.aG.aA.a.b.E.aG | q.c.aG.aA.a.b.R.a | |
| q.c.aG.aA.a.b.R.aA | q.c.aG.aA.a.b.R.aG | q.c.aG.aA.a.b.aw.a | |
| q.c.aG.aA.a.b.aw.aA | | q.c.aG.aA.a.b.aw.aG | |
| q.c.aG.aA.a.b.aA.a | q.c.aG.aA.a.b.aA.aA | | |
| q.c.aG.aA.a.b.aA.aG | | q.c.aG.aA.a.b.aG.a | |
| q.c.aG.aA.a.b.aG.aA | | q.c.aG.aA.a.b.aG.aG | q.c.aG.aA.b.b.a.a |
| q.c.aG.aA.b.b.a.aA | q.c.aG.aA.b.b.a.aG | q.c.aG.aA.b.b.e.a | |
| q.c.aG.aA.b.b.e.aA | q.c.aG.aA.b.b.e.aG | q.c.aG.aA.b.b.m.a | |
| q.c.aG.aA.b.b.m.aA | q.c.aG.aA.b.b.m.aG | q.c.aG.aA.b.b.ao.a | |
| q.c.aG.aA.b.b.o.aA | q.c.aG.aA.b.b.o.aG | q.c.aG.aA.b.b.E.a | |
| q.c.aG.aA.b.b.E.aA | q.c.aG.aA.b.b.E.aG | q.c.aG.aA.b.b.R.a | |
| q.c.aG.aA.b.b.R.aA | q.c.aG.aA.b.b.R.aG | q.c.aG.aA.b.b.aw.a | |
| q.c.aG.aA.b.b.aw.aA | | q.c.aG.aA.b.b.aw.aG | |
| q.c.aG.aA.b.b.aA.a | q.c.aG.aA.b.b.aA.aA | | |
| q.c.aG.aA.b.b.aA.aG | | q.c.aG.aA.b.b.aG.a | |

TABLE 14-continued

Exemplary Compounds of the Invention

| | | | |
|---|---|---|---|
| q.c.aG.aA.b.b.aG.aA | | q.c.aG.aA.b.b.aG.aG | q.c.aG.aG.a.b.a.a |
| q.c.aG.aG.a.b.a.aA | q.c.aG.aG.a.b.a.aG | q.c.aG.aG.a.b.e.a | |
| q.c.aG.aG.a.b.e.aA | q.c.aG.aG.a.b.e.aG | q.c.aG.aG.a.b.m.a | |
| q.c.aG.aG.a.b.m.aA | q.c.aG.aG.a.b.m.aG | q.c.aG.aG.a.b.ao.a | |
| q.c.aG.aG.a.b.o.aA | q.c.aG.aG.a.b.o.aG | q.c.aG.aG.a.b.E.a | |
| q.c.aG.aG.a.b.E.aA | q.c.aG.aG.a.b.E.aG | q.c.aG.aG.a.b.R.a | |
| q.c.aG.aG.a.b.R.aA | q.c.aG.aG.a.b.R.aG | q.c.aG.aG.a.b.aw.a | |
| q.c.aG.aG.a.b.aw.aA | | q.c.aG.aG.a.b.aw.aG | |
| q.c.aG.aG.a.b.aA.a | q.c.aG.aG.a.b.aA.aA | | |
| q.c.aG.aG.a.b.aA.aG | | q.c.aG.aG.a.b.aG.a | |
| q.c.aG.aG.a.b.aG.aA | | q.c.aG.aG.a.b.aG.aG | q.c.aG.aG.b.a.a.a |
| q.c.aG.aG.b.a.a.aA | q.c.aG.aG.b.a.a.aG | q.c.aG.aG.b.a.e.a | q.c.aG.aG.b.a.e.aA |
| q.c.aG.aG.b.a.e.aG | q.c.aG.aG.b.a.m.a | q.c.aG.aG.b.a.m.aA | |
| q.c.aG.aG.b.a.m.aG | q.c.aG.aG.b.a.ao.a | q.c.aG.aG.b.a.o.aA | q.c.aG.aG.b.a.o.aG |
| q.c.aG.aG.b.a.E.a | q.c.aG.aG.b.a.E.aA | q.c.aG.aG.b.a.E.aG | q.c.aG.aG.b.a.R.a |
| q.c.aG.aG.b.a.R.aA | q.c.aG.aG.b.a.R.aG | q.c.aG.aG.b.a.aw.a | |
| q.c.aG.aG.b.a.aw.aA | | q.c.aG.aG.b.a.aw.aG | |
| q.c.aG.aG.b.a.aA.a | q.c.aG.aG.b.a.aA.aA | | |
| q.c.aG.aG.b.a.aA.aG | | q.c.aG.aG.b.a.aG.a | |
| q.c.aG.aG.b.a.aG.aA | | q.c.aG.aG.b.a.aG.aG | q.c.aG.aG.b.b.a.a |
| q.c.aG.aG.b.b.a.aA | q.c.aG.aG.b.b.a.aG | q.c.aG.aG.b.b.e.a | q.c.aG.aG.b.b.e.aA |
| q.c.aG.aG.b.b.e.aG | q.c.aG.aG.b.b.m.a | q.c.aG.aG.b.b.m.aA | |
| q.c.aG.aG.b.b.m.aG | q.c.aG.aG.b.b.ao.a | q.c.aG.aG.b.b.o.aA | q.c.aG.aG.b.b.o.aG |
| q.c.aG.aG.b.b.E.a | q.c.aG.aG.b.b.E.aA | q.c.aG.aG.b.b.E.aG | q.c.aG.aG.b.b.R.a |
| q.c.aG.aG.b.b.R.aA | q.c.aG.aG.b.b.R.aG | q.c.aG.aG.b.b.aw.a | |
| q.c.aG.aG.b.b.aw.aA | | q.c.aG.aG.b.b.aw.aG | |
| q.c.aG.aG.b.b.aA.a | q.c.aG.aG.b.b.aA.aA | | |
| q.c.aG.aG.b.b.aA.aG | | q.c.aG.aG.b.b.aG.a | |
| q.c.aG.aG.b.b.aG.aA | | q.c.aG.aG.b.b.aG.aG | |
| k.c.aN.o.a.b.a.a | k.c.aN.o.a.b.a.aA | k.c.aN.o.a.b.a.aG | k.c.aN.o.a.b.e.a |
| k.c.aN.o.a.b.e.aA | k.c.aN.o.a.b.e.aG | k.c.aN.o.a.b.m.a. | |
| k.c.aN.o.a.b.m.aA | k.c.aN.o.a.b.m.aG | k.c.aN.o.b.a.a.a | k.c.aN.o.b.a.a.aA |
| k.c.aN.o.b.a.a.aG | k.c.aN.o.b.a.e.a | k.c.aN.o.b.a.e.aA | k.c.aN.o.b.a.e.aG |
| k.c.aN.o.b.a.m.a | k.c.aN.o.b.a.m.aA | k.c.aN.o.b.a.m.aG | k.c.aN.o.b.b.a.a |
| k.c.aN.o.b.b.a.aA | k.c.aN.o.b.b.a.aG | k.c.aN.o.b.b.e.a | k.c.aN.o.b.b.e.aA |
| k.c.aN.o.b.b.e.aG | k.c.aN.o.b.b.m.a | k.c.aN.o.b.b.m.aA | |
| k.c.aN.o.b.b.m.aG | k.c.aN.q.a.b.a.a | k.c.aN.q.a.b.a.aA | k.c.aN.q.a.b.a.aG |
| k.c.aN.q.a.b.e.a | k.c.aN.q.a.b.e.aA | k.c.aN.q.a.b.e.aG | k.c.aN.q.a.b.m.a |
| k.c.aN.q.a.b.m.aA | k.c.aN.q.a.b.m.aG | k.c.aN.q.b.a.a.a | k.c.aN.q.b.a.a.aA |
| k.c.aN.q.b.a.a.aG | k.c.aN.q.b.a.e.a | k.c.aN.q.b.a.e.aA | k.c.aN.q.b.a.e.aG |
| k.c.aN.q.b.a.m.a | k.c.aN.q.b.a.m.aA | k.c.aN.q.b.a.m.aG | k.c.aN.q.b.b.a.a |
| k.c.aN.q.b.b.a.aA | k.c.aN.q.b.b.a.aG | k.c.aN.q.b.b.e.a | k.c.aN.q.b.b.e.aA |
| k.c.aN.q.b.b.e.aG | k.c.aN.q.b.b.m.a | k.c.aN.q.b.b.m.aA | |
| k.c.aN.q.b.b.m.aG | q.c.aN.o.a.b.a.a | q.c.aN.o.a.b.a.aA | q.c.aN.o.a.b.a.aG |
| q.c.aN.o.a.b.e.a | q.c.aN.o.a.b.e.aA | q.c.aN.o.a.b.e.aG | q.c.aN.o.a.b.m.a |
| q.c.aN.o.a.b.m.aA | q.c.aN.o.a.b.m.aG | q.c.aN.o.b.a.a.a | q.c.aN.o.b.a.a.aA |
| q.c.aN.o.b.a.a.aG | q.c.aN.o.b.a.e.a | q.c.aN.o.b.a.e.aA | q.c.aN.o.b.a.e.aG |
| q.c.aN.o.b.a.m.a | q.c.aN.o.b.a.m.aA | q.c.aN.o.b.a.m.aG | q.c.aN.o.b.b.a.a |
| q.c.aN.o.b.b.a.aA | q.c.aN.o.b.b.a.aG | q.c.aN.o.b.b.e.a | q.c.aN.o.b.b.e.aA |
| q.c.aN.o.b.b.e.aG | q.c.aN.o.b.b.m.a | q.c.aN.o.b.b.m.aA | |
| q.c.aN.o.b.b.m.aG | q.c.aN.q.a.b.a.a | q.c.aN.q.a.b.a.aA | q.c.aN.q.a.b.a.aG |
| q.c.aN.q.a.b.e.a | q.c.aN.q.a.b.e.aA | q.c.aN.q.a.b.e.aG | q.c.aN.q.a.b.m.a |
| q.c.aN.q.a.b.m.aA | q.c.aN.q.a.b.m.aG | q.c.aN.q.b.a.a.a | q.c.aN.q.b.a.a.aA |
| q.c.aN.q.b.a.a.aG | q.c.aN.q.b.a.e.a | q.c.aN.q.b.a.e.aA | q.c.aN.q.b.a.e.aG |
| q.c.aN.q.b.a.m.a | q.c.aN.q.b.a.m.aA | q.c.aN.q.b.a.m.aG | q.c.aN.q.b.a.a.a |
| q.c.aN.q.b.a.aA | q.c.aN.q.a.b.a.aG | q.c.aN.q.a.b.e.a | q.c.aN.q.a.b.e.aA |
| q.c.aN.q.a.b.e.aG | q.c.aN.q.a.b.m.a | q.c.aN.q.a.b.m.aA | q.c.aN.q.a.b.m.aG |
| k.c.a.a.a.b.o.aN | k.c.a.a.a.b.q.aN | k.c.a.a.b.a.o.aN | k.c.a.a.b.a.q.aN |
| k.c.a.a.b.b.o.aN | k.c.a.a.b.b.q.aN | k.c.a.e.a.b.o.aN | k.c.a.e.a.b.q.aN |
| k.c.a.e.b.a.o.aN | k.c.a.e.b.a.q.aN | k.c.a.e.b.b.o.aN | k.c.a.e.b.b.q.aN |
| k.c.a.m.a.b.o.aN | k.c.a.m.a.b.q.aN | k.c.a.m.b.a.o.aN | k.c.a.m.b.a.q.aN |
| k.c.a.m.b.b.o.aN | k.c.a.m.b.b.q.aN | k.c.aA.a.a.b.o.aN | |
| k.c.aA.a.a.b.q.aN | k.c.aA.a.b.a.o.aN | k.c.aA.a.b.a.q.aN | |
| k.c.aA.a.b.b.o.aN | k.c.aA.a.b.b.q.aN | k.c.aA.e.a.b.o.aN | |
| k.c.aA.e.a.b.q.aN | k.c.aA.e.a.b.o.aN | k.c.aA.m.a.b.q.aN | |
| k.c.aA.m.a.b.o.aN | k.c.aA.m.b.a.q.aN | k.c.aA.m.b.a.o.aN | |
| k.c.aA.m.b.b.q.aN | k.c.aA.m.b.a.o.aN | k.c.aA.m.b.a.q.aN | |
| k.c.aA.m.b.b.o.aN | k.c.aA.m.b.b.q.aN | k.c.aG.a.a.b.o.aN | |
| k.c.aG.a.a.b.q.aN | k.c.aG.a.b.a.o.aN | k.c.aG.a.b.a.q.aN | |
| k.c.aG.a.b.b.o.aN | k.c.aG.a.b.b.q.aN | k.c.aG.e.a.b.o.aN | |
| k.c.aG.e.a.b.q.aN | k.c.aG.e.b.a.o.aN | k.c.aG.e.b.a.q.aN | |
| k.c.aG.e.b.b.o.aN | k.c.aG.e.b.b.q.aN | k.c.aG.m.a.b.o.aN | |
| k.c.aG.m.a.b.q.aN | k.c.aG.m.b.a.o.aN | k.c.aG.m.b.a.q.aN | |
| k.c.aG.m.b.b.o.aN | k.c.aG.m.b.b.q.aN | q.c.a.a.a.b.o.aN | q.c.a.a.a.b.q.aN |
| q.c.a.a.b.a.o.aN | q.c.a.a.b.a.q.aN | q.c.a.a.b.b.o.aN | q.c.a.a.b.b.q.aN |
| q.c.a.e.a.b.o.aN | q.c.a.e.a.b.q.aN | q.c.a.e.b.a.o.aN | q.c.a.e.b.a.q.aN |
| q.c.a.e.b.b.o.aN | q.c.a.e.b.b.q.aN | q.c.a.m.a.b.o.aN | q.c.a.m.a.b.q.aN |

TABLE 14-continued

Exemplary Compounds of the Invention

| | | | |
|---|---|---|---|
| q.c.a.m.b.a.o.aN | q.c.a.m.b.a.q.aN | q.c.a.m.b.b.o.aN | q.c.a.m.b.b.q.aN |
| q.c.aA.a.a.b.o.aN | q.c.aA.a.a.b.q.aN | q.c.aA.a.b.a.o.aN | |
| q.c.aA.a.b.a.q.aN | q.c.aA.a.b.b.o.aN | q.c.aA.a.bb.q.aN | |
| q.c.aA.e.a.b.o.aN | q.c.aA.e.a.b.q.aN | q.c.aA.e.b.a.o.aN | |
| q.c.aA.e.b.a.q.aN | q.c.aA.e.b.b.o.aN | q.c.aA.eb.b.q.aN | |
| q.c.aA.m.a.b.o.aN | q.c.aA.m.a.b.q.aN | q.c.aA.m.b.a.o.aN | |
| q.c.aA.m.b.a.q.aN | q.c.aA.m.b.b.o.aN | q.c.aA.m.b.b.q.aN | |
| q.c.aG.a.a.b.o.aN | q.c.aG.a.a.b.q.aN | q.c.aG.a.b.a.o.aN | |
| q.c.aG.a.b.a.q.aN | q.c.aG.a.b.b.o.aN | q.c.aG.a.b.b.q.aN | |
| q.c.aG.e.a.b.o.aN | q.c.aG.e.ab.q.aN | q.c.aG.e.b.a.o.aN | |
| q.c.aG.e.b.a.q.aN | q.c.aG.e.b.b.o.aN | q.c.aG.e.b.b.q.aN | |
| q.c.aG.m.a.b.o.aN | q.c.aG.m.a.b.q.aN | q.c.aG.m.b.a.o.aN | |
| q.c.aG.m.b.a.q.aN | q.c.aG.m.b.b.o.aN | q.c.aG.m.b.b.q.aN | k.c.a.aT.b.b.aT.a |
| k.c.a.aT.b.b.a.a | k.c.a.aU.b.b.aU.a | k.c.a.aU.b.b.a.a | k.c.a.bB.b.b.bB.a |
| k.c.a.bB.b.b.a.a | k.c.a.bF.b.b.bF.a | k.c.a.bF.b.b.a.a | k.c.a.bG.b.b.bG.a |
| k.c.a.bG.b.b.a.a | k.c.a.cE.b.b.cE.a | k.c.a.cE.b.b.a.a | k.c.a.cG.b.b.cG.a |
| k.c.a.cG.b.b.a.a | k.c.a.cH.b.b.cH.a | k.c.a.cH.b.b.a.a | k.c.a.cJ.b.b.cJ.a |
| k.c.a.cJ.b.b.a.a | k.c.a.cL.b.b.cL.a | k.c.a.cL.b.b.a.a | k.c.a.cN.b.b.cN.a |
| k.c.a.cN.b.b.a.a | k.c.a.cS.b.b.cS.a | k.c.a.cS.b.b.a.a | k.c.a.cU.b.b.cU.a |
| k.c.a.cU.b.b.a.a | k.c.a.cY.b.b.cY.a | k.c.a.cY.b.b.a.a | k.c.a.dB.b.b.dB.a |
| k.c.a.dB.b.b.a.a | k.c.a.dD.b.b.dD.a | k.c.a.dD.b.b.a.a | k.c.a.fF.b.b.fF.a |
| k.c.a.fF.b.b.a.a | k.c.a.fK.b.b.fK.a | k.c.a.fK.b.b.a.a | k.c.a.fP.b.b.fP.a |
| k.c.a.fP.b.b.a.a | k.c.a.fR.b.b.fR.a | k.c.a.fR.b.b.a.a | k.c.a.jA.b.b.jA.a |
| k.c.a.jA.b.b.a.a | k.c.a.kB.b.b.kB.a | k.c.a.kB.b.b.a.a | k.c.a.kC.b.b.kC.a |
| k.c.a.kC.b.b.a.a | k.c.a.kL.b.b.kL.a | k.c.a.kL.b.b.a.a | k.c.a.kM.bb.kM.a |
| k.c.a.kM.b.b.a.a | k.c.a.kN.b.b.kN.a | k.c.a.kN.b.b.a.a | k.c.a.kO.b.b.kO.a |
| k.c.a.kO.b.b.a.a | k.c.a.kP.b.b.kP.a | k.c.a.kP.b.b.a.a | k.c.a.kQ.b.b.kQ.a |
| k.c.a.kQ.b.b.a.a | q.c.a.aT.b.b.aT.a | q.c.a.aT.b.b.a.a | q.c.a.aU.b.b.aU.a |
| q.c.a.aU.b.b.a.a | q.c.aabB.b.b.bB.a | q.c.a.bB.b.b.a.a | q.c.a.bF.b.b.bF.a |
| q.c.a.bF.b.b.a.a | q.c.a.bG.b.b.bG.a | q.c.a.bG.b.b.a.a | q.c.a.cE.b.b.cE.a |
| q.c.a.cE.b.b.a.a | q.c.a.cG.b.b.cG.a | q.c.a.cG.b.b.a.a | q.c.a.cH.b.b.cH.a |
| q.c.a.cH.b.b.a.a | q.c.a.cJ.b.b.cJ.a | q.c.a.cJ.b.b.b.a | q.c.a.cL.b.b.cL.a |
| q.c.a.cL.b.b.a.a | q.c.a.cN.b.b.cN.a | q.c.a.cN.b.b.a.a | q.c.a.cS.b.b.cS.a |
| q.c.a.cS.b.b.a.a | q.c.a.cU.b.b.cU.a | q.c.a.cU.b.b.a.a | q.c.a.cY.b.b.cY.a |
| q.c.a.cY.b.b.a.a | q.c.a.dB.b.b.dB.a | q.c.a.dB.b.b.a.a | q.c.a.dD.b.b.dD.a |
| q.c.a.dD.b.b.a.a | q.c.a.fF.b.b.fF.a | q.c.a.fF.b.b.a.a | q.c.a.fK.b.b.fK.a |
| q.c.a.fK.b.b.a.a | q.c.a.fP.b.b.fP.a | q.c.a.fP.b.b.a.a | q.c.a.fR.b.b.fR.a |
| q.c.a.fR.b.b.a.a | q.c.a.jA.b.b.jA.a | q.c.a.jA.b.b.a.a | q.c.a.kB.b.b.kB.a |
| q.c.a.kB.b.b.a.a | q.c.a.kC.b.b.kC.a | q.c.a.kC.b.b.a.a | q.c.a.kL.b.b.kL.a |
| q.c.a.kL.b.b.a.a | q.c.a.kM.b.b.kM.a | q.c.a.kM.b.b.a.a | q.c.a.kN.b.b.kN.a |
| q.c.a.kN.b.b.a.a | q.c.a.kO.b.b.kO.a | q.c.a.kO.b.b.a.a | q.c.a.kP.b.b.kP.a |
| q.c.a.kP.b.b.a.a | q.c.a.kQ.b.b.kQ.a | q.c.a.kQ.b.b.a.a | k.c.a.aT.b.b.e.a |
| k.c.a.aU.b.b.e.a | k.c.a.bB.b.b.e.a | k.c.a.bF.b.b.e.a | k.c.a.bG.b.b.e.a |
| k.c.a.cE.b.b.e.a | k.c.a.cG.b.b.e.a | k.c.a.cH.b.b.e.a | k.c.a.cJ.b.b.b.a |
| k.c.a.cL.b.b.e.a | k.c.a.cN.b.b.e.a | k.c.a.cS.b.b.e.a | k.c.a.cU.b.b.e.a |
| k.c.a.cY.b.b.e.a | k.c.a.dB.b.b.e.a | k.c.a.dD.b.b.e.a | k.c.a.fF.b.b.e.a |
| k.c.a.fK.b.b.e.a | k.c.a.fP.b.b.e.a | k.c.a.fR.b.b.e.a | k.c.a.jA.b.b.e.a |
| k.c.a.kB.b.b.e.a | k.c.a.kC.b.b.e.a | k.c.a.kL.b.b.e.a | k.c.a.kM.b.b.e.a |
| k.c.a.kN.b.b.e.a | k.c.a.kO.b.b.e.a | k.c.a.kP.b.b.e.a | k.c.a.kQ.b.b.e.a |
| q.c.a.aT.b.b.e.a | q.c.a.aU.b.b.e.a | q.c.a.bB.b.b.e.a | q.c.a.bF.b.b.e.a |
| q.c.a.bG.b.b.e.a | q.c.a.cE.b.b.e.a | q.c.a.cG.b.b.e.a | q.c.a.cH.b.b.e.a |
| q.c.a.cJ.b.b.b.a | q.c.a.cL.b.b.e.a | q.c.a.cN.b.b.e.a | q.c.a.cS.b.b.e.a |
| q.c.a.cU.b.b.e.a | q.c.a.cY.b.b.e.a | q.c.a.dB.b.b.e.a | q.c.a.dD.b.b.e.a |
| q.c.a.fF.b.b.e.a | q.c.a.fK.b.b.e.a | q.c.a.fP.b.b.e.a | q.c.a.fR.b.b.e.a |
| q.c.a.jA.b.b.e.a | q.c.a.kB.b.b.e.a | q.c.a.kC.b.b.e.a | q.c.a.kL.b.b.e.a |
| q.c.a.kM.b.b.e.a | q.c.a.kN.b.b.e.a | q.c.a.kO.b.b.e.a | q.c.a.kP.b.b.e.a |
| q.c.a.kQ.b.b.e.a | k.c.a.aT.b.b.m.a | k.c.a.aU.b.b.m.a | k.c.a.bB.b.b.m.a |
| k.c.a.bF.b.b.m.a | k.c.a.bG.b.b.m.a | k.c.a.cE.b.b.m.a | k.c.a.cG.b.b.m.a |
| k.c.a.cH.b.b.m.a | k.c.a.cJ.b.b.b.a | k.c.a.cL.b.b.m.a | k.c.a.cN.b.b.m.a |
| k.c.a.cS.b.b.m.a | k.c.a.cU.b.b.m.a | k.c.a.cY.b.b.m.a | k.c.a.dB.b.b.m.a |
| k.c.a.dD.b.b.m.a | k.c.a.fF.b.b.m.a | k.c.a.fK.b.b.m.a | k.c.a.fP.b.b.m.a |
| k.c.a.fR.b.b.m.a | k.c.a.jA.b.b.m.a | k.c.a.kB.b.b.m.a | k.c.a.kC.b.b.m.a |
| k.c.a.kL.b.b.m.a | k.c.a.kM.b.b.m.a | k.c.a.kN.b.b.m.a | k.c.a.kO.b.b.m.a |
| k.c.a.kP.b.b.m.a | k.c.a.kQ.b.b.m.a | q.c.a.aT.b.b.m.a | q.c.a.aU.b.b.m.a |
| q.c.a.bB.b.b.m.a | q.c.a.bF.b.b.m.a | q.c.a.bG.b.b.m.a | q.c.a.cE.b.b.m.a |
| q.c.a.cG.b.b.m.a | q.c.a.cH.b.b.m.a | q.c.a.cJ.b.b.b.a | q.c.a.cL.b.b.m.a |
| q.c.a.cN.b.b.m.a | q.c.a.cS.b.b.m.a | q.c.a.cU.b.b.m.a | q.c.a.cY.b.b.m.a |
| q.c.a.dB.b.b.m.a | q.c.a.dD.b.b.m.a | q.c.a.fF.b.b.m.a | q.c.a.fK.b.b.m.a |
| q.c.a.fP.b.b.m.a | q.c.a.fR.b.b.m.a | q.c.a.jA.b.b.m.a | q.c.a.kB.b.b.m.a |
| q.c.a.kC.b.b.m.a | q.c.a.kL.b.b.m.a | q.c.a.kM.b.b.m.a | q.c.a.kN.b.b.m.a |
| q.c.a.kO.b.b.m.a | q.c.a.kP.b.b.m.a | q.c.a.kQ.b.b.m.a | k.c.a.aT.b.b.ah.a |
| k.c.a.aU.b.b.ah.a | k.c.a.bB.b.b.ah.a | k.c.a.bF.b.b.ah.a | k.c.a.bG.b.b.ah.a |
| k.c.a.cE.b.b.ah.a | k.c.a.cG.b.b.ah.a | k.c.a.cH.b.b.ah.a | k.c.a.cJ.b.b.b.a |
| k.c.a.cL.b.b.ah.a | k.c.a.cN.b.b.ah.a | k.c.a.cS.b.b.ah.a | k.c.a.cU.b.b.ah.a |
| k.c.a.cY.b.b.ah.a | k.c.a.dB.b.b.ah.a | k.c.a.dD.b.b.ah.a | k.c.a.fF.b.b.ah.a |
| k.c.a.fK.b.b.ah.a | k.c.a.fP.b.b.ah.a | k.c.a.fR.b.b.ah.a | k.c.a.jA.b.b.ah.a |
| k.c.a.kB.b.b.ah.a | k.c.a.kC.b.b.ah.a | k.c.a.kL.b.b.ah.a | k.c.a.kM.b.b.ah.a |

TABLE 14-continued

Exemplary Compounds of the Invention

| | | | |
|---|---|---|---|
| k.c.a.kN.b.b.ah.a | k.c.a.kO.b.b.ah.a | k.c.a.kP.b.b.ah.a | k.c.a.kQ.b.b.ah.a |
| q.c.a.aT.b.b.ah.a | q.c.a.aU.b.b.ah.a | q.c.a.bB.b.b.ah.a | q.c.a.bF.b.b.ah.a |
| q.c.a.bG.b.b.ah.a | q.c.a.cE.b.b.ah.a | q.c.a.cG.b.b.ah.a | q.c.a.cH.b.b.ah.a |
| q.c.a.cJ.b.b.b.a | q.c.a.cL.b.b.ah.a | q.c.a.cN.b.b.ah.a | q.c.a.cS.b.b.ah.a |
| q.c.a.cU.b.b.ah.a | q.c.a.cY.b.b.ah.a | q.c.a.dB.b.b.ah.a | q.c.a.dD.b.b.ah.a |
| q.c.a.fF.b.b.ah.a | q.c.a.fK.b.b.ah.a | q.c.a.fP.b.b.ah.a | q.c.a.fR.b.b.ah.a |
| q.c.a.jA.b.b.ah.a | q.c.a.kB.b.b.ah.a | q.c.a.kC.b.b.ah.a | q.c.a.kL.b.b.ah.a |
| q.c.a.kM.b.b.ah.a | q.c.a.kN.b.b.ah.a | q.c.a.kO.b.b.ah.a | q.c.a.kP.b.b.ah.a |
| q.c.a.kQ.b.b.ah.a | k.c.a.aT.b.b.ak.a | k.c.a.aU.b.b.ak.a | k.c.a.bB.b.b.ak.a |
| k.c.a.bF.b.b.ak.a | k.c.a.bG.b.b.ak.a | k.c.a.cE.b.b.ak.a | k.c.a.cG.b.b.ak.a |
| k.c.a.cH.b.b.ak.a | k.c.a.cJ.b.b.b.a | k.c.a.cL.b.b.ak.a | k.c.a.cN.b.b.ak.a |
| k.c.a.cS.b.b.ak.a | k.c.a.cU.b.b.ak.a | k.c.a.cY.b.b.ak.a | k.c.a.dB.b.b.ak.a |
| k.c.a.dD.b.b.ak.a | k.c.a.fF.b.b.ak.a | k.c.a.fK.b.b.ak.a | k.c.a.fP.b.b.ak.a |
| k.c.a.fR.b.b.ak.a | k.c.a.jA.b.b.ak.a | k.c.a.kB.b.b.ak.a | k.c.a.kC.b.b.ak.a |
| k.c.a.kL.b.b.ak.a | k.c.a.kM.b.b.ak.a | k.c.a.kN.b.b.ak.a | k.c.a.kO.b.b.ak.a |
| k.c.a.kP.b.b.ak.a | k.c.a.kQ.b.b.ak.a | q.c.a.aT.b.b.ak.a | q.c.a.aU.b.b.ak.a |
| q.c.a.bB.b.b.ak.a | q.c.a.bF.b.b.ak.a | q.c.a.bG.b.b.ak.a | q.c.a.cE.b.b.ak.a |
| q.c.a.cG.b.b.ak.a | q.c.a.cH.b.b.ak.a | q.c.a.cJ.b.b.b.a | q.c.a.cL.b.b.ak.a |
| q.c.a.cN.b.b.ak.a | q.c.a.cS.b.b.ak.a | q.c.a.cU.b.b.ak.a | q.c.a.cY.b.b.ak.a |
| q.c.a.dB.b.b.ak.a | q.c.a.dD.b.b.ak.a | q.c.a.fF.b.b.ak.a | q.c.a.fK.b.b.ak.a |
| q.c.a.fP.b.b.ak.a | q.c.a.fR.b.b.ak.a | q.c.a.jA.b.b.ak.a | q.c.a.kB.b.b.ak.a |
| q.c.a.kC.b.b.ak.a | q.c.a.kL.b.b.ak.a | q.c.a.kM.b.b.ak.a | q.c.a.kN.b.b.ak.a |
| q.c.a.kO.b.b.ak.a | q.c.a.kP.b.b.ak.a | q.c.a.kQ.b.b.ak.a | k.c.a.aT.b.b.ao.a |
| k.c.a.aU.b.b.ao.a | k.c.a.bB.b.b.ao.a | k.c.a.bF.b.b.ao.a | k.c.a.bG.b.b.ao.a |
| k.c.a.cE.b.b.ao.a | k.c.a.cG.b.b.ao.a | k.c.a.cH.b.b.ao.a | k.c.a.cJ.b.b.b.a |
| k.c.a.cL.b.b.ao.a | k.c.a.cN.b.b.ao.a | k.c.a.cS.b.b.ao.a | k.c.a.cU.b.b.ao.a |
| k.c.a.cY.b.b.ao.a | k.c.a.dB.b.b.ao.a | k.c.a.dD.b.b.ao.a | k.c.a.fF.b.b.ao.a |
| k.c.a.fK.b.b.ao.a | k.c.a.fP.b.b.ao.a | k.c.a.fR.b.b.ao.a | k.c.a.jA.b.b.ao.a |
| k.c.a.kB.b.b.ao.a | k.c.a.kC.b.b.ao.a | k.c.a.kL.b.b.ao.a | k.c.a.kM.b.b.ao.a |
| k.c.a.kN.b.b.ao.a | k.c.a.kO.b.b.ao.a | k.c.a.kP.b.b.ao.a | k.c.a.kQ.b.b.ao.a |
| q.c.a.aT.b.b.ao.a | q.c.a.aU.b.b.ao.a | q.c.a.bB.b.b.ao.a | q.c.a.bF.b.b.ao.a |
| q.c.a.bG.b.b.ao.a | q.c.a.cE.b.b.ao.a | q.c.a.cG.b.b.ao.a | q.c.a.cH.b.b.ao.a |
| q.c.a.cJ.b.b.b.a | q.c.a.cL.b.b.ao.a | q.c.a.cN.b.b.ao.a | q.c.a.cS.b.b.ao.a |
| q.c.a.cU.b.b.ao.a | q.c.a.cY.b.b.ao.a | q.c.a.dB.b.b.ao.a | q.c.a.dD.b.b.ao.a |
| q.c.a.fF.b.b.ao.a | q.c.a.fK.b.b.ao.a | q.c.a.fP.b.b.ao.a | q.c.a.fR.b.b.ao.a |
| q.c.a.jA.b.b.ao.a | q.c.a.kB.b.b.ao.a | q.c.a.kC.b.b.ao.a | q.c.a.kL.b.b.ao.a |
| q.c.a.kM.b.b.ao.a | q.c.a.kN.b.b.ao.a | q.c.a.kO.b.b.ao.a | q.c.a.kP.b.b.ao.a |
| q.c.a.kQ.b.b.ao.a | k.c.a.aT.b.b.aw.a | k.c.a.aU.b.b.aw.a | k.c.a.bB.b.b.aw.a |
| k.c.a.bF.b.b.aw.a | k.c.a.bG.b.b.aw.a | k.c.a.cE.b.b.aw.a | k.c.a.cG.b.b.aw.a |
| k.c.a.cH.b.b.aw.a | k.c.a.cJ.b.b.b.a | k.c.a.cL.b.b.aw.a | k.c.a.cN.b.b.aw.a |
| k.c.a.cS.b.b.aw.a | k.c.a.cU.b.b.aw.a | k.c.a.cY.b.b.aw.a | k.c.a.dB.b.b.aw.a |
| k.c.a.dD.b.b.aw.a | k.c.a.fF.b.b.aw.a | k.c.a.fK.b.b.aw.a | k.c.a.fP.b.b.aw.a |
| k.c.a.fR.b.b.aw.a | k.c.a.jA.b.b.aw.a | k.c.a.kB.b.b.aw.a | |
| k.c.a.kC.b.b.aw.a | k.c.a.kL.b.b.aw.a | k.c.a.kM.b.b.aw.a | |
| k.c.a.kN.b.b.aw.a | k.c.a.kO.b.b.aw.a | k.c.a.kP.b.b.aw.a | |
| k.c.a.kQ.b.b.aw.a | q.c.a.aT.b.b.aw.a | q.c.a.aU.b.b.aw.a | q.c.a.bB.b.b.aw.a |
| q.c.a.bF.b.b.aw.a | q.c.a.bG.b.b.aw.a | q.c.a.cE.b.b.aw.a | q.c.a.cG.b.b.aw.a |
| q.c.a.cH.b.b.aw.a | q.c.a.cJ.b.b.b.a | q.c.a.cL.b.b.aw.a | q.c.a.cN.b.b.aw.a |
| q.c.a.cS.b.b.aw.a | q.c.a.cU.b.b.aw.a | q.c.a.cY.b.b.aw.a | q.c.a.dB.b.b.aw.a |
| q.c.a.dD.b.b.aw.a | q.c.a.fF.b.b.aw.a | q.c.a.fK.b.b.aw.a | q.c.a.fP.b.b.aw.a |
| q.c.a.fR.b.b.aw.a | q.c.a.jA.b.b.aw.a | q.c.a.kB.b.b.aw.a | q.c.a.kC.b.b.aw.a |
| q.c.a.kL.b.b.aw.a | q.c.a.kM.b.b.aw.a | q.c.a.kN.b.b.aw.a | |
| q.c.a.kO.b.b.aw.a | q.c.a.kP.b.b.aw.a | q.c.a.kQ.b.b.aw.a | k.c.a.aU.b.b.aT.a |
| k.c.a.bB.b.b.aT.a | k.c.a.bF.b.b.aT.a | k.c.a.bG.b.b.aT.a | k.c.a.cE.b.b.aT.a |
| k.c.a.cG.b.b.aT.a | k.c.a.cH.b.b.aT.a | k.c.a.cJ.b.b.b.a | k.c.a.cL.b.b.aT.a |
| k.c.a.cN.b.b.aT.a | k.c.a.cS.b.b.aT.a | k.c.a.cU.b.b.aT.a | k.c.a.cY.b.b.aT.a |
| k.c.a.dB.b.b.aT.a | k.c.a.dD.b.b.aT.a | k.c.a.fF.b.b.aT.a | k.c.a.fK.b.b.aT.a |
| k.c.a.fP.b.b.aT.a | k.c.a.fR.b.b.aT.a | k.c.a.jA.b.b.aT.a | k.c.a.kB.b.b.aT.a |
| k.c.a.kC.b.b.aT.a | k.c.a.kL.b.b.aT.a | k.c.a.kM.b.b.aT.a | k.c.a.kN.b.b.aT.a |
| k.c.a.kO.b.b.aT.a | k.c.a.kP.b.b.aT.a | k.c.a.kQ.b.b.aT.a | q.c.a.aU.b.b.aT.a |
| q.c.a.bB.b.b.aT.a | q.c.a.bF.b.b.aT.a | q.c.a.bG.b.b.aT.a | q.c.a.cE.b.b.aT.a |
| q.c.a.cG.b.b.aT.a | q.c.a.cH.b.b.aT.a | q.c.a.cJ.b.b.b.a | q.c.a.cL.b.b.aT.a |
| q.c.a.cN.b.b.aT.a | q.c.a.cS.b.b.aT.a | q.c.a.cU.b.b.aT.a | q.c.a.cY.b.b.aT.a |
| q.c.a.dB.b.b.aT.a | q.c.a.dD.b.b.aT.a | q.c.a.fF.b.b.aT.a | q.c.a.fK.b.b.aT.a |
| q.c.a.fP.b.b.aT.a | q.c.a.fR.b.b.aT.a | q.c.a.jA.b.b.aT.a | q.c.a.kB.b.b.aT.a |
| q.c.a.kC.b.b.aT.a | q.c.a.kL.b.b.aT.a | q.c.a.kM.b.b.aT.a | q.c.a.kN.b.b.aT.a |
| q.c.a.kO.b.b.aT.a | q.c.a.kP.b.b.aT.a | q.c.a.kQ.b.b.aT.a | k.c.a.aT.b.b.aU.a |
| k.c.a.bB.b.b.aU.a | k.c.a.bF.b.b.aU.a | k.c.a.bG.b.b.aU.a | k.c.a.cE.b.b.aU.a |
| k.c.a.cG.b.b.aU.a | k.c.a.cH.b.b.aU.a | k.c.a.cJ.b.b.b.a | k.c.a.cL.b.b.aU.a |
| k.c.a.cN.b.b.aU.a | k.c.a.cS.b.b.aU.a | k.c.a.cU.b.b.aU.a | k.c.a.cY.b.b.aU.a |
| k.c.a.dB.b.b.aU.a | k.c.a.dD.b.b.aU.a | k.c.a.fF.b.b.aU.a | k.c.a.fK.b.b.aU.a |
| k.c.a.fP.b.b.aU.a | k.c.a.fR.b.b.aU.a | k.c.a.jA.b.b.aU.a | k.c.a.kB.b.b.aU.a |
| k.c.a.kC.b.b.aU.a | k.c.a.kL.b.b.aU.a | k.c.a.kM.b.b.aU.a | |
| k.c.a.kN.b.b.aU.a | k.c.a.kO.b.b.aU.a | k.c.a.kP.b.b.aU.a | |
| k.c.a.kQ.b.b.aU.a | q.c.a.aT.b.b.aU.a | q.c.a.bB.b.b.aU.a | q.c.a.bF.b.b.aU.a |
| q.c.a.bG.b.b.aU.a | q.c.a.cE.b.b.aU.a | q.c.a.cG.b.b.aU.a | q.c.a.cH.b.b.aU.a |
| q.c.a.cJ.b.b.b.a | q.c.a.cL.b.b.aU.a | q.c.a.cN.b.b.aU.a | q.c.a.cS.b.b.aU.a |

TABLE 14-continued

Exemplary Compounds of the Invention

| | | | |
|---|---|---|---|
| q.c.a.cU.b.b.aU.a | q.c.a.cY.b.b.aU.a | q.c.a.dB.b.b.aU.a | q.c.a.dD.b.b.aU.a |
| q.c.a.fF.b.b.aU.a | q.c.a.fK.b.b.aU.a | q.c.a.fP.b.b.aU.a | q.c.a.fR.b.b.aU.a |
| q.c.a.jA.b.b.aU.a | q.c.a.kB.b.b.aU.a | q.c.a.kC.b.b.aU.a | q.c.a.kL.b.b.aU.a |
| q.c.a.kM.b.b.aU.a | q.c.a.kN.b.b.aU.a | q.c.a.kO.b.b.aU.a | q.c.a.kP.b.b.aU.a |
| q.c.a.kQ.b.b.aU.a | K.c.a.a.b.b.a.a | K.c.a.a.b.b.a.aA | K.c.a.a.b.b.m.a |
| K.c.a.a.b.b.m.aA | K.c.a.ab.b.b.ak.a | K.c.a.ab.b.b.ak.aA | K.c.a.a.b.b.cP.a |
| K.c.a.a.b.b.cP.aA | K.c.a.a.b.b.cS.a | K.c.a.a.b.b.cS.aA | K.c.a.a.b.b.cT.a |
| K.c.a.a.b.b.cT.aA | K.c.a.a.b.b.kr.a | K.c.a.a.b.b.kr.aA | K.c.a.m.b.b.a.a |
| K.c.a.m.b.b.a.aA | K.c.a.m.b.b.m.a | K.c.a.m.b.b.m.aA | K.c.a.m.b.b.ak.a |
| K.c.a.m.b.b.ak.aA | K.c.a.m.b.b.cP.a | K.c.a.m.b.b.cP.aA | K.c.a.m.b.b.cS.a |
| K.c.a.m.b.b.cS.aA | K.c.a.m.b.b.cT.a | K.c.a.m.b.b.cT.aA | K.c.a.m.b.b.kr.a |
| K.c.a.m.b.b.kr.aA | K.c.a.ak.b.b.a.a | K.c.a.ak.b.b.a.aA | K.c.a.ak.b.b.m.a |
| K.c.a.ak.b.b.m.aA | K.c.a.ak.b.b.ak.a | K.c.a.ak.b.b.ak.aA | K.c.a.ak.b.b.cP.a |
| K.c.a.ak.b.b.cP.aA | K.c.a.ak.b.b.cS.a | K.c.a.ak.b.b.cS.aA | K.c.a.ak.b.b.cT.a |
| K.c.a.ak.b.b.cT.aA | K.c.a.ak.b.b.kr.a | K.c.a.ak.b.b.kr.aA | K.c.a.cP.b.b.a.a |
| K.c.a.cP.b.b.a.aA | K.c.a.cP.b.b.m.a | K.c.a.cP.b.b.m.aA | K.c.a.cP.b.b.ak.a |
| K.c.a.cP.b.b.ak.aA | K.c.a.cP.b.b.cP.a | K.c.a.cP.b.b.cP.aA | K.c.a.cP.b.b.cS.a |
| K.c.a.cP.b.b.cS.aA | K.c.a.cP.b.b.cT.a | K.c.a.cP.b.b.cT.aA | K.c.a.cP.b.b.kr.a |
| K.c.a.cP.b.b.kr.aA | K.c.a.cS.b.b.a.a | K.c.a.cS.b.b.a.aA | K.c.a.cS.b.b.m.a |
| K.c.a.cS.b.b.m.aA | K.c.a.cS.b.b.ak.a | K.c.a.cS.b.b.ak.aA | K.c.a.cS.b.b.cP.a |
| K.c.a.cS.b.b.cP.aA | K.c.a.cS.b.b.cS.a | K.c.a.cS.b.b.cS.aA | K.c.a.cS.b.b.cT.a |
| K.c.a.cS.b.b.cT.aA | K.c.a.cS.b.b.kr.a | K.c.a.cS.b.b.kr.aA | K.c.a.cT.b.b.a.a |
| K.c.a.cT.b.b.a.aA | K.c.a.cT.b.b.m.a | K.c.a.cT.b.b.m.aA | K.c.a.cT.b.b.ak.a |
| K.c.a.cT.b.b.ak.aA | K.c.a.cT.b.b.cP.a | K.c.a.cT.b.b.cP.aA | K.c.a.cT.b.b.cS.a |
| K.c.a.cT.b.b.cS.aA | K.c.a.cT.b.b.cT.a | K.c.a.cT.b.b.cT.aA | K.c.a.cT.b.b.kr.a |
| K.c.a.cT.b.b.kr.aA | K.c.a.kr.b.b.a.a | K.c.a.kr.b.b.a.aA | K.c.a.kr.b.b.m.a |
| K.c.a.kr.b.b.m.aA | K.c.a.kr.b.b.ak.a | K.c.a.kr.b.b.ak.aA | K.c.a.kr.b.b.cP.a |
| K.c.a.kr.b.b.cP.aA | K.c.a.kr.b.b.cS.a | K.c.a.kr.b.b.cS.aA | K.c.a.kr.b.b.cT.a |
| K.c.a.kr.b.b.cT.aA | K.c.a.kr.b.b.kr.a | K.c.a.kr.b.b.kr.aA | K.c.aA.a.b.b.a.a |
| K.c.aA.a.b.b.a.aA | K.c.aA.a.b.b.m.a | K.c.aA.a.b.b.m.aA | |
| K.c.aA.a.b.b.ak.a | K.c.aA.a.b.b.ak.aA | K.c.aA.a.b.b.cP.a | |
| K.c.aA.a.b.b.cP.aA | K.c.aA.a.b.b.cS.a | K.c.aA.a.b.b.cS.aA | |
| K.c.aA.a.b.b.cT.a | K.c.aA.a.b.b.cT.aA | K.c.aA.a.b.b.kr.a | |
| K.c.aA.a.b.b.kr.aA | K.c.aA.m.b.b.a.a | K.c.aA.m.b.b.a.aA | |
| K.c.aA.m.b.b.m.a | K.c.aA.m.b.b.m.aA | K.c.aA.m.b.b.ak.a | |
| K.c.aA.m.b.b.ak.aA | K.c.aA.m.b.b.cP.a | K.c.aA.m.b.b.cP.aA | |
| K.c.aA.m.b.b.cS.a | K.c.aA.m.b.b.cS.aA | K.c.aA.m.b.b.cT.a | |
| K.c.aA.m.b.b.cT.aA | K.c.aA.m.b.b.kr.a | K.c.aA.m.b.b.kr.aA | |
| K.c.aA.ak.b.b.a.a | K.c.aA.ak.b.b.a.aA | K.c.aA.ak.b.b.m.a | |
| K.c.aA.ak.b.b.m.aA | K.c.aA.ak.b.b.ak.a | K.c.aA.ak.b.b.ak.aA | |
| K.c.aA.ak.b.b.cP.a | K.c.aA.ak.b.b.cP.aA | K.c.aA.ak.b.b.cS.a | |
| K.c.aA.ak.b.b.cS.aA | K.c.aA.ak.b.b.cT.a | K.c.aA.ak.b.b.cT.aA | |
| K.c.aA.ak.b.b.kr.a | K.c.aA.ak.b.b.kr.aA | K.c.aA.cP.b.b.a.a | |
| K.c.aA.cP.b.b.a.aA | K.c.aA.cP.b.b.m.a | K.c.aA.cP.b.b.m.aA | |
| K.c.aA.cP.b.b.ak.a | K.c.aA.cP.b.b.ak.aA | K.c.aA.cP.b.b.cP.a | |
| K.c.aA.cP.b.b.cP.aA | K.c.aA.cP.b.b.cS.a | K.c.aA.cP.b.b.cS.aA | |
| K.c.aA.cP.b.b.cT.aA | K.c.aA.cP.b.b.cT.aA | K.c.aA.cP.b.b.kr.a | |
| K.c.aA.cP.b.b.kr.aA | K.c.aA.cS.b.b.a.a | K.c.aA.cS.b.b.a.aA | |
| K.c.aA.cS.b.b.m.a | K.c.aA.cS.b.b.m.aA | K.c.aA.cS.b.b.ak.a | |
| K.c.aA.cS.b.b.ak.aA | K.c.aA.cS.b.b.cP.a | K.c.aA.cS.b.b.cP.aA | |
| K.c.aA.cS.b.b.cS.a | K.c.aA.cS.b.b.cS.aA | K.c.aA.cS.b.b.cT.a | |
| K.c.aA.cS.b.b.cT.aA | K.c.aA.cS.b.b.kr.a | K.c.aA.cS.b.b.kr.aA | |
| K.c.aA.cT.b.b.a.a | K.c.aA.cT.b.b.a.aA | K.c.aA.cT.b.b.m.a | |
| K.c.aA.cT.b.b.m.aA | K.c.aA.cT.b.b.ak.a | K.c.aA.cT.b.b.ak.aA | |
| K.c.aA.cT.b.b.cP.a | K.c.aA.cT.b.b.cP.aA | K.c.aA.cT.b.b.cS.a | |
| K.c.aA.cT.b.b.cS.aA | K.c.aA.cT.b.b.cT.a | K.c.aA.cT.b.b.cT.aA | |
| K.c.aA.cT.b.b.kr.a | K.c.aA.cT.b.b.kr.aA | K.c.aA.kr.b.b.a.a | |
| K.c.aA.kr.b.b.a.aA | K.c.aA.kr.b.b.m.a | K.c.aA.kr.b.b.m.aA | |
| K.c.aA.kr.b.b.ak.a | K.c.aA.kr.b.b.ak.aA | K.c.aA.kr.b.b.cP.a | |
| K.c.aA.kr.b.b.cP.aA | K.c.aA.kr.b.b.cS.a | K.c.aA.kr.b.b.cS.aA | |
| K.c.aA.kr.b.b.cT.a | K.c.aA.kr.b.b.cT.aA | K.c.aA.kr.b.b.kr.a | |
| K.c.aA.kr.b.b.kr.aA | L.c.a.a.b.b.a.a | L.c.a.a.b.b.a.aA | L.c.a.a.b.b.m.a |
| L.c.a.a.b.b.m.aA | L.c.a.a.b.b.ak.a | L.c.a.a.b.b.ak.aA | L.c.a.a.b.b.cP.a |
| L.c.a.a.b.b.cP.aA | L.c.a.a.b.b.cS.a | L.c.a.a.b.b.cS.aA | L.c.a.a.b.b.cT.a |
| L.c.a.a.b.b.cT.aA | L.c.a.a.b.b.kr.a | L.c.a.a.b.b.kr.aA | L.c.a.m.b.b.a.a |
| L.c.a.m.b.b.a.aA | L.c.a.m.b.b.m.a | L.c.a.m.b.b.m.aA | L.c.a.m.b.b.ak.a |
| L.c.a.m.b.b.ak.aA | L.c.a.m.b.b.cP.a | L.c.a.m.b.b.cP.aA | L.c.a.m.b.b.cS.a |
| L.c.a.m.b.b.cS.aA | L.c.a.m.b.b.cT.a | L.c.a.m.b.b.cT.aA | L.c.a.m.b.b.kr.a |
| L.c.a.m.b.b.kr.aA | L.c.a.ak.b.b.a.a | L.c.a.ak.b.b.a.aA | L.c.a.ak.b.b.m.a |
| L.c.a.ak.b.b.m.aA | L.c.a.ak.b.b.ak.a | L.c.a.ak.b.b.ak.aA | L.c.a.ak.b.b.cP.a |
| L.c.a.ak.b.b.cP.aA | L.c.a.ak.b.b.cS.a | L.c.a.ak.b.b.cS.aA | L.c.a.ak.b.b.cT.a |
| L.c.a.ak.b.b.cT.aA | L.c.a.ak.b.b.kr.a | L.c.a.ak.b.b.kr.aA | L.c.a.cP.b.b.a.a |
| L.c.a.cP.b.b.a.aA | L.c.a.cP.b.b.m.a | L.c.a.cP.b.b.m.aA | L.c.a.cP.b.b.ak.a |
| L.c.a.cP.b.b.ak.aA | L.c.a.cP.b.b.cP.a | L.c.a.cP.b.b.cP.aA | L.c.a.cP.b.b.cS.a |
| L.c.a.cP.b.b.cS.aA | L.c.a.cP.b.b.cT.a | L.c.a.cP.b.b.cT.aA | L.c.a.cP.b.b.kr.a |
| L.c.a.cP.b.b.kr.aA | L.c.a.cS.b.b.a.a | L.c.a.cS.b.b.a.aA | L.c.a.cS.b.b.m.a |
| L.c.a.cS.b.b.m.aA | L.c.a.cS.b.b.ak.a | L.c.a.cS.b.b.ak.aA | L.c.a.cS.b.b.cP.a |

TABLE 14-continued

| Exemplary Compounds of the Invention | | | |
|---|---|---|---|
| L.c.a.cS.b.b.cP.aA | L.c.a.cS.b.b.cS.a | L.c.a.cS.b.b.cS.aA | L.c.a.cS.b.b.cT.a |
| L.c.a.cS.b.b.cT.aA | L.c.a.cS.b.b.kr.a | L.c.a.cS.b.b.kr.aA | L.c.a.cT.b.b.a.a |
| L.c.a.cT.b.b.a.aA | L.c.a.cT.b.b.m.a | L.c.a.cT.b.b.m.aA | L.c.a.cT.b.b.ak.a |
| L.c.a.cT.b.b.ak.aA | L.c.a.cT.b.b.cP.a | L.c.a.cT.b.b.cP.aA | L.c.a.cT.b.b.cS.a |
| L.c.a.cT.b.b.cS.aA | L.c.a.cT.b.b.cT.a | L.c.a.cT.b.b.cT.aA | L.c.a.cT.b.b.kr.a |
| L.c.a.cT.b.b.kr.aA | L.c.a.kr.b.b.a.a | L.c.a.kr.b.b.a.aA | L.c.a.kr.b.b.m.a |
| L.c.a.kr.b.b.m.aA | L.c.a.kr.b.b.ak.a | L.c.a.kr.b.b.ak.aA | L.c.a.kr.b.b.cP.a |
| L.c.a.kr.b.b.cP.aA | L.c.a.kr.b.b.cS.a | L.c.a.kr.b.b.cS.aA | L.c.a.kr.b.b.cT.a |
| L.c.a.kr.b.b.cT.aA | L.c.a.kr.b.b.kr.a | L.c.a.kr.b.b.kr.aA | L.c.aA.a.b.b.a.a |
| L.c.aA.a.b.b.a.aA | L.c.aA.a.b.b.m.a | L.c.aA.a.b.b.m.aA | L.c.aA.a.b.b.ak.a |
| L.c.aA.a.b.b.ak.aA | L.c.aA.a.b.b.cP.a | L.c.aA.a.b.b.cP.aA | L.c.aA.a.b.b.cS.a |
| L.c.aA.a.b.b.cS.aA | L.c.aA.a.b.b.cT.a | L.c.aA.a.b.b.cT.aA | L.c.aA.a.b.b.kr.a |
| L.c.aA.a.b.b.kr.aA | L.c.aA.m.b.b.a.a | L.c.aA.m.b.b.a.aA | L.c.aA.m.b.b.m.a |
| L.c.aA.m.b.b.m.aA | L.c.aA.m.b.b.ak.a | L.c.aA.m.b.b.ak.aA | |
| L.c.aA.m.b.b.cP.a | L.c.aA.m.b.b.cP.aA | L.c.aA.m.b.b.cS.a | |
| L.c.aA.m.b.b.cS.aA | L.c.aA.m.b.b.cT.a | L.c.aA.m.b.b.cT.aA | |
| L.c.aA.m.b.b.kr.a | L.c.aA.m.b.b.kr.aA | L.c.aA.ak.b.b.a.a | |
| L.c.aA.ak.b.b.a.aA | L.c.aA.ak.b.b.m.a | L.c.aA.ak.b.b.m.aA | |
| L.c.aA.ak.b.b.ak.a | L.c.aA.ak.b.b.ak.aA | L.c.aA.ak.b.b.cP.a | |
| L.c.aA.ak.b.b.cP.aA | L.c.aA.ak.b.b.cS.a | L.c.aA.ak.b.b.cS.aA | |
| L.c.aA.ak.b.b.cT.a | L.c.aA.ak.b.b.cT.aA | L.c.aA.ak.b.b.kr.a | |
| L.c.aA.ak.b.b.kr.aA | L.c.aA.cP.b.b.a.a | L.c.aA.cP.b.b.a.aA | L.c.aA.cP.b.b.m.a |
| L.c.aA.cP.b.b.m.aA | L.c.aA.cP.b.b.ak.a | L.c.aA.cP.b.b.ak.aA | |
| L.c.aA.cP.b.b.cP.a | L.c.aA.cP.b.b.cP.aA | L.c.aA.cP.b.b.cS.a | |
| L.c.aA.cP.b.b.cS.aA | L.c.aA.cP.b.b.cT.a | L.c.aA.cP.b.b.cT.aA | |
| L.c.aA.cP.b.b.kr.a | L.c.aA.cP.b.b.kr.aA | L.c.aA.cS.b.b.a.a | L.c.aA.cS.b.b.a.aA |
| L.c.aA.cS.b.b.m.a | L.c.aA.cS.b.b.m.aA | L.c.aA.cS.b.b.ak.a | |
| L.c.aA.cS.b.b.ak.aA | L.c.aA.cS.b.b.cP.a | L.c.aA.cS.b.b.cP.aA | |
| L.c.aA.cS.b.b.cS.a | L.c.aA.cS.b.b.cS.aA | L.c.aA.cS.b.b.cT.a | |
| L.c.aA.cS.b.b.cT.aA | L.c.aA.cS.b.b.kr.a | L.c.aA.cS.b.b.kr.aA | L.c.aA.cT.b.b.a.a |
| L.c.aA.cT.b.b.a.aA | L.c.aA.cT.b.b.m.a | L.c.aA.cT.b.b.m.aA | |
| L.c.aA.cT.b.b.ak.a | L.c.aA.cT.b.b.ak.aA | L.c.aA.cT.b.b.cP.a | |
| L.c.aA.cT.b.b.cP.aA | L.c.aA.cT.b.b.cS.a | L.c.aA.cT.b.b.cS.aA | |
| L.c.aA.cT.b.b.cT.a | L.c.aA.cT.b.b.cT.aA | L.c.aA.cT.b.b.kr.a | |
| L.c.aA.cT.b.b.kr.aA | L.c.aA.kr.b.b.a.a | L.c.aA.kr.b.b.a.aA | L.c.aA.kr.b.b.m.a |
| L.c.aA.kr.b.b.m.aA | L.c.aA.kr.b.b.ak.a | L.c.aA.kr.b.b.ak.aA | |
| L.c.aA.kr.b.b.cP.a | L.c.aA.kr.b.b.cP.aA | L.c.aA.kr.b.b.cS.a | |
| L.c.aA.kr.b.b.cS.aA | L.c.aA.kr.b.b.cT.a | L.c.aA.kr.b.b.cT.aA | |
| L.c.aA.kr.b.b.kr.a | L.c.aA.kr.b.b.kr.aA | M.c.a.a.b.b.a.a | M.c.a.a.b.b.a.aA |
| M.c.a.a.b.b.m.a | M.c.a.a.b.b.m.aA | M.c.a.a.b.b.ak.a | M.c.a.a.b.b.ak.aA |
| M.c.a.a.b.b.cP.a | M.c.a.a.b.b.cP.aA | M.c.a.a.b.b.cS.a | M.c.a.a.b.b.cS.aA |
| M.c.a.a.b.b.cT.a | M.c.a.a.b.b.cT.aA | M.c.a.a.b.b.kr.a | M.c.a.a.b.b.kr.aA |
| M.c.a.m.b.b.a.a | M.c.a.m.b.b.a.aA | M.c.a.m.b.b.m.a | M.c.a.m.b.b.m.aA |
| M.c.a.m.b.b.ak.a | M.c.a.m.b.b.ak.aA | M.c.a.m.b.b.cP.a | |
| M.c.a.m.b.b.cP.aA | M.c.a.m.b.b.cS.a | M.c.a.m.b.b.cS.aA | M.c.a.m.b.b.cT.a |
| M.c.a.m.b.b.cT.aA | M.c.a.m.b.b.kr.a | M.c.a.m.b.b.kr.aA | M.c.a.ak.b.b.a.a |
| M.c.a.ak.b.b.a.aA | M.c.a.ak.b.b.m.a | M.c.a.ak.b.b.m.aA | |
| M.c.a.ak.b.b.ak.a | M.c.a.ak.b.b.ak.aA | M.c.a.ak.b.b.cP.a | |
| M.c.a.ak.b.b.cP.aA | M.c.a.ak.b.b.cS.a | M.c.a.ak.b.b.cS.aA | |
| M.c.a.ak.b.b.cT.a | M.c.a.ak.b.b.cT.aA | M.c.a.ak.b.b.kr.a | |
| M.c.a.ak.b.b.kr.aA | M.c.a.cP.b.b.a.a | M.c.a.cP.b.b.a.aA | M.c.a.cP.b.b.m.a |
| M.c.a.cP.b.b.m.aA | M.c.a.cP.b.b.ak.a | M.c.a.cP.b.b.ak.aA | M.c.a.cP.b.b.cP.a |
| M.c.a.cP.b.b.cP.aA | M.c.a.cP.b.b.cS.a | M.c.a.cP.b.b.cS.aA | M.c.a.cP.b.b.cT.a |
| M.c.a.cP.b.b.cT.aA | M.c.a.cP.b.b.kr.a | M.c.a.cP.b.b.kr.aA | M.c.a.cS.b.b.a.a |
| M.c.a.cS.b.b.a.aA | M.c.a.cS.b.b.m.a | M.c.a.cS.b.b.m.aA | M.c.a.cS.b.b.ak.a |
| M.c.a.cS.b.b.ak.aA | M.c.a.cS.b.b.cP.a | M.c.a.cS.b.b.cP.aA | M.c.a.cS.b.b.cS.a |
| M.c.a.cS.b.b.cS.aA | M.c.a.cS.b.b.cT.a | M.c.a.cS.b.b.cT.aA | M.c.a.cS.b.b.kr.a |
| M.c.a.cS.b.b.kr.aA | M.c.a.cT.b.b.a.a | M.c.a.cT.b.b.a.aA | M.c.a.cT.b.b.m.a |
| M.c.a.cT.b.b.m.aA | M.c.a.cT.b.b.ak.a | M.c.a.cT.b.b.ak.aA | M.c.a.cT.b.b.cP.a |
| M.c.a.cT.b.b.cP.aA | M.c.a.cT.b.b.cS.a | M.c.a.cT.b.b.cS.aA | |
| M.c.a.cT.b.b.cT.a | M.c.a.cT.b.b.cT.aA | M.c.a.cT.b.b.kr.a | |
| M.c.a.cT.b.b.kr.aA | M.c.a.kr.b.b.a.a | M.c.a.kr.b.b.a.aA | M.c.a.kr.b.b.m.a |
| M.c.a.kr.b.b.m.aA | M.c.a.kr.b.b.ak.a | M.c.a.kr.b.b.ak.aA | M.c.a.kr.b.b.cP.a |
| M.c.a.kr.b.b.cP.aA | M.c.a.kr.b.b.cS.a | M.c.a.kr.b.b.cS.aA | M.c.a.kr.b.b.cT.a |
| M.c.a.kr.b.b.cT.aA | M.c.a.kr.b.b.kr.a | M.c.a.kr.b.b.kr.aA | M.c.aA.a.b.b.a.a |
| M.c.aA.a.b.b.a.aA | M.c.aA.a.b.b.m.a | M.c.aA.a.b.b.m.aA | |
| M.c.aA.a.b.b.ak.a | M.c.aA.a.b.b.ak.aA | M.c.aA.a.b.b.cP.a | |
| M.c.aA.a.b.b.cP.aA | M.c.aA.a.b.b.cS.a | M.c.aA.a.b.b.cS.aA | |
| M.c.aA.a.b.b.cT.a | M.c.aA.a.b.b.cT.aA | M.c.aA.a.b.b.kr.a | |
| M.c.aA.a.b.b.kr.aA | M.c.aA.m.b.b.a.a | M.c.aA.m.b.b.a.aA | |
| M.c.aA.m.b.b.m.a | M.c.aA.m.b.b.m.aA | M.c.aA.m.b.b.ak.a | |
| M.c.aA.m.b.b.ak.aA | M.c.aA.m.b.b.cP.a | M.c.aA.m.b.b.cP.aA | |
| M.c.aA.m.b.b.cS.a | M.c.aA.m.b.b.cS.aA | M.c.aA.m.b.b.cT.a | |
| M.c.aA.m.b.b.cT.aA | M.c.aA.m.b.b.kr.a | M.c.aA.m.b.b.kr.aA | |
| M.c.aA.ak.b.b.a.a | M.c.aA.ak.b.b.a.aA | M.c.aA.ak.b.b.m.a | |
| M.c.aA.ak.b.b.m.aA | M.c.aA.ak.b.b.ak.a | M.c.aA.ak.b.b.ak.aA | |
| M.c.aA.ak.b.b.cP.a | M.c.aA.ak.b.b.cP.aA | M.c.aA.ak.b.b.cS.a | |

TABLE 14-continued

| Exemplary Compounds of the Invention | | | |
|---|---|---|---|
| M.c.aA.ak.b.b.cS.aA | M.c.aA.ak.b.b.cT.a | M.c.aA.ak.b.b.cT.aA | |
| M.c.aA.ak.b.b.kr.a | M.c.aA.ak.b.b.kr.aA | M.c.aA.cP.b.b.a.a | |
| M.c.aA.cP.b.b.a.aA | M.c.aA.cP.b.b.m.a | M.c.aA.cP.b.b.m.aA | |
| M.c.aA.cP.b.b.ak.a | M.c.aA.cP.b.b.ak.aA | M.c.aA.cP.b.b.cP.a | |
| M.c.aA.cP.b.b.cP.aA | M.c.aA.cP.b.b.cS.a | M.c.aA.cP.b.b.cS.aA | |
| M.c.aA.cP.b.b.cT.a | M.c.aA.cP.b.b.cT.aA | M.c.aA.cP.b.b.kr.a | |
| M.c.aA.cP.b.b.kr.aA | M.c.aA.cS.b.b.a.a | M.c.aA.cS.b.b.a.aA | |
| M.c.aA.cS.b.b.m.a | M.c.aA.cS.b.b.m.aA | M.c.aA.cS.b.b.ak.a | |
| M.c.aA.cS.b.b.ak.aA | M.c.aA.cS.b.b.cP.a | M.c.aA.cS.b.b.cP.aA | |
| M.c.aA.cS.b.b.cS.a | M.c.aA.cS.b.b.cS.aA | M.c.aA.cS.b.b.cT.a | |
| M.c.aA.cS.b.b.cT.aA | M.c.aA.cS.b.b.kr.a | M.c.aA.cS.b.b.kr.aA | |
| M.c.aA.cT.b.b.a.a | M.c.aA.cT.b.b.a.aA | M.c.aA.cT.b.b.m.a | |
| M.c.aA.cT.b.b.m.aA | M.c.aA.cT.b.b.ak.a | M.c.aA.cT.b.b.ak.aA | |
| M.c.aA.cT.b.b.cP.a | M.c.aA.cT.b.b.cP.aA | M.c.aA.cT.b.b.cS.a | |
| M.c.aA.cT.b.b.cS.aA | M.c.aA.cT.b.b.cT.a | M.c.aA.cT.b.b.cT.aA | |
| M.c.aA.cT.b.b.kr.a | M.c.aA.cT.b.b.kr.aA | M.c.aA.kr.b.b.a.a | |
| M.c.aA.kr.b.b.a.aA | M.c.aA.kr.b.b.m.a | M.c.aA.kr.b.b.m.aA | |
| M.c.aA.kr.b.b.ak.a | M.c.aA.kr.b.b.ak.aA | M.c.aA.kr.b.b.cP.a | |
| M.c.aA.kr.b.b.cP.aA | M.c.aA.kr.b.b.cS.a | M.c.aA.kr.b.b.cS.aA | |
| M.c.aA.kr.b.b.cT.a | M.c.aA.kr.b.b.cT.aA | M.c.aA.kr.b.b.kr.a | |
| M.c.aA.kr.b.b.kr.aA | N.c.a.a.b.b.a.a | N.c.a.a.b.b.a.aA | N.c.a.a.b.b.m.a |
| N.c.a.a.b.b.m.aA | N.c.a.a.b.b.ak.a | N.c.a.a.b.b.ak.aA | N.c.a.a.b.b.cP.a |
| N.c.a.a.b.b.cP.aA | N.c.a.a.b.b.cS.a | N.c.a.a.b.b.cS.aA | N.c.a.a.b.b.cT.a |
| N.c.a.a.b.b.cT.aA | N.c.a.a.b.b.kr.a | N.c.a.a.b.b.kr.aA | N.c.a.m.b.b.a.a |
| N.c.a.m.b.b.a.aA | N.c.a.m.b.b.m.a | N.c.a.m.b.b.m.aA | N.c.a.m.b.b.ak.a |
| N.c.a.m.b.b.ak.aA | N.c.a.m.b.b.cP.a | N.c.a.m.b.b.cP.aA | N.c.a.m.b.b.cS.a |
| N.c.a.m.b.b.cS.aA | N.c.a.m.b.b.cT.a | N.c.a.m.b.b.cT.aA | N.c.a.m.b.b.kr.a |
| N.c.a.m.b.b.kr.aA | N.c.a.ak.b.b.a.a | N.c.a.ak.b.b.a.aA | N.c.a.ak.b.b.m.a |
| N.c.a.ak.b.b.m.aA | N.c.a.ak.b.b.ak.a | N.c.a.ak.b.b.ak.aA | N.c.a.ak.b.b.cP.a |
| N.c.a.ak.b.b.cP.aA | N.c.a.ak.b.b.cS.a | N.c.a.ak.b.b.cS.aA | N.c.a.ak.b.b.cT.a |
| N.c.a.ak.b.b.cT.aA | N.c.a.ak.b.b.kr.a | N.c.a.ak.b.b.kr.aA | N.c.a.cP.b.b.a.a |
| N.c.a.cP.b.b.a.aA | N.c.a.cP.b.b.m.a | N.c.a.cP.b.b.m.aA | N.c.a.cP.b.b.ak.a |
| N.c.a.cP.b.b.ak.aA | N.c.a.cP.b.b.cP.a | N.c.a.cP.b.b.cP.aA | N.c.a.cP.b.b.cS.a |
| N.c.a.cP.b.b.cS.aA | N.c.a.cP.b.b.cT.a | N.c.a.cP.b.b.cT.aA | N.c.a.cP.b.b.kr.a |
| N.c.a.cP.b.b.kr.aA | N.c.a.cS.b.b.a.a | N.c.a.cS.b.b.a.aA | N.c.a.cS.b.b.m.a |
| N.c.a.cS.b.b.m.aA | N.c.a.cS.b.b.ak.a | N.c.a.cS.b.b.ak.aA | N.c.a.cS.b.b.cP.a |
| N.c.a.cS.b.b.cP.aA | N.c.a.cS.b.b.cS.a | N.c.a.cS.b.b.cS.aA | N.c.a.cS.b.b.cT.a |
| N.c.a.cS.b.b.cT.aA | N.c.a.cS.b.b.kr.a | N.c.a.cS.b.b.kr.aA | N.c.a.cT.b.b.a.a |
| N.c.a.cT.b.b.a.aA | N.c.a.cT.b.b.m.a | N.c.a.cT.b.b.m.aA | N.c.a.cT.b.b.ak.a |
| N.c.a.cT.b.b.ak.aA | N.c.a.cT.b.b.cP.a | N.c.a.cT.b.b.cP.aA | N.c.a.cT.b.b.cS.a |
| N.c.a.cT.b.b.cS.aA | N.c.a.cT.b.b.cT.a | N.c.a.cT.b.b.cT.aA | N.c.a.cT.b.b.kr.a |
| N.c.a.cT.b.b.kr.aA | N.c.a.kr.b.b.a.a | N.c.a.kr.b.b.a.aA | N.c.a.kr.b.b.m.a |
| N.c.a.kr.b.b.m.aA | N.c.a.kr.b.b.ak.a | N.c.a.kr.b.b.ak.aA | N.c.a.kr.b.b.cP.a |
| N.c.a.kr.b.b.cP.aA | N.c.a.kr.b.b.cS.a | N.c.a.kr.b.b.cS.aA | N.c.a.kr.b.b.cT.a |
| N.c.a.kr.b.b.cT.aA | N.c.a.kr.b.b.kr.a | N.c.a.kr.b.b.kr.aA | N.c.aA.a.b.b.a.a |
| N.c.aA.a.b.b.a.aA | N.c.aA.a.b.b.m.a | N.c.aA.a.b.b.m.aA | |
| N.c.aA.a.b.b.ak.a | N.c.aA.a.b.b.ak.aA | N.c.aA.a.b.b.cP.a | |
| N.c.aA.a.b.b.cP.aA | N.c.aA.a.b.b.cS.a | N.c.aA.a.b.b.cS.aA | |
| N.c.aA.a.b.b.cT.a | N.c.aA.a.b.b.cT.aA | N.c.aA.a.b.b.kr.a | |
| N.c.aA.a.b.b.kr.aA | N.c.aA.m.b.b.a.a | N.c.aA.m.b.b.a.aA | |
| N.c.aA.m.b.b.m.a | N.c.aA.m.b.b.m.aA | N.c.aA.m.b.b.ak.a | |
| N.c.aA.m.b.b.ak.aA | N.c.aA.m.b.b.cP.a | N.c.aA.m.b.b.cP.aA | |
| N.c.aA.m.b.b.cS.a | N.c.aA.m.b.b.cS.aA | N.c.aA.m.b.b.cT.a | |
| N.c.aA.m.b.b.cT.aA | N.c.aA.m.b.b.kr.a | N.c.aA.m.b.b.kr.aA | |
| N.c.aA.ak.b.b.a.a | N.c.aA.ak.b.b.a.aA | N.c.aA.ak.b.b.m.a | |
| N.c.aA.ak.b.b.m.aA | N.c.aA.ak.b.b.ak.a | N.c.aA.ak.b.b.ak.aA | |
| N.c.aA.ak.b.b.cP.a | N.c.aA.ak.b.b.cP.aA | N.c.aA.ak.b.b.cS.a | |
| N.c.aA.ak.b.b.cS.aA | N.c.aA.ak.b.b.cT.a | N.c.aA.ak.b.b.cT.aA | |
| N.c.aA.ak.b.b.kr.a | N.c.aA.ak.b.b.kr.aA | N.c.aA.cP.b.b.a.a | |
| N.c.aA.cP.b.b.a.aA | N.c.aA.cP.b.b.m.a | N.c.aA.cP.b.b.m.aA | |
| N.c.aA.cP.b.b.ak.a | N.c.aA.cP.b.b.ak.aA | N.c.aA.cP.b.b.cP.a | |
| N.c.aA.cP.b.b.cP.aA | N.c.aA.cP.b.b.cS.a | N.c.aA.cP.b.b.cS.aA | |
| N.c.aA.cP.b.b.cT.a | N.c.aA.cP.b.b.cT.aA | N.c.aA.cP.b.b.kr.a | |
| N.c.aA.cP.b.b.kr.aA | N.c.aA.cS.b.b.a.a | N.c.aA.cS.b.b.a.aA | |
| N.c.aA.cS.b.b.m.a | N.c.aA.cS.b.b.m.aA | N.c.aA.cS.b.b.ak.a | |
| N.c.aA.cS.b.b.ak.aA | N.c.aA.cS.b.b.cP.a | N.c.aA.cS.b.b.cP.aA | |
| N.c.aA.cS.b.b.cS.a | N.c.aA.cS.b.b.cS.aA | N.c.aA.cS.b.b.cT.a | |
| N.c.aA.cS.b.b.cT.aA | N.c.aA.cS.b.b.kr.a | N.c.aA.cS.b.b.kr.aA | |
| N.c.aA.cT.b.b.a.a | N.c.aA.cT.b.b.a.aA | N.c.aA.cT.b.b.m.a | |
| N.c.aA.cT.b.b.m.aA | N.c.aA.cT.b.b.ak.a | N.c.aA.cT.b.b.ak.aA | |
| N.c.aA.cT.b.b.cP.a | N.c.aA.cT.b.b.cP.aA | N.c.aA.cT.b.b.cS.a | |
| N.c.aA.cT.b.b.cS.aA | N.c.aA.cT.b.b.cT.a | N.c.aA.cT.b.b.cT.aA | |
| N.c.aA.cT.b.b.kr.a | N.c.aA.cT.b.b.kr.aA | N.c.aA.kr.b.b.a.a | |
| N.c.aA.kr.b.b.a.aA | N.c.aA.kr.b.b.m.a | N.c.aA.kr.b.b.m.aA | |
| N.c.aA.kr.b.b.ak.a | N.c.aA.kr.b.b.ak.aA | N.c.aA.kr.b.b.cP.a | |
| N.c.aA.kr.b.b.cP.aA | N.c.aA.kr.b.b.cS.a | N.c.aA.kr.b.b.cS.aA | |
| N.c.aA.kr.b.b.cT.a | N.c.aA.kr.b.b.cT.aA | N.c.aA.kr.b.b.kr.a | |

TABLE 14-continued

Exemplary Compounds of the Invention

| | | | |
|---|---|---|---|
| N.c.aA.kr.b.b.kr.aA | O.c.a.a.b.b.a.a | O.c.a.a.b.b.a.aA | O.c.a.a.b.b.m.a |
| O.c.a.a.b.b.m.aA | O.c.a.a.b.b.ak.a | O.c.a.a.b.b.ak.aA | O.c.a.a.b.b.cP.a |
| O.c.a.a.b.b.cP.aA | O.c.a.a.b.b.cS.a | O.c.a.a.b.b.cS.aA | O.c.a.a.b.b.cT.a |
| O.c.a.a.b.b.cT.aA | O.c.a.a.b.b.kr.a | O.c.a.a.b.b.kr.aA | O.c.a.m.b.b.a.a |
| O.c.a.m.b.b.a.aA | O.c.a.m.b.b.m.a | O.c.a.m.b.b.m.aA | O.c.a.m.b.b.ak.a |
| O.c.a.m.b.b.ak.aA | O.c.a.m.b.b.cP.a | O.c.a.m.b.b.cP.aA | O.c.a.m.b.b.cS.a |
| O.c.a.m.b.b.cS.aA | O.c.a.m.b.b.cT.a | O.c.a.m.b.b.cT.aA | O.c.a.m.b.b.kr.a |
| O.c.a.m.b.b.kr.aA | O.c.a.ak.b.b.a.a | O.c.a.ak.b.b.a.aA | O.c.a.ak.b.b.m.a |
| O.c.a.ak.b.b.m.aA | O.c.a.ak.b.b.ak.a | O.c.a.ak.b.b.ak.aA | O.c.a.ak.b.b.cP.a |
| O.c.a.ak.b.b.cP.aA | O.c.a.ak.b.b.cS.a | O.c.a.ak.b.b.cS.aA | O.c.a.ak.b.b.cT.a |
| O.c.a.ak.b.b.cT.aA | O.c.a.ak.b.b.kr.a | O.c.a.ak.b.b.kr.aA | O.c.a.cP.b.b.a.a |
| O.c.a.cP.b.b.a.aA | O.c.a.cP.b.b.m.a | O.c.a.cP.b.b.m.aA | O.c.a.cP.b.b.ak.a |
| O.c.a.cP.b.b.ak.aA | O.c.a.cP.b.b.cP.a | O.c.a.cP.b.b.cP.aA | O.c.a.cP.b.b.cS.a |
| O.c.a.cP.b.b.cS.aA | O.c.a.cPb.b.cT.a | O.c.a.cP.b.b.cT.aA | O.c.a.cP.b.b.kr.a |
| O.c.a.cP.b.b.kr.aA | O.c.a.cS.b.b.a.a | O.c.a.cS.b.b.a.aA | O.c.a.cS.b.b.m.a |
| O.c.a.cS.b.b.m.aA | O.c.a.cS.b.b.ak.a | O.c.a.cS.b.b.ak.aA | O.c.a.cS.b.b.cP.a |
| O.c.a.cS.b.b.cP.aA | O.c.a.cS.b.b.cS.a | O.c.a.cS.b.b.cS.aA | O.c.a.cS.b.b.cT.a |
| O.c.a.cS.b.b.cT.aA | O.c.a.cS.b.b.kr.a | O.c.a.cS.b.b.kr.aA | O.c.a.cT.b.b.a.a |
| O.c.a.cT.b.b.a.aA | O.c.a.cT.b.b.m.a | O.c.a.cT.b.b.m.aA | O.c.a.cT.b.b.ak.a |
| O.c.a.cT.b.b.ak.aA | O.c.a.cT.b.b.cP.a | O.c.a.cT.b.b.cP.aA | O.c.a.cT.b.b.cS.a |
| O.c.a.cT.b.b.cS.aA | O.c.a.cT.b.b.cT.a | O.c.a.cT.b.b.cT.aA | O.c.a.cT.b.b.kr.a |
| O.c.a.cT.b.b.kr.aA | O.c.a.kr.b.b.a.a | O.c.a.kr.b.b.a.aA | O.c.a.kr.b.b.m.a |
| O.c.a.kr.b.b.m.aA | O.c.a.kr.b.b.ak.a | O.c.a.kr.b.b.ak.aA | O.c.a.kr.b.b.cP.a |
| O.c.a.kr.b.b.cP.aA | O.c.a.kr.b.b.cS.a | O.c.a.kr.bb.cS.aA | O.c.a.kr.b.b.cT.a |
| O.c.a.kr.b.b.cT.aA | O.c.a.kr.b.b.kr.a | O.c.a.kr.b.b.kr.aA | O.c.aA.a.b.b.a.a |
| O.c.aA.a.b.b.a.aA | O.c.aA.a.b.b.m.a | O.c.aA.a.b.b.m.aA | |
| O.c.aA.a.b.b.ak.a | O.c.aA.a.b.b.ak.aA | O.c.aA.a.b.b.cP.a | |
| O.c.aA.a.b.b.cP.aA | O.c.aA.a.b.b.cS.a | O.c.aA.a.b.b.cS.aA | |
| O.c.aA.a.b.b.cT.a | O.c.aA.a.b.b.cT.aA | O.c.aA.a.b.b.kr.a | |
| O.c.aA.a.b.b.kr.aA | O.c.aA.m.b.b.a.a | O.c.aA.m.b.b.a.aA | |
| O.c.aA.m.b.b.m.a | O.c.aA.m.b.b.m.aA | O.c.aA.m.b.b.ak.a | |
| O.c.aA.m.b.b.ak.aA | O.c.aA.m.b.b.cP.a | O.c.aA.m.b.b.cP.aA | |
| O.c.aA.m.b.b.cS.a | O.c.aA.m.b.b.cS.aA | O.c.aA.m.b.b.cT.a | |
| O.c.aA.m.b.b.cT.aA | O.c.aA.m.b.b.kr.a | O.c.aA.m.b.b.kr.aA | |
| O.c.aA.ak.b.b.a.a | O.c.aA.ak.b.b.a.aA | O.c.aA.ak.b.b.m.a | |
| O.c.aA.ak.b.b.m.aA | O.c.aA.ak.b.b.ak.a | O.c.aA.ak.b.b.ak.aA | |
| O.c.aA.ak.b.b.cP.a | O.c.aA.ak.b.b.cP.aA | O.c.aA.ak.b.b.cS.a | |
| O.c.aA.ak.b.b.cS.aA | O.c.aA.ak.b.b.cT.a | O.c.aA.ak.b.b.cT.aA | |
| O.c.aA.ak.b.b.kr.a | O.c.aA.ak.b.b.kr.aA | O.c.aA.cP.b.b.a.a | |
| O.c.aA.cP.b.b.a.aA | O.c.aA.cP.b.b.m.a | O.c.aA.cP.b.b.m.aA | |
| O.c.aA.cP.b.b.ak.a | O.c.aA.cP.b.b.ak.aA | O.c.aA.cP.b.b.cP.a | |
| O.c.aA.cP.b.b.cP.aA | O.c.aA.cP.b.b.cS.a | O.c.aA.cP.b.b.cS.aA | |
| O.c.aA.cP.b.b.cT.a | O.c.aA.cP.b.b.cT.aA | O.c.aA.cP.b.b.kr.a | |
| O.c.aA.cP.b.b.kr.aA | O.c.aA.cS.b.b.a.a | O.c.aA.cS.b.b.a.aA | |
| O.c.aA.cS.b.b.m.a | O.c.aA.cS.b.b.m.aA | O.c.aA.cS.b.b.ak.a | |
| O.c.aA.cS.b.b.ak.aA | O.c.aA.cS.b.b.cP.a | O.c.aA.cS.b.b.cP.aA | |
| O.c.aA.cS.b.b.cS.a | O.c.aA.cS.b.b.cS.aA | O.c.aA.cS.b.b.cT.a | |
| O.c.aA.cS.b.b.cT.aA | O.c.aA.cS.b.b.kr.a | O.c.aA.cS.b.b.kr.aA | |
| O.c.aA.cT.b.b.a.a | O.c.aA.cT.b.b.a.aA | O.c.aA.cT.b.b.m.a | |
| O.c.aA.cT.b.b.m.aA | O.c.aA.cT.b.b.ak.a | O.c.aA.cT.b.b.ak.aA | |
| O.c.aA.cT.b.b.cP.a | O.c.aA.cT.b.b.cP.aA | O.c.aA.cT.b.b.cS.a | |
| O.c.aA.cT.b.b.cS.aA | O.c.aA.cT.b.b.cT.a | O.c.aA.cT.b.b.cT.aA | |
| O.c.aA.cT.b.b.kr.a | O.c.aA.cT.b.b.kr.aA | O.c.aA.kr.b.b.a.a | |
| O.c.aA.kr.b.b.a.aA | O.c.aA.kr.b.b.m.a | O.c.aA.kr.b.b.m.aA | |
| O.c.aA.kr.b.b.ak.a | O.c.aA.kr.b.b.ak.aA | O.c.aA.kr.b.b.cP.a | |
| O.c.aA.kr.b.b.cP.aA | O.c.aA.kr.b.b.cS.a | O.c.aA.kr.b.b.cS.aA | |
| O.c.aA.kr.b.b.cT.a | O.c.aA.kr.b.b.cT.aA | O.c.aA.kr.b.b.kr.a | |
| O.c.aA.kr.b.b.kr.aA | P.c.a.a.b.b.a.a | P.c.a.a.b.b.a.aA | P.c.a.a.b.b.m.a |
| P.c.a.a.b.b.m.aA | P.c.a.a.b.b.ak.a | P.c.a.a.b.b.ak.aA | P.c.a.a.b.b.cP.a |
| P.c.a.a.b.b.cP.aA | P.c.a.a.b.b.cS.a | P.c.a.a.b.b.cS.aA | P.c.a.a.b.b.cT.a |
| P.c.a.a.b.b.cT.aA | P.c.a.a.b.b.kr.a | P.c.a.a.b.b.kr.aA | P.c.a.m.b.b.a.a |
| P.c.a.m.b.b.a.aA | P.c.a.m.b.b.m.a | P.c.a.m.b.b.m.aA | P.c.a.m.b.b.ak.a |
| P.c.a.m.b.b.ak.aA | P.c.a.m.b.b.cP.a | P.c.a.m.b.b.cP.aA | P.c.a.m.b.b.cS.a |
| P.c.a.m.b.b.cS.aA | P.c.a.m.b.b.cT.a | P.c.a.m.b.b.cT.aA | P.c.a.m.b.b.kr.a |
| P.c.a.m.b.b.kr.aA | P.c.a.ak.b.b.a.a | P.c.a.ak.b.b.a.aA | P.c.a.ak.b.b.m.a |
| P.c.a.ak.b.b.m.aA | P.c.a.ak.b.b.ak.a | P.c.a.ak.b.b.ak.aA | P.c.a.ak.b.b.cP.a |
| P.c.a.ak.b.b.cP.aA | P.c.a.ak.b.b.cS.a | P.c.a.ak.b.b.cS.aA | P.c.a.ak.b.b.cT.a |
| P.c.a.ak.b.b.cT.aA | P.c.a.ak.b.b.kr.a | P.c.a.ak.b.b.kr.aA | P.c.a.cP.b.b.a.a |
| P.c.a.cP.b.b.a.aA | P.c.a.cP.b.b.m.a | P.c.a.cP.b.b.m.aA | P.c.a.cP.b.b.ak.a |
| P.c.a.cP.b.b.ak.aA | P.c.a.cP.b.b.cP.a | P.c.a.cP.b.b.cP.aA | P.c.a.cP.b.b.cS.a |
| P.c.a.cP.b.b.cS.aA | P.c.a.cP.b.b.cT.a | P.c.a.cP.b.b.cT.aA | P.c.a.cP.b.b.kr.a |
| P.c.a.cP.b.b.kr.aA | P.c.a.cS.b.b.a.a | P.c.a.cS.b.b.a.aA | P.c.a.cS.b.b.m.a |
| P.c.a.cS.b.b.m.aA | P.c.a.cS.b.b.ak.a | P.c.a.cS.b.b.ak.aA | P.c.a.cS.b.b.cP.a |
| P.c.a.cS.b.b.cP.aA | P.c.a.cS.b.b.cS.a | P.c.a.cS.b.b.cS.aA | P.c.a.cS.b.b.cT.a |
| P.c.a.cS.b.b.cT.aA | P.c.a.cS.b.b.kr.a | P.c.a.cS.b.b.kr.aA | P.c.a.cT.b.b.a.a |
| P.c.a.cT.b.b.a.aA | P.c.a.cT.b.b.m.a | P.c.a.cT.b.b.m.aA | P.c.a.cT.b.b.ak.a |
| P.c.a.cT.b.b.ak.aA | P.c.a.cT.b.b.cP.a | P.c.a.cT.b.b.cP.aA | P.c.a.cT.b.b.cS.a |

TABLE 14-continued

Exemplary Compounds of the Invention

| | | | |
|---|---|---|---|
| P.c.a.cT.b.b.cS.aA | P.c.a.cT.b.b.cT.a | P.c.a.cT.b.b.cT.aA | P.c.a.cT.b.b.kr.a |
| P.c.a.cT.b.b.kr.aA | P.c.a.kr.b.b.a.a | P.c.a.kr.b.b.a.aA | P.c.a.kr.b.b.m.a |
| P.c.a.kr.b.b.m.aA | P.c.a.kr.b.b.ak.a | P.c.a.kr.b.b.ak.aA | P.c.a.kr.b.b.cP.a |
| P.c.a.kr.b.b.cP.aA | P.c.a.kr.b.b.cS.a | P.c.a.kr.b.b.cS.aA | P.c.a.kr.b.b.cT.a |
| P.c.a.kr.b.b.cT.aA | P.c.a.kr.b.b.kr.a | P.c.a.kr.b.b.kr.aA | P.c.aA.a.b.b.a.a |
| P.c.aA.a.b.b.a.aA | P.c.aA.a.b.b.m.a | P.c.aA.a.b.b.m.aA | P.c.aA.a.b.b.ak.a |
| P.c.aA.a.b.b.ak.aA | P.c.aA.a.b.b.cP.a | P.c.aA.a.b.b.cP.aA | P.c.aA.a.b.b.cS.a |
| P.c.aA.a.b.b.cS.aA | P.c.aA.a.b.b.cT.a | P.c.aA.a.b.b.cT.aA | P.c.aA.a.b.b.kr.a |
| P.c.aA.a.b.b.kr.aA | P.c.aA.m.b.b.a.a | P.c.aA.m.b.b.a.aA | P.c.aA.m.b.b.m.a |
| P.c.aA.m.b.b.m.aA | P.c.aA.m.b.b.ak.a | P.c.aA.m.b.b.ak.aA | |
| P.c.aA.m.b.b.cP.a | P.c.aA.m.b.b.cP.aA | P.c.aA.m.b.b.cS.a | |
| P.c.aA.m.b.b.cS.aA | P.c.aA.m.b.b.cT.a | P.c.aA.m.b.b.cT.aA | |
| P.c.aA.m.b.b.kr.a | P.c.aA.m.b.b.kr.aA | P.c.aA.ak.b.b.a.a | |
| P.c.aA.ak.b.b.a.aA | P.c.aA.ak.b.b.m.a | P.c.aA.ak.b.b.m.aA | |
| P.c.aA.ak.b.b.ak.a | P.c.aA.ak.b.b.ak.aA | P.c.aA.ak.b.b.cP.a | |
| P.c.aA.ak.b.b.cP.aA | P.c.aA.ak.b.b.cS.a | P.c.aA.ak.b.b.cS.aA | |
| P.c.aA.ak.b.b.cT.a | P.c.aA.ak.b.b.cT.aA | P.c.aA.ak.b.b.kr.a | |
| P.c.aA.ak.b.b.kr.aA | P.c.aA.cP.b.b.a.a | P.c.aA.cP.b.b.a.aA | P.c.aA.cP.b.b.m.a |
| P.c.aA.cP.b.b.m.aA | P.c.aA.cP.b.b.ak.a | P.c.aA.cP.b.b.ak.aA | |
| P.c.aA.cP.b.b.cP.a | P.c.aA.cP.b.b.cP.aA | P.c.aA.cP.b.b.cS.a | |
| P.c.aA.cP.b.b.cS.aA | P.c.aA.cP.b.b.cT.a | P.c.aA.cP.b.b.cT.aA | |
| P.c.aA.cP.b.b.kr.a | P.c.aA.cP.b.b.kr.aA | P.c.aA.cS.b.b.a.a | P.c.aA.cS.b.b.a.aA |
| P.c.aA.cS.b.b.m.a | P.c.aA.cS.b.b.m.aA | P.c.aA.cS.b.b.ak.a | |
| P.c.aA.cS.b.b.ak.aA | P.c.aA.cS.b.b.cP.a | P.c.aA.cS.b.b.cP.aA | |
| P.c.aA.cS.b.b.cS.a | P.c.aA.cS.b.b.cS.aA | P.c.aA.cS.b.b.cT.a | |
| P.c.aA.cS.b.b.cT.aA | P.c.aA.cS.b.b.kr.a | P.c.aA.cS.b.b.kr.aA | P.c.aA.cT.b.b.a.a |
| P.c.aA.cT.b.b.a.aA | P.c.aA.cT.b.b.m.a | P.c.aA.cT.b.b.m.aA | |
| P.c.aA.cT.b.b.ak.a | P.c.aA.cT.b.b.ak.aA | P.c.aA.cT.b.b.cP.a | |
| P.c.aA.cT.b.b.cP.aA | P.c.aA.cT.b.b.cS.a | P.c.aA.cT.b.b.cS.aA | |
| P.c.aA.cT.b.b.cT.a | P.c.aA.cT.b.b.cT.aA | P.c.aA.cT.b.b.kr.a | |
| P.c.aA.cT.b.b.kr.aA | P.c.aA.kr.b.b.a.a | P.c.aA.kr.b.b.a.aA | P.c.aA.kr.b.b.m.a |
| P.c.aA.kr.b.b.m.aA | P.c.aA.kr.b.b.ak.a | P.c.aA.kr.b.b.ak.aA | |
| P.c.aA.kr.b.b.cP.a | P.c.aA.kr.b.b.cP.aA | P.c.aA.kr.b.b.cS.a | |
| P.c.aA.kr.b.b.cS.aA | P.c.aA.kr.b.b.cT.a | P.c.aA.kr.b.b.cT.aA | |
| P.c.aA.kr.b.b.kr.a | P.c.aA.kr.b.b.kr.aA | K.c.a.aw.b.b.aw.a | |
| K.c.a.aw.b.b.aw.aA | K.c.aA.aw.b.b.aw.a | K.c.aA.aw.b.b.aw.aA | |
| L.c.a.aw.b.b.aw.a | L.c.a.aw.b.b.aw.aA | L.c.aA.aw.b.b.aw.a | |
| L.c.aA.aw.b.b.aw.aA | M.c.a.aw.b.b.aw.a | M.c.a.aw.b.b.aw.aA | |
| M.c.aA.aw.b.b.aw.a | M.c.aA.aw.b.b.aw.aA | N.c.a.aw.b.b.aw.a | |
| N.c.a.aw.b.b.aw.aA | N.c.aA.aw.b.b.aw.a | N.c.aA.aw.b.b.aw.aA | |
| O.c.a.aw.b.b.aw.a | O.c.a.aw.b.b.aw.aA | O.c.aA.aw.b.b.aw.a | |
| O.c.aA.aw.b.b.aw.aA | P.c.a.aw.b.b.aw.a | P.c.a.aw.b.b.aw.aA | |
| P.c.aA.aw.b.b.aw.a | P.c.aA.aw.b.b.aw.aA | Q.c.a.a.b.b.a.a | Q.c.a.a.b.b.a.aA |
| Q.c.a.a.b.b.m.a | Q.c.a.a.b.b.m.aA | Q.c.a.a.b.b.ak.a | Q.c.a.a.b.b.ak.aA |
| Q.c.a.a.b.b.cP.a | Q.c.a.a.b.b.cP.aA | Q.c.a.a.b.b.cS.a | Q.c.a.a.b.b.cS.aA |
| Q.c.a.a.b.b.cT.a | Q.c.a.a.b.b.cT.aA | Q.c.a.a.b.b.kr.a | Q.c.a.a.b.b.kr.aA |
| Q.c.a.m.b.b.a.a | Q.c.a.m.b.b.a.aA | Q.c.a.m.b.b.m.a | Q.c.a.m.b.b.m.aA |
| Q.c.a.m.b.b.ak.a | Q.c.a.m.b.b.ak.aA | Q.c.a.m.b.b.cP.a | Q.c.a.m.b.b.cP.aA |
| Q.c.a.m.b.b.cS.a | Q.c.a.m.b.b.cS.aA | Q.c.a.m.b.b.cT.a | Q.c.a.m.b.b.cT.aA |
| Q.c.a.m.b.b.kr.a | Q.c.a.m.b.b.kr.aA | Q.c.a.ak.b.b.a.a | Q.c.a.ak.b.b.a.aA |
| Q.c.a.ak.b.b.m.a | Q.c.a.ak.b.b.m.aA | Q.c.a.ak.b.b.ak.a | Q.c.a.ak.b.b.ak.aA |
| Q.c.a.ak.b.b.cP.a | Q.c.a.ak.b.b.cP.aA | Q.c.a.ak.b.b.cS.a | Q.c.a.ak.b.b.cS.aA |
| Q.c.a.ak.b.b.cT.a | Q.c.a.ak.b.b.cT.aA | Q.c.a.ak.b.b.kr.a | Q.c.a.ak.b.b.kr.aA |
| Q.c.a.cP.b.b.a.a | Q.c.a.cP.b.b.a.aA | Q.c.a.cP.b.b.m.a | Q.c.a.cP.b.b.m.aA |
| Q.c.a.cP.b.b.ak.a | Q.c.a.cP.b.b.ak.aA | Q.c.a.cP.b.b.cP.a | Q.c.a.cP.b.b.cP.aA |
| Q.c.a.cP.b.b.cS.a | Q.c.a.cP.b.b.cS.aA | Q.c.a.cP.b.b.cT.a | Q.c.a.cP.b.b.cT.aA |
| Q.c.a.cP.b.b.kr.a | Q.c.a.cP.b.b.kr.aA | Q.c.a.cS.b.b.a.a | Q.c.a.cS.b.b.a.aA |
| Q.c.a.cS.b.b.m.a | Q.c.a.cS.b.b.m.aA | Q.c.a.cS.b.b.ak.a | Q.c.a.cS.b.b.ak.aA |
| Q.c.a.cS.b.b.cP.a | Q.c.a.cS.b.b.cP.aA | Q.c.a.cS.b.b.cS.a | Q.c.a.cS.b.b.cS.aA |
| Q.c.a.cS.b.b.cT.a | Q.c.a.cS.b.b.cT.aA | Q.c.a.cS.b.b.kr.a | Q.c.a.cS.b.b.kr.aA |
| Q.c.a.cT.b.b.a.a | Q.c.a.cT.b.b.a.aA | Q.c.a.cT.b.b.m.a | Q.c.a.cT.b.b.m.aA |
| Q.c.a.cT.b.b.ak.a | Q.c.a.cT.b.b.ak.aA | Q.c.a.cT.b.b.cP.a | Q.c.a.cT.b.b.cP.aA |
| Q.c.a.cT.b.b.cS.a | Q.c.a.cT.b.b.cS.aA | Q.c.a.cT.b.b.cT.a | Q.c.a.cT.b.b.cT.aA |
| Q.c.a.cT.b.b.kr.a | Q.c.a.cT.b.b.kr.aA | Q.c.a.kr.b.b.a.a | Q.c.a.kr.b.b.a.aA |
| Q.c.a.kr.b.b.m.a | Q.c.a.kr.b.b.m.aA | Q.c.a.kr.b.b.ak.a | Q.c.a.kr.b.b.ak.aA |
| Q.c.a.krb.b.cP.a | Q.c.a.kr.b.b.cP.aA | Q.c.a.kr.b.b.cS.a | Q.c.a.kr.b.b.cS.aA |
| Q.c.a.kr.b.b.cT.a | Q.c.a.kr.b.b.cT.aA | Q.c.a.kr.b.b.kr.a | Q.c.a.kr.b.b.kr.aA |
| Q.c.aA.a.b.b.a.a | Q.c.aA.a.b.b.a.aA | Q.c.aA.a.b.b.m.a | Q.c.aA.a.b.b.m.aA |
| Q.c.aA.a.b.b.ak.a | Q.c.aA.a.b.b.ak.aA | Q.c.aA.a.b.b.cP.a | |
| Q.c.aA.a.b.b.cP.aA | Q.c.aA.a.b.b.cS.a | Q.c.aA.a.b.b.cS.aA | |
| Q.c.aA.a.b.b.cT.a | Q.c.aA.a.b.b.cT.aA | Q.c.aA.a.b.b.kr.a | |
| Q.c.aA.a.b.b.kr.aA | Q.c.aA.m.b.b.a.a | Q.c.aA.m.b.b.a.aA | |
| Q.c.aA.m.b.b.m.a | Q.c.aA.m.b.b.m.aA | Q.c.aA.m.b.b.ak.a | |
| Q.c.aA.m.b.b.ak.aA | Q.c.aA.m.b.b.cP.a | Q.c.aA.m.b.b.cP.aA | |
| Q.c.aA.m.b.b.cS.a | Q.c.aA.m.b.b.cS.aA | Q.c.aA.m.b.b.cT.a | |
| Q.c.aA.m.b.b.cT.aA | Q.c.aA.m.b.b.kr.a | Q.c.aA.m.b.b.kr.aA | |
| Q.c.aA.ak.b.b.a.a | Q.c.aA.ak.b.b.a.aA | Q.c.aA.ak.b.b.m.a | |

TABLE 14-continued

Exemplary Compounds of the Invention

| | | | |
|---|---|---|---|
| Q.c.aA.ak.b.b.m.aA | Q.c.aA.ak.b.b.ak.a | Q.c.aA.ak.b.b.ak.aA | |
| Q.c.aA.ak.b.b.cP.a | Q.c.aA.ak.b.b.cP.aA | Q.c.aA.ak.b.b.cS.a | |
| Q.c.aA.ak.b.b.cS.aA | Q.c.aA.ak.b.b.cT.a | Q.c.aA.ak.b.b.cT.aA | |
| Q.c.aA.ak.b.b.kr.a | Q.c.aA.ak.b.b.kr.aA | Q.c.aA.cP.b.b.a.a | |
| Q.c.aA.cP.b.b.a.aA | Q.c.aA.cP.b.b.m.a | Q.c.aA.cP.b.b.m.aA | |
| Q.c.aA.cP.b.b.ak.a | Q.c.aA.cP.b.b.ak.aA | Q.c.aA.cP.b.b.cP.a | |
| Q.c.aA.cP.b.b.cP.aA | Q.c.aA.cP.b.b.cS.a | Q.c.aA.cP.b.b.cS.aA | |
| Q.c.aA.cP.b.b.cT.a | Q.c.aA.cP.b.b.cT.aA | Q.c.aA.cP.b.b.kr.a | |
| Q.c.aA.cP.b.b.kr.aA | Q.c.aA.cS.b.b.a.a | Q.c.aA.cS.b.b.a.aA | |
| Q.c.aA.cS.b.b.m.a | Q.c.aA.cS.b.b.m.aA | Q.c.aA.cS.b.b.ak.a | |
| Q.c.aA.cS.b.b.ak.aA | Q.c.aA.cS.b.b.cP.a | Q.c.aA.cS.b.b.cP.aA | |
| Q.c.aA.cS.b.b.cS.a | Q.c.aA.cS.b.b.cS.aA | Q.c.aA.cS.b.b.cT.a | |
| Q.c.aA.cS.b.b.cT.aA | Q.c.aA.cS.b.b.kr.a | Q.c.aA.cS.b.b.kr.aA | |
| Q.c.aA.cT.b.b.a.a | Q.c.aA.cT.b.b.a.aA | Q.c.aA.cT.b.b.m.a | |
| Q.c.aA.cT.b.b.m.aA | Q.c.aA.cT.b.b.ak.a | Q.c.aA.cT.b.b.ak.aA | |
| Q.c.aA.cT.b.b.cP.a | Q.c.aA.cT.b.b.cP.aA | Q.c.aA.cT.b.b.cS.a | |
| Q.c.aA.cT.b.b.cS.aA | Q.c.aA.cT.b.b.cT.a | Q.c.aA.cT.b.b.cT.aA | |
| Q.c.aA.cT.b.b.kr.a | Q.c.aA.cT.b.b.kr.aA | Q.c.aA.kr.b.b.a.a | |
| Q.c.aA.kr.b.b.a.aA | Q.c.aA.kr.b.b.m.a | Q.c.aA.kr.b.b.m.aA | |
| Q.c.aA.kr.b.b.ak.a | Q.c.aA.kr.b.b.ak.aA | Q.c.aA.kr.b.b.cP.a | |
| Q.c.aA.kr.b.b.cP.aA | Q.c.aA.kr.b.b.cS.a | Q.c.aA.kr.b.b.cS.aA | |
| Q.c.aA.kr.b.b.cT.a | Q.c.aA.kr.b.b.cT.aA | Q.c.aA.kr.b.b.kr.a | |
| Q.c.aA.kr.b.b.kr.aA | R.c.a.a.b.b.a.a | R.c.a.a.b.b.a.aA | R.c.a.a.b.b.m.a |
| R.c.a.a.b.b.m.aA | R.c.a.a.b.b.ak.a | R.c.a.a.b.b.ak.aA | R.c.a.a.b.b.cP.a |
| R.c.a.a.b.b.cP.aA | R.c.a.a.b.b.cS.a | R.c.a.a.b.b.cS.aA | R.c.a.a.b.b.cT.a |
| R.c.a.a.b.b.cT.aA | R.c.a.a.b.b.kr.a | R.c.a.a.b.b.kr.aA | R.c.a.m.b.b.a.a |
| R.c.a.m.b.b.a.aA | R.c.a.m.b.b.m.a | R.c.a.m.b.b.m.aA | R.c.a.m.b.b.ak.a |
| R.c.a.m.b.b.ak.aA | R.c.a.m.b.b.cP.a | R.c.a.m.b.b.cP.aA | R.c.a.m.b.b.cS.a |
| R.c.a.m.b.b.cS.aA | R.c.a.m.b.b.cT.a | R.c.a.m.b.b.cT.aA | R.c.a.m.b.b.kr.a |
| R.c.a.m.b.b.kr.aA | R.c.a.ak.b.b.a.a | R.c.a.ak.b.b.a.aA | R.c.a.ak.b.b.m.a |
| R.c.a.ak.b.b.m.aA | R.c.a.ak.b.b.ak.a | R.c.a.ak.b.b.ak.aA | R.c.a.ak.b.b.cP.a |
| R.c.a.ak.b.b.cP.aA | R.c.a.ak.b.b.cS.a | R.c.a.ak.b.b.cS.aA | R.c.a.ak.b.b.cT.a |
| R.c.a.ak.b.b.cT.aA | R.c.a.ak.b.b.kr.a | R.c.a.ak.b.b.kr.aA | R.c.a.cP.b.b.a.a |
| R.c.a.cP.b.b.a.aA | R.c.a.cP.b.b.m.a | R.c.a.cP.b.b.m.aA | R.c.a.cP.b.b.ak.a |
| R.c.a.cP.b.b.ak.aA | R.c.a.cP.b.b.cP.a | R.c.a.cP.b.b.cP.aA | R.c.a.cP.b.b.cS.a |
| R.c.a.cP.b.b.cS.aA | R.c.a.cP.b.b.cT.a | R.c.a.cP.b.b.cT.aA | R.c.a.cP.b.b.kr.a |
| R.c.a.cP.b.b.kr.aA | R.c.a.cS.b.b.a.a | R.c.a.cS.b.b.a.aA | R.c.a.cS.b.b.m.a |
| R.c.a.cS.b.b.m.aA | R.c.a.cS.b.b.ak.a | R.c.a.cS.b.b.ak.aA | R.c.a.cS.b.b.cP.a |
| R.c.a.cS.b.b.cP.aA | R.c.a.cS.b.b.cS.a | R.c.a.cS.b.b.cS.aA | R.c.a.cS.b.b.cT.a |
| R.c.a.cS.b.b.cT.aA | R.c.a.cS.b.b.kr.a | R.c.a.cS.b.b.kr.aA | R.c.a.cT.b.b.a.a |
| R.c.a.cT.b.b.a.aA | R.c.a.cT.b.b.m.a | R.c.a.cT.b.b.m.aA | R.c.a.cT.b.b.ak.a |
| R.c.a.cT.b.b.ak.aA | R.c.a.cT.b.b.cP.a | R.c.a.cT.b.b.cP.aA | R.c.a.cT.b.b.cS.a |
| R.c.a.cT.b.b.cS.aA | R.c.a.cT.b.b.cT.a | R.c.a.cT.b.b.cT.aA | R.c.a.cT.b.b.kr.a |
| R.c.a.cT.b.b.kr.aA | R.c.a.kr.b.b.a.a | R.c.a.kr.b.b.a.aA | R.c.a.kr.b.b.m.a |
| R.c.a.kr.b.b.m.aA | R.c.a.kr.b.b.ak.a | R.c.a.kr.b.b.ak.aA | R.c.a.kr.b.b.cP.a |
| R.c.a.kr.b.b.cP.aA | R.c.a.kr.b.b.cS.a | R.c.a.kr.b.b.cS.aA | R.c.a.kr.b.b.cT.a |
| R.c.a.kr.b.b.cT.aA | R.c.a.kr.b.b.kr.a | R.c.a.kr.b.b.kr.aA | R.c.aA.b.b.a.a |
| R.c.aA.a.b.b.a.aA | R.c.aA.a.b.b.m.a | R.c.aA.a.b.b.m.aA | |
| R.c.aA.a.b.b.ak.a | R.c.aA.a.b.b.ak.aA | R.c.aA.a.b.b.cP.a | |
| R.c.aA.a.b.b.cP.aA | R.c.aA.a.b.b.cS.a | R.c.aA.a.b.b.cS.aA | |
| R.c.aA.a.b.b.cT.a | R.c.aA.a.b.b.cT.aA | R.c.aA.a.b.b.kr.a | |
| R.c.aA.a.b.b.kr.aA | R.c.aA.m.b.b.a.a | R.c.aA.m.b.b.a.aA | |
| R.c.aA.m.b.b.m.a | R.c.aA.m.b.b.m.aA | R.c.aA.m.b.b.ak.a | |
| R.c.aA.m.b.b.ak.aA | R.c.aA.m.b.b.cP.a | R.c.aA.m.b.b.cP.aA | |
| R.c.aA.m.b.b.cS.a | R.c.aA.m.b.b.cS.aA | R.c.aA.m.b.b.cT.a | |
| R.c.aA.m.b.b.cT.aA | R.c.aA.m.b.b.kr.a | R.c.aA.m.b.b.kr.aA | |
| R.c.aA.ak.b.b.a.a | R.c.aA.ak.b.b.a.aA | R.c.aA.ak.b.b.m.a | |
| R.c.aA.ak.b.b.m.aA | R.c.aA.ak.b.b.ak.a | R.c.aA.ak.b.b.ak.aA | |
| R.c.aA.ak.b.b.cP.a | R.c.aA.ak.b.b.cP.aA | R.c.aA.ak.b.b.cS.a | |
| R.c.aA.ak.b.b.cS.aA | R.c.aA.ak.b.b.cT.a | R.c.aA.ak.b.b.cT.aA | |
| R.c.aA.ak.b.b.kr.a | R.c.aA.ak.b.b.kr.aA | R.c.aA.cP.b.b.a.a | |
| R.c.aA.cP.b.b.a.aA | R.c.aA.cP.b.b.m.a | R.c.aA.cP.b.b.m.aA | |
| R.c.aA.cP.b.b.ak.a | R.c.aA.cP.b.b.ak.aA | R.c.aA.cP.b.b.cP.a | |
| R.c.aA.cP.b.b.cP.aA | R.c.aA.cP.b.b.cS.a | R.c.aA.cP.b.b.cS.aA | |
| R.c.aA.cP.b.b.cT.a | R.c.aA.cP.b.b.cT.aA | R.c.aA.cP.b.b.kr.a | |
| R.c.aA.cP.b.b.kr.aA | R.c.aA.cS.b.b.a.a | R.c.aA.cS.b.b.a.aA | |
| R.c.aA.cS.b.b.m.a | R.c.aA.cS.b.b.m.aA | R.c.aA.cS.b.b.ak.a | |
| R.c.aA.cS.b.b.ak.aA | R.c.aA.cS.b.b.cP.a | R.c.aA.cS.b.b.cP.aA | |
| R.c.aA.cS.b.b.cS.a | R.c.aA.cS.b.b.cS.aA | R.c.aA.cS.b.b.cT.a | |
| R.c.aA.cS.b.b.cT.aA | R.c.aA.cS.b.b.kr.a | R.c.aA.cS.b.b.kr.aA | |
| R.c.aA.cT.b.b.a.a | R.c.aA.cT.b.b.a.aA | R.c.aA.cT.b.b.m.a | |
| R.c.aA.cT.b.b.m.aA | R.c.aA.cT.b.b.ak.a | R.c.aA.cT.b.b.ak.aA | |
| R.c.aA.cT.b.b.cP.a | R.c.aA.cT.b.b.cP.aA | R.c.aA.cT.b.b.cS.a | |
| R.c.aA.cT.b.b.cS.aA | R.c.aA.cT.b.b.cT.a | R.c.aA.cT.b.b.cT.aA | |
| R.c.aA.cT.b.b.kr.a | R.c.aA.cT.b.b.kr.aA | R.c.aA.kr.b.b.a.a | |
| R.c.aA.kr.b.b.a.aA | R.c.aA.kr.b.b.m.a | R.c.aA.kr.b.b.m.aA | |
| R.c.aA.kr.b.b.ak.a | R.c.aA.kr.b.b.ak.aA | R.c.aA.kr.b.b.cP.a | |

TABLE 14-continued

Exemplary Compounds of the Invention

| | | | |
|---|---|---|---|
| R.c.aA.kr.b.b.cP.aA | R.c.aA.kr.b.b.cS.a | R.c.aA.kr.b.b.cS.aA | |
| R.c.aA.kr.b.b.cT.a | R.c.aA.kr.b.b.cT.aA | R.c.aA.kr.b.b.kr.a | |
| R.c.aA.kr.b.b.kr.aA | S.c.a.a.b.b.a.a | S.c.a.a.b.b.a.aA | S.c.a.a.b.b.m.a |
| S.c.a.a.b.b.m.aA | S.c.a.a.b.b.ak.a | S.c.a.a.b.b.ak.aA | S.c.a.a.b.b.cP.a |
| S.c.a.a.b.b.cP.aA | S.c.a.a.b.b.cS.a | S.c.a.a.b.b.cS.aA | S.c.a.a.b.b.cT.a |
| S.c.a.a.b.b.cT.aA | S.c.a.a.b.b.kr.a | S.c.a.a.b.b.kr.aA | S.c.a.m.b.b.a.a |
| S.c.a.m.b.b.a.aA | S.c.a.m.b.b.m.a | S.c.a.m.b.b.m.aA | S.c.a.m.b.b.ak.a |
| S.c.a.m.b.b.ak.aA | S.c.a.m.b.b.cP.a | S.c.a.m.b.b.cP.aA | S.c.a.m.b.b.cS.a |
| S.c.a.m.b.b.cS.aA | S.c.a.m.b.b.cT.a | S.c.a.m.b.b.cT.aA | S.c.a.m.b.b.kr.a |
| S.c.a.m.b.b.kr.aA | S.c.a.ak.b.b.a.a | S.c.a.ak.b.b.a.aA | S.c.a.ak.b.b.m.a |
| S.c.a.ak.b.b.m.aA | S.c.a.ak.b.b.ak.a | S.c.a.ak.b.b.ak.aA | S.c.a.ak.b.b.cP.a |
| S.c.a.ak.b.b.cP.aA | S.c.a.ak.b.b.cS.a | S.c.a.ak.b.b.cS.aA | S.c.a.ak.b.b.cT.a |
| S.c.a.ak.b.b.cT.aA | S.c.a.ak.b.b.kr.a | S.c.a.ak.b.b.kr.aA | S.c.a.cP.b.b.a.a |
| S.c.a.cP.b.b.a.aA | S.c.a.cP.b.b.m.a | S.c.a.cP.b.b.m.aA | S.c.a.cP.b.b.ak.a |
| S.c.a.cP.b.b.ak.aA | S.c.a.cP.b.b.cP.a | S.c.a.cP.b.b.cP.aA | S.c.a.cP.b.b.cS.a |
| S.c.a.cP.b.b.cS.aA | S.c.a.cP.b.b.cT.a | S.c.a.cP.b.b.cT.aA | S.c.a.cP.b.b.kr.a |
| S.c.a.cP.b.b.kr.aA | S.c.a.cS.b.b.a.a | S.c.a.cS.b.b.a.aA | S.c.a.cS.b.b.m.a |
| S.c.a.cS.b.b.m.aA | S.c.a.cS.b.b.ak.a | S.c.a.cS.b.b.ak.aA | S.c.a.cS.b.b.cP.a |
| S.c.a.cS.b.b.cP.aA | S.c.a.cS.b.b.cS.a | S.c.a.cS.b.b.cS.aA | S.c.a.cS.b.b.cT.a |
| S.c.a.cS.b.b.cT.aA | S.c.a.cS.b.b.kr.a | S.c.a.cS.b.b.kr.aA | S.c.a.cT.b.b.a.a |
| S.c.a.cT.b.b.a.aA | S.c.a.cT.b.b.m.a | S.c.a.cT.b.b.m.aA | S.c.a.cT.b.b.ak.a |
| S.c.a.cT.b.b.ak.aA | S.c.a.cT.b.b.cP.a | S.c.a.cT.b.b.cP.aA | S.c.a.cT.b.b.cS.a |
| S.c.a.cT.b.b.cS.aA | S.c.a.cT.b.b.cT.a | S.c.a.cT.b.b.cT.aA | S.c.a.cT.b.b.kr.a |
| S.c.a.cT.b.b.kr.aA | S.c.a.kr.b.b.a.a | S.c.a.kr.b.b.a.aA | S.c.a.kr.b.b.m.a |
| S.c.a.kr.b.b.m.aA | S.c.a.kr.b.b.ak.a | S.c.a.kr.b.b.ak.aA | S.c.a.kr.b.b.cP.a |
| S.c.a.kr.b.b.cP.aA | S.c.a.kr.b.b.cS.a | S.c.a.kr.b.b.cS.aA | S.c.a.kr.b.b.cT.a |
| S.c.a.kr.b.b.cT.aA | S.c.a.kr.b.b.kr.a | S.c.a.kr.b.b.kr.aA | S.c.aA.a.b.b.a.a |
| S.c.aA.a.b.b.a.aA | S.c.aA.a.b.b.m.a | S.c.aA.a.b.b.m.aA | S.c.aA.a.b.b.ak.a |
| S.c.aA.a.b.b.ak.aA | S.c.aA.a.b.b.cP.a | S.c.aA.a.b.b.cP.aA | S.c.aA.a.b.b.cS.a |
| S.c.aA.a.b.b.cS.aA | S.c.aA.a.b.b.cT.a | S.c.aA.a.b.b.cT.aA | S.c.aA.a.b.b.kr.a |
| S.c.aA.a.b.b.kr.aA | S.c.aA.m.b.b.a.a | S.c.aA.m.b.b.a.aA | S.c.aA.m.b.b.m.a |
| S.c.aA.m.b.b.m.aA | S.c.aA.m.b.b.ak.a | S.c.aA.m.b.b.ak.aA | |
| S.c.aA.m.b.b.cP.a | S.c.aA.m.b.b.cP.aA | S.c.aA.m.b.b.cS.a | |
| S.c.aA.m.b.b.cS.aA | S.c.aA.m.b.b.cT.a | S.c.aA.m.b.b.cT.aA | |
| S.c.aA.m.b.b.kr.a | S.c.aA.m.b.b.kr.aA | S.c.aA.ak.b.b.a.a | |
| S.c.aA.ak.b.b.a.aA | S.c.aA.ak.b.b.m.a | S.c.aA.ak.b.b.m.aA | |
| S.c.aA.ak.b.b.ak.a | S.c.aA.ak.b.b.ak.aA | S.c.aA.ak.b.b.cP.a | |
| S.c.aA.ak.b.b.cP.aA | S.c.aA.ak.b.b.cS.a | S.c.aA.ak.b.b.cS.aA | |
| S.c.aA.ak.b.b.cT.a | S.c.aA.ak.b.b.cT.aA | S.c.aA.ak.b.b.kr.a | |
| S.c.aA.ak.b.b.kr.aA | S.c.aA.cP.b.b.a.a | S.c.aA.cP.b.b.a.aA | S.c.aA.cP.b.b.m.a |
| S.c.aA.cP.b.b.m.aA | S.c.aA.cP.b.b.ak.a | S.c.aA.cP.b.b.ak.aA | |
| S.c.aA.cP.b.b.cP.a | S.c.aA.cP.b.b.cP.aA | S.c.aA.cPh.b.cS.a | |
| S.c.aA.cP.b.b.cS.aA | S.c.aA.cP.b.b.cT.a | S.c.aA.cP.b.b.cT.aA | |
| S.c.aA.cP.b.b.kr.a | S.c.aA.cP.b.b.kr.aA | S.c.aA.cS.b.b.a.a | S.c.aA.cS.b.b.a.aA |
| S.c.aA.cS.b.b.m.a | S.c.aA.cS.b.b.m.aA | S.c.aA.cS.b.b.ak.a | |
| S.c.aA.cS.b.b.ak.aA | S.c.aA.cS.b.b.cP.a | S.c.aA.cS.b.b.cP.aA | |
| S.c.aA.cS.b.b.cS.a | S.c.aA.cS.b.b.cS.aA | S.c.aA.cS.b.b.cT.a | |
| S.c.aA.cS.b.b.cT.aA | S.c.aA.cS.b.b.kr.a | S.c.aA.cS.b.b.kr.aA | S.c.aA.cT.b.b.a.a |
| S.c.aA.cT.b.b.a.aA | S.c.aA.cT.b.b.m.a | S.c.aA.cT.b.b.m.aA | |
| S.c.aA.cT.b.b.ak.a | S.c.aA.cT.b.b.ak.aA | S.c.aA.cT.b.b.cP.a | |
| S.c.aA.cT.b.b.cP.aA | S.c.aA.cT.b.b.cS.a | S.c.aA.cT.b.b.cS.aA | |
| S.c.aA.cT.b.b.cT.a | S.c.aA.cT.b.b.cT.aA | S.c.aA.cT.b.b.kr.a | |
| S.c.aA.cT.b.b.kr.aA | S.c.aA.kr.b.b.a.a | S.c.aA.kr.b.b.a.aA | S.c.aA.kr.b.b.m.a |
| S.c.aA.kr.b.b.m.aA | S.c.aA.kr.b.b.ak.a | S.c.aA.kr.b.b.ak.aA | |
| S.c.aA.kr.b.b.cP.a | S.c.aA.kr.b.b.cP.aA | S.c.aA.kr.b.b.cS.a | |
| S.c.aA.kr.b.b.cS.aA | S.c.aA.kr.b.b.cT.a | S.c.aA.kr.b.b.cT.aA | |
| S.c.aA.kr.b.b.kr.a | S.c.aA.kr.b.b.kr.aA | T.c.a.a.b.b.a.a | T.c.a.a.b.b.a.aA |
| T.c.a.a.b.b.m.a | T.c.a.a.b.b.m.aA | T.c.a.a.b.b.ak.a | T.c.a.a.b.b.ak.aA |
| T.c.a.a.b.b.cP.a | T.c.a.a.b.b.cP.aA | T.c.a.ab.b.cS.a | T.c.a.a.b.b.cS.aA |
| T.c.a.a.b.b.cT.a | T.c.a.a.b.b.cT.aA | T.c.a.a.b.b.kr.a | T.c.a.a.b.b.kr.aA |
| T.c.a.m.b.b.a.a | T.c.a.m.b.b.a.aA | T.c.a.m.b.b.m.a | T.c.a.m.b.b.m.aA |
| T.c.a.m.b.b.ak.a | T.c.a.m.b.b.ak.aA | T.c.a.m.b.b.cP.a | T.c.a.m.b.b.cP.aA |
| T.c.a.m.b.b.cS.a | T.c.a.m.b.b.cS.aA | T.c.a.m.b.b.cT.a | T.c.a.m.b.b.cT.aA |
| T.c.a.m.b.b.kr.a | T.c.a.m.b.b.kr.aA | T.c.a.ak.b.b.a.a | T.c.a.ak.b.b.a.aA |
| T.c.a.ak.b.b.m.a | T.c.a.ak.b.b.m.aA | T.c.a.ak.b.b.ak.a | T.c.a.ak.b.b.ak.aA |
| T.c.a.ak.b.b.cP.a | T.c.a.ak.b.b.cP.aA | T.c.a.ak.b.b.cS.a | T.c.a.ak.b.b.cS.aA |
| T.c.a.ak.b.b.cT.a | T.c.a.ak.b.b.cT.aA | T.c.a.ak.b.b.kr.a | T.c.a.ak.b.b.kr.aA |
| T.c.a.cP.b.b.a.a | T.c.a.cP.b.b.a.aA | T.c.a.cP.b.b.m.a | T.c.a.cP.b.b.m.aA |
| T.c.a.cP.b.b.ak.a | T.c.a.cP.b.b.ak.aA | T.c.a.cP.b.b.cP.a | T.c.a.cP.b.b.cP.aA |
| T.c.a.cP.b.b.cS.a | T.c.a.cP.b.b.cS.aA | T.c.a.cP.b.b.cT.a | T.c.a.cP.b.b.cT.aA |
| T.c.a.cP.b.b.kr.a | T.c.a.cP.b.b.kr.aA | T.c.a.cS.b.b.a.a | T.c.a.cS.b.b.a.aA |
| T.c.a.cS.b.b.m.a | T.c.a.cS.b.b.m.aA | T.c.a.cS.b.b.ak.a | T.c.a.cS.b.b.ak.aA |
| T.c.a.cS.b.b.cS.a | T.c.a.cS.b.b.cS.aA | T.c.a.cS.b.b.cS.a | T.c.a.cS.b.b.cS.aA |
| T.c.a.cS.b.b.cT.a | T.c.a.cS.b.b.cT.aA | T.c.a.cS.b.b.kr.a | T.c.a.cS.b.b.kr.aA |
| T.c.a.cT.b.b.a.a | T.c.a.cT.b.b.a.aA | T.c.a.cT.b.b.m.a | T.c.a.cT.b.b.m.aA |
| T.c.a.cT.b.b.ak.a | T.c.a.cT.b.b.ak.aA | T.c.a.cT.b.b.cT.a | T.c.a.cT.b.b.cT.aA |
| T.c.a.cT.b.b.cS.a | T.c.a.cT.b.b.cS.aA | T.c.a.cT.b.b.cT.a | T.c.a.cT.b.b.cT.aA |

TABLE 14-continued

Exemplary Compounds of the Invention

| | | | |
|---|---|---|---|
| T.c.a.cT.b.b.kr.a | T.c.a.cT.b.b.kr.aA | T.c.a.kr.b.b.a.a | T.c.a.kr.b.b.a.aA |
| T.c.a.kr.b.b.m.a | T.c.a.kr.b.b.m.aA | T.c.a.kr.b.b.ak.a | T.c.a.kr.b.b.ak.aA |
| T.c.a.kr.b.b.kr.a | T.c.a.kr.b.b.kr.aA | T.c.a.kr.b.b.kr.a | T.c.a.kr.b.b.kr.aA |
| T.c.a.kr.b.b.cT.a | T.c.a.kr.b.b.cT.aA | T.c.a.kr.b.b.kr.a | T.c.a.kr.b.b.kr.aA |
| T.c.Aa.a.b.b.a.a | T.c.Aa.a.b.b.a.aA | T.c.Aa.a.b.b.m.a | T.c.Aa.a.b.b.m.aA |
| T.c.Aa.a.b.b.ak.a | T.c.Aa.a.b.b.ak.aA | T.c.Aa.a.b.b.cP.a | |
| T.c.Aa.a.b.b.cP.aA | T.c.Aa.a.b.b.cS.a | T.c.Aa.a.b.b.cS.aA | T.c.Aa.a.b.b.cT.a |
| T.c.Aa.a.b.b.cT.aA | T.c.Aa.a.b.b.kr.a | T.c.Aa.a.b.b.kr.aA | T.c.Aa.m.b.b.a.a |
| T.c.Aa.m.b.b.a.aA | T.c.Aa.m.b.b.m.a | T.c.Aa.m.b.b.m.aA | |

TABLE 14-continued

Exemplary Compounds of the Invention

| | | | |
|---|---|---|---|
| V.c.a.m.b.b.kr.aA | V.c.a.ak.b.b.a.a | V.c.a.ak.b.b.a.aA | V.c.a.ak.b.b.m.a |
| V.c.a.ak.b.b.m.aA | V.c.a.ak.b.b.ak.a | V.c.a.ak.b.b.ak.aA | V.c.a.ak.b.b.cP.a |
| V.c.a.ak.b.b.cP.aA | V.c.a.ak.b.b.cS.a | V.c.a.ak.b.b.cS.aA | V.c.a.ak.b.b.cT.a |
| V.c.a.ak.b.b.cT.aA | V.c.a.ak.b.b.kr.a | V.c.a.ak.b.b.kr.aA | V.c.a.cP.b.b.a.a |
| V.c.a.cP.b.b.a.aA | V.c.a.cP.b.b.m.a | V.c.a.cP.b.b.m.aA | V.c.a.cP.b.b.ak.a |
| V.c.a.cP.b.b.ak.aA | V.c.a.cP.b.b.cP.a | V.c.a.cP.b.b.cP.aA | V.c.a.cP.b.b.cS.a |
| V.c.a.cP.b.b.cS.aA | V.c.a.cP.b.b.cT.a | V.c.a.cP.b.b.cT.aA | V.c.a.cP.b.b.kr.a |
| V.c.a.cP.b.b.kr.aA | V.c.a.cS.b.b.a.a | V.c.a.cS.b.b.a.aA | V.c.a.cS.b.b.m.a |
| V.c.a.cS.b.b.m.aA | V.c.a.cS.b.b.ak.a | V.c.a.cS.b.b.ak.aA | V.c.a.cS.b.b.cP.a |
| V.c.a.cS.b.b.cP.aA | V.c.a.cS.b.b.cS.a | V.c.a.cS.b.b.cS.aA | V.c.a.cS.b.b.cT.a |
| V.c.a.cS.b.b.cT.aA | V.c.a.cS.b.b.kr.a | V.c.a.cS.b.b.kr.aA | V.c.a.cT.b.b.a.a |
| V.c.a.cT.b.b.a.aA | V.c.a.cT.b.b.m.a | V.c.a.cT.b.b.m.aA | V.c.a.cT.b.b.ak.a |
| V.c.a.cT.b.b.ak.aA | V.c.a.cT.b.b.cP.a | V.c.a.cT.b.b.cP.aA | V.c.a.cT.b.b.cS.a |
| V.c.a.cT.b.b.cS.aA | V.c.a.cT.b.b.cT.a | V.c.a.cT.b.b.cT.aA | V.c.a.cT.b.b.kr.a |
| V.c.a.cT.b.b.kr.aA | V.c.a.kr.b.b.a.a | V.c.a.kr.b.b.a.aA | V.c.a.kr.b.b.m.a |
| V.c.a.kr.b.b.m.aA | V.c.a.kr.b.b.ak.a | V.c.a.kr.b.b.ak.aA | V.c.a.kr.b.b.cP.a |
| V.c.a.kr.b.b.cP.aA | V.c.a.kr.b.b.cS.a | V.c.a.kr.b.b.cS.aA | V.c.a.kr.b.b.cT.a |
| V.c.a.kr.b.b.cT.aA | V.c.a.kr.b.b.kr.a | V.c.a.kr.b.b.kr.aA | V.c.aA.b.b.a.a |
| V.c.aA.b.b.a.aA | V.c.aA.b.b.m.a | V.c.aA.b.b.m.aA | |
| V.c.aA.b.b.ak.a | V.c.aA.b.b.ak.aA | V.c.aA.b.b.cP.a | |
| V.c.aA.b.b.cP.aA | V.c.aA.b.b.cS.a | V.c.aA.b.b.cS.aA | |
| V.c.aA.b.b.cT.a | V.c.aA.b.b.cT.aA | V.c.aA.b.b.kr.a | |
| V.c.aA.b.b.kr.aA | V.c.aA.m.b.b.a.a | V.c.aA.m.b.b.a.aA | |
| V.c.aA.m.b.b.m.a | V.c.aA.m.b.b.m.aA | V.c.aA.m.b.b.ak.a | |
| V.c.aA.m.b.b.ak.aA | V.c.aA.m.b.b.cP.a | V.c.aA.m.b.b.cP.aA | |
| V.c.aA.m.b.b.cS.a | V.c.aA.m.b.b.cS.aA | V.c.aA.m.b.b.cT.a | |
| V.c.aA.m.b.b.cT.aA | V.c.aA.m.b.b.kr.a | V.c.aA.m.b.b.kr.aA | |
| V.c.aA.ak.b.b.a.a | V.c.aA.ak.b.b.a.aA | V.c.aA.ak.b.b.m.a | |
| V.c.aA.ak.b.b.m.aA | V.c.aA.ak.b.b.ak.a | V.c.aA.ak.b.b.ak.aA | |
| V.c.aA.ak.b.b.cP.a | V.c.aA.ak.b.b.cP.aA | V.c.aA.ak.b.b.cS.a | |
| V.c.aA.ak.b.b.cS.aA | V.c.aA.ak.b.b.cT.a | V.c.aA.ak.b.b.cT.aA | |
| V.c.aA.ak.b.b.kr.a | V.c.aA.ak.b.b.kr.aA | V.c.aA.cP.b.b.a.a | |
| V.c.aA.cP.b.b.a.aA | V.c.aA.cP.b.b.m.a | V.c.aA.cP.b.b.m.aA | |
| V.c.aA.cP.b.b.ak.a | V.c.aA.cP.b.b.ak.aA | V.c.aA.cP.b.b.cP.a | |
| V.c.aA.cP.b.b.cP.aA | V.c.aA.cP.b.b.cS.a | V.c.aA.cP.b.b.cS.aA | |
| V.c.aA.cP.b.b.cT.a | V.c.aA.cP.b.b.cT.aA | V.c.aA.cP.b.b.kr.a | |
| V.c.aA.cP.b.b.kr.aA | V.c.aA.cS.b.b.a.a | V.c.aA.cS.b.b.a.aA | |
| V.c.aA.cS.b.b.m.a | V.c.aA.cS.b.b.m.aA | V.c.aA.cS.b.b.ak.a | |
| V.c.aA.cS.b.b.ak.aA | V.c.aA.cS.b.b.cP.a | V.c.aA.cS.b.b.cP.aA | |
| V.c.aA.cS.b.b.cS.a | V.c.aA.cS.b.b.cS.aA | V.c.aA.cS.b.b.cT.a | |
| V.c.aA.cS.b.b.cT.aA | V.c.aA.cS.b.b.kr.a | V.c.aA.cS.b.b.kr.aA | |
| V.c.aA.cT.b.b.a.a | V.c.aA.cT.b.b.a.aA | V.c.aA.cT.b.b.m.a | |
| V.c.aA.cT.b.b.m.aA | V.c.aA.cT.b.b.ak.a | V.c.aA.cT.b.b.ak.aA | |
| V.c.aA.cT.b.b.cP.a | V.c.aA.cT.b.b.cP.aA | V.c.aA.cT.b.b.cS.a | |
| V.c.aA.cT.b.b.cS.aA | V.c.aA.cT.b.b.cT.a | V.c.aA.cT.b.b.cT.aA | |
| V.c.aA.cT.b.b.kr.a | V.c.aA.cT.b.b.kr.aA | V.c.aA.kr.b.b.a.a | |
| V.c.aA.kr.b.b.a.aA | V.c.aA.kr.b.b.m.a | V.c.aA.kr.b.b.m.aA | |
| V.c.aA.kr.b.b.ak.a | V.c.aA.kr.b.b.ak.aA | V.c.aA.kr.b.b.cP.a | |
| V.c.aA.kr.b.b.cP.aA | V.c.aA.kr.b.b.cS.a | V.c.aA.kr.b.b.cS.aA | |
| V.c.aA.kr.b.b.cT.a | V.c.aA.kr.b.b.cT.aA | V.c.aA.kr.b.b.kr.a | |
| V.c.aA.kr.b.b.kr.aA | W.c.a.a.b.b.a.a | W.c.a.a.b.b.a.aA | W.c.a.a.b.b.m.a |
| W.c.a.a.b.b.m.aA | W.c.a.a.b.b.ak.a | W.c.a.a.b.b.ak.aA | W.c.a.a.b.b.cP.a |
| W.c.a.a.b.b.cP.aA | W.c.a.a.b.b.cS.a | W.c.a.a.b.b.cS.aA | W.c.a.a.b.b.cT.a |
| W.c.a.a.b.b.cT.aA | W.c.a.a.b.b.kr.a | W.c.a.a.b.b.kr.aA | W.c.a.m.b.b.a.a |
| W.c.a.m.b.b.a.aA | W.c.a.m.b.b.m.a | W.c.a.m.b.b.m.aA | |
| W.c.a.m.b.b.ak.a | W.c.a.m.b.b.ak.aA | W.c.a.m.b.b.cP.a | |
| W.c.a.m.b.b.cP.aA | W.c.a.m.b.b.cS.a | W.c.a.m.b.b.cS.aA | |
| W.c.a.m.b.b.cT.a | W.c.a.m.b.b.cT.aA | W.c.a.m.b.b.kr.a | |
| W.c.a.m.b.b.kr.aA | W.c.a.ak.b.b.a.a | W.c.a.ak.b.b.a.aA | W.c.a.ak.b.b.m.a |
| W.c.a.ak.b.b.m.aA | W.c.a.ak.b.b.ak.a | W.c.a.ak.b.b.ak.aA | |
| W.c.a.ak.b.b.cP.a | W.c.a.ak.b.b.cP.aA | W.c.a.ak.b.b.cS.a | |
| W.c.a.ak.b.b.cS.aA | W.c.a.ak.b.b.cT.a | W.c.a.ak.b.b.cT.aA | |
| W.c.a.ak.b.b.kr.a | W.c.a.ak.b.b.kr.aA | W.c.a.cP.b.b.a.a | W.c.a.cP.b.b.a.aA |
| W.c.a.cP.b.b.m.a | W.c.a.cP.b.b.m.aA | W.c.a.cP.b.b.ak.a | |
| W.c.a.cP.b.b.ak.aA | W.c.a.cP.b.b.cP.a | W.c.a.cP.b.b.cP.aA | |
| W.c.a.cP.b.b.cS.a | W.c.a.cP.b.b.cS.aA | W.c.a.cP.b.b.cT.a | |
| W.c.a.cP.b.b.cT.aA | W.c.a.cP.b.b.kr.a | W.c.a.cP.b.b.kr.aA | W.c.a.cS.b.b.a.a |
| W.c.a.cS.b.b.a.aA | W.c.a.cS.b.b.m.a | W.c.a.cS.b.b.m.aA | |
| W.c.a.cS.b.b.ak.a | W.c.a.cS.b.b.ak.aA | W.c.a.cS.b.b.cP.a | |
| W.c.a.cS.b.b.cP.aA | W.c.a.cS.b.b.cS.a | W.c.a.cS.b.b.cS.aA | |
| W.c.a.cS.b.b.cT.a | W.c.a.cS.b.b.cT.aA | W.c.a.cS.b.b.kr.a | |
| W.c.a.cS.b.b.kr.aA | W.c.a.cT.b.b.a.a | W.c.a.cT.b.b.a.aA | W.c.a.cT.b.b.m.a |
| W.c.a.cT.b.b.m.aA | W.c.a.cT.b.b.ak.a | W.c.a.cT.b.b.ak.aA | |
| W.c.a.cT.b.b.cP.a | W.c.a.cT.b.b.cP.aA | W.c.a.cT.b.b.cS.a | |
| W.c.a.cT.b.b.cS.aA | W.c.a.cT.b.b.cT.a | W.c.a.cT.b.b.cT.aA | |
| W.c.a.cT.b.b.kr.a | W.c.a.cT.b.b.kr.aA | W.c.a.kr.b.b.a.a | W.c.a.kr.b.b.a.aA |
| W.c.a.kr.b.b.m.a | W.c.a.kr.b.b.m.aA | W.c.a.kr.b.b.ak.a | |

TABLE 14-continued

Exemplary Compounds of the Invention

| | | | |
|---|---|---|---|
| W.c.a.kr.b.b.ak.aA | W.c.a.kr.b.b.cP.a | W.c.a.kr.b.b.cP.aA | |
| W.c.a.kr.b.b.cS.a | W.c.a.kr.b.b.cS.aA | W.c.a.kr.b.b.cT.a | |
| W.c.a.kr.b.b.cT.aA | W.c.a.kr.b.b.kr.a | W.c.a.kr.b.b.kr.aA | W.c.aA.a.b.b.a.a |
| W.c.aA.a.b.b.a.aA | W.c.aA.a.b.b.m.a | W.c.aA.a.b.b.m.aA | |
| W.c.aA.a.b.b.ak.a | W.c.aA.a.b.b.ak.aA | W.c.aA.a.b.b.cP.a | |
| W.c.aA.a.b.b.cP.aA | W.c.aA.a.b.b.cS.a | W.c.aA.a.b.b.cS.aA | |
| W.c.aA.a.b.b.cT.a | W.c.aA.a.b.b.cT.aA | W.c.aA.a.b.b.kr.a | |
| W.c.aA.a.b.b.kr.aA | W.c.aA.m.b.b.a.a | W.c.aA.m.b.b.a.aA | |
| W.c.aA.m.b.b.m.a | W.c.aA.m.b.b.m.aA | W.c.aA.m.b.b.ak.a | |
| W.c.aA.m.b.b.ak.aA | W.c.aA.m.b.b.cP.a | W.c.aA.m.b.b.cP.aA | |
| W.c.aA.m.b.b.cS.a | W.c.aA.m.b.b.cS.aA | W.c.aA.m.b.b.cT.a | |
| W.c.aA.m.b.b.cT.aA | W.c.aA.m.b.b.kr.a | W.c.aA.m.b.b.kr.aA | W.c.aA.ak.b.b.a.a |
| W.c.aA.ak.b.b.a.aA | W.c.aA.ak.b.b.m.a | W.c.aA.ak.b.b.m.aA | |
| W.c.aA.ak.b.b.ak.a | W.c.aA.ak.b.b.ak.aA | W.c.aA.ak.b.b.cP.a | |
| W.c.aA.ak.b.b.cP.aA | W.c.aA.ak.b.b.cS.a | W.c.aA.ak.b.b.cS.aA | |
| W.c.aA.ak.b.b.cT.a | W.c.aA.ak.b.b.cT.aA | W.c.aA.ak.b.b.kr.a | |
| W.c.aA.ak.b.b.kr.aA | W.c.aA.cP.b.b.a.a | W.c.aA.cP.b.b.a.aA | |
| W.c.aA.cP.b.b.m.a | W.c.aA.cP.b.b.m.aA | W.c.aA.cP.b.b.ak.a | |
| W.c.aA.cP.b.b.ak.aA | W.c.aA.cP.b.b.cP.a | W.c.aA.cP.b.b.cP.aA | |
| W.c.aA.cP.b.b.cS.a | W.c.aA.cP.b.b.cS.aA | W.c.aA.cP.b.b.cT.a | |
| W.c.aA.cP.b.b.cT.aA | W.c.aA.cP.b.b.kr.a | W.c.aA.cP.b.b.kr.aA | W.c.aA.cS.b.b.a.a |
| W.c.aA.cS.b.b.a.aA | W.c.aA.cS.b.b.m.a | W.c.aA.cS.b.b.m.aA | |
| W.c.aA.cS.b.b.ak.a | W.c.aA.cS.b.b.ak.aA | W.c.aA.cS.b.b.cP.a | |
| W.c.aA.cS.b.b.cP.aA | W.c.aA.cS.b.b.cS.a | W.c.aA.cS.b.b.cS.aA | |
| W.c.aA.cS.b.b.cT.a | W.c.aA.cS.b.b.cT.aA | W.c.aA.cS.b.b.kr.a | |
| W.c.aA.cS.b.b.kr.aA | W.c.aA.cT.b.b.a.a | W.c.aA.cT.b.b.a.aA | |
| W.c.aA.cT.b.b.m.a | W.c.aA.cT.b.b.m.aA | W.c.aA.cT.b.b.ak.a | |
| W.c.aA.cT.b.b.ak.aA | W.c.aA.cT.b.b.cP.a | W.c.aA.cT.b.b.cP.aA | |
| W.c.aA.cT.b.b.cS.a | W.c.aA.cT.b.b.cS.aA | W.c.aA.cT.b.b.cT.a | |
| W.c.aA.cT.b.b.cT.aA | W.c.aA.cT.b.b.kr.a | W.c.aA.cT.b.b.kr.aA | |
| W.c.aA.kr.b.b.a.a | W.c.aA.kr.b.b.a.aA | W.c.aA.kr.b.b.m.a | |
| W.c.aA.kr.b.b.m.aA | W.c.aA.kr.b.b.ak.a | W.c.aA.kr.b.b.ak.aA | |
| W.c.aA.kr.b.b.cP.a | W.c.aA.kr.b.b.cP.aA | W.c.aA.kr.b.b.cS.a | |
| W.c.aA.kr.b.b.cS.aA | W.c.aA.kr.b.b.cT.a | W.c.aA.kr.b.b.cT.aA | |
| W.c.aA.kr.b.b.kr.a | W.c.aA.kr.b.b.kr.aA | Y.c.a.a.b.b.a.a | Y.c.a.a.b.b.a.aA |
| Y.c.a.a.b.b.m.a | Y.c.a.a.b.b.m.aA | Y.c.a.a.b.b.ak.a | Y.c.a.a.b.b.ak.aA |
| Y.c.a.a.b.b.cP.a | Y.c.a.a.b.b.cP.aA | Y.c.a.a.b.b.cS.a | Y.c.a.a.b.b.cS.aA |
| Y.c.a.a.b.b.cT.a | Y.c.a.a.b.b.cT.aA | Y.c.a.a.b.b.kr.a | Y.c.a.a.b.b.kr.aA |
| Y.c.a.m.b.b.a.a | Y.c.a.m.b.b.a.aA | Y.c.a.m.b.b.m.a | Y.c.a.m.b.b.m.aA |
| Y.c.a.m.b.b.ak.a | Y.c.a.m.b.b.ak.aA | Y.c.a.m.b.b.cP.a | Y.c.a.m.b.b.cP.aA |
| Y.c.a.m.b.b.cS.a | Y.c.a.m.b.b.cS.aA | Y.c.a.m.b.b.cT.a | Y.c.a.m.b.b.cT.aA |
| Y.c.a.m.b.b.kr.a | Y.c.a.m.b.b.kr.aA | Y.c.a.ak.b.b.a.a | Y.c.a.ak.b.b.a.aA |
| Y.c.a.ak.b.b.m.a | Y.c.a.ak.b.b.m.aA | Y.c.a.ak.b.b.ak.a | Y.c.a.ak.b.b.ak.aA |
| Y.c.a.ak.b.b.cP.a | Y.c.a.ak.b.b.cP.aA | Y.c.a.ak.b.b.cS.a | Y.c.a.ak.b.b.cS.aA |
| Y.c.a.ak.b.b.cT.a | Y.c.a.ak.b.b.cT.aA | Y.c.a.ak.b.b.kr.a | Y.c.a.ak.b.b.kr.aA |
| Y.c.a.cP.b.b.a.a | Y.c.a.cP.b.b.a.aA | Y.c.a.cP.b.b.m.a | Y.c.a.cP.b.b.m.aA |
| Y.c.a.cP.b.b.ak.a | Y.c.a.cP.b.b.ak.aA | Y.c.a.cP.b.b.cP.a | Y.c.a.cP.b.b.cP.aA |
| Y.c.a.cP.b.b.cS.a | Y.c.a.cP.b.b.cS.aA | Y.c.a.cP.b.b.cT.a | Y.c.a.cP.b.b.cT.aA |
| Y.c.a.cP.b.b.kr.a | Y.c.a.cP.b.b.kr.aA | Y.c.a.cS.b.b.a.a | Y.c.a.cS.b.b.a.aA |
| Y.c.a.cS.b.b.m.a | Y.c.a.cS.b.b.m.aA | Y.c.a.cS.b.b.ak.a | Y.c.a.cS.b.b.ak.aA |
| Y.c.a.cS.b.b.cP.a | Y.c.a.cS.b.b.cP.aA | Y.c.a.cS.b.b.cS.a | Y.c.a.cS.b.b.cS.aA |
| Y.c.a.cS.b.b.cT.a | Y.c.a.cS.b.b.cT.aA | Y.c.a.cS.b.b.kr.a | Y.c.a.cS.b.b.kr.aA |
| Y.c.a.cT.b.b.a.a | Y.c.a.cT.b.b.a.aA | Y.c.a.cT.b.b.m.a | Y.c.a.cT.b.b.m.aA |
| Y.c.a.cT.b.b.ak.a | Y.c.a.cT.b.b.ak.aA | Y.c.a.cT.b.b.cP.a | Y.c.a.cT.b.b.cP.aA |
| Y.c.a.cT.b.b.cS.a | Y.c.a.cT.b.b.cS.aA | Y.c.a.cT.b.b.cT.a | Y.c.a.cT.b.b.cT.aA |
| Y.c.a.cT.b.b.kr.a | Y.c.a.cT.b.b.kr.aA | Y.c.a.kr.b.b.a.a | Y.c.a.kr.b.b.a.aA |
| Y.c.a.kr.b.b.m.a | Y.c.a.kr.b.b.m.aA | Y.c.a.kr.b.b.ak.a | Y.c.a.kr.b.b.ak.aA |
| Y.c.a.kr.b.b.cP.a | Y.c.a.kr.b.b.cP.aA | Y.c.a.kr.b.b.cS.a | Y.c.a.kr.b.b.cS.aA |
| Y.c.a.kr.b.b.cT.a | Y.c.a.kr.b.b.cT.aA | Y.c.a.kr.b.b.kr.a | Y.c.a.kr.b.b.kr.aA |
| Y.c.aA.a.b.b.a.a | Y.c.aA.a.b.b.a.aA | Y.c.aA.a.b.b.m.a | Y.c.aA.a.b.b.m.aA |
| Y.c.aA.a.b.b.ak.a | Y.c.aA.a.b.b.ak.aA | Y.c.aA.a.b.b.cP.a | |
| Y.c.aA.a.b.b.cP.aA | Y.c.aA.a.b.b.cS.a | Y.c.aA.a.b.b.cS.aA | Y.c.aA.a.b.b.cT.a |
| Y.c.aA.a.b.b.cT.aA | Y.c.aA.a.b.b.kr.a | Y.c.aA.a.b.b.kr.aA | Y.c.aA.m.b.b.a.a |
| Y.c.aA.m.b.b.a.aA | Y.c.aA.m.b.b.m.a | Y.c.aA.m.b.b.m.aA | |
| Y.c.aA.m.b.b.ak.a | Y.c.aA.m.b.b.ak.aA | Y.c.aA.m.b.b.cP.a | |
| Y.c.aA.m.b.b.cP.aA | Y.c.aA.m.b.b.cS.a | Y.c.aA.m.b.b.cS.aA | |
| Y.c.aA.m.b.b.cT.a | Y.c.aA.m.b.b.cT.aA | Y.c.aA.m.b.b.kr.a | |
| Y.c.aA.m.b.b.kr.aA | Y.c.aA.ak.b.b.a.a | Y.c.aA.ak.b.b.a.aA | |
| Y.c.aA.ak.b.b.m.a | Y.c.aA.ak.b.b.m.aA | Y.c.aA.ak.b.b.ak.a | |
| Y.c.aA.ak.b.b.ak.aA | Y.c.aA.ak.b.b.cP.a | Y.c.aA.ak.b.b.cP.aA | |
| Y.c.aA.ak.b.b.cS.a | Y.c.aA.ak.b.b.cS.aA | Y.c.aA.ak.b.b.cT.a | |
| Y.c.aA.ak.b.b.cT.aA | Y.c.aA.ak.b.b.kr.a | Y.c.aA.ak.b.b.kr.aA | |
| Y.c.aA.cP.b.b.a.a | Y.c.aA.cP.b.b.a.aA | Y.c.aA.cP.b.b.m.a | |
| Y.c.aA.cP.b.b.m.aA | Y.c.aA.cP.b.b.ak.a | Y.c.aA.cP.b.b.ak.aA | |
| Y.c.aA.cP.b.b.cP.a | Y.c.aA.cP.b.b.cP.aA | Y.c.aA.cP.b.b.cS.a | |
| Y.c.aA.cP.b.b.cS.aA | Y.c.aA.cP.b.b.cT.a | Y.c.aA.cP.b.b.cT.aA | |
| Y.c.aA.cP.b.b.kr.a | Y.c.aA.cP.b.b.kr.aA | Y.c.aA.cS.b.b.a.a | |

TABLE 14-continued

| Exemplary Compounds of the Invention | | |
|---|---|---|
| Y.c.aA.cS.b.b.a.aA | Y.c.aA.cS.b.b.m.a | Y.c.aA.cS.b.b.m.aA |
| Y.c.aA.cS.b.b.ak.a | Y.c.aA.cS.b.b.ak.aA | Y.c.aA.cS.b.b.cP.a |
| Y.c.aA.cS.b.b.cP.aA | Y.c.aA.cS.b.b.cS.a | Y.c.aA.cS.b.b.cS.aA |
| Y.c.aA.cS.b.b.cT.a | Y.c.aA.cS.b.b.cT.aA | Y.c.aA.cS.b.b.kr.a |
| Y.c.aA.cS.b.b.kr.aA | Y.c.aA.cT.b.b.a.a | Y.c.aA.cT.b.b.a.aA |
| Y.c.aA.cT.b.b.m.a | Y.c.aA.cT.b.b.m.aA | Y.c.aA.cT.b.b.ak.a |
| Y.c.aA.cT.b.b.ak.aA | Y.c.aA.cT.b.b.cP.a | Y.c.aA.cT.b.b.cP.aA |
| Y.c.aA.cT.b.b.cS.a | Y.c.aA.cT.b.b.cS.aA | Y.c.aA.cT.b.b.cT.a |
| Y.c.aA.cT.b.b.cT.aA | Y.c.aA.cT.b.b.kr.a | Y.c.aA.cT.b.b.kr.aA |
| Y.c.aA.kr.b.b.a.a | Y.c.aA.kr.b.b.a.aA | Y.c.aA.kr.b.b.m.a |
| Y.c.aA.kr.b.b.m.aA | Y.c.aA.kr.b.b.ak.a | Y.c.aA.kr.b.b.ak.aA |
| Y.c.aA.kr.b.b.cP.a | Y.c.aA.kr.b.b.cP.aA | Y.c.aA.kr.b.b.cS.a |
| Y.c.aA.kr.b.b.cS.aA | Y.c.aA.kr.b.b.cT.a | Y.c.aA.kr.b.b.cT.aA |
| Y.c.aA.kr.b.b.kr.a | Y.c.aA.kr.b.b.kr.aA | |

Pharmaceutical Formulations and Administration.

Another aspect of the invention relates to compositions comprising compound(s) of this invention plus one or more pharmaceutically-acceptable carriers. One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with, for example, the condition of the recipient.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.) which is incorporated by reference herein. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally are coated or scored and optionally are formulated so as to provide slow or controlled release of the active ingredient therefrom.

For administration to the eye or other external tissues e.g. mouth and skin, the formulations are preferably applied as a topical ointment or cream if; containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc.), which is administered by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for inhalation therapy are prepared as aerosols or powders having a particle size small enough to dose the alveoli. Such powders and aerosols are prepared by any of the methods common in the art. Ordinarily aerosols are aqueous aerosols.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends on the nature of the condition being treated, the method of treatment, pharmaceutical formulation, and the like. It can be expected to be from about 0.001 to about 30 mg/kg body weight per day. Particular dose ranges are determined by the methods common in the art. Such methods include dose escalation studies involving animal models such as SIV in monkeys or HIV IN SCID mouse systems. Studies of this type take into account effectiveness and toxicity of a particular dose among other variables commonly studied in the art.

Active ingredients of the invention are also used in combination with other active ingredients heretofore employed or useful in the treatment of HIV, including nucleotide or nucleoside analogues such as PMEA, PMPA, PMEDAP, PMPDAP, DDI, AZT, DDC, D4T, D4AP, bis (POM) PMEA and the like. Such combinations are selected based on the condition to be treated, cross-reactivities of ingredients and pharmaco-properties of the combination.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of structure I, II, or III with a mammal for a period of time sufficient to yield a metabolic product of the compound. Such products typically are identified by preparing a radiolabeled (e.g. $C^{14}$ or $H^3$) compound of structure I, II, or III, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of structure I, II, or III—even if they possess no HIV protease inhibitory activity of their own. Particular compounds are products of cytochrome-mediated oxidation. These include oxidation of aryl groups to phenolic groups and amino to hydroxyl. They are identified by incubating the compounds described herein with liver cytochrome preparations in conventional fashion.

Immunogens Antibodies, and Assays.

The compounds of this invention, or the biologically active substances produced from these compounds by hydrolysis or metabolism in vivo, are used as immunogens to prepare antibodies capable of binding specifically to the compounds or their metabolic products which retain immunologically recognized epitopes (sites of antibody binding). The immunogenic compositions therefore are useful as intermediates in the preparation of antibodies for use in diagnostic, quality control, or the like methods or in assays for the compounds or their novel metabolic products.

The hydrolysis products of interest include products of the hydrolysis of protected acidic groups (such as carboxylic acids and phenols), hydroxy groups, and basic groups (such as amines). The metabolic products described above may retain a substantial degree of immunological cross reactivity with the compounds of the invention. Thus, the antibodies of this invention will be capable of binding to the inhibitor compounds of the invention without binding to the non-inhibitory protected compounds; alternatively the metabolic products, will be capable of binding to the non-inhibitory protected compounds and/or the metabolitic products without binding to the inhibitory compounds of the invention, or will be capable of binding specifically to any one or all three. The antibodies desirably will not substantially cross-react with naturally-occurring materials (other than naturally produced metabolites as discussed above). Substantial cross-reactivity is reactivity under specific assay conditions for specific analytes such that it interferes with the assay results.

The immunogens of this invention contain the compound presenting the desired epitope in association with an immunogenic substance such as an antigenic polypeptide. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1–100, typically, 1–25, more typically 1–10 carbon atoms to the immunogenic substance. The conjugates are separated from starting materials and by products using chromatography or the like, and then are sterile filtered and vialed for storage.

The compounds of this invention are cross-linked for example through any one or more of the following groups: a hydroxyl group of E, G, J, L, T, or U; a carboxyl group of E, G, T, or T; a carbon atom of the compound of formulas I, II, or III in substitution of H and/or an amine group of E, G, J, L, T, or U.

Animals are typically immunized against the immunogenic conjugates or derivatives by combining 1 mg or 1 $\mu$g of conjugate (for rabbits or mice, respectively) with 3 volumes of Freund's complete adjuvant and injecting the solution intradermally at multiple sites. One month later the animals are boosted with $\frac{1}{5}$ to $\frac{1}{10}$ the original amount of conjugate in Freund's complete adjuvant (or other suitable adjuvant) by subcutaneous injection at multiple sites. 7 to 14 days later animals are bled and the serum is assayed for the desired antibody titer. Animals are boosted until the titer plateaus. Preferably, the animal is boosted with the conjugate in which the precursor or product is linked to a different protein, through a different cross-linking agent or both. Optionally, aggregating agents such as alum are used to enhance the immune response.

After immunization, monoclonal antibodies are prepared by recovering immune lymphoid cells (typically spleen cells or lymphocytes from lymph node tissue) from immunized animals and immortalizing the cells in conventional fashion, e.g., by fusion with myeloma cells or by Epstein-Barr virus transformation and screening for clones expressing the desired antibody. The hybridoma technique described originally be Kohler and Milstein, *Eur. T. Immunol.* (1976) 6:511 has been widely applied to produce hybrid cell lines that secrete high levels of monoclonal antibodies against many specific antigens.

It is possible to fuse cells of one species with another. However, it is preferably that the source of the immunized antibody producing cells and the myeloma be from the same species.

The hybrid cell lines are maintained in culture in vitro. The cell lines of this invention are selected or maintained in a hypoxanthine-aminopterin thymidine (HAT) medium. However, the established hybridoma cell line can be maintained on a variety of nutritionally adequate media. The secreted antibody is recovered from culture by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of test samples.

The antibodies of this invention are obtained from any animal species, but ordinarily are from murine or rat. Once a monoclonal antibody having the desired specificity and affinity is obtained, other conventional modifications of the antibodies are within the scope of this invention. For example, the complementarity determining regions of an animal antibody, together with as much of the framework domain as is needed, are substituted into an antibody of another animal species or class to produce a cross-class or cross-species chimeric antibody. Fragments or other amino acid sequence variants of monoclonal antibodies also are encompassed within the meaning of antibody as that term is used herein, for example, Fab, Fab' or (Fab')2 fragments, single chain antibodies, bi or poly specific antibodies, and the like.

The antibodies of this invention are from any suitable class or isotype, e.g. IgG, IgM, IgA, IgD or IgE. They may or may not participate in complement binding or ADCC.

Typically, hybridomas which are capable of binding to the immunogen are screened for the ability to bind to the hapten itself in typical test samples (plasma, serum and the like) with the requisite degree of affinity. The desired affinity will depend upon the use intended for the antibody, but should be adequate to function in a conventional competitive-type ELISA or radioimmunoassays, or in conventional EMIT immunoassays.

The antibodies of this invention are used in such assays together with a labeled form of the compounds of the invention. Alternatively, the antibody is labeled. Suitable labels are well-known and include radioisotopes, enzymes, stable free radicals, fluorophors, chemiluminescent moieties and other detectable groups heretofore employed to prepare covalent conjugates for use in assays. Methods for linking the labels to ligand amino groups, or amino acid side chains or termini of polypeptides, are known and are suitable for use herein. Other suitable linking methods will be apparent to the ordinary artisan. Labels are conveniently bound to the thiepanes herein at the same sites used for bonding to antigenic polypeptides.

The antibodies and labeled ligands herein optionally are assembled into kits for use in therapeutic drug monitoring or evaluation, or for process quality control, and used in the conventional manner.

The invention also relates to methods of detecting HIV protease in a sample suspected of containing HIV protease comprising the steps of: treating a sample suspected of containing HIV protease with a composition comprising a compound of the invention bound to a label; and observing the effect of the sample on the activity of the label.

Compositions of the invention are inhibitors of HIV protease. As such frequently the compositions will bind to locations on the surface or in a cavity of HIV protease having a geometry unique to HIV protease. Compositions binding HIV protease may bind with varying degrees of reversibility. Those compounds binding substantially irreversibly are ideal candidates for use in this method of the invention. Once labeled, the substantially irreversibly binding compositions become probes for the detection of HIV protease.

Uses of the Compounds of the Invention.

Compositions of the invention are screened for inhibitory activity against HIV protease by any of the conventional techniques for evaluating enzyme activity. Within the context of the invention, typically compositions are first screened for inhibition of HIV protease in vitro and compositions showing inhibitory activity are then screened for activity in vivo. Compositions having in vitro Ki (inhibitory constants) of less then about $5 \times 10^6 M$, typically less than about $5 \times 10^7 M$ and more typically less than about $5 \times 10^8 M$ are excellent candidates for in vivo screening.

Useful in vitro screens have been described in detail and will not be elaborated here. However, the above cited work of Billich, A.; Billich, S.; and Rosenwirth, B; *Antiviral Chem. & Chemoth.*, 1991, 2(2), 65–73, discloses suitable assays for HIV protease.

Useful in vivo screens have also been described. The above cited work of Wong, Y.; Burcham, D.; Saxton, P.; Erickson-Viitanen, S.; Grubb, M.; Quon, C.; and Huang, S.-M.; *Biopharm. & Drug Disp.*, 1994, 15, 535–544, discloses suitable pharmacokinetic evaluation of HIV protease inhibitors in rats and dogs.

Another typical assay is described below in the Examples section of this specification.

The compositions of the invention bind HIV protease. Accordingly, they are useful in any of the assay methods described. They are also inhibitors of HIV protease, and as a result are useful as negative controls and analytical standards in any of the described methods of assay for HIV protease activity. These uses are distinct in that a composition of the invention which binds HIV protease, whether in an inhibitory manner or not, is useful for immobilizing HIV protease in any heterogeneous assay system. A composition which inhibits HIV protease is useful for suppressing HIV protease in an assay which detects HIV protease activity, thereby acting as a negative control or analytical standard.

Another aspect of the invention relates to methods of inhibiting the activity of HIV protease comprising the step of treating a sample suspected of containing HIV protease with a composition of the invention.

Within the context of the invention samples suspected of containing HIV protease include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells; and the like. Typically the sample will be suspected of containing an organism which produces HIV protease, frequently a pathogenic organism such as a virus, most typically, HIV. Samples can be contained in any medium including water and organic solvent/water mixtures. Typically, samples include living organisms such as mammals and man made materials such as bioproduct samples, more typically, samples include humans.

The treating step of the invention can involve adding the composition of the invention to the sample or it can involve adding a precursor of the composition to the sample. The addition step comprises any method of administration as described above.

If desired, the activity of HIV protease after application of the composition can be observed by any method including direct and indirect methods of detecting HIV protease activity. Quantitative, qualitative, and semiquantitative methods of determining HIV protease activity are all contemplated. Typically one of the screening methods described above are applied, however, any other method such as observation of the physiological properties of a living organism are also applicable.

The compounds of the invention are polyfunctional. As such they represent a unique class of monomers for the synthesis of polymers. By way of example and not limitation, the polymers could include polyamides and polyesters. Polyamides and polyesters are materials of well known utility and the present monomers provide access to polymers having unique pendent functionalities.

Polymers are prepared from the compounds of the invention by conventional techniques. Polyesters are prepared from the compounds having a carboxylic acid group and an alcohol or other leaving group. Alternatively, a diol composition of the invention is reacted with a diacid monomer. Polyamides are prepared from the compounds of the invention containing one or more amine groups.

The compounds of the invention are also a unique class of polyfunctional surfactants. The sulfur group Qa and the groups comprising E, G, T, and U having a chain of carbon atoms are spatially separated by the 7-membered ring structure and thus have the properties of bi-functional surfactants. As such they have useful surfactant, surface coating, emulsion modifying, rheology modifying and surface wetting properties.

As polyfunctional compounds with defined geometry and simultaneously carrying polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms in groups E, G, T, or U. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters with a compound of the invention having one or more —OH groups; 2) separating the diastereomers; and 3) hydrolyzing the ester structure. Racemic acids are also separated by amide formation with an amine function of the molecule of the invention. Further, such a method can be used to resolve the compounds of the invention themselves if optically active acids, bases or alcohols are used instead of racemic starting materials.

Exemplary Methods of Making the Compositions of the Invention General

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985); as well as "Comprehensive Organic Synthesis. Selectivity, Strategy & Efficiency in Modern Organic Chemistry. In 9 Volumes.", Barry M. Trost, Editor-in-Chief (Pergamon Press, New York, 1993 printing). Many known techniques for manipulating the sulfur atom of the compositions of the invention are described in Reid, E. Emmet; "Organic Chemistry of Bivalent Sulfur", vol. 1, 1958, vol. 2, 1960, vol.3, 1960, vol. 4, 1962, vol. 5, 1963, and vol. 6, 1965 (Chemical Publishing Company, New York).

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, workup procedures, and the like, will be those common in the art for the particular reaction to be performed. The incorporated reference material, together with material cited therein, contains detailed descriptions of such conditions. Typically the temperatures will be $-100°$ C. to $200°$ C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about $20°$ C.) or at temperatures corresponding to the boiling point of solvents used in the reaction, although for metal hydride reductions frequently the temperature is reduced to $0°$ C. to $-100°$ C. Solvents are typically protic for sodium borohydride reductions and may be either protic or aprotic for oxidations. More typically, oxidations of hydroxy groups pendant on the thiepane ring to form corresponding carbonyls are carried out in refluxing toluene. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. More typically, Claisen-Schmidt condensations are carried out in refluxing toluene. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

In the schemes P indicates a hydrolytic ally cleavable protecting group. Such groups have been described in the above cited work of Greene. Ordinarily such groups include silyl ethers, esters, amides and the like.

Scheme 1

The starting thiepane diols for these preparations are available from D-mannitol and D-sorbitol by literature methods. U. Kuszmann and P. Sohar. Carb Res. 56, 105–115 (1977) for D-manno and L-idito and J. Kuszmann and P. Sohar. Carb Res. 48, 23–32 (1976) for D-sorbito.) The enantiomeric series (illustrated as diols 1) is available in analogous fashion from L-mannonolactone and L-glucuronolactone after sodium borohydride reduction by the method of H. L. Frush, H. S. Isbell, J. Am. Chem. Soc. 78, 2844–2846 (1956).

Combined Oppenhauer oxidation, C. Djerassi Org. Reactions, 6, 207 (1951) and Claisen-Schmidt condensation, House p 633, Modern Synthetic Reactions 2nd ed., W. A. Benjamin, Menlo Park Ca (1972); G. A. Hill and G. M. Bramann, Org. Syn. Coll Vol 1, 81 (1944); C. S. Marvel and W. B. King Org. Syn. Coll Vol 1, 252 (1944) provide the α-β unsaturated ketones 2.

Simultaneous conjugate reduction and ketone reduction by methods such as those described in N. Greeves "Reductions of C=O to CHOH by Metal Hydrides" p 1–78 in Vol. 6 sect 1.1 of Comprehensive Organic Synthesis, Trost and Fleming Ed. Pergamon Press (1991) provides the saturated alcohols 3. In particular, nickel based conjugate reduction, L. Mordenti, J. J. Brunet and P. Caubere, JOC, 44, 2203 (1979); J. J. Brunet, L. Mordenti and P. Caubere, JOC, 43, 4804 (1979); and P. Caubere, Ang. Chem. Int. Ed. Engl. 22, 599 (1983) minimizes the amount of allylic alcohol obtained in the reduction.

Repeating this two step sequence appends the second carbon bound substituent in a less stereoselective fashion from which the diastereomeric thiepane diols 5, 6 and 7 are obtained, readily separable by chromatography.

Scheme 2

Diols 5, 6 or 7 are individually alkylated by methods such as the Williamson ether synthesis described in March Advanced Organic Chemistry Org. 2nd, reaction 0–14 p 357 and Feuer and Hooz, pp446–450, 460–468 in The Chemistry of the Ether Linkage, S. Patai Ed., Interscience Pub., New York, N.Y. (1967) or arylated C. Paradisi "Arene Substitution via Nucleophilic Addition to Electron Deficient Arenes" p423–450 in Comprehensive Organic Synthesis V4 sect 2.1, Trost and Fleming Ed., Pergamon Press, (1991); J. B. Hynes, J. Heterocyclic Chem. 25, 1173–1177 (1988); or reductively alkylated such as is described by S. Hatakeyama, H. Mori, K. Kitano, H. Yamada and M. Nishizawa, Tet. Lett. 35, 4367–4370 (1994) to provide mono- or diethers 8. Monoethers may be etherified with the different groups to provide unsymetrically substituted diethers 8.

Diols 5–7 may also be acylated with a variety of methods to form esters or carbamates 8.

Removal of the acetonide group under standard conditions, L. F. Wiggins, J. Chem. Soc. 13 (1946) gives the thiepane diol 9.

Oxidation, B. M. Trost, D. P. Curran, Tet. Lett. 22, 1287 (1981); K. S. Webb., Tet. Lett. 35, 3457–3460 (1994) gives the corresponding sulfoxide 10 or sulfone 11 analogs depending on the reaction stoichiometry.

Alternatively the acetonide may be retained to the end and removed after sulfur oxidation. This sequence is advantageous for those stereochemical relationships (idito) which favor sulfur participation and resulting ring contraction, J. Kuszmann and P. Sohar., Carb Res. 56, 105–115 (1977).

The diols 9 are converted to the corresponding epoxides 11 by methods such as those described in O. Mitsunobu "Synthesis of Alcohols and Ethers" p25–31 in Vol. 1 sect 1.1.3.2 of Comprehensive Organic Synthesis, Trost and Fleming Ed., Pergamon Press (1991); D. R. Hicks and B. Fraser-Reid, Synthesis 203 (1974); and 0. Mitsunobu et al. Chem. Lett. 1613 (1980)).

The corresponding epoxy sulfoxides 12 and sulfones 13 are obtained by oxidation as described above.
Scheme 3

Alternatively, the thiepane diols 1 are oxidized by Dess-Martin reagent R. E. Ireland and L. Liu, J. Org. Chem. 58, 2899 (1993); D. B. Dess and J. C. Martin, J. Am. Chem. Soc. 113, 7277 (1991) to the symmetrical diketone 14 which is converted to its bis lithium or silyl enolate, E. J. Corey and A. W. Gross, Tet. Lett. 25, 495 (1984) and T. H. Chan "Enol Ethers" p 595–628 in Vol. 2 sect 2.3 of Comprehensive Organic Synthesis, Trost and Fleming Ed., Pergamon Press (1991) and then mono or bis-alkylated by methods such as those discussed in Drury Caine "Alkylation of Enolates" p 1–63 in Vol. 3 sect 1.1 of Comprehensive Organic Synthesis, Trost and Fleming Ed., Pergamon Press (1991) to give the diketone 15. 15 is also obtained by Dess-Martin oxidation of the unsymmetrical diol 7. Reduction with sodium borohydride in methanol stereoselectively provides the symmetrical diol 5.
Scheme 4

The initial thiepane diols 1 may also be oxidized to the diastereotopic sulfones 16, 17 or 18 by methods described earlier. Generation of the sulfone polyanion and carbon alkylation, A. Krief "Alkylation of Sulfur and Selenium Containing Carbanions" p 85–191 in Vol. 3 sect 1.3 of Comprehensive Organic Synthesis, Trost and Fleming Ed., Pergamon Press (1991); V. Cere, Tet. Lett. 5239 (1978); R. Tanikaga et al., Tet. Lett. 28, 3705 (1987); T. Sato et al., Tet. Lett. 28, 5677 (1987) provides the diastereomeric relationships 19, 20 and 21. Subsequent O-alkylation, arylation or acylation and acetonide removal as discussed for Scheme 2 provide the sulfone diols 22, 23 or 24. Alternatively, the thiepane diols 1 can be O-alkylated, converted to the sulfones and then C-alkylated to provide the same isomers, H. Altenbach, pp 359–372 in Antibiotics and Antiviral Compounds, K. Krohn, H. A. Kirst and H. Maag Ed., VCH Publishers, Inc., New York, N.Y. (1993). The choice of reaction sequences depends on the physical and mechanical properties of the intermediates.
Scheme 5

The epoxy derivatives 25 are converted to azido alcohols 26 or 27 or amino alcohols 28 or 29 by methods such as those discussed in O. Mitsunobu "Synthesis of Amines and Ammonium Salts" p65–101 in Vol. 6 sect 1.3 of Comprehensive Organic Synthesis, Trost and Fleming Ed., Pergamon Press (1991).

The epoxides are also reduced by methods such as those discussed in S. Murai "Reduction of Epoxides" p871–893 in Vol. 8 sect 4.4 of Comprehensive Organic Synthesis, Trost and Fleming Ed., Pergamon Press (1991) and Y. Fort et al. Tet. Lett. 26, 3111 (1985) to provide the monoalcohol analogs 30 and 31.

Azido alcohols 26 or 27 after adjustment of the sulfur oxidation state are reduced to the corresponding amino alcohols 28 or 29 by methods such as those listed in R. C. Larock, p 409–410 in Comprehensive Organic Transformations, VCH Publishers, New York, N.Y. (1989).
Scheme 6

The acetonide of dimethyl L-tartrate 32 is converted into the diketone 33 by the method of I. Kikkawa and T. Yorifuji, Synthesis 877–880 (1980). The bis-silyl enol ether 34 is prepared by the methods of H. Emde et al., Liebigs Ann. Chem. 1643 (1981); S. Torkelson and C. Ainsworth, Synthesis 431 (1977); or other methods as discussed in T. H. Chan "Enol Ethers" p 595–628 in Vol. 2 sect 2.3 of Comprehensive Organic Synthesis, Trost and Fleming Ed., Pergamon Press (1991).

The bis-enol ether 34 is cyclized via SCl2 according to the method of M. Muehlstaedt, D. Martinez and P. Schneider, J. Prakt. Chemie. 315, 940–948 (1973) to diketone 15 which is reduced to diol 5 as discussed before.

Alternatively 34 is halogenated by methods such as J. Org. Chem. 39, 1785 (1974), J. Org. Chem. 52, 3346 (1987) and Synthesis 194 (1976) to the bis haloketone and cyclized with sulfide reagents such as NaHS or Na2S to give the cyclic diketone 15.
Scheme 7

The lactol 35 obtained from an inositol derivative according to Fujami, Tet. Lett. 4771 (1967) is converted by the method of I. Kikkawa and T. Yorifuji, Synthesis 877–880 (1980) to the keto alcohol 36. Stereoselective reduction by methods such as T. Nakata et al., Tet. Lett. 24, 2653 (1983) or others as discussed in N. Greeves "Reductions of C=O to CHOH by Metal Hydrides" p 1–78 in Vol. 6 sect 1.1 of Comprehensive Organic Synthesis, Trost and Fleming Ed., Pergamon Press (1991) provides the diol 37. Activation with tosylate and displacement by sulfide provides the thiepane bisacetonide 38. Partial deprotection and equilibration of the acetonide in analogy to J. Kuszmann, P. Sohar, C. Horvath, Carb. Res. 50, 45–52 (1976) provides the thiepane diol 39 which is manipulated in accord with Schemes 2 and 5.
Scheme 8

Diol 7 obtained as described in Scheme 1 is monoalkylated to ether 40, either directly or via a monoprotected intermediate. After oxidation to the sulfone 41, the equatorial alcohol is eliminated via methanesulfonylchloride and triethyl amine in methylene chloride to vinyl sulfone 42. Michael addition of various nucleophiles such as amines, thiols or carbon based nucleophiles such as cuprates provides structures such as 43 or its stereoisomers. Deprotection provides the diol sulfones 44. The preparation and reactions of vinyl sulfones are reviewed in Simpkins, N. S. "Sulphones in Organic Synthesis", Pergamon Press, Oxford (1993).

Scheme 9

Diol 5 is activated by acylation or alkylation to 45 followed by oxidation to the corresponding sulfone 46. Base induced elimination provides the divinyl sulfone 47. Other diol stereoisomers may be oxidized to the sulfone first and then dehydrated to the desired sulfone 47. Nucleophilic addition with amines, or thiols gives 48, or 50. Alkoxy nucleophiles will provide O-linked structures such as 64 (Scheme 12). With some nucleophiles, the elimination and Michael addition may occur in the same pot to provide the adducts directly from 46. Acetonide removal provides the sulfone diol 49, or 51.

Scheme 10

An alternative route to the divinyl sulfone 47 involves condensation of sulfone 54 with L-tartaric ester-derived dialdehyde 55 followed by dehydration.

Scheme 11

Tosyl acetate 56, derived from L-mannitol as described in Example 1 is converted to the thioether 57. Alkylation or arylation of the free hydroxyls to 58 followed by sulfur oxidation to diastereomeric sulfoxides 59 and Pummerer rearrangement gives 60 as a protected version of the dialdehyde 61. Nucleophilic addition to the aldehyde function provides the diol 62. Stereoselectivity in this addition can be controlled by the adjacent chiral centers and by the use of various additives such as Lewis acids or cosolvents to enhance or diminish inherent directing affects. Alternatively, diastereomers of diol 62 can be oxidized to the corresponding diketone and reduced to the desired stereochemistry. After activation of the hydroxyls to structures 63, ring closure to structures 8 will occur. Oxidation to sulfones 64 and deprotection provides the sulfone diols 11.

Scheme 12

The order of sulfur oxidation and acetonide removal can be altered at will as illustrated. Diastereomers of 8 with equatorial oxysubstituents may undergo ring contraction under acid catalysed deprotection at the sulfide oxidation state. Such rearrangements are minimized from the sulfoxide 65 or sulfone 64 oxidation states.

Scheme 13

The dialdehyde 61 is a versatile intermediate which can be olefinated to the diene 65 or epoxidized to 66, directly or via 65. Thiepane ring formation can occur to provide diol 67 (R=H). Regioselectivity of the epoxide opening and ring closure reactions can be moderated by the steric and electronic characteristics of the R" substituent as well as by solvent and counter ion effects. Thiepane 67 can be converted to diol sulfones in a variety of routes, retaining the extra alkoxy substituents or eliminating them to olefin or saturated side chains as illustrated in structures 8 or 68. Divinyl sulfone 68 can be further elaborated by conjugate addition reactions similar to those described in Scheme 8 or by conjugate reduction to provide saturated structures such as 64 (Scheme 11).

Scheme 14

The tartrate derived silyl enol ether may be condensed with thionyl chloride to give the diketosulfoxide 70 which can be reduced to thiepane diol 5 or oxidized to the sulfone 71 and then reduced and eliminated to give the divinyl sulfone 47. The reaction of silyl enolethers with thionyl chloride is described in B. Zwanenburg, "Phosphorus, Sulfur and Silica" 43, 1–24 (1989).

Scheme 15

Chiral 102 is readily available by routes described in C. R. Johnson, P. A. Ple, L. Su, M. J. Heeg, J. P. Adam., Synlett 338 (1992) and L. Dumortier, P. Liu, S. Dobbelarere, J. Van der Eycken, M. Vanderwalle., Synlett, 243 (1992). Another preparation of 104 is described by H-J Altenbach in Antibiotics and Antiviral Compounds, Chemical Synthesis and Modification, Eds.; K. Krohn, H. A. Kirst, H. Maag: VCH Publishning Inc., p. 359 (1993). Saponification of acetate 104 followed by alkylation with benzylbromide in the presence of sodium hydride in THF provides 105 which is subjected to ozonolysis to produce 106. Chelation controlled addition of benzyl Grignard reagent to aldehyde 106 leads to 107. Mesylation of 107 and hydrogenolysis of benzyl groups followed by treatment of the hydroxy mesylate with DBU generates epoxide 108. Formation of the seven membered ring sulfide 109 is accomplished by epoxide opening with Na2S.

Scheme 16

The mixture of ketoalcohols (Table 101, compounds 31 and 32) are condensed with alkyl amines under conditions of reductive amination to provide the amino alcohols 201. Etherification of the hydroxy function followed by oxidation with Oxone in methanol without buffering, provides the sulfone 203. Deprotection gives the aminodiol sulfone 204.

Schemes 17

Treatment of vinyl sulfone 42 with benzyl amine in refluxing ethanol affords the amino sulfone 205. Deprotection in 95% TFA/water at 85° for 2 hrs affords the diol 206.

Scheme 18

Alternatively 42 is deprotected in 50% TFA/30% methanol/20% water for 30 minutes to provide the vinyl sulfone diol 207. Treatment of 207 with various primary amines in refluxing solvents such as ethanol or toluene provides the aminosulfones 208.

Scheme 19

Monoalcohols 209 or 41 are oxidized to the keto sulfones 210. Enamine formation to the vinylogous sulfonamides 211 will occur under dehydrating conditions such as azeotropic removal of water, or treatment with drying agents such as molecular sieves or magnesium sulfate. Reduction of the enamine provides the aminosulfones 212.

Scheme 20

The bis-nitrone 215 derived from the corresponding known tartaric dialdehyde derivative, A. Krief, et al., Tetrahedron, 45, 3039–3052 (1989) by methods such as those described in A. Dondoni, Syn. Comm. 24, 2537–2550 (1994) is condensed with divinyl sulfones 216, prepared from aldehydes according to H. J. Backer, Recueil, 72, 119 (1953), to afford the bisisoxazolidines 217 in analogy to P. Deshong et al., JACS 106, 5598 (1984). Reductive cleavage of the N—O bond affords the diol 218 which is dehydrated to the exocyclic divinylsulfone 219. Michael addition of N, S, O or C based nucleophiles provides the aminosulfones 220. Alternatively, when R" is not hydrogen, hydrogenolysis or dehydration/reduction may afford the corresponding amionosulfones 220. Deprotection provides the aminodiols 221.

Scheme 21

Alternatively the bisisoxazolidines 217 can be built sequentially by the condensation of known nitrones 222, S. Saito et al., Synlett, 282–284 (1994) with divinylsulfones 216 to provide the monocyclic isoxazolidine 223. Deprotection of the protected primary alcohol function is followed by oxidation to the aldehyde 224. Condensation with an N-substituted hydroxylamine provides the nitrone 225 which can then undergo an intramolecular cycloaddition reaction to 217 optionally deprotected to sulfone diol 226.

Scheme 25

The starting tartrate esters 251 are available from natural L-tartaric acid by literature methods, L. T. Rossaano, Tet. Lett., 36, 4967 (1995).

Treatment with N,O-dimethylhydroxylamine, S. Nahm, Tet. Lett., 39, 3815 (1981) provide the bis-amides 252 which can be used to acylate metalated sulfides, sulfoxides or sulfones 253, to afford keto amides 254 after acid hydrolysis. Subsequent α-thio metalation and intramolecular acylation provide diketones 255. Additionally, diketones 255 may be available directly from bis-amides 252 via acylation of thio 1,3-dianions, E. M. Kaiser, Tet. Lett., 3341 (1967); S. Patai, Ed., "The Syntheses of Sulphones, Sulphoxides and Cyclic Sulphides", J. Wiley & Sons, New York, N.Y. (1994).

Reduction with sodium borohydride in methanol stereoselectively provides the symmetric diols 256.

O-alkylation, arylation or acylation (as discussed herein) followed by sulfer oxidation, B. M. Trost, Tet. Lett. 22, 1287 (1981) afford the corresponding sulfone analogs 257.

Scheme 26

Keto amides 254 are also available in sequential fashion starting from diols 258, S. Terashima, Tet. Lett. 23, 4107 (1982) and L. J. Rubin, J. Am. Chem. Soc. 74, 425 (1952).

Mono protection followed by oxidation and esterification provide esters 259 which are converted to the corresponding N-methoxy-N-methyl amides 260 as described in Scheme 25. Acylation of sulfer reagents 253 then provide ketones 261.

Deprotection of the remaining primary alcohol provides an appropriate substrate on which to repeat the oxidation, esterification and amide formation sequence, which provide the keto amides 254.

Scheme 27

Tartrate esters 251 are reduced to dialdehydes 262 with DIBAL, A. Krief, Tetrahedron, 45, 3039 (1989).

Alkylation of metalated sulfer reagents 253 provide alcohols 263 or diols 264 directly if 1,3-dianions are utilized (as discussed in Scheme 25).

Oxidation of diols 264 by the Dess-Martin periodinane reagent, D. B. Dess, J. Am. Chem. Soc. 113, 7277 (1991) provide diones 255.

Scheme 28

Mono protection and oxidation of diols 258 provide aldehydes 265 (H. Iida, J. Org. Chem., 52, 3337 (1987) and T. Mukaiyama, Tetrahedron, 46, 265 (1990). Treatment of aldehydes 265 with metalated sulfer reagents 253 allow access to the mono protected diols 266. Protecting group removal followed by oxidation provide aldehyde intermediates 263.

Scheme 29

Acylation, B. M. Trost, Ed., Comp. Org. Synth. Vol 2, Pergamon Press, Tarrytown, N.Y. (1991) of the bis-enol ethers derived from sulfer reagents 267, M. T. Reetz, Org. Syn. Coll. Vol. VII, 424 (1990) afford the bis-1, 3-diketones 269.

Conjugate reduction, C. M. Belisle, Tet. Lett. 35, 5595 (1994) and E. Yoshii, Chem. Pharm. Bull. 25, 1468 (1977) provides diols 270. O-alkylation, arylation or acylation and sulfer oxidation (described herein) provide sulfones 271.

Scheme 30

Acylation of the mono enol ether derived from sulfer reagents 267 with N-methoxy-N-methyl amides 260 (Scheme 26) as described in Scheme 29, provide the 1,3-diketones 272.

Alcohol deprotection and conversion to the corresponding N-methoxy-N-methyl amides as described in Scheme 26 allow access to keto intermediates 269.

Scheme 31

Wittig olefination of dialdehydes 262, A. Krief, Tetrahedron, 45, 3039 (1989) stereo selectively provide (Z,Z)-1,5-dienes 273.

Directed epoxidation, J. Rokash, Tet. Lett. 22, 979 (1981) afford di-epoxides 274 which provide thiepanes 256 upon treatment with $Na_2S$. Alternatively, epoxide opening can be performed sequentially via basic hydrolysis of intermediates 275.

Scheme 32

A stepwise route toward intermediate 279 also allow access to thiepane 256.

Wittig olefination of aldehydes 265 provide (Z)-olefins 276. Directed epoxidation followed by nucleophilic opening affords alcohols 278.

O-alkylation, arylation or acylation of the secondary alcohol and deprotection/oxidation of the primary alcohol give aldehydes 279 which can be converted to oxiranes 275 by repeating the initial two step sequence described in Scheme 31.

Scheme 33

Horner-Emmons olefination with (2,2,2-trifluoroethoxy) phosphonates selectively afford the symmetrical α,β-unsaturated esters 280, D. Boschelli, Tet. Lett., 26, 5239 (1985) and H. Kotsuki, J. Org. Chem., 54, 5153 (1989).

Lithium aluminum hydride reduction, G. R. Newkome, J. Org. Chem., 52, 5480 (1987) give allylic alcohols 281 which undergo Sharpless asymmetric epoxidation, T. Katsuki, J. Org. Chem., 47, 1373 (1982) to provide 282.

Hydroxyl protection followed by epoxide opening as described in Schemes 31 and 32 afford thiepanes 285.

O-alkylation, arylation or acylation provide the bis-hydroxymethyl thiepanes 286.

Interconversion of the free hydroxyls to suitable leaving groups (e.g. mesylates, tosylates, halides, etc.), nucleophilic displacement and sulfide oxidation afford sulfones 257.

Scheme 34

Epoxides 284 can also be assembled in stepwise fashion following the general protocol described in Scheme 32.

Horner-Emmons reaction of aldehydes 265 with (2,2,2-trifluoroethoxy)phosphonates provide (Z)-olefins 287.

Ester reduction followed by Sharpless asymmetric epoxidation afford oxiranes 288. Nucleophilic ring opening and primary alcohol protection give intermediates 289 which can be homologated to epoxides 284 as described in Scheme 32.

Scheme 35

An optional method to stereo selectively prepare bis-(Z)-olefins 273 involve a formyl to ethynyl conversion as described by E. J. Corey, Tet. Lett. 3769 (1972). Treatment of dialdehydes 262 with $CBr_4$ and $PPh_3$ afford intermediate bis-vinylidene dibromides which undergo elimination and metal halogen exchange upon treatment with alkyllithium bases. The resultant terminal alkynes can be isolated, remetalated, and homologated to provide bis-alkynes 290 or obtained directly by alkylation of the intermediate alkynyllithium.

Partial reduction of 290 utilizing the Lindlar protocol, H. Lindlar, Org. Syn. Coll. Vol. V, 880 (1973) provide bis-(Z)-olefins 273 which can be further manipulated as described in Scheme 31.

Scheme 36

An alternative method to stereo selectively prepare (Z)-olefins 276 involve a formyl to ethynyl conversion as described by E. J. Corey, Tet. Lett. 3769 (1972). Treatment of aldehydes 265 (described herein) with $CBr_4$ and $PPh_3$ afford intermediate vinylidene dibromides which undergo elimination and metal halogen exchange upon treatment with alkyllithium bases. The resultant terminal alkynes can be isolated, remetalated, and homologated to provide alkynes 291 or obtained directly by alkylation of the intermediate alkynyllithium.

Partial reduction of 291 utilizing the Lindlar protocol, H. Lindlar, Org. Syn. Coll. Vol. V, 880 (1973) provide (Z)-olefins 276 which can be further manipulated as described in Scheme 32.

Scheme 37

Conversion of diols 258 to bis-halomethyl compounds 292 can be accomplished by treatment with $PPh_3$ and $CX_4$, M. Falorni, J. Org. Chem. 51, 5291 (1986). Treatment of 292 with $PPh_3$ provide the Wittig salts 293.

Access to olefins 273 (Scheme 31) is possible by Wittig reaction between 293 and suitable aldehydes.

Scheme 38

Utilizing mono protected diol 294 (described herein), Wittig salt 296 can be prepared according to the procedure described in Scheme 37.

Olefination of 296 provide 276 which is elaborated to compounds 278 according to Scheme 32. O-alkylation, arylation or acylation of the secondary alcohol, followed by deprotection of the primary alcohol afford compounds which can be subjected to the above sequence (halogenation, Wittig olefination) allowing entry to compounds 275.

Scheme 50

Alkylation of dianion of 54 with allyl bromide affords diene 310. Formation of the seven membered ring compound 311 is accomplished by ring-closing-metathesis (RCM) of 310 by methods described by Grubbs and coworkers, J. Am. Chem. Soc., 114, 7324 (1992). Oxidation of 311 leads to diketone 312, Comprehensive Organic Transformations, Ed. R. C. Larock: VCH Publishers, Inc., pp. 593–594 (1989) and references cite therein which can be reduced to diol 313 ($R_1$, $R_2$=OH). Reductive amination of 312 leads to Diamine 313 ($R_1$, $R_2$=$NHR_5$). In the sequence of reduction and reductive amination affords amino alcohol 313 ($R_1$=$NHR_5$, $R_2$=OH). Di hydroxylation of 313 affords cis-diol 314 ($R_3$=$R_4$=OH). Epoxidation of 313 followed by opening of epoxide gives trans-diol. Hydroboration of 313 provides mono-alcohol 314 ($R_3$=H, $R_4$=OH). R groups depicted in Scheme 50, in particular those of compound 314, are selected to be consistent with the disclosure of the compositions herein. Separation of isomers of compound 314 are performed by conventional methods.

Scheme 51

Condensation of α,β-unsaturated aldehyde and dianion of 54 affords corresponding diene alcohol 315 which is protected to form ether 316. Formation of the seven membered ring compound 317 is accomplished by ring-closing-metathesis (RCM) of 316 by methods described by Grubbs and coworkers, J. Am. Chem. Soc., 114, 7324 (1992). Di hydroxylation of 317 affords cis-diol 318 ($R_3$=$R_4$=OH). Epoxidation of 317 followed by opening of epoxide gives the trans-diol. Hydroboration of 317 provides mono-alcohol 318 ($R_3$=H, $R_4$=OH). R groups depicted in Scheme 51, in particular those of compound 318, are selected to be consistent with the disclosure of the compositions herein. Separation of isomers of compound 318 are performed by conventional methods.

In each of the above exemplary schemes it may be advantageous to separate reaction products from one another and/or from starting materials. The desired products of each step or series of steps are separated and/or purified (hereinafter separated) to the desired degree of homogeneity by techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involve treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Each of the cited works above is incorporated by reference in its entirety. Specifically cited sections or pages of the above cited works are incorporated by reference with specificity at the location of the citation and for the purpose appropriate for the context of the citation. The invention has been described in detail sufficient to allow one of ordinary skill in the art to make and use the subject matter of the following claims. It is obvious that certain modifications of the methods and compositions of the following claims can be made within the scope and spirit of the invention.

Scheme 60

Chiral aldol condensation of butenoic acid derivatives such as 400 using any number of chiral auxiliaries Xc such as those developed by Evans with various aldehydes 401 such as phenylacetaldehyde gives the non-racemic aldol product 402. Hydrolysis provides the β-hydroxyacid 403. Curtius rearrangement provides the cis substituted oxazolidinone 404 which may be optionally alkylated on nitrogen to provide 405. Manipulation of the heterocycle by direct attack by sulfide anion or optionally by hydrolysis of the ring followed by optional protection of the nitrogen and activation of the hydroxyl group and displacement with sulfide dianion provides the symmetrical sulfide 406. Optionally unsymmetrical analogs can be prepared by appropriate manipulation of these intermediates. Optional protection of the nitrogens of 407 followed by ring closure via olefin metathesis as illustrated by H. Schmalz, Angew. Chem. Int. Ed. Engl, 34, 1833 (1995) provides the cyclic sulfides 407 or 408. The oxidation state of these intermediates may be either the sulfide, sulfoxide or sulphone.

Scheme 61

Cis dihydroxylation of 408 provides a single diastereomer 409 which may be deprotected and adjusted to the cis diol diastereomer 413. Cyclization of 409 into the cis protecting group provides the oxazolidinone 410 which allows activation of the remaining hydroxyl and displacement via neighboring group participation to the symmetrical 411. Hydrolysis of the carbamate rings provide the trans diols 412. Final adjustment of sulfur oxidation state may be accomplished at this point if not earlier.

Scheme 62

Methylenation of dialdehydes 450 (prepared by conventional means) afford bis-olefins 451, J. Am. Chem. Soc., 106, 7514 (1984).

Metal carbene facilitated metathesis, G. C. Fu, J. Am. Chem. Soc., 115, 9856 (1993), provide alkenes 452 which undergo cis-dihydroxylation to afford diols 453.

Selective protection of the equitorial hydroxyl followed by oxidation of the remaining axial hydroxyl group provide access to ketones 454. Directed reduction from the least hindered face return diols 455 following alcohol deprotection.

X is selected from:
—N(R)C(=O)N(R)—;
—C(H)(R)C(=O)C(H)(R)—;
—C(H)(R)SC(H)(R)—;
—C(H)(R)S(=O)C(H)(R)—;
—C(H)(R)S(=O)$_2$C(H)(R)—;
—C(H)(R)P(R)C(H)(R)—;
—C(H)(R)P(=O)C(H)(R)—

Other embodiments of X are those found as W on p. 12 of the above cited work of Lam; et. al. (WO 94/19329).

Scheme 63

Compounds 456 are prepared in a manner consistent with Scheme 1, p. 351 of the above cited work of Lam, et. al. (WO 94/19329); Scheme 1 and supporting disclosure of which are incorporated herein by reference.

Methylenation of dialdehydes 456 afford bis-olefins 457, J. Am. Chem. Soc., 106, 7514 (1984).

Metal carbene facilitated metathesis, G. C. Fu, J. Am. Chem. Soc., 115, 9856 (1993), provide alkenes 458 which undergo cis-dihydroxylation to afford diols 459.

Selective protection of the equitorial hydroxyl followed by oxidation of the remaining axial hydroxyl group provide access to ketones 460. Directed reduction from the least hindered face return diols 461 following alcohol deprotection.

Scheme 64

An alternative preparation of bis-olefins 457 is as follows. Condensation of aldehydes 462 with amines 463 provide imines 464. Nucleophilic addition of a vinyl group (e.g. Vinyl lithium, grignard, cuprate, etc.) afford the allylic amines 465 which are resolved to provide optically active 466, J. D. Morrison, Ed., Asymmetric Synthesis, Vol 1, Academic Press, Inc., New York, N.Y. (1983). Alternatively, amines 466 may be available directly from imine 464 via stereoselective organometallic addition. Coupling of amines 466 with an appropriate acylating reagent (e.g. CDI, phosgene, etc.) afford bis olefins 457.

Scheme 1

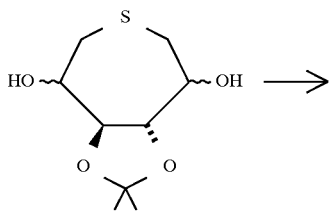

1

-continued

Scheme 1

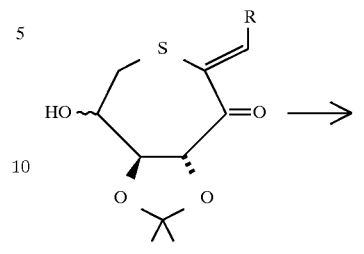

2

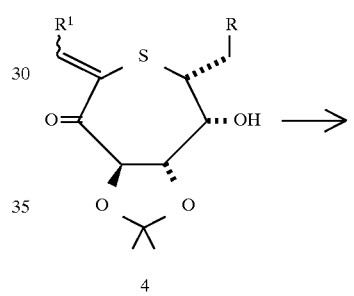

3

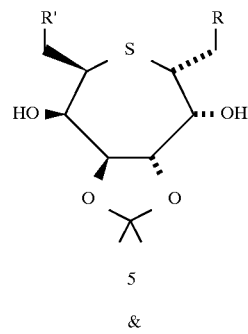

4

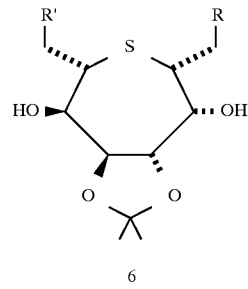

5
&

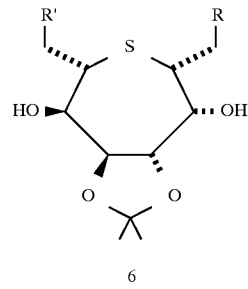

6
&

Scheme 1
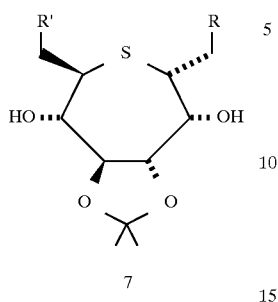
Scheme 2
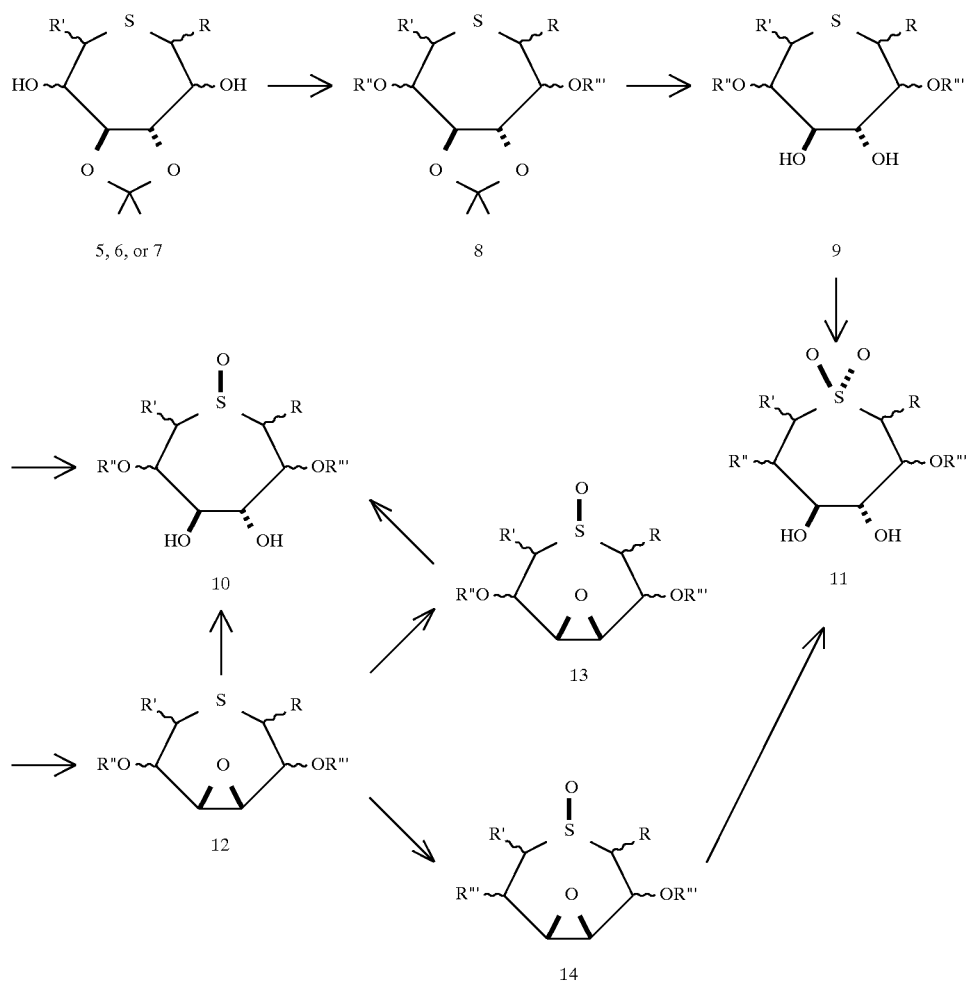

Scheme 3
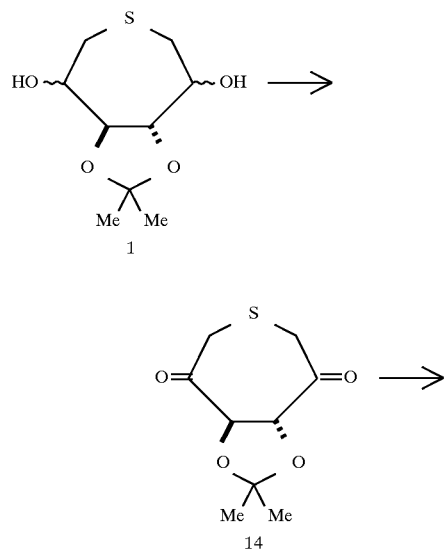
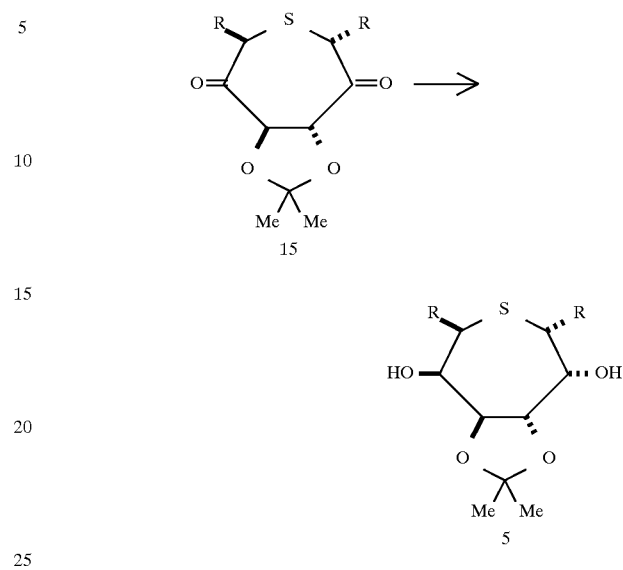
Scheme 4
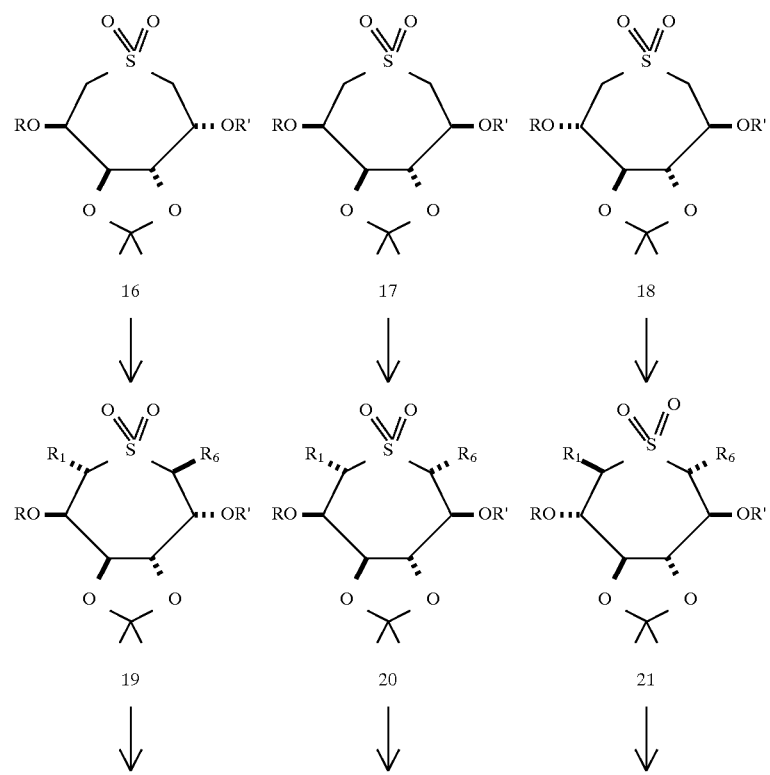

-continued
Scheme 4
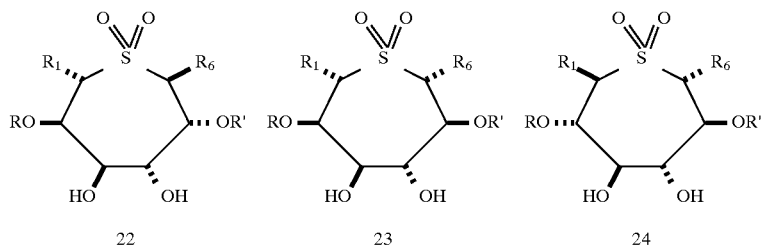
Scheme 5
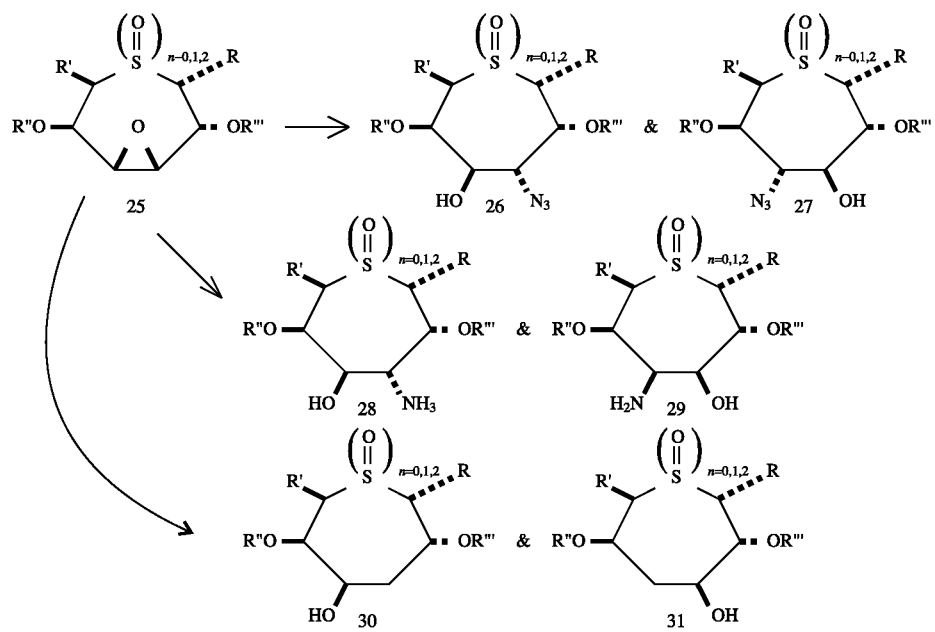
Scheme 6
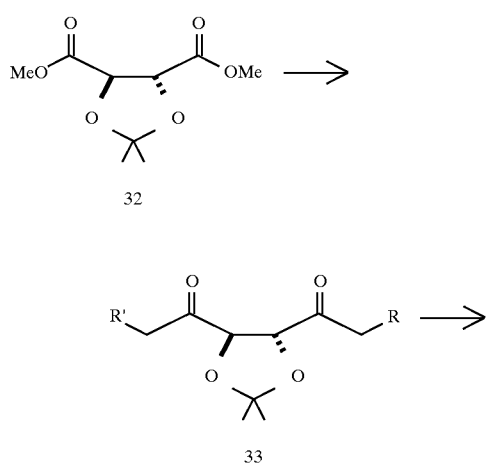
-continued
Scheme 6
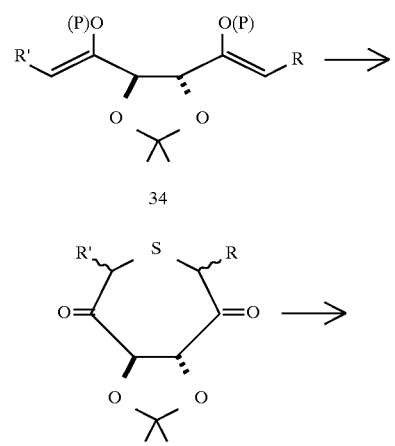

-continued
Scheme 6
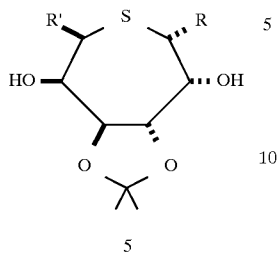
5
(P) = hydroxy protecting group
Scheme 7
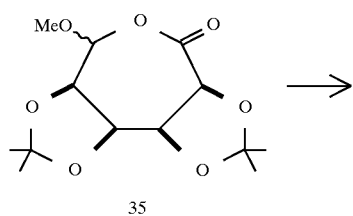
35
Fujami, Tet Lett. 1967, 4771
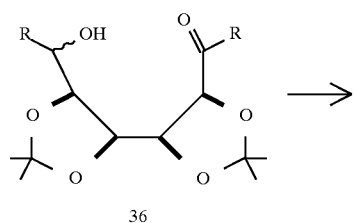
36
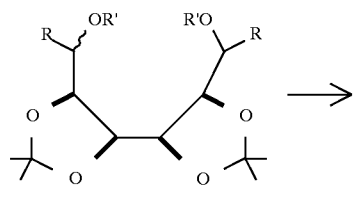
37
R' = H
R' = Ts
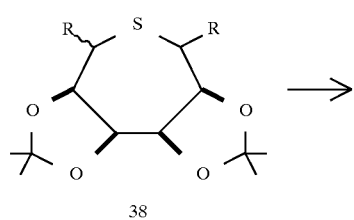
38
-continued
Scheme 7
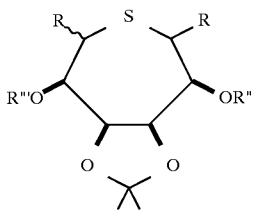
39: R", R''' = H
then alkylation
Scheme 8
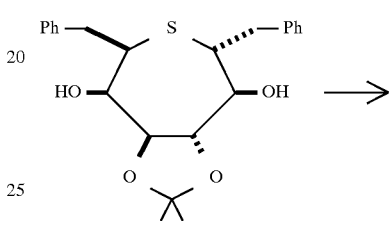
7
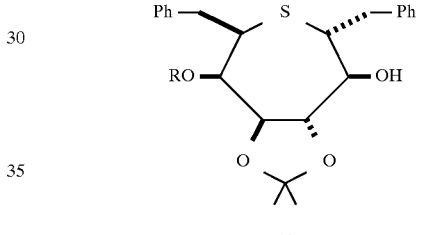
40
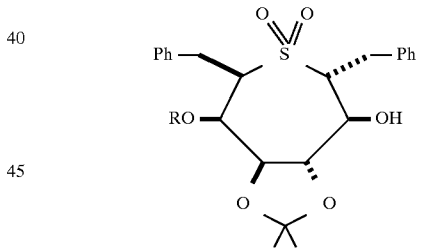
41
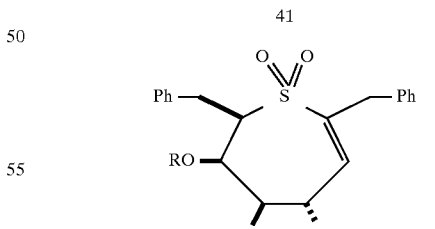
42

Scheme 8
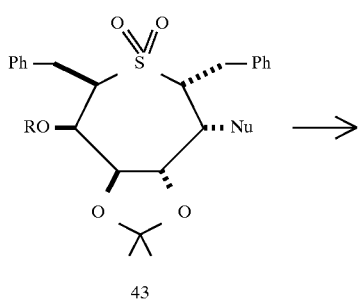
43
Scheme 8
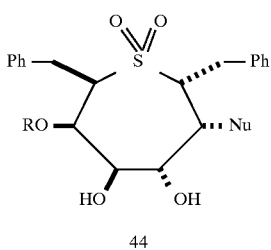
44
Scheme 9
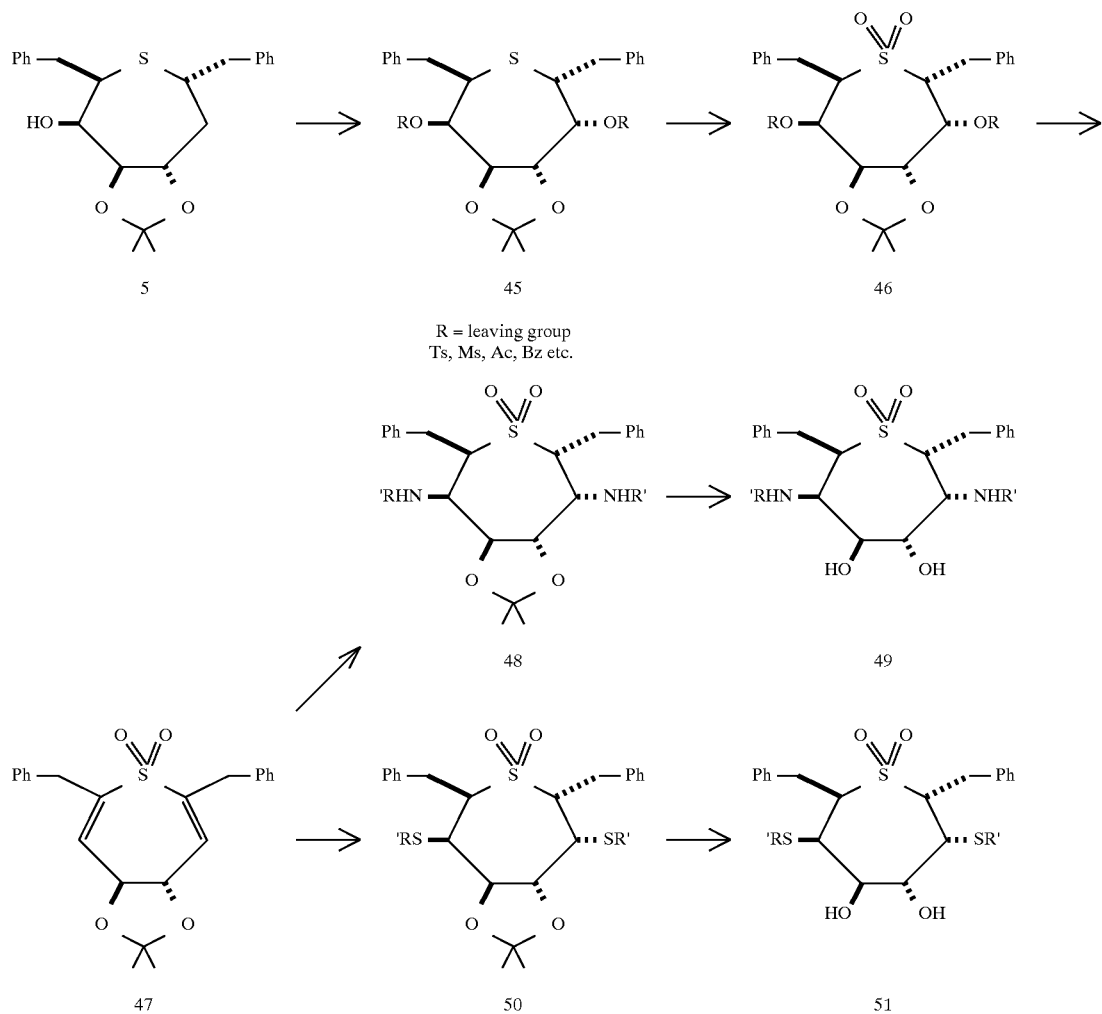

5,811,450
Scheme 10
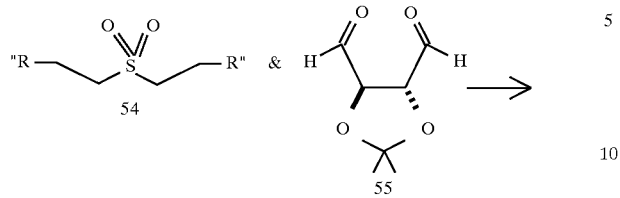
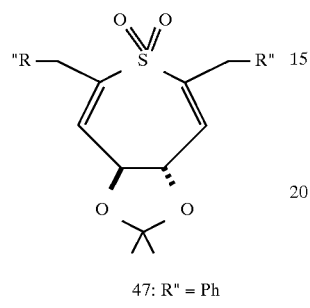
47: R" = Ph
Scheme 11
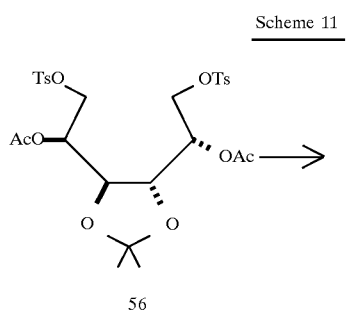
56
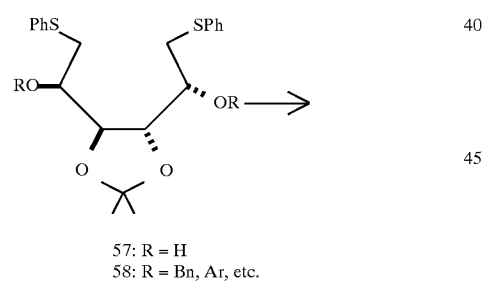
57: R = H
58: R = Bn, Ar, etc.
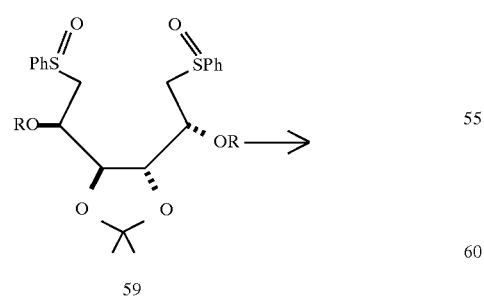
59
-continued
Scheme 11
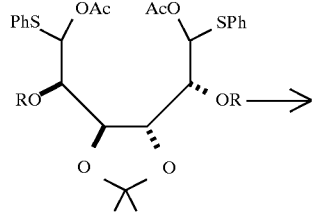
60
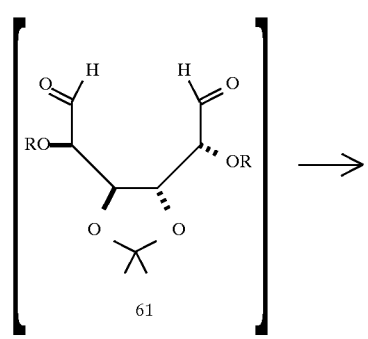
61
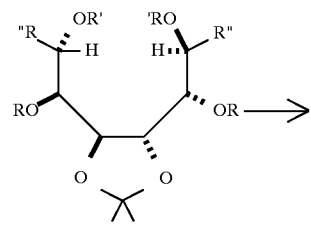
62: R' = H
63: R' = Ts, Ms etc
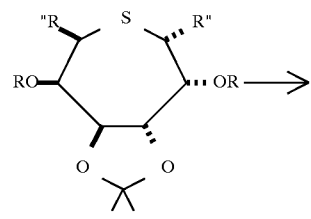
8
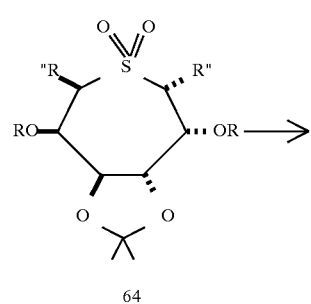
64

-continued
Scheme 11
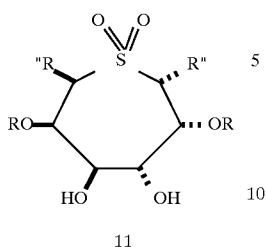
Scheme 12
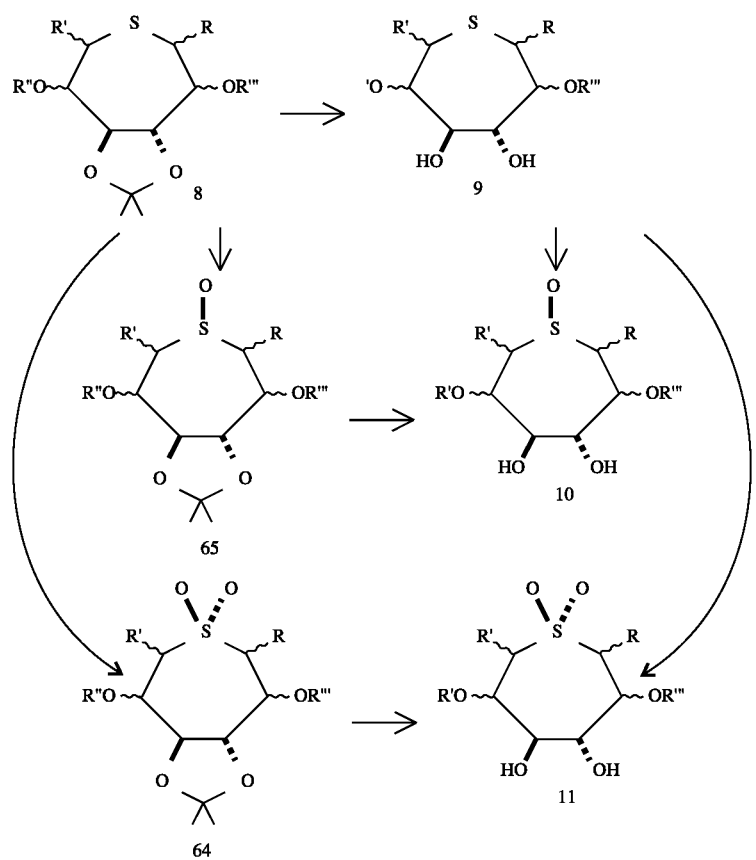
Scheme 13
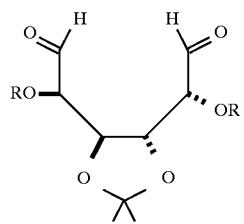
-continued
Scheme 13
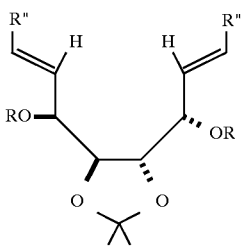

5,811,450
-continued
Scheme 13
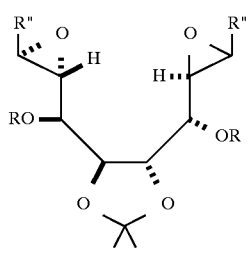
66
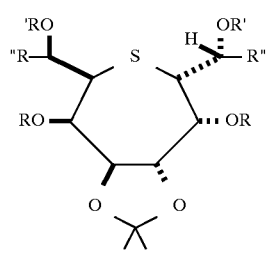
67
R = H, Me, Ac, etc
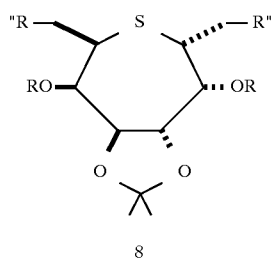
8
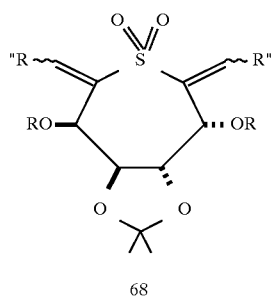
68
Scheme 14
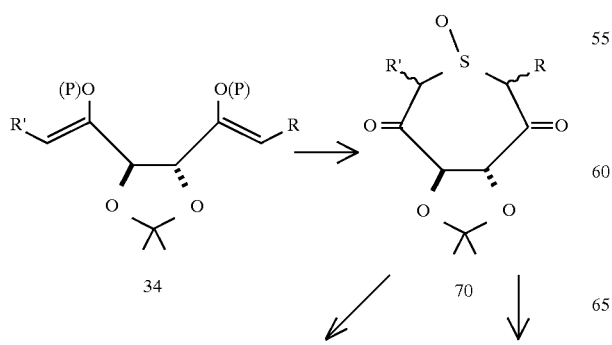
34    70
-continued
Scheme 14
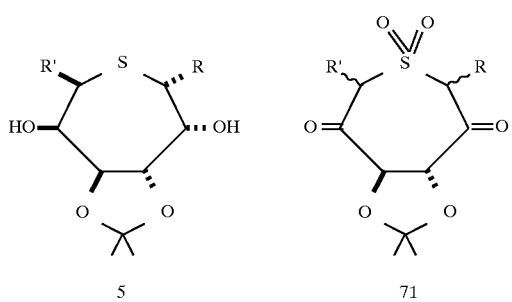
5    71
Scheme 15
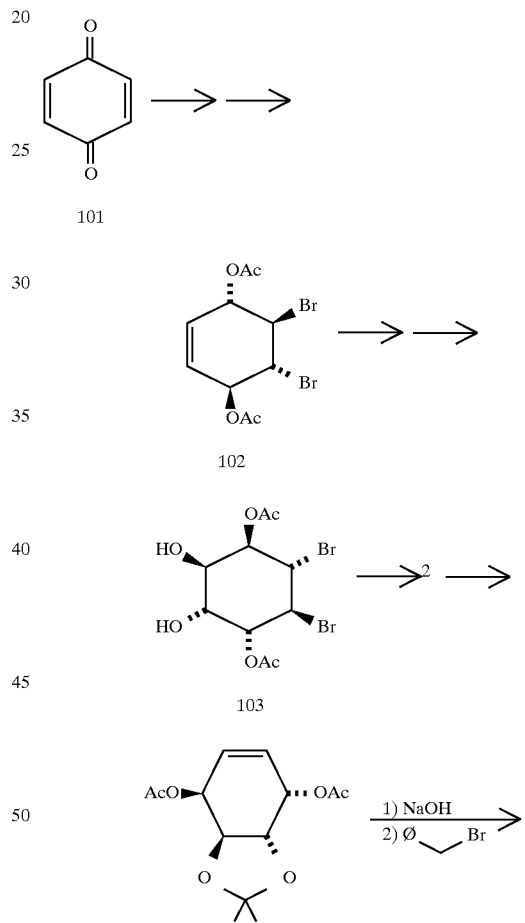
101
102
103
104
105

Scheme 15
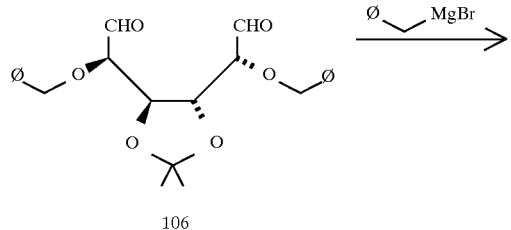
106
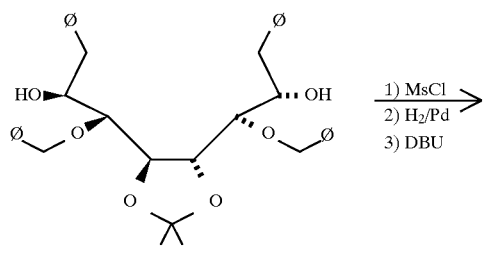
107
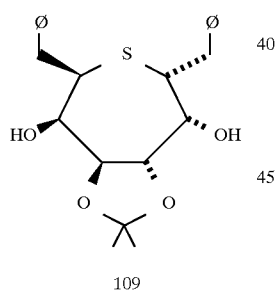
108
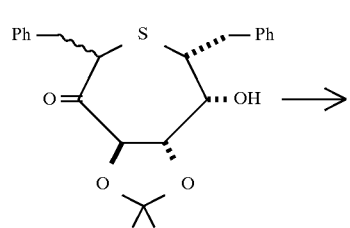
109
Scheme 16
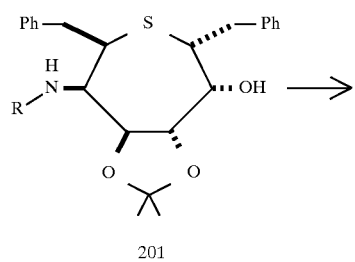
201
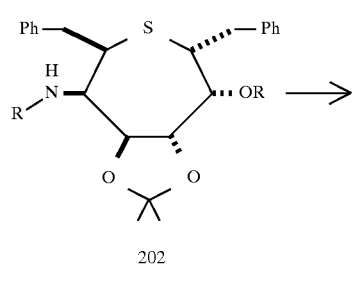
202
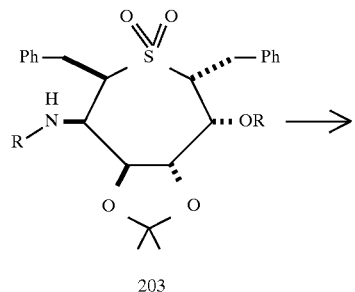
203
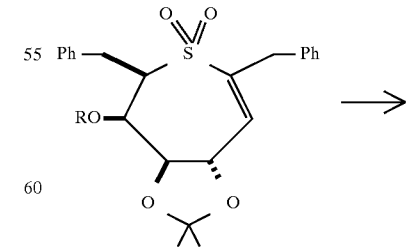
204
Scheme 16
200
Scheme 17
42

Scheme 17
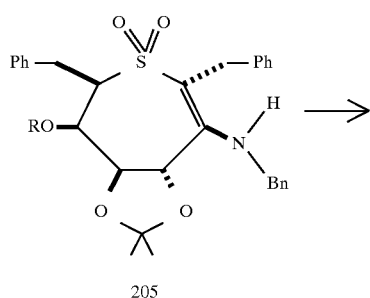
205
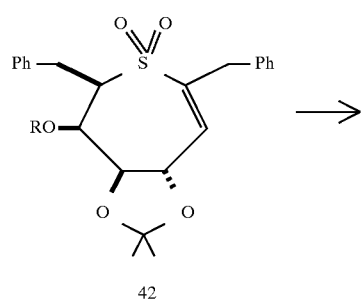
206
Scheme 18
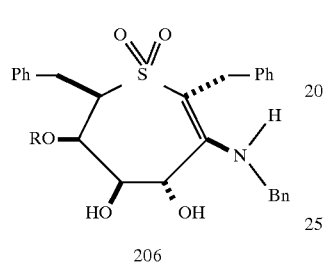
42
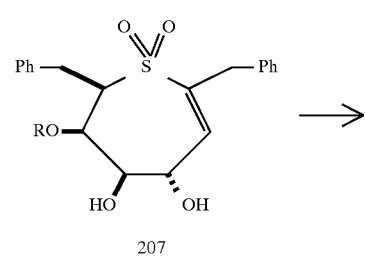
207
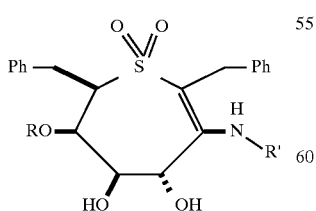
208
Scheme 19
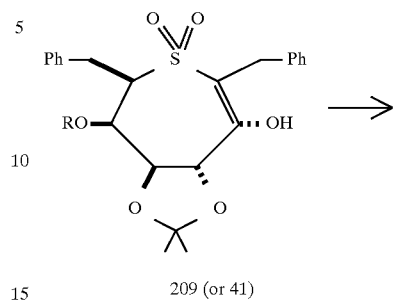
209 (or 41)
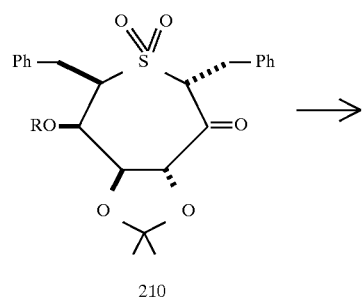
210
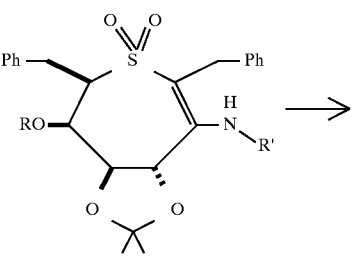
211
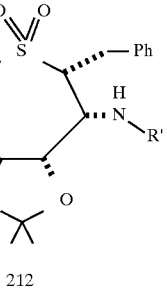
212

Scheme 20
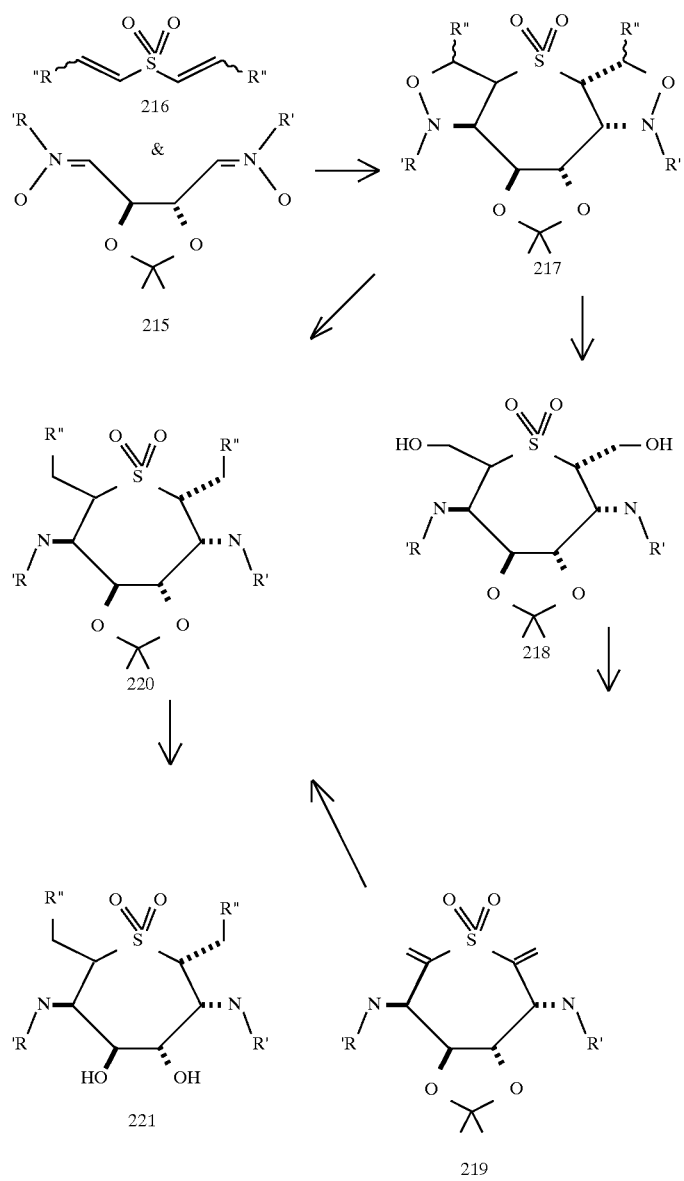
Scheme 21
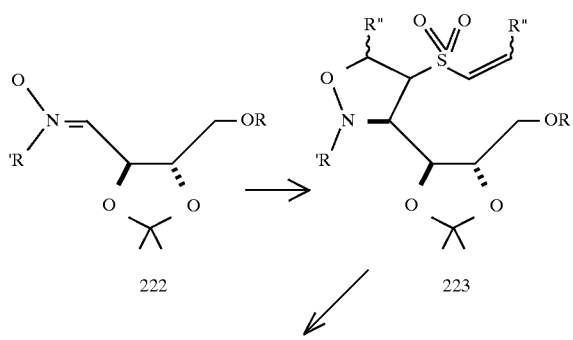

-continued
Scheme 21
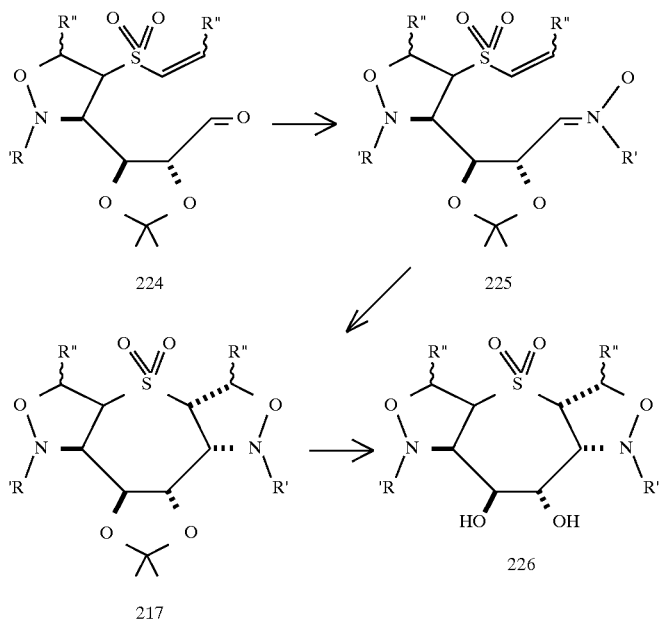
Scheme 25
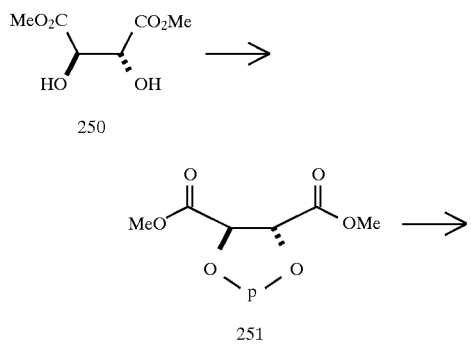
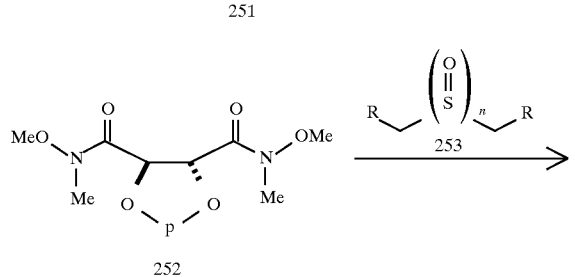
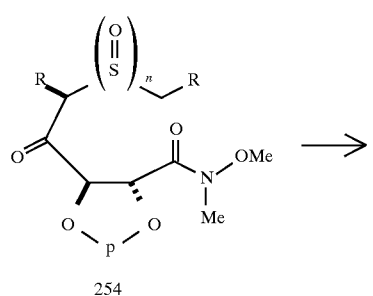
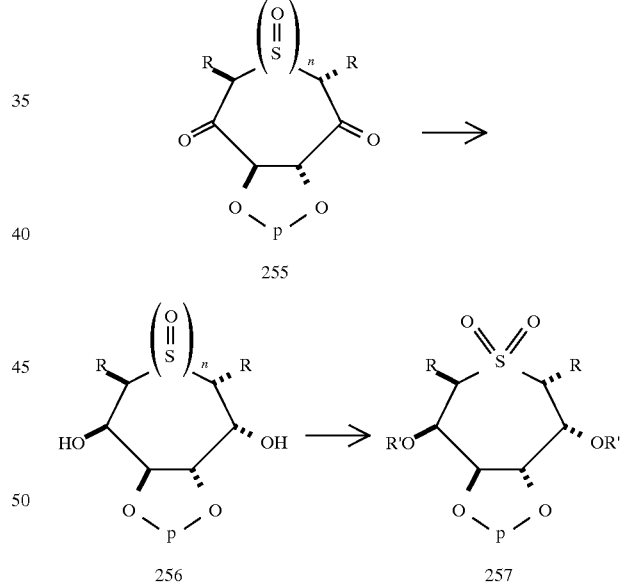
p = diol protecting group
n = 0–2
Scheme 26
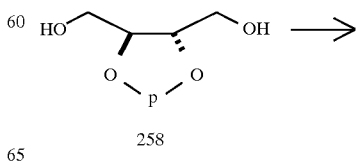

Scheme 26
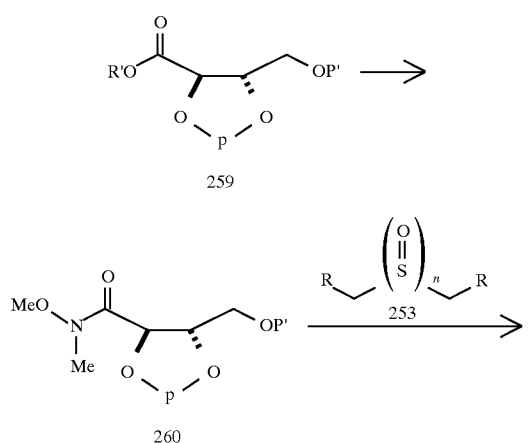
p = diol protecting group
P' = hydroxy protecting group
n = 0–2
Scheme 27
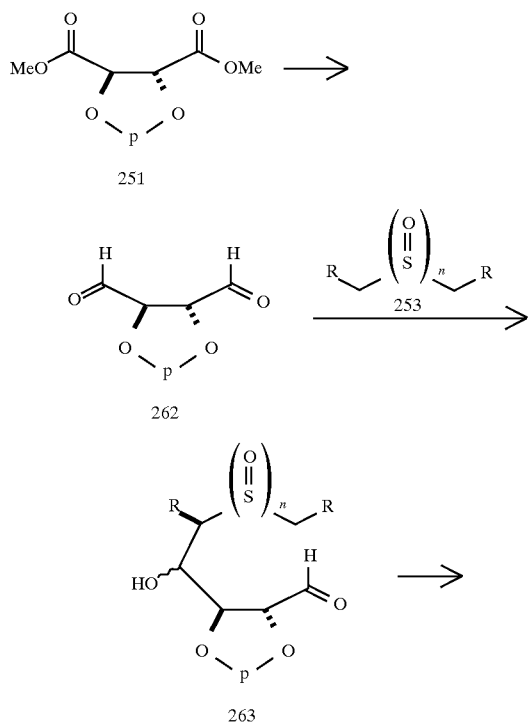
Scheme 27
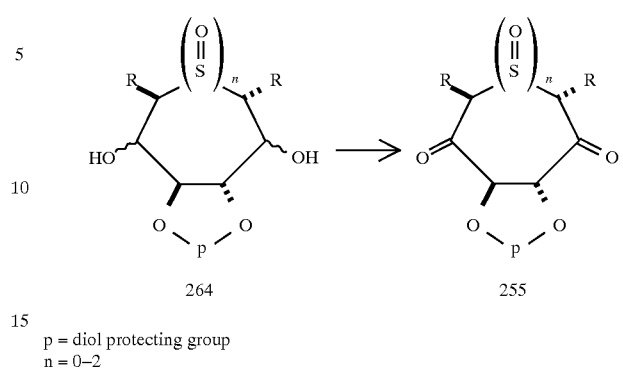
p = diol protecting group
n = 0–2
Scheme 28
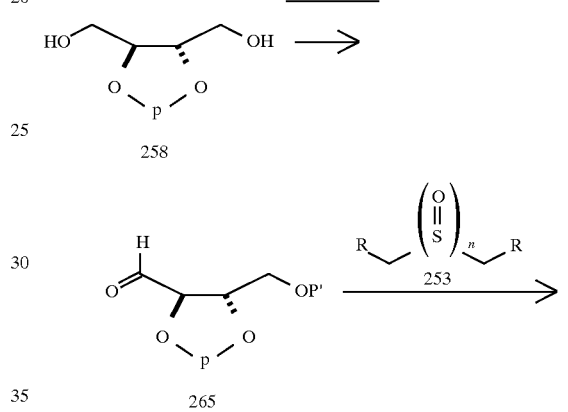
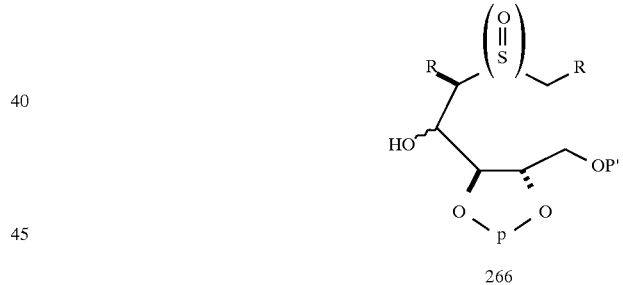
p = diol protecting group
P' = hydroxy protecting group
n = 0–2
Scheme 29
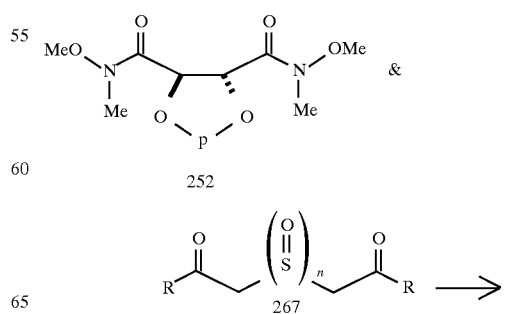

-continued
Scheme 29
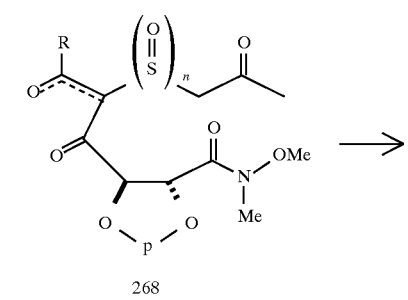
268
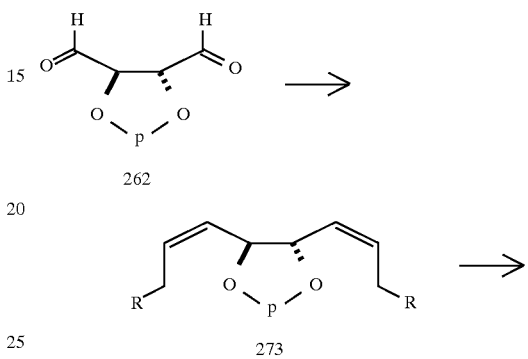
269
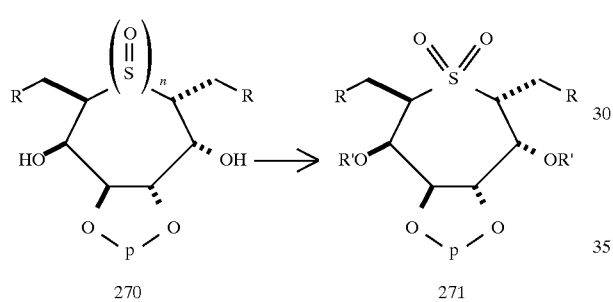
270 271
p = diol protecting group
n = 0–2
Scheme 30
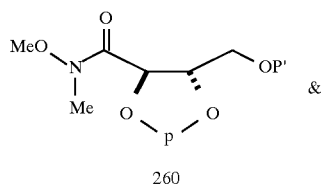
260
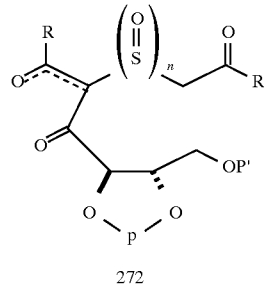
267
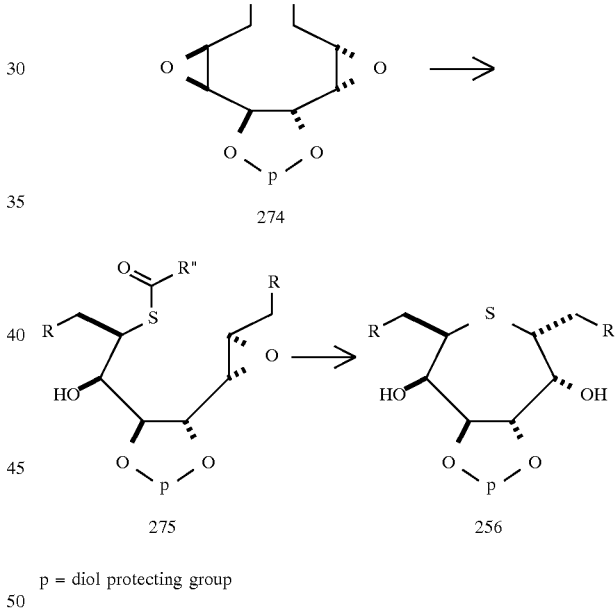
272
-continued
Scheme 30
p = diol protecting group
P' = hydroxy protecting group
n = 0–2
Scheme 31
262
273
274
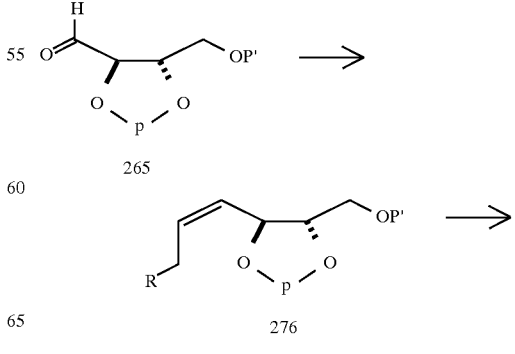
275 256
p = diol protecting group
Scheme 32
265
276

167
-continued
Scheme 32
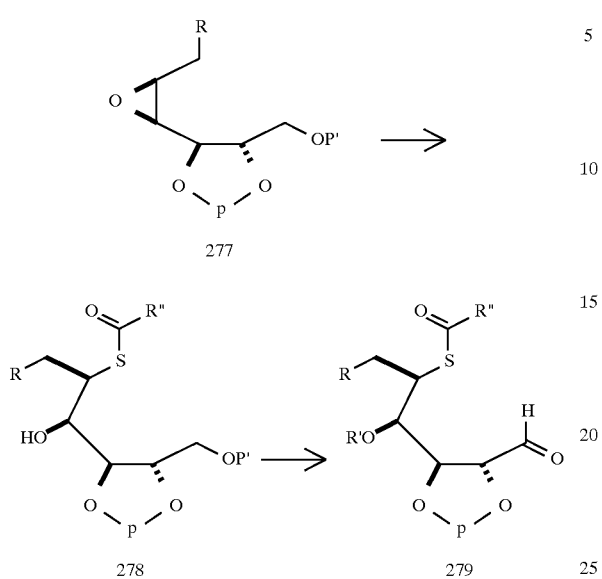
p = diol protecting group
P' = hydroxy protecting group
Scheme 33
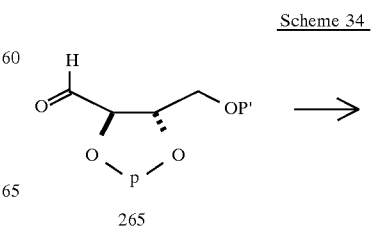
168
-continued
Scheme 33
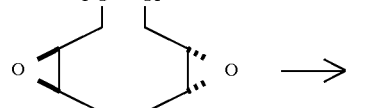
283
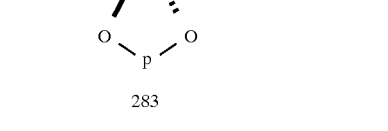
284
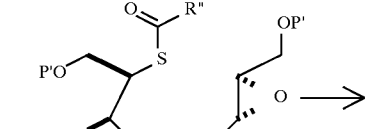
285
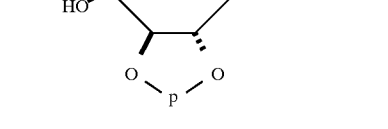
286
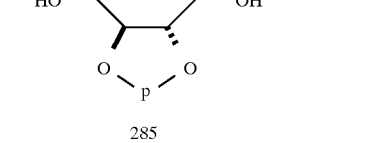
257
p = diol protecting group
P' = hydroxy protecting group
Scheme 34
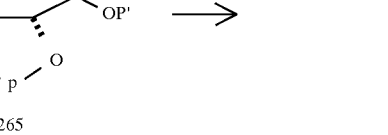
265

5,811,450
169
-continued
Scheme 34
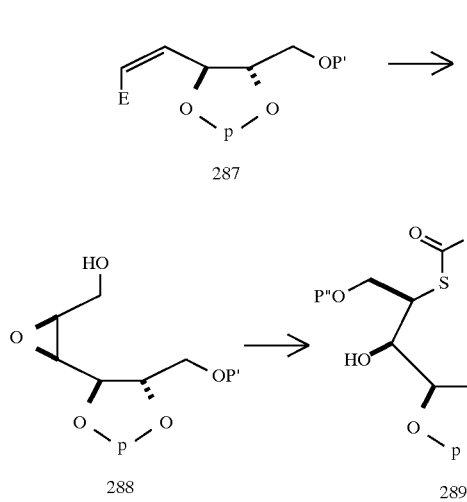
p = diol protecting group
P' = hydroxy protecting group
Scheme 35
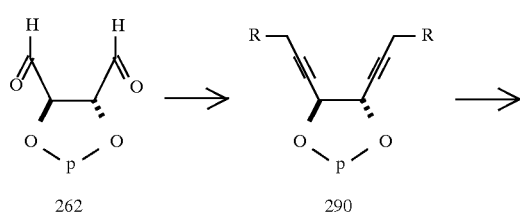
p = diol protecting group
Scheme 36
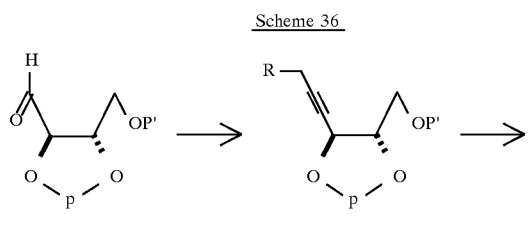
p = diol protecting group
P' = hydroxy protecting group
170
Scheme 37
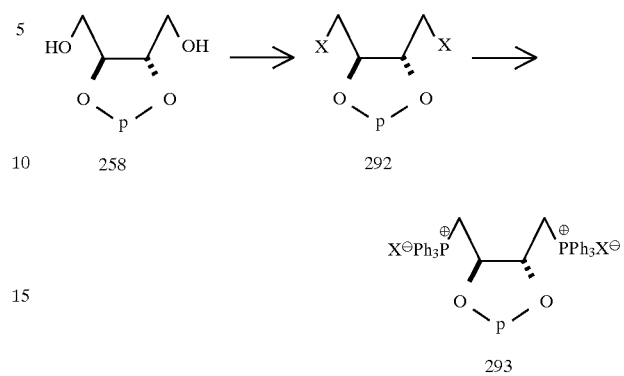
p = diol protecting group
Scheme 38
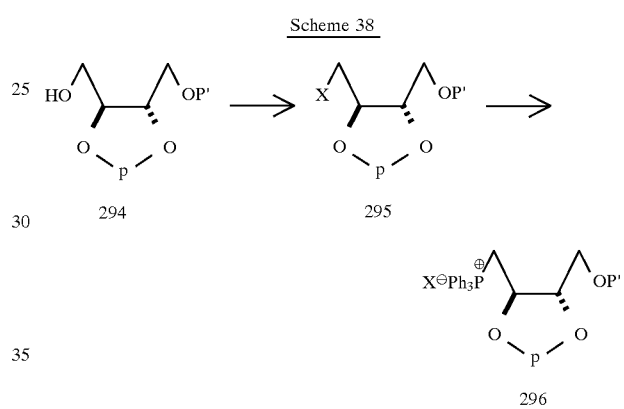
p = diol protecting group
P' = hydroxy protecting group
Scheme 50
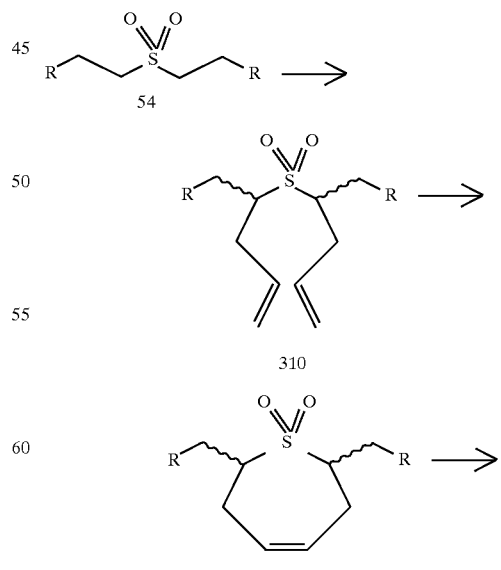

171
-continued
Scheme 50
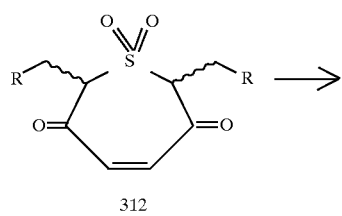
312
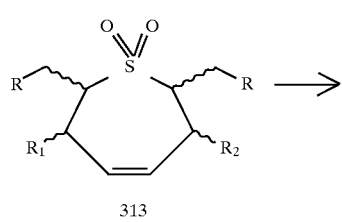
313
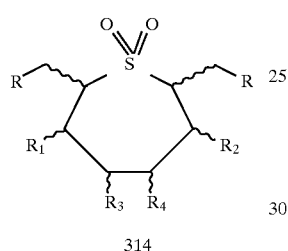
314
Scheme 51
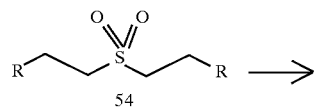
54
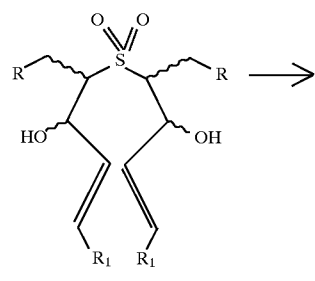
315
172
-continued
Scheme 51
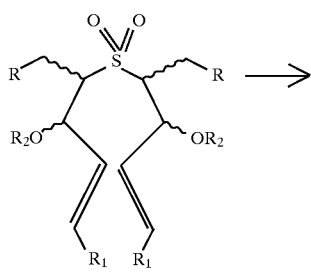
316
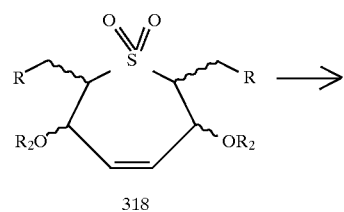
318
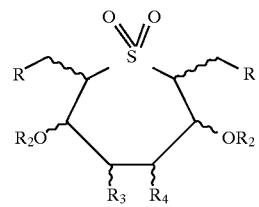
317

Scheme 60
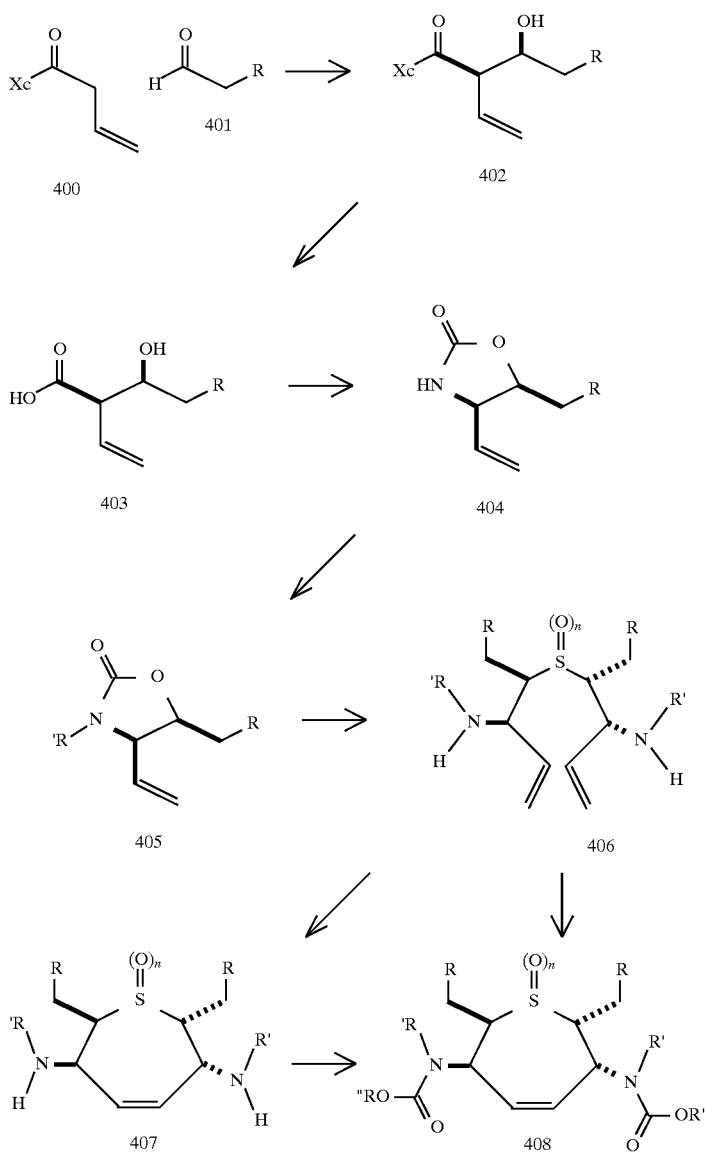
Scheme 61
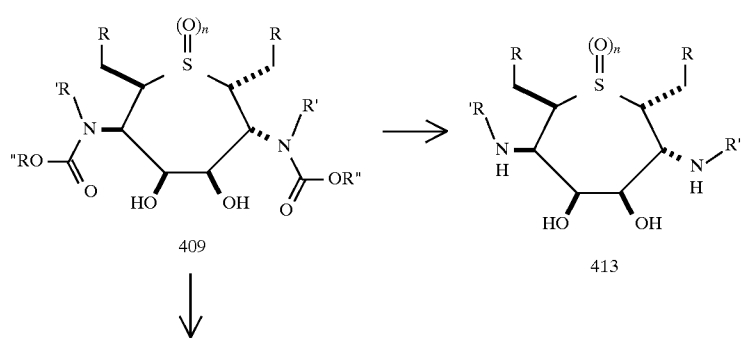

-continued
Scheme 61
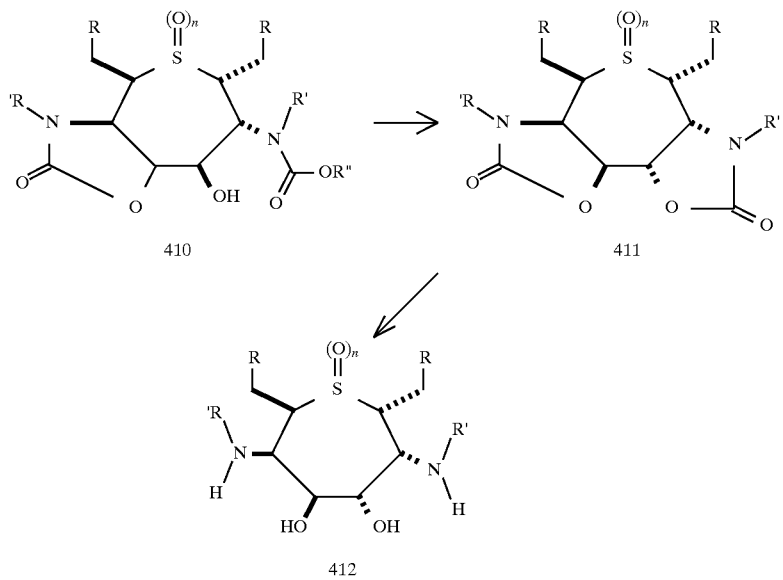
Scheme 62
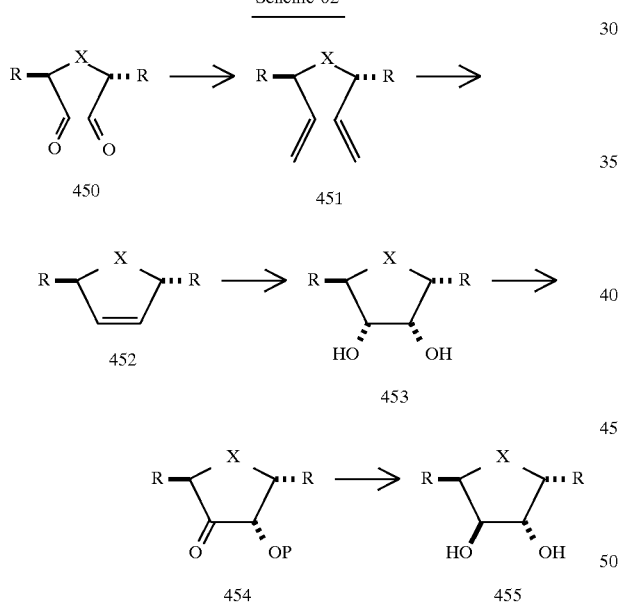
-continued
Scheme 63
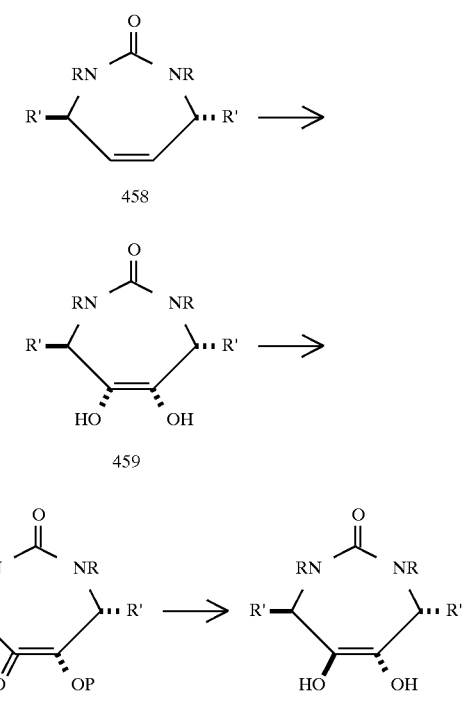
Scheme 63
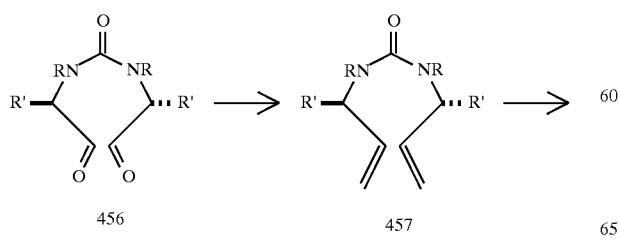
Scheme 64
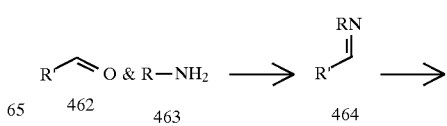

-continued
Scheme 64

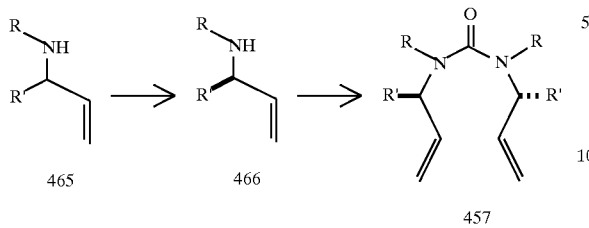

EXAMPLES

Compositions

The compositions described in the Examples are uniquely designated as indicated in Tables 101, 107 and 108 based on the following formula:

TABLE 101

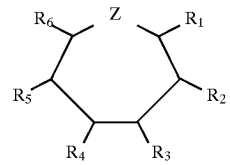

| # | Z | R1 | R2 | R3 | R4 | R5 | R6 | Z | 1 | 2 | 3 | 4 | 5 | 6 |
|---|---|---|---|---|---|---|---|---|---|---|---|---|---|---|
| 1  | —S— | H     | —OH | —OC(Me)$_2$O— | —OH | H     | — | — | α | α | β | β | — |
| 13 | —S— | PhCH= | O=  | —OC(Me)$_2$O— | —OH | H     | — | z | — | α | β | β | — |
| 15 | —S— | —Bn   | —OH | —OC(Me)$_2$O— | —OH | H     | — | α | α | α | β | β | — |
| 25 | —S— | —Bn   | —OH | —OC(Me)$_2$O— | O=  | PhCH= | — | α | α | α | β | — | z |
| 27 | —S— | —Bn   | O=  | —OC(Me)$_2$O— | O=  | —Bn   | — | α | — | α | β | — | β |
| 28 | —S— | —Bn   | —OH | —OC(Me)$_2$O— | —OH | —Bn   | — | α | α | α | β | β | β |
| 29 | —S— | —Bn   | —OH | —OC(Me)$_2$O— | —OH | —Bn   | — | α | α | α | β | β | α |
| 30 | —S— | —Bn   | —OH | —OC(Me)$_2$O— | —OH | —BN   | — | α | α | α | β | α | β |
| 31 | —S— | —Bn   | —OH | —OC(Me)$_2$O— | O=  | —Bn   | — | α | α | β | — | β |   |
| 32 | —S— | —Bn   | —OH | —OC(Me)$_2$O— | O=  | —Bn   | — | α | α | α | β | — | α |

TABLE 107

| # | Z | R1 | R2 | R3 | R4 | R5 | R6 | Z | 1 | 2 | 3 | 4 | 5 | 6 |
|---|---|---|---|---|---|---|---|---|---|---|---|---|---|---|
| 1  | —S—   | —Bn | —OBn  | —OC(Me)$_2$O— | —OBn | H | — | α | α | α | β | β | — |
| 2  | —S—   | —Bn | —OBn  | —OH | —OH | —OBn  | H | — | α | α | α | β | β | — |
| 3  | —SO—  | —Bn | —OBn  | —OH | —OH | —OBn  | H | β | α | α | α | β | β | — |
| 4  | —SO—  | —Bn | —OBn  | —OH | —OH | —OBn  | H | α | α | α | α | β | β | — |
| 5  | —SO$_2$— | —Bn | —OBn | —OH | —OH | —OBn  | H | — | α | α | α | β | β | — |
| 6  | —S—   | —Bn | —OoCN | —OC(Me)$_2$O— | —OoCN | H | — | α | α | α | β | β | — |
| 7  | —S—   | —Bn | —OoCN | —OH | —OH | —OoCN | H | — | α | α | α | β | β | — |
| 8  | —SO—  | —Bn | —OoCN | —OH | —OH | —OoCN | H | α | α | α | α | β | β | — |
| 9  | —SO—  | —Bn | —OoCN | —OH | —OH | —OoCN | H | β | α | α | α | β | β | — |
| 10 | —SO$_2$— | —Bn | —OoCN | —OH | —OH | —OoCN | H | — | α | α | α | β | β | — |
| 11 | —S—   | —Bn | —OpCN | —OC(Me)$_2$O— | —OpCN | H | — | α | α | α | β | β | — |
| 12 | —S—   | —Bn | —OpCN | —OH | —OH | —OpCN | H | — | α | α | α | β | β | — |
| 13 | —SO—  | —Bn | —OpCN | —OH | —OH | —OpCN | H | β | α | α | α | β | β | — |
| 14 | —SO—  | —Bn | —OpCN | —OH | —OH | —OpCN | H | α | α | α | α | β | β | — |
| 15 | —SO$_2$— | —Bn | —OpCN | —OH | —OH | —OpCN | H | — | α | α | α | β | β | — |

TABLE 108

| # | Z | R1 | R2 | R3 | R4 | R5 | R6 | Z | 1 | 2 | 3 | 4 | 5 | 6 |
|---|---|---|---|---|---|---|---|---|---|---|---|---|---|---|
| 1  | —S—   | —Bn | —OBn  | —OC(Me)$_2$O— | —OBn  | —Bn | — | α | α | α | β | β | β |
| 2  | —S—   | —Bn | —OBn  | —OC(Me)$_2$O— | —OH   | —Bn | — | α | α | α | β | β | β |
| 3  | —S—   | —Bn | —OBn  | —OH | —OH | —OBn  | —Bn | — | α | α | α | β | β | β |
| 4  | —SO—  | —Bn | —OBn  | —OH | —OH | —OBn  | —Bn | — | α | α | α | β | β | β |
| 5  | —SO$_2$— | —Bn | —OBn | —OH | —OH | —OBn  | —Bn | — | α | α | α | β | β | β |
| 6  | —S—   | —Bn | —OBn  | —O— | —OBn | —Bn | — | α | α | β | β | β | β |
| 7  | —SO—  | —Bn | —OBn  | —O— | —OBn | —Bn | — | α | α | β | β | β | β |
| 8  | —SO$_2$— | —Bn | —OBn | —O— | —OBn | —Bn | — | α | α | β | β | β | β |
| 9  | —S—   | —Bn | —O3PM | —OC(Me)$_2$O— | —O3PM | —Bn | — | α | α | α | β | β | β |
| 10 | —SO—  | —Bn | —O3PM | —OC(Me)$_2$O— | —O3PM | —Bn | — | α | α | α | β | β | β |
| 11 | —SO$_2$— | —Bn | —O3PM | —OC(Me)$_2$O— | —O3PM | —Bn | — | α | α | α | β | β | β |

TABLE 108-continued

| # | Z | R1 | R2 | R3 | R4 | R5 | R6 | Z | 1 | 2 | 3 | 4 | 5 | 6 |
|---|---|---|---|---|---|---|---|---|---|---|---|---|---|---|
| 14 | —SO₂— | —Bn | —O3PM | —OH | —OH | —O3PM | —Bn | — | α | α | α | β | β | β |
| 15 | —S— | —Bn | —OBn | —OC(Me)2O— | | —OBn | —Bn | — | α | α | α | β | β | α |
| 16 | —S— | —Bn | —OBn | —OH | —OH | —OBn | —Bn | — | α | α | α | β | β | α |
| 17 | —SO— | —Bn | —OBn | —OH | —OH | —OBn | —Bn | β | α | α | α | β | β | α |
| 18 | —SO₂— | —Bn | —OBn | —OH | —OH | —OBn | —Bn | — | α | α | α | β | β | α |
| 19 | S | Bn | OBn | —OC(Me)₂O— | | OBn | Bn | — | α | α | α | β | α | β |
| 20 | SO₂ | Bn | OBn | —Oc(Me)₂O— | | OBn | Bn | — | α | α | α | β | α | β |
| 21 | SO₂ | Bn | OBn | —OH | OH | OBn | Bn | — | α | α | α | β | α | β |
| 22 | S | Bn | OBn | —OC(Me)₂O— | | OBn | Bn | — | α | α | α | β | α | α |
| 23 | SO₂ | Bn | OBn | —OC(Me)₂O— | | OBn | Bn | — | α | α | α | β | α | α |
| 24 | SO₂ | Bn | OBn | —OH | OH | OBn | Bn | — | α | α | α | β | α | α |
| 25 | S | Bn | OBn | —OC(Me)₂O— | | OBn | Bn | — | β | β | β | α | α | α |
| 26 | SO₂ | Bn | OBn | —OC(Me)₂O— | | OBn | Bn | — | β | β | β | α | α | α |
| 27 | SO₂ | Bn | OBn | —OH | OH | OBn | Bn | — | β | β | β | α | α | α |

TABLE 120

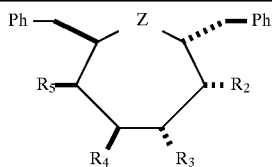

| # | Z | R2 | R3 | R4 | R5 |
|---|---|---|---|---|---|
| 1 | S | OBn | —OC(Me)₂O— | | OBn |
| 2 | S | OBn | —OH | —OH | OBn |
| 3 | SO | OBn | —OH | —OH | OBn |
| 4 | SO₂ | OBn | —OH | —OH | OBn |
| 5 | S | O2PM | —OC(Me)2O— | | O2PM |
| 6 | SO₂ | O2PM | —OC(Me)2O— | | O2PM |
| 7 | SO₂ | O2PM | —OC(Me)2O— | | O2PMNO |
| 8 | SO₂ | O2PM | —OH | —OH | O2PM |
| 9 | SO₂ | O2PM | —OH | —OH | O2PMNO |
| 10 | S | O3PM | —OC(Me)2O— | | O3PM |
| 11 | SO | O3PM | —OC(Me)2O— | | O3PM |
| 12 | SO₂ | O3PM | —OC(Me)2O— | | O3PM |
| 13 | SO₂ | O3PM | —OC(Me)2O— | | O3PMNO |
| 14 | SO₂ | O3PMNO | —OC(Me)2O— | | O3PMNO |
| 15 | SO₂ | O3PM | —OH | —OH | O3PM |
| 16 | SO₂ | O3PM | —OH | —OH | O3PMNO |
| 17 | S | O4PM | —OC(Me)2O— | | O4PM |
| 18 | SO₂ | O4PM | —OC(Me)2O— | | O4PM |
| 19 | SO₂ | O4PM | —OH | —OH | O4PM |
| 20 | S | O2MT4M | —OC(Me)2O— | | O2MT4M |
| 21 | SO₂ | O2MT4M | —OC(Me)2O— | | O2MT4M |
| 22 | SO₂ | O2MT4M | —OH | —OH | O2MT4M |
| 23 | S | OT5M | —OC(Me)2O— | | OT5M |
| 24 | SO₂ | OT5M | —OC(Me)2O— | | OT5M |
| 25 | SO₂ | OT5M | —OH | —OH | OT5M |
| 26 | S | O2P | —OC(Me)2O— | | O2P |
| 27 | SO₂ | O2P | —OC(Me)2O— | | O2P |
| 28 | SO₂ | O2P | —OH | —OH | O2P |
| 29 | S | OmMe | —OC(Me)2O— | | OmMe |
| 30 | SO₂ | OmMe | —OC(Me)2O— | | OmMe |
| 31 | SO₂ | OmMe | —OH | —OH | OmMe |
| 32 | S | OmOMe | —OC(Me)2O— | | OmOMe |
| 33 | SO₂ | OmOMe | —OC(Me)2O— | | OmOMe |
| 34 | SO₂ | OmOMe | —OH | —OH | OmOMe |
| 35 | S | OmBr | —OC(Me)2O— | | OmBr |
| 36 | SO₂ | OmBr | —OC(Me)2O— | | OmBr |
| 37 | SO₂ | OmBr | —OH | —OH | OmBr |
| 38 | S | OmOBn | —OC(Me)2O— | | OmOBn |
| 39 | SO₂ | OmOBn | —OC(Me)2O— | | OmOBn |
| 40 | SO₂ | OmOBn | —OH | —OH | OmOBn |
| 41 | SO₂ | OmOH | —OH | —OH | OmOH |
| 42 | S | OmNO₂ | —OC(Me)2O— | | OmNO₂ |
| 43 | SO₂ | OmNO₂ | —OC(Me)2O— | | OmNO₂ |
| 44 | SO | OmNO₂ | —OH | —OH | OmNO₂ |
| 45 | SO₂ | OmNO₂ | —OH | —OH | OmNO₂ |

TABLE 120-continued

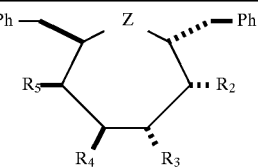

| # | Z | R2 | R3 | R4 | R5 |
|---|---|---|---|---|---|
| 46 | SO₂ | OmNH₂ | —OH | —OH | OmNH₂ |
| 47 | SO₂ | OmNH₂s | —OH | —OH | OmNH₂s |

TABLE 125

| # | X | R3 | R4 | R2 |
|---|---|---|---|---|
| 1 | S | —OC(Me)₂O— | | ![thiazole] |
| 2 | SO₂ | —OC(Me)₂O— | | |
| 3 | SO₂ | —OH | —OH | |
| 4 | S | —OC(Me)₂O— | | Me-thiazole |
| 5 | SO₂ | —OC(Me)₂O— | | |
| 6 | SO₂ | —OH | —OH | |
| 7 | S | —OC(Me)₂O— | | Cl-thiazole |
| 8 | S | —OC(Me)₂O— | | Me₂N-thiazole |
| 9 | SO₂ | —OC(Me)₂O— | | |
| 10 | SO₂ | —OH | —OH | |
| 11 | S | —OC(Me)₂O— | | Br-thiazole |
| 12 | S | —OC(Me)₂O— | | Me₂N-thiazole |
| 13 | SO₂ | —OC(Me)₂O— | | |
| 14 | SO₂ | —OH | —OH | |

TABLE 125-continued

[Structure: seven-membered ring with Ph, X, Ph, R₂O, OR₂, R₄, R₃ substituents]

| # | X | R₃ | R₄ | R₂ |
|---|---|---|---|---|
| 15 | S | —OC(Me)₂O— | | |
| 16 | SO₂ | —OC(Me)₂O— | | |
| 17 | SO₂ | —OH | —OH | 4-nitrophenyl (O₂N-C₆H₄-) |
| 18 | SO₂ | —OH | —OH | 4-aminophenyl (H₂N-C₆H₄-) |
| 19 | S | —OC(Me)₂O— | | |
| 20 | SO₂ | —OC(Me)₂O— | | |
| 21 | SO₂ | —OH | —OH | 6-methylpyridin-3-yl (Me-pyridyl) |
| 22 | S | —OC(Me)₂O— | | |
| 23 | SO₂ | —OC(Me)₂O— | | |
| 24 | SO₂ | —OH | —OH | 3-methylpyridin-2-yl |
| 25 | S | —OC(Me)₂O— | | |
| 26 | SO₂ | —OC(Me)₂O— | | |
| 27 | SO₂ | —OH | —OH | 2-nitro-4-trifluoromethylphenyl |
| 28 | SO₂ | —OH | —OH | 2-amino-4-trifluoromethylphenyl |
| 29 | S | —OC(Me)₂O— | | |
| 30 | SO₂ | —OC(Me)₂O— | | |
| 31 | SO₂ | —OH | —OH | 6-methylpyridin-2-yl |
| 32 | SO₂ | —OH | —OH | 3-(methanesulfonylamino)phenyl (HN(SO₂Me)-C₆H₄-) |
| 33 | S | —OC(Me)₂O— | | |
| 34 | SO₂ | —OC(Me)₂O— | | |
| 35 | SO₂ | —OH | —OH | 4-methylpyridin-3-yl |
| 36 | S | —OC(Me)₂O— | | isoprenyl |
| 37 | S | —OC(Me)₂O— | | |
| 38 | SO₂ | —OC(Me)₂O— | | |
| 39 | SO₂ | —OH | —OH | isobutyl/isopentyl |

Bn = benzyl-
mMe = meta xylylmOMe = meta methoxybenzyl-
mOBn = meta Benzyloxybenzyl-
mOH = meta hydroxybenzyl-
mBr = meta bromobenzyl-
mNO₂ = meta nitrobenzyl-
mNH₂ = meta aminobenzyl-
mNH₂s = meta aminobenzyl-, methanesulfonate salt
2P = 2-pyridyl-
2PM = 2-pyridylmethyl-
2PMNO = 2-pyridylmethyl-, N-oxide
3PM = 3-pyridylmethyl-
3PMNO = 3-pyridylmethyl-, N-oxide
4PM = 4-pyridylmethyl-
2MT4M = 2-methylthiazol-4-ylmethyl-
T5M = thiazol-5-ylmethyl- Abbreviations Ac=acetyl Bn=benzyl Bz=benzoyl oCN=ortho-cyanophenyl pCN=para-cyanophenyl Me=methyl Ph=phenyl Ts=toluenesulfonyl 3P=3-pyridylmethyl Example 1

D-manno thiepane diol acetonide and L-manno thiepane diol acetonide Table 101, compound 1.

D-manno thiepane diol acetonide was prepared from D-mannitol by the procedure of Kutzman, (Carb. Res. 56, 105–115 (1977)). An improvement uses the 1,6 ditosyl 2,5 diacetyl 3,4 isopropylidene derivative (described in L. F. Wiggins, J. Chem. Soc. 1946, 384–388) in the thiepane forming reaction in place of the diepoxide.

L-manno thiepane diol acetonide (Table 101, compound 1) was prepared in an analogous way. L-mannolactone is the commercial starting material. Reduction by the method of Frush (JACS 78, 2844–2846 (1956)) is combined with acetonide formation to provide 1,2:3,4:5,6-Triisopropylidene-L-mannitol.

Part 1 1,2:3,4:5,6-Triisopropylidene-L-mannitol A 5-liter 3-necked flask equipped with solids addition funnel with nitrogen stream, reflux condensor and thermometer is charged with 178.1 g (1 mol) of L-mannono-1,4-lactone (Pfahnstiehl) suspended in methanol (2.7 liter) with vigorous stirring. Sodium borohydride (81.2 g, 2 mol) is added cautiously as a solid so that gas evolution is maintained at a safe rate (45 min). [A nitrogen stream is used to sweep methanol vapor away from the solid addition funnel to prevent caking. Caked material is occasionally rinsed into the reaction with additional methanol.] The temperature of the reaction rises to and is maintained between 50° and 60° C. by the continuous addition of borohydride. Complete solution occurs early during the addition, then a slurry forms. After addition is complete, the reaction temperature is maintained at 50° C. for 60 minutes. After cooling to 35°

C., hydrochloric acid (358 ml, 6N, 2 mol) is added carefully (no gas evolution is observed but the character of the slurry changes). The slurried reaction is concentrated at reduced pressure by rotary evaporation in a 3 liter pear flask. The residue is thoroughly suspended in methanol (700 mL) and then reconcentrated under vacuum to remove boron as trimethyl borate. This is repeated a total of three times. At this point the residue consists of L-mannitol and sodium chloride.

To the residue in the concentration flask is added acetone (2 liter), dimethoxypropane (120 mL), acetic acid (15 mL) and finally concentrated sulfuric acid (27.7 mL). The suspension is shaken on an orbit shaker overnight. The solution is filtered though a sintered-glass funnel to remove the salt. The filtrate is treated with 86 mL of concentrated ammonium hydroxide, refiltered, concentrated by rotary evaporation and redissolved in 900 ml of acetone. The acetone solution is poured slowly into 2.7 l of cold, vigorously stirred water. Stirring is continued for 1 hr. The resulting white triacetonide is collected by filtration, washed with 450 mL of water and dried under vacuum overnight at room temperature to yield 195 g (66%) of white plates. mp 66.5°–68° C. ( a]20 D=-12.6° c=1, ethanol).

[The triacetonide of D-mannitol has reported values of (lit.2 m.p. 70°–71°, [a]20 D=+14.70° (c=1, ethanol); lit.6 m.p. 69°–70°, [a]20 D=+12.5°(c=9.6, ethanol) ] 2. Kuszmann, J.; Tomori, E. Carb. Res. 1985, 137, 276–281. 6. Wiggins, L. J. Chem. Soc. 1946, 13–14.

Part 2: 3, 4-isopropylidene-L-mannitol

Partial deblocking by the method of L.F. Wiggins, J. Chem. Soc., 1946, 13–14 gives the tetraol: 3, 4-isopropylidene-L-mannitol.

Part 3: From 3, 4-isopropylidene-L-mannitol 1, 6 ditosyl 2, 5 diacetyl 3, 4 isopropylidene L-mannitol was prepared by the method of L.F. Wiggins, J. Chem. Soc., 1946, 384–388 as described for the D-isomer. In general, longer tosylation times (5 days at 0° C. ) were preferred. See example 74 for the use of this ditosylate to prepare thiepane diol acetonide

Example 2

Table 101, compound 13

L-Mannothiepane diol (Table 101, compound 1)(12.4 g) dried by azeotropic distillation of toluene, was dissolved in toluene (1700 mL). Toluene (100 mL) was distilled from the reaction. Benzaldehyde (184 mL) was added to the refluxing solution followed by aluminum t-butoxide (15.3 g) as a powdered solid. The reaction was continued at reflux for 45 min, cooled, filtered through a celite plug and concentrated. The residue was then carefully chromatographed on silica gel with methylene chloride followed by 3% ethyl acetate/methylene chloride to afford the hydroxyenone (Table 101, compound 13)(9.17 g) which was recrystallized from ether/hexane.

mp 132°–133° C.

$^1$H NMR 300 MHz (CDCl$_3$) d 8.053 (s, 1H), 7.87 (m, 2 H), 7.4–7.2 (m, 3 H), 5 5.94 ( d, J=9.3 Hz, 1H), 4.35 ( br q, 1H), 3.84 (dd, J=9.6, 2.4 Hz, 1H), 3,15 (dd, J=15.3, 4.5 Hz, 1H), 2.92 (br s, 1H), 2.87 ( d, J=15.3 Hz, 1H), 1.54 (s, 3H), 1.53 (s, 3H)

$^{13}$C NMR 75 MHz (CDCl$_3$) d 194.27, 143.80, 133.81, 131.56, 130.26, 129.44, 128.24, 110.30, 80.58, 77.90, 65.28, 37.38, 26.73, 26.25.

UV (methanol) 1=303 nm, e=9000.

Example 3

Table 101, compound 15

Enone (Table 101, compound 13)(5.11 g) and Ni(AcAc)$_2$ (8.55 g) were dissolved in methylene chloride (350 mL) and ethanol (500 mL) and cooled in an ice bath. Solid sodium borohydride (1.88 g) was added. After 30 min, the mixture was concentrated under vacuum and filtered through a silica plug with ethyl acetate to elute the product. After concentration, careful chromatography on silica gel eluting with 3% ethyl acetate/methylene chloride gave diol (Table 101, compound 15)(3.18 g) accompanied by other isomers (0.58 g).

$^1$H NMR 300 MHz (CDCl$_3$) d 7.3–7.2 (m, 5 H), 4.76 ( dd, J=9.0, 4.0 Hz, 1H), 4.31 ( ddd, J=9.0, 4.5, 4.0 Hz, 1H), 4.06 (dt, J=4.5, 2.0 Hz, 1H), 3.94 (dd, J=9.5, 1.5 Hz, 1H), 3.32 (dd, J=15.0, 8.0 Hz, 1H), 3.0–2.9 ( m, 3H), 2.72 ( br s, 1H), 2.41 (dd, J=15.0, 9.0 Hz, 1H), 2.30 (br s, 1H), 1.47 (s, 3H), 1.41 (s, 3H).

$^{13}$C NMR 75 MHz (CDCl$_3$) d 138.73, 129.18, 128.71, 126.98, 110.0, 77.10, 75.02, 68.23, 66.32, 54.37, 37.82, 35.84, 27.36, 27.03.

UV (methanol) 1=259 nm, e=48; 1=214 nm, e=640.

Example 4

Table 101, compound 25

Diol (Table 101, compound 15)(1.3 g) was dissolved in toluene (250 mL) and dried by azeotropic distillation of 60 mL of toluene. Benzaldehyde (22 mL) was added. An additional 55 ml of toluene was removed by distillation. Aluminum isopropoxide (2.1 g) was added as a solid. The reaction was heated to reflux for 7 h, cooled, filtered through a Celite plug and concentrated. The residue was then carefully chromatographed on silica with 5% ethyl acetate/methylene chloride to afford the enone (Table 101, compound 25)(0.688 g). along with recovered starting material (0.335 g). A portion of the enone was recrystallized to give yellow crystals. mp 180°–182° C.

$^1$H NMR 300 MHz (CDCl$_3$) d 8.044 (s, 1H), 7.71 (d, J=7.2 Hz, 2 H), 7.3–7.2 (m, 8 H), 5.96 ( d, J=9.3 Hz, 1H), 4.23 (br s, 1H), 3.83 (dd, J=9.3, 2.4 Hz, 1H), 3.11 (m, 2H), 2.61 ( d, J=3.3 Hz, 2H), 1.59 (s, 3H), 1.50 (s, 3H).

$^{13}$C NMR 75 MHz (CDCl$_3$) d 194.49, 144.77, 138.07, 133.75, 131.91, 130.45, 129.35, 128.65, 128.35, 126.91, 110.26, 80.94, 77.95, 68.27, 53.38, 38.77, 26.79, 26.34.

UV (methanol) 1=304 nm, e=22800.

Example 5

Table 101, compounds 26, 28, and 29

Enone (Table 101, compound 25)(1.1 g) with Ni (AcAc)$_2$ (1.42 g) was dissolved in methylene chloride (60 mL) and ethanol (110 mL) and cooled in an ice bath. Solid sodium borohydride (315 mg) was added. The reaction turns dark over 10 min. After 30 min, the mixture was concentrated under vacuum and filtered through a silica plug with ethyl acetate to elute the product. After concentration, careful chromatography on silica gel eluting with 2% to 20% ethyl acetate/methylene chloride gave the symmetrical diol (Table 101, compound 28)(407 mg), accompanied by other diastereomers (200 mg)(including Table 101, compounds 29 and 30).

Symmetrical diol (Table 101, compound 28):

$^1$H NMR 300 MHz (CDCl$_3$) d 7.3–7.15 (m, 10 H), 4.22 (dd, J=4.8, 4.2 Hz, 2H), 4.14 (br s, 2H), 3.37 (m, 2H), 3.07 (dd, J=13.8, 9.0 Hz, 2H), 2.78 (dd, J=1.38, 6.9 Hz, 2H), 2.44 ( d, J=5.4 Hz, 2H), 1.38 (s, 6H).

$^{13}$C NMR 75 MHz (CDCl$_3$) d 138.92, 129.14, 128.51, 126.57, 107.81, 76.90, 67.64, 46.51, 39.14, 26.78.

Example 6

Table 101, compound 27

To a solution of diol (Table 101, compound 30)(18 mg) in methylene chloride (0.5 mL) was added a solution of Dess- Martin reagent (~2M in methylene chloride)(1 mL). Additional reagent was added after 4 and 5 hours until the reaction was complete. After completion, the reaction was quenched with sodium bicarbonate solution and extracted with methylene chloride. The crude diketone was dissolved in methanol (3 mL). Sodium borohydride (3.8 mg) was added to afford, after workup, the symmetrical diol (Table 101, compound 28).

The diketone (Table 101, compound 27) was characterized by NMR and used directly in the reduction:

$^1$H NMR 300 MHz (CDCl$_3$) d 7.4–7.1 (m, 8H), 6.89 (m, 2H), 4.8 (s, 2H), 3.45–3.2 (m, 4H), 2.7 (dd, J=15, 6 Hz, 2H), 1.48 (s, 6H).

$^{13}$C NMR 75 MHz (CDCl$_3$) d 199.54, 137.30, 129.61, 128.58, 126.97, 112.76,

Example 7
Table 107, compound 1

Diol (Table 101, compound 15)(0.51g) was dissolved in THF (40 mL) and DMSO (20 mL) at 0° C. Sodium hydride (0.48 gm, 60% in oil) was added, followed after 15 min. by benzyl bromide (0.45 mL). After 24 hours, the reaction was quenched with water and extracted into methylene chloride. Chromatography on silica gel with hexane followed by methylene chloride afforded dibenzyl ether (Table 107, compound 1)(0.81 g) as yellow oil.

$^1$H NMR 300 MHz (CDCl$_3$) d 7.5–7.0 (m, 15 H), 5.094 ( d, J=12 Hz, 1H), 5.086 (dd, J=8.4, 4.2 Hz, 1H),4.85 ( d, J=12.3 Hz, 1H), 4.59 ( d, J=12 Hz, 2H), 4.23 (dd, J=8.7, 1.5 Hz, 1H), 4.10 ( td, J=8.7, 3.9 Hz, 2H), 4.03 (t, J=1.5 Hz, 1H), 3.12 (dd, J=15.3, 8.4 Hz, 1H), 2.99 (ddd, J=11.7, 6.6, 1.5 Hz, 1H), 2.89 (dd, J=15.3, 6.6 Hz, 1H), 2.79 (dd, J=15.3, 8.4 Hz, 1H), 2.46 (dd, J=15.3, 8.4 Hz, 1H), 1.45 (s, 3H), 1.43 (s,3H).

Example 8
Table 107, compound 2

Acetonide (Table 107, compound 1)(0.81 g) was dissolved in methanol (60 mL), water (5 mL) and TFA (100 mL) and heated to reflux for 5 h. The reaction was concentrated under vacuum and chromatographed on silica with 10% ethyl acetate/methylene chloride to give diol (Table 107, compound 2)(0.36 g) as an oil.

$^1$H NMR 300 MHz (CDCl$_3$) d 7.5–7.0 (m, 15H), 5.00 ( d, J=12 Hz, 1H), 4.67 (d, J=11.4 Hz, 1H), 4.61 ( d, J=12.Hz, 1H), 4.44 (d, J=11.1 Hz, 1H), 4.29 (td, J=8.7, 4.5 Hz, 1H), 4.10 ( dt, J=9.0, 4.5 Hz, 1H), 4.04 (t, J=1.2 Hz, 1H), 3.82 (d, J=9.0 Hz, 1H), 3.22 (br s, 1H), 3.16 ( td, J=7.5, 2.4 Hz, 1H), 3.14 (dd, J=15,4.5 Hz, 1H), 2.91 (m, 3H), 2.62 (dd, J=15, 5.7 Hz, 1H).

Example 9
Table 107, compounds 3, and 4

To a solution of sulfide (Table 107, compound 2)(107 mg) in methanol (12 mL) was added a solution of OXONE (73 mg) in water (3 mL). After stirring 1 h, the product was extracted into methylene chloride and chromatographed on silica with 2% methanol/methylene chloride to give a mixture (85 mg) of sulfoxides as a foam. These were resolved by preparative reverse phase HPLC to give sulfoxides (Table 107, compound 3)(34 mg). and (Table 107, compound 4)(17 mg).

HPLC diastereomer 1 (Table 107, compound 3) 16.958 min; diastereomer 2 (Table 107, compound 4) 16.321 min; 20% to 97% methanol/water gradient over 25 minutes, UV 248 nm detection, Rainin Dynamax 3 uM, 4.6 mm×5 cm. C18 column, 1 ml/min flow rate. Diastereomer 1 (Table 107, compound 3):

$^1$H NMR 500 MHz (CDCl$_3$) d 7.5–7.1 (m, 15H), 4.80 (d, J=12 Hz, 1H), 4.71 (d, J=12Hz, 1H), 4.69 ( d, J=12 Hz, 1H), 4.59 ( d, J=11.5 Hz, 1H), 4.51 (ddd, J=10, 3, 1.5 Hz, 1H), 4.22 ( dd, J=3.5, 1Hz, 1H), 4.10 (dd, J=8, 2.5 Hz, 1H), 3.92 (br d, J=6.5 Hz, 1H), 3.54 (br s, 1H), 3.44 ( dd, J=14.5, 1Hz, 1H), 3.43 (dd, J=14.5, 7 Hz, 1H), 3.30 (dd, J=14.5, 10 Hz, 1H), 3.25 (dd, J=14.5, 7 Hz, lH),3.13 (ddd, J=9, 7.5, 3.5 Hz, 1H).

$^{13}$C NMR 125 MHz HMQC (CDCl$_3$) d 129.44, 128.89, 128.75, 128.25, 128.09, 127.15, 79.63, 75.79, 75.79, 73.70, 73.54, 72.58, 71.30, 62.97, 33.74. Diastereomer 2 (Table 107, compound 4):

$^1$H NMR 500 MHz (CDCl$_3$) d 7.5–7.1 (m, 13 H), 6.96 (d, J=6.5 Hz, 2H), 5.00 (d, J=11Hz, 1H), 4.80 (d, J=12.5 Hz, 1H), 4.61 (d, J=11.5 Hz, 1H), 4.52 (d, J=11 Hz, 1H), 4.32 (dt, J=8.5, 2 Hz, 1H), 3.98 (br s, 1H), 3.77 (br m, 1H), 3.68 (d, J=8.5 Hz, 1H), 3.56 (dd, J=11.5,3.5 Hz, 1H), 3.51 (m, 2H), 3.31 (d, J=15 Hz, 1H), 2.84 (dd, J=13, 12 Hz, 1H), 2.83 (br s, 1H), 2.71 (d, J=6 Hz, 1H).

$^{13}$C NMR 125 MHz HMQC (CDCl$_3$) d 77.42, 77.22, 75.56, 74.90, 74.86, 72.23, 67.21, 50.61, 35.39.

Example 10
Table 107, compound 5

To a solution of sulfide (Table 107, compound 2)(98 mg) in methanol (11 mL) was added a solution of OXONE (176 mg) in water (3 mL). After stirring 15 h, the product was extracted into methylene chloride and chromatographed on silica with 5% methanol in methylene chloride to give sulfone (Table 107, compound 5)( 94 mg) as a foam.

$^1$H NMR 300 MHz (CDCl$_3$) d 7.5–7.1 (m, 13H), 6.93 (m, 2H), 4.94 ( d, J=11.1Hz, 1H), 4.83 (s, 2H), 4.58 (d, J=11.1Hz, 1H), 4.25 (dd, J=8.4, 2.7 Hz, 1H 3.91 (s, 1H), 3.80 ( dd, J=11.7, 2.7 Hz, 1H), 3.73 (dd, J=14.7, 8.7 Hz, 1H), 3.64 (d, J=8.4 Hz, 1H), 3.50 (m, 3H), 2.95 (dd, J=14.7, 12 Hz, 1H), 2.51 (m, 2H).

Example 11
Table 107, compound 6

Sodium hydride (60% in oil, 0.1 g) was washed 2× with hexane (5 mL) and suspended in DMSO (6 mL) and THF ( 6 mL) under argon. After cooling in ice, thiepane diol (Table 101, compound 15)(0.144 g) was added as a solution in THF (6 mL). After gas evolution ceased, o-fluorobenzonitrile (0.2 mL) was added. More THF was added to keep the mixture stirrable. After 3.5 h the mixture was cautiously quenched into 5% citric acid solution. After extraction into methylene chloride, the product was chromatographed on silica gel with methylene chloride to afford diaryl ether (Table 107, compound 6)(0.2 g) as a foam. m.p. 81–84 ° C.

$^1$H NMR 500 MHz (CDCl$_3$) d 7.6–6.9 (m, 13H), 5.41 (dd, J=9, 4 Hz, 1H), 5.19 (ddd, J=8, 8, 3.5 Hz, 1H), 4.94 (br s, lH), 4.50 (dd, J=9, 2 Hz, 1H), 3.47 (dd, J=15.5, 9 Hz, 1H), 3.34 (ddd, J=9.5, 6, 1Hz, 1H), 3.12 (dd, J=14, 6.5 Hz, 1H), 2.86 (dd, J=14, 10.5 Hz, 1H), 2.855 (dd, J=15.5, 7 Hz, 1H) 1.20 (s, 3H), 1.01 (s, 3H).

$^{13}$C NMR 125 MHz HMQC (CDCl$_3$) d 134.19, 133.72, 133.48, 133.12, 129.3, 128.82, 127.15, 121.53, 116.15, 115.08, 77.69, 76.25, 75.67, 74.52, 53.77, 38.2, 35.32, 26.96, 26.38.

Example 12
Table 107, compound 7

Acetonide (Table 107, compound 6)(187 mg) was suspended in water (10 mL) and solubilized with methanol (16 mL) and methylene chloride (5 mL). TFA ( 26 mL) was added and the reaction heated to gentle reflux until complete by TLC. The solvents were removed by vacuum to afford after chromatography, diol (Table 107, compound 7)(106 mg).

¹H NMR 500 MHz (CDCl₃) d 7.591 (d, J=7.5 Hz, 1H), 7.586 (d, J=7.5 Hz, 1H), 7.466 (dd, J=9, 7.5 Hz, 1H), 7.463 (dd, J=9, 7.5 Hz, 1H), 7.225 (m, 4H), 7.17 (d, J=8.5 Hz, 1H), 7.13 (d, J=8 Hz, 1H), 7.089 (t, J=7 Hz, 1H), 7.04 (m, 2H), 5.24 (ddd, J=8.5, 4, 4 Hz, 1H), 5.01 (br s, 1H), 4.54 (dd, J=9,4 Hz, 1H), 4.27 (dd, J=8.5, 1Hz, 1H), 3.62 (ddd, J=9.5, 6.5, 2 Hz, 1H), 3.36 (dd, J=15.5,4 Hz, 1H), 3.03 (dd, J=13.5, 6.5 Hz, 1H), 3.02 (dd, J=15, 8.5 Hz, 1H), 2.95 (dd, J=14, 8.5 Hz, 1H).
¹³C NMR 125 MHz HMQC (CDCl₃) d 134.71, 134.36 (2C), 133.67, 129.39, 128.81, 127.07, 122.39, 121.99, 115.85, 114.81, 81.39, 78.91, 73.29, 71.47, 49.88, 39.28, 30.46.

Example 13
Table 107, compound 8
Sulfide (Table 107, compound 7)(72 mg) in methanol (8 mL) and water (2 mL) was cooled to 0° C. OXONE (46 mg) as a solid was added followed by methanol (1 mL). After 2 h, the solvent was removed under vacuum and the mixture extracted between methylene chloride and water. The product was a mixture of sulfoxides. The unpurified mixture showed by HPLC, a diastereomeric ratio of 93:7. After chromatography on silica gel the major sulfoxide (54 mg), believed to have the stereochemistry indicated (Table 107, compound 8), was characterized as a solid. m.p. 183°–186° C.
¹H NMR 500 MHz (CDCl₃) d 7.49 (m, 4H), 7.26 (m, 2H), 7.20 (m, 1H), 7.14 (m, 4H), 7.03 (t, J=7.5 Hz, 1H), 6.99 (t, J=7.5 Hz, 1H), 5.31 (d, J=7.5 Hz, 1H) 5.00 (br s, 1H), 4.12 (d, J=8.5 Hz, 1H), 3.98 (dd, J=11.5,4 Hz, 1H), 3.96 (dd, J=8.5, 2 Hz, 1H), 3.76 (d, J=15 Hz, 1H), 3.64 (dd, J=15, 8 Hz, 1H), 3.56 (dd, J=14, 4 Hz, 1H), 2.87 (dd, J=14, 12 Hz, 1H).
¹³C NMR 125 MHz HMQC (CDCl₃) d 134.83, 134.43, 133., 129.68, 129.16, 127.43, 122.39, 122.22, 114.58, 113.43, 78.21, 75.09, 73.86, 65.73, 49.80, 35.55.
HPLC major diastereomer 11.453 min; minor diastereomer 11.916 min, 20% to 97% methanol/water gradient over 25 minutes, UV 292 nm detection, Rainin Dynamax 3 uM, 4.6 mm X 5 cm. C18 column, 1 ml/min flow rate.

Example 14
Table 107, compound 10
Sulfide (Table 107, compound 7)(29 mg) in methanol (3 mL) and water (1 mL) was cooled to 0° C. OXONE (50 mg) in water (1 mL) was added followed by methanol (1 mL). After warming to ambient and stirring overnight, the mixture was extracted between methylene chloride and water. After concentration the residue was chromatographed on silica gel with 2% methanol in methylene chloride to give sulfone (Table 107, compound 10)(27 mg).
¹H NMR 500 MHz (CDCl₃) d 7.63 ( td, J=8.5, 1Hz, 1H), 7.58 (dd, J=8, 1 Hz, 1H), 7.55 ( dd, J=7.5, 1Hz, 1H), 7.52 ( td, J=8.5, 1Hz, 1H), 7.34 (m, 2H), 7.32 (d, J=7.5 Hz, 1H), 7.30 (m,2H), 7.19 ( d, J=7.5 Hz, 1H), 7.1 ( m, 1H), 7.08 (m, 1H), 7.07 ( d, J=9 Hz, 1H), 5.49 (ddd, J=6.5, 3, 3 Hz, 1H), 4.99 (br s, 1H), 4.25 (m, 1H), 4.20 (d, J=8 Hz, 1H), 4.12 (dd, J=11.5,3 Hz, 1H), 3.94 (m, 2H), 3.58 (dd, J=14.5,3 Hz, 1H), 3.32 (d, J=4.5 Hz, 1H), 3.10 (d, J=2 Hz, 1H), 3.01 (dd, J=14.5, 12 Hz, 1H).
¹³C NMR 125 MHz HMQC (CDCl₃) d 160.19, 158.10, 135.2, 134.53 (2C), 133.59, 129.48, 129.23, 127.64, 122.34, 122.23, 113.54, 112.89, 75.88, 75.66, 74.02, 72.07, 67.17, 53.74, 30.17.

Example 15
Table 107, compound 11
By the method of Example 11, compound 15, Table 101, (0.48 g) was converted with p-fluorobenzonitrile (0.43 g) into diaryl ether (Table 107, compound 11)(0.55 g) after chromatography on silica gel with methylene chloride.
¹H NMR 300 MHz (CDCl₃) d 7.54 (d, J=8.7 Hz, 2H), 7.53 (d, J=9 Hz, 2H), 7.20 (m, 3 H), 7.05 (d, J=8.7, 2H), 6.98 (d, J=8.7, 2H), 6.90 (m, 2H), 5.27 (dd, J=8.7, 3.9 Hz, 1H), 5.08 (td, J=8.1, 3.9 Hz, 1H), 4.87 (s, 1H), 4.38 (dd, J=8.4, 1.5 Hz, 1.5 Hz, 1H), 3.45(dd, J=15.6, 8.4 Hz, 1H), 3.25 (ddd, J=9.9, 5.7, 1.5 Hz, 1H), 3.04 (dd, J=14.1, 6 Hz, 1H), 2.75 (m, 2H). 1.10( s, 3H), 0.95 (s, 3H).

Example 16
Table 107, compound 12
By the method of Example 8, compound 11, Table 107, (550 mg) was converted to diol (Table 107, compound 12)(201 mg) after chromatography.
¹H NMR 300 MHz (CDCl₃) d 7.61 ( d, J=9 Hz, 2H), 7.55 (d, J=8.7 Hz, 2H), 7.18 (m, 5H), 7.02 (d, J=9, 2H), 6.91 ( m, 2H), 5.08 (dd, J=9, 4.8, 3.9 Hz, 1H), 4.88 (dd, J=1.8, 1.5 Hz, 1H), 4.58 (dd, J=8.4, 3.9 Hz, 1H), 4.14 (dd, J=8.4, 1.5 Hz, 1H), 3.40 (ddd, J=8.7, 6.3, 2.1Hz, 1H), 3.20 (dd, J=15.3, 5.4 Hz, 1H), 2.95 (dd, J=13.8, 6 Hz, 1H), 2.83 (dd, J=9, 7.5 Hz, 1H), 2.80 (dd, J=9.3, 6 Hz, 1H).

Example 17
Table 107, compounds 13 and 14
By the method of Example 9, compound 12, Table 107, (67 mg) was converted to a mixture of sulfoxides. The unpurified mixture showed by HPLC, a diastereomeric ratio of 80:20. After careful chromatography on silica gel the more polar major diastereomer (14 mg), assigned the stereochemistry indicated (Table 107, compound 13), was obtained. The mixed fractions (50 mg) were separated on reverse phase HPLC to provide the less polar diastereomer (Table 107, compound 14) 2.5 mg for NMR characterization.
HPLC major diastereomer 11.856 min; minor diastereomer 12.438 min, 20% to 97% methanol/water gradient over 25 minutes, UV 248 nm detection, Rainin Dynamax 3 uM, 4.6 mm X 5 cm. C18 column, 1 ml/min flow rate.
Major diastereomer (Table 107, compound 13):
¹H NMR 500 MHz (CDC13/D4-methanol) d 7.54 ( d, J=8.5 Hz, 1H), 7.50 ( d, J=8.5 Hz, 1H), 7.15 (m, 1H), 7.14 (m, 1H), 7.08 ( d, J=8.5 Hz, 2H), 6.90 ( d, J=7 Hz, 1H), 5.13 (br d, J=8 Hz, 1H), 4.82 (br s, 1H), 3.98 (d, J=8 Hz, 1H), 3.93 (d, J=8, 1H), 3.66 (ddd, J=11.5,4, 1.5 Hz, 1H), 3.55 (dd, J=14.5, 8 Hz, 1H), 3.47 (dd, J=14.5, 2 Hz, 1H), 3.42 (dd, J=14.5, 4 Hz, 1H), 2.82 (dd, J=13, 12 Hz, 1H).
¹³C NMR 125 MHz HMQC (CDCl₃) d 134.24, 134.13, 129.22, 128.99, 127.35, 116.95, 78.49, 74.6, 74.34, 72.79, 67.34, 50.99, 34.39.
UV (methanol) 1=248 nm, e=23500.
Minor diastereomer (Table 107, compound 14):
¹H NMR 500 MHz (CDC13/D4-methanol) d 7.52 (d, J=7 Hz, 1H), 7.51 ( d, J=7 Hz, lH), 7.16 ( d, J=7Hz, 2H), 7.13 (m, 1H), 7.11 (d, J=9 Hz, 1H), 7.0 ( d, J=6.5 Hz, 1H), 5.57 (ddd, J=6.5, 4.5, 3 Hz, 1H), 5.0 (br s, 1H), 4.14 (dd, J=7, 3 Hz, 1H), 3.98 (dd, J=7, 1H), 3.65 (m, 1H), 3.42 (m, 1H), 3.39 (m, 1H), 3.31 (m, 1H), 3.15 (dd, J=16.5, 11Hz, 1H).
¹³C NMR 125 MHz HMQC (CDCl₃) d 134.26, 129.23, 116.56, 80.73, 74.55, 72.78, 68.96, 63.07, 45.12, 33.64.

Example 18 Table 107, compound 15
By the method of Example 11, compound 11, Table 107, (79 mg) was converted to sulfone (Table 107, compound 15)(66 mg) after chromatography on silica gel with 2% methanol in methylene chloride.

m.p. 117°–122° C.

$^1$H NMR 300 MHz (CDCl$_3$) d 7.64 ( d, J=8.7 Hz, 2H), 7.59 (d, J=8.7 Hz, 2H), 7.25 (m, 7 H), 6.85 ( m, 2H), 5.36 (dd, J=9.3, 3 Hz, 1H), 4.7 (br s, 1H), 4.12 (br d, J=7.5 Hz, 1H), 4.05 (dd, J=7.8, 1.5 Hz, 1H), 3.86 (dd, J=15.3, 9.6 Hz, 1H), 3.65 (ddd, J=10.8, 2.4, 2.1Hz, 1H), 3.52 (d, J=15.6 Hz, 1H), 3.51 (dd, J=14.1, 3.9 Hz, 1H), 3.15 (dd, J=9.9, 2.4 Hz, 1H), 2.91 (dd, J=14.1, 11.7 Hz, 1H).

Example 19
Table 108, compound 1

Sodium hydride (107 mg, 60% in oil) was added to a THF (5 mL) solution of diol (Table 101, compound 28)(270 mg). Benzyl bromide (250 uL) was added after 10 minutes. DMSO (250 uL) was added and the reaction warmed to 45° C. for 3 h. After extraction between water and methylene chloride, the product was chromatographed on silica gel with 20% ethyl acetate/hexane to provide dibenzyl ether (Table 108, compound 1)(360 mg) as an oil.

$^1$H NMR 300 MHz (CDCl$_3$) d 7.4–7.1 (m, 16H), 6.94 ( dd, J=7.8, 1.8 Hz, 4H), 4.97 ( d, J=12 Hz, 2H), 4.55 ( d, J=12 Hz, 2H), 4.28 (s, 2H), 4.07 ( d, J=2.7 Hz, 2H), 3.44 (td, J=7.8, 2.7 Hz, 2H), 2.85 ( d, J=7.8 Hz, 4H), 1.39 (s, 6H).

UV (methanol) 1=258 nm, e=800

Example 20
Table 108, compounds 1, 2

Sodium hydride (60% in oil, 180 mg) was washed 3× with hexane (5 mL) and suspended in THF (12 mL) and DMSO (12 mL) under argon. A solution of diol (Table 101, compound 28)(364 mg) in THF (13 mL) was added slowly. After gas evolution subsided, the mixture was cooled with an ice bath. Benzyl bromide (0.25 mL) was added via syringe. The reaction was warmed to 40° C. and stirred overnight. After extraction between water and methylene chloride, the product was chromatographed on silica gel with 50% hexane/methylene chloride, 100% methylene chloride and finally 10% ethyl acetate/methylene chloride to afford the dibenzyl ether (Table 108, compound 1)(210 mg) as an oil, monobenzyl ether (Table 108, compound 2) (155 mg) and starting diol (62 mg).

Monobenzyl ether (Table 108, compound 2):

$^1$H NMR 300 MHz (CDCl$_3$) d 7.4–7.1 (m, 13 H), 6.98 ( dd, J=7.8, 1.8 Hz, 2H), 4.89 (d, J=11.7 Hz, 1H), 4.36 (d, J=11.7 Hz, 1H), 4.24 (d, J=9.3 Hz, 1H), 4.18 ( d, J=4.8 Hz, 1H), 4.07 (dd, J=4.8, 2.7 Hz, 1H), 3.99 ( dd, J=9.3, 3 Hz, 1H), 3.69 (dd, J=8.7, 7.5 Hz, 1H), 3.19 (ddd, J=7.8, 7.2, 5.1Hz, 1H), 3.08 (dd, J=13.2, 8.4 Hz, 1H), 2.96–2.76 (m, 3H), 2.91 (dd, J=13.8, 7.2 Hz, 1H), 2.85 (dd, J=13.8, 9.3 Hz, 1H) 2.77 (d, J=7.8 Hz, 1H), 1.39 (s, 6H).

Example 21
Table 108, compound 3

Acetonide (Table 108, compound 1)(210 mg) was dissolved in methanol (15 mL) and methylene chloride (1 mL) with added TFA (22 mL). After heating to 65° C., the solvent was removed under vacuum. The residue was chromatographed on silica gel with 5% ethyl acetate/methylene chloride to give 165 mg of diol (Table 108, compound 3) as a white foam.

$^1$H NMR 300 MHz (CDCl$_3$/D$_2$O) d 7.4–7.15 (m, 16H), 7.37 (d, J=6.6 Hz, 4H ), 4.76 (s, 4H), 4.06 (br s, 2H), 3.76 (br s, 2H), 3.63 (td, J=7.5, 1.2 Hz, 2H), 2.89 (m, 4H).

$^{13}$C NMR 75 MHz (CDCl$_3$/D$_2$O) d 139.22, 138.43, 129.11, 128.48, 128.41, 127.76, 127.60, 126.46, 80.99, 75.13, 74.37, 46.68, 40.97.

UV (methanol) 1=258.6 nm, e=840.

Example 22
Table 108, compound 4

To a solution of sulfide (Table 108, compound 3)(34.5 mg) in methanol (5 mL) was added a solution of OXONE (20 mg) in water (0.5 mL) and stirred for 1.5 h. After extraction with methylene chloride, the product was chromatographed on silica gel with 10% ethyl acetate/methylene chloride to provide 30.6 mg of sulfoxide (Table 108, compound 4).

$^1$H NMR 300 MHz (CDCl$_3$/D$_2$O) d 7.5–7.1 (m, 16H), 6.96 (m, 2H ), 5.11 (d, J=11.1 Hz, 1H), 4.79 (d, J=11.7 Hz, 1H), 4.71 (d, J=11.1 Hz, 1H), 4.64 (d, J=11.7 Hz, 1H), 4.22 (s, 1H), 3.99 (s, 1H), 3.86 (dd, J=12, 3.3 Hz, 1H), 3.60 (s, 2H), 3.55 (m, 2H), 3.43 (t, J=7.8 Hz, 1H), 3.09 (dd, J=14.1, 8.4 Hz, 1H), 2.81 (dd, J=16.5, 12 Hz, 1H).

$^{13}$C NMR 75 MHz (CDCl$_3$/D$_2$O) d 138.25, 138.04, 137.99, 137.92, 129.30 (2C), 128.74, 128.70, 128.47, 128.12, 127.93, 127.85, 126.72, 126.83, 82.04, 77.22, 74.68, 74.63, 65.04, 59.41, 36.57, 36.44.

UV (methanol) 1=258.6 nm, e=610.

Example 23
Table 108, compound 5

To a solution of sulfide (Table 108, compound 3)(35.7 mg) in methanol (5 mL) was added a solution of OXONE (53 mg) in water (1 mL) and stirred for 24 hours. After extraction with methylene chloride, the product was chromatographed on silica gel with 8% ethyl acetate/methylene chloride to provide 32.2 mg of sulfone (Table 108, compound 5) which was then recrystallized from hexane.

mp 164–165.

$^1$H NMR 300 MHz (CDCl$_3$/D$_2$O) d 7.5–7.2 (m, 16H), 7.00 (d, J=6 Hz, 4H), 5.04 (d, J=11.4 Hz, 2H), 4.79 (d, J=11.4 Hz, 2H), 3.96 (s, 2H), 3.78 (dd, J=11.7, 3.0 Hz, 2H), 3.63 (dd, J=11.4,3.0 Hz, 2H), 3.56 (s, 2H), 3.03 (dd, J=14.1, 12.0 Hz, 2H).

$^{13}$C NMR 75 MHz (CDCl$_3$/D$_2$O) d 137.82, 136.80, 129.40, 128.93, 128.56, 128.14, 128.05, 127.05, 76.58, 76.36, 74.95, 66.95, 31.76.

UV (methanol) 1=258.6 nm, e=780.

Example 24
Table 108, compound 6

Sodium hydride (75 mg, 60% in oil) under argon was washed with hexane (2×4 mL). A solution of diol (Table 108, compound 3) in THF (15 mL) was added. After gas evolution ceased, a solution of tosyl chloride (75 mg) in THF (30 mL) was added slowly over 75 min. After stirring an additional 3 h, the reaction was quenched with water and extracted into methylene chloride. Chromatography on silica with 10% ethyl acetate/hexane afforded epoxide (Table 108, compound 6)(131 mg).

$^1$H NMR 300 MHz (CDCl$_3$) d 7.5–7.1 (m, 16H), 7.06 (m, 2H ), 6.84 (m, 2H) 4.91 (d, J=12 Hz, 1H), 4.79 (d, J=11.7 Hz, 1H), 4.67 (d, J=12 Hz, 1H), 4.53 (d, J=12 Hz, 1H), 4.39 (dd, J=6.3, 1.8 Hz, 1H), 4.01 (d, J=4.2 Hz, 1H), 3.29 (m, 2H), 3.16 (dd, J=6.3, 4.5 Hz, 1H), 2.97 (m, 2H), 2.83–2.7 (m, 3H)

Example 25
Table 108, compound 7

By the method of Example 22, compound 6, Table 108, (10 mg) was converted to sulfoxide (Table 108, compound 7)(4 mg) after chromatography on silica gel with 5% ethyl acetate in methylene chloride. A single diastereomer was obtained, assigned the stereochemistry depicted.

$^1$H NMR 300 MHz (CDCl$_3$) d 7.4–7.2 (m, 16H), 7.1–7.04 (m, 4H ), 4.77 (br d, J=12 Hz, 1H), 4.71 (d, J=11.7 Hz, 1H), 4.62 (d, J=11.7 Hz, 1H), 4.59 (dd, J=5.7, 1.5 Hz, 1H), 4.37 (d, J=11.7 Hz, 1H), 4.26 (dd, J=4.2,0.9 Hz, 1H), 3.83 (br td, J=7.5, 0.9 Hz, 1H), 3.42 (br dd, J=12, 2.7 Hz, 1H), 3.243.05 (m, 6H).

Example 26
Table 108, compound 8

Epoxide (Table 108, compound 6)(33 mg) was suspended in acetone (6 ml) and water (3 mL), then treated with sodium bicarbonate (800 mg) and OXONE (60 mg) at RT for 25 min. After quenching with sodium thiosulphate (100 mg) the mixture was reduced under vacuum to 2 mL volume, diluted with water (10 mL) and extracted with methylene chloride (3×10 mL). The organic layer was dried over sodium sulfate, filtered and concentrated under vacuum. The residue was triturated with hexane. The solid was collected by centrifugation and dried under vacuum to provide epoxy sulfone (Table 108, compound 8)(31 mg).

$^1$H NMR 300 MHz (CDCl$_3$) d 7.4–7.1 (m, 19H), 6.89 (br s, 1H), 4.89 (d, J=11.7 Hz, 1H), 4.7–4.5 (m, 2H), 4.41 (d, J=12 Hz, 1H), 4.01 (br s, 1H), 3.91 (br t, J=6.6 Hz, 1H), 3.57–3.50 (m, 2H), 3.38–3.29 (m, 4H), 3.1–3.0 (m, 2H).

Example 27
Table 108, compound 9

By the method of Example 20, compound 28, Table 101, (100 mg) was alkylated with 3-chloromethylpyridine hydrochloride (300 mg) and NaH (500 mg) to give dipyridyl ether (Table 108, compound 9)(82 mg) after chromatography on silica with 10% methanol/methylene chloride.

$^1$H NMR 300 MHz (CDCl$_3$) d 8.62 (s, 2H), 8.58 (d, J=4.5 Hz, 2H), 7.71 (d, J=7.5 Hz, 2H), 7.35–7.1 (m, 10H), 6.98 (d, J=6.9 Hz, 2H), 4.97 (d, J=12 Hz, 2H), 4.52 (d, J=12 Hz, 2H), 4.28 (s, 2H), 4.1 (d, J=2.7 Hz, 2H), 3.41 (td, J=8.1, 2.7 Hz, 2H), 2.86 (d, J=8.1Hz, 4H), 1.37 (s, 6H).

$^{13}$C NMR 125 MHz HMQC (CDCl$_3$) d 149.7, 149.5, 149.2, 135.71, 135.57, 129.55, 129.41, 129.28, 127.11, 123.86, 79.33, 74.93, 72.39, 72.25, 71.94, 65.99, 62.30, 34.87, 32.03, 26.83.

Example 28
Table 108, compound 10

The sulfide (Table 108, compound 9)(70 mg) was dissolved in water (3 ml) and acetone (5 mL) with sodium bicarbonate (800 mg). The solution was cooled to −5° C. and OXONE (90 mg) was added as a solid. After 10 min, the reaction was quenched with sodium thiosulfate (100 mg), diluted with water (10 mL), then concentrated to half its volume under vacuum and extracted with methylene chloride (3×5 mL). The organic layer was dried over sodium sulfate and concentrated to leave sulfoxide (Table 108, compound 10)(73 mg) which was used directly in the next reaction.

$^1$H NMR 300 MHz (CDCl$_3$) d 8.62 (d, J=4.5 Hz, 1H), 8.61 (d, J=4.5 Hz, 1H), 8.58 (s, 1H), 8.55 (s, 1H), 7.75 ( d, J=7.8 Hz, 1H), 7.68 ( d, J=7.5 Hz, 1H), 8H), 7.12 ( d, J=6.9 Hz, 2H), 7.01 ( d, J=6.9 Hz, 2H), 4.94 (d, J=12.3 Hz, 1H), 4.87 (d, J=12.3 Hz, 1H), 4.66 (d, J=12 Hz, 1H), 4.56 (d, J=12 Hz, 1H), 4.29 (s, 1H), 4.14 (s, 2H), 4.07 (s, 2H), 3.51 (m, 4H), 2.91 (m, 2H), 1.35 (s, 6H).

Example 29
Table 108, compound 11

Sulfoxide (Table 108, compound 10)(65 mg) was dissolved in acetone (5 mL) and water (3 mL) with sodium bicarbonate (800 mg). At room temperature, OXONE (45 mg) was added as a solid. After 30 min, the reaction was quenched with sodium thiosulfate (100 mg), diluted with water (10 mL), then concentrated to half its volume under vacuum and extracted with methylene chloride (3×5 mL). The organic layer was dried over sodium sulfate and concentrated to afford after chromatography on silica with 5% methanol/ethyl acetate the sulfone (Table 108, compound 11)(18 mg).

$^1$H NMR 300 MHz (CDCl$_3$) d 8.62 (d, J=6.3 Hz, 2H), 8.61 (s, 2H), 7.86 ( d, J=7.8 Hz, 2H), 7.38 (dd, J=7.5, 4.8 Hz, 2H), 7.26 (m, 6H), 6.98 ( d, J=7.5 Hz, 4H), 4.97 (d, J=12 Hz, 2H), 4.79 (d, J=12 Hz, 2H), 4.09 (s, 2H), 4.01 (s, 2H), 3.60 (dd, J=14.1, 2.4 Hz, 2H), 3.49 (dd, J=11.4, 2.7 Hz, 2H), 3.04 (dd, J=13.8, 11.1Hz, 4H), 1.35 (s, 6H).

Example 30
Table 108, compound 14

By the method of Example 21, compound 11, Table 108, (15 mg) was converted to diol (Table 108, compound 14)(10 mg) $^1$H NMR 300 MHz (CDCl$_3$) d 8.50 (s, 2H), 8.45 (d, J=4.5 Hz, 2H), 7.91 ( d, J=7.8 Hz, 2H), 7.26 (m, 8H), 7.02 ( d, J=7.2 Hz, 4H), 5.02 (d, J=11.7 Hz, 2H), 4.87 (d, J=11.7 Hz, 2H), 4.01 (s, 2H), 3.73 (dd, J=11.7, 3 Hz, 2H), 3.70 (m, 4H), 3.65 (s, 2H), 3.02 (dd, J=13.8, 12 Hz, 2H).

Example 31
Table 108, compounds 15 and 19

By the method of Example 19, a mixture of diastereomers (330 mg) containing compound 29, Table 101, and compound 30, Table 101, was benzylated to the corresponding diethers. After chromatography on silica with methylene chloride, (Table 108, compound 15)(79 mg) and (Table 108, compound 19)(107 mg) were obtained.

Table 108, compound 15:

$^1$H NMR 300 MHz (CDCl$_3$) d 7.5–6.8 (m, 20H), 4.97 (d, J=11.7 Hz, 1H), 4.871 (d, J=12.3 Hz, 1H), 4.867 (dd, J=9,5.7 Hz, 1H), 4.48 (d J=12 Hz, 1H), 4.39 (d, J=12 Hz, 1H), 3.98 (br s, 1H), 3.79 (dd, J=9.3, 1.2 Hz, 1H), 3.56 (dd, J=5.4, 0.9 Hz, 1H), 2.92 (td, J=7.8, 1.5 Hz, 1H), 2.81 (s, 3H), 2.78 (dd, J=14.4, 7.2 Hz, 1H), 2.64 (dd, J=14.1, 7.8 Hz, 1H), 1.29 (s, 3H), 1.25 (s, 3H).

Table 108, compound 19:

$^1$H NMR 300 MHz (CDCl$_3$) d 7.4–6.8 (m, 20H), 5.05 (d, J=12 Hz, 1H), 4.88 (7, J=8.7 Hz, 1H), 4.60 (d, J=12. Hz, 1H), 4.54 (d, J=11.7 Hz, 1H), 4.36 (d J=12 Hz, 1H), 4.07 (br s, 1H), 4.03 (d, J=9 Hz, 1H), 3.56 (dd, J=8.1, 3.6 Hz, 1H), 3.11 (m, 3H), 2.76 (m, 3H), 1.42 (s, 3H), 1.37 (s, 3H).

$^{13}$C NMR 125 MHz HMQC* (CDCl$_3$) d 84.2, 81.8, 79.3, 76.6, 74.8, 72.4, 48.1, 45.5, 40.5, 38.5, 27.2, 27*.

Example 32
Table 108, compound 16

By the method of Example 21, compound 15, Table 108, (58 mg) was converted to diol (Table 108, compound 16)(28 mg).

$^1$H NMR 300 MHz (CDCl$_3$) d 7.5–6.9 (m, 20H), 4.98 (d, J=12 Hz, 1H), 4.74 (d, J=11.7 Hz, 1H), 4.67 (d J=12 Hz, 1H), 4.66 (d, J=12 Hz, 1H), 4.55 (m, 1H), 3.98 (br s, 1H), 3.63 (br s, 1H), 3.61 (br d, J=9.3 Hz, 1H), 3.22 (s, 1H), 3.02 (m, 1H), 3.00 (s, 3H), 2.84 (d, J=7.2 Hz, 2H), 2.61 (d, J=3.6 Hz, 1H).

$^{13}$C NMR 75 MHz (CDCl$_3$) d 139.61, 139.03, 138.58, 129.0, 128.93, 128.50, 128.32, 128.23, 127.72, 127.61, 127.52, 127.43, 126.35, 126.22, 85.20, 80.99, 74.65, 73.90, 73.24, 72.02, 52.21, 49.26, 38.75, 37.57.

UV (methanol) 1=258.2 nm, e=1100.

Example 33
Table 108, compound 17

By the method of method 22, compound 16, Table 108, (21 mg) was converted to a single sulfoxide diastereomer (Table 108, compound 17)(17 mg).

$^1$H NMR 500 MHz (CDCl$_3$) d 7.4–7.3 (m, 8H), 7.3–7.2 (m, 8H), 7.01 (d, J=7 Hz, 2H), 6.96 (d, J=7 Hz, 1H), 4.99 (d, J=11Hz, 1H), 4.78 (d, J=12Hz, 1H), 4.68 (d

Docket No. 216.PC J=11Hz, 1H) 4.64 (d, J=12 Hz, 1H), 4.1–4.0 (m, 3 H), 3.51 (m, 2H), 3.45 (ddd, J=10, 5, 2 Hz, 1H), 3.18 (m, 3H), 2.92 (m, 3H).

$^{13}$C NMR 75 MHz (CDCl$_3$) d 137.65, 137.08, 129.28, 129.11, 128.83, 128.71, 128.60, 128.23, 127.99, 126.95, 126.62, 78.90, 76.75, 76.18, 75.28, 72.86, 70.86, 68.34, 68.29, 35.76, 30.34.

UV (methanol) 1=258.4 nm, e=1100.

Example 34
Enzyme Assay

HIV protease assay was performed using the method and materials of Molecular Probes, Inc., 4849 Pitchford Ave., Eugene, Oreg., 97402–9144, or P.O. BOX 22010, Eugene, Oreg., 97402–0414, (503) 344–3007, FAX (503) 344–6504.

Compositions to be subjected to enzyme assay are lyophilited and diluted in DMSO to 100–1000 μM. Compositions having apparent IC$_{50}$<1 μm are diluted to 100 μM.

General

The assay is a fluorometric method for measurement of HIV-protease (HIV-PR) activity utilizing a synthetic peptide substrate for HIV-PR based on that described by Matayoshi, E.D.; Wang, G.T.; Krafft, G.A.; and Erickson, J.W.; Science, 1990, 247, 954–958; and Wang, G.T.; Huffker, J.A.; Matayoshi, E.; and Krafft, G.A.; Tetrahedron Lett., 1990, 165 6493–6496.

Material

Structure: Arg-Glu(EDANS)-Ser-Gln-Asn-Tyr-Pro-Ile-Val-Lys(DABCYL)-Arg.

Buffer: 0.1M sodium acetate 1.0M sodium chloride 1.0 mM ethylenediaminetetraacetic acid (EDTA)

1.0 mM dithiothreitol (DTT)

10% dimethyl sulfoxide (DMSO)

1 mg/mL bovine serum albumin (BSA) adjusted to pH 4.7

Enzyme Assay Protocol

1. Prepare a solution of 2 μM HIV Protease Substrate 1 in the Assay Buffer.

2. Dispense the substrate solution into UV-pass fluorescence cuvettes (1 cm pathlength).

3. Set the excitation and emission monochromators of the spectrofluorimeter to 340 nm and 490 nm, respectively. To obtain the same kinetic constants as reported, cuvettes should be held at 37° C. throughout the assay.

4. Begin each assay by adding a small amount (<3% of the final volume) of HIV-PR-containing solution diluted tin the Assay Buffer.

5. Measure the initial rate of cleavage of fluorogenic substrate by monitoring the increase in fluorescence signal at 490 nm for 5–8 min at 37° C.

Example 35
XTT Cell Culture Assay

The method of Weislow, O.S.; Kiser, R.; Fine, D.L.; Bader, J.; Shoemaker, R.H.; and Boyd, M.R.; I. Nat. Cancer Institute, 1989, 81(8) 577–586 was applied with the following minor modifications:. Infection of cells with HIV IIIB was performed without polybrene. Cells were distributed to Microtiter wells containing the compound of the invention 4 h after infection with HIV IIIB. 2×XTT was added at 5–6 days post infection. 20 μl 2% Triton X-100 was added 1 hour after XTT addition.

XTT Assay Protocol

1. Add 4 ml of XTT (5 mg/ml) to 8 ml of Deficient RPMI medium (no phenol red, no serum). Mix briefly at 45° C. to dissolve XTT.

2. Add 800 μl of PMS (0.2 mg/ml) to XTT/RPMI mixture.

3. Remove 100 4 μl of cell free media from each well of a 96 well plate and replace with 100 μl of the XTT/PMS mixture.

4. Incubate at 37° C. for 1.5–2 h.

5. Read absorbance at 450 nm. Absorbance values are directly proportional to cell viability.

Cytotoxic Effects Assay Protocol

1. Place 100 4 μl of RPMI+10% FBS into the wells of columns 2–11 of a 96 well plate. Do not use outside wells.

2. Make a stock of the compound of the invention that is 10× the desired high concentration to use in a drug dilution series across the plate.

3. Add 25 4 μl of the 10× stock to the appropriate triplicate wells of column 2 (results in a 1:5 initial stock compound dilution; 2× final stock compound concentration). Routinely a 500 μM starting stock compound concentration is used for the cytotoxic effect assay.

4. Mix thoroughly by pipetting, then transfer 25 4 μl across the plate to give ⅕ dilutions through column 10. Column 11 does not get the stock compound.

5. Pipette 2×10$^4$ MT2 cells/well (1004 μl) into columns 2–11.

6. Incubate at 37° C. for 5–6 days.

7. Perform XTT assay as described.

Example 36
Activity

The apparent IC$_{50}$ and IC$_{50}$ values reported below in Table 25 were determined using the assays of Example 34 and 35, respectively. The values are indicated as follows: +=10–50 μM, ++2–10 μM, and +++<2 μM.

Example 37
Table 120 compound 12 and 13

To a solution of 3-pyridylmethylsulfide (Table 120, compound 10)(505 mg) in acetone /water (40 mL; 25:15 containing sodium bicarbonate (800 mg) was added, in 50 mg portions every 10 min., Oxone (500 mg). After the addition was complete, water (20 mL) was added, and additional portions of Oxone (400 mg) were added in the same manner. TLC (acetonitrile/water 9:1) showed three predominant products (Rf=0.63, 0.48 and 0.27). The mixture was evaporated to a volume of 50 mL. The solution extracted with methylene chloride (5×20 mL). The extracts were evaporated and chromatographed on silica gel using acetonitrile/water 19:1 to afford sulfone (Table 120, compound 12)(117 mg) corresponding to Rf=0.68. $^1$H-NMR (CDCL$_3$) d 8.63 (m, 2H); 7.87(m, 1H); 7.40–6.95(3m, 5H); 4.97 and 4.79 (2d, 2H); 4.01 and 4.09 (2s, 2H); 3.65–3.4 (m, 2H); 3.05 (m, 1H); 1.35 (s, 3H).

Further elution with acetonitrile/water 9:1 afforded the mono-N-oxide (Table 120, compound 13)(191 mg) corresponding to the product with Rf=0.48. $^1$H-NMR (CDCL$_3$) d 8.63 (2s, 2H); 8.26 (s, 1H); 8.20 (d, 1H); 7.86 (d, 1H); 7.47(d, 1H); 7.38–6.99 (m, 10H); 4.99–4.70 (4d, 4H); 4.11 (s, 1H); 4.10 (s, 1H); 4.01 (q, 2H); 3.72–3.50 (m, 5H); 3.16–3.05 (m, 3H); 1.35 (s, 6H).

Example 38
Table 120 compound 15

To a solution of 95 mg of sulfone (Table 120, compound 12) in methanol (2 mL) and water (0.2 mL) was added trifluoroacetic acid (3 mL). The mixture was stirred at room temperature for 45 min., then evaporated and coevaporated with water (2×2 mL). The residue was chromatographed on silica gel using ethyl acetate/methanol/triethylamine (9:1:1) to afford the diol (Table 120, compound 15)(77 mg). $^1$H-NMR (CDCL$_3$) d 8.50–8.53 (m, 2H); 7.90 (d, 1H); 7.0–7.37 (m, 5H); 4.86, 5.04 (d, 2H); 4.00 (2, 1H); 3.64–3.76 (m, 3H); 3.03 (m, 1H).

UV (methanol) 1 259 e 3190

Example 39
Table 120 compound 16K

Mono-N-oxide sulfone (Table 120, compound 13)(50 mg) was treated by the method of example 38 to afford diol (Table 120, compound 16)(31 mg) as a solid after chromatography using acetonitrile/water (9:1). $^1$H-NMR (CDCL$_3$) d 8.55 (s, 1H;); 8.48 (d, 1H); 8.35 (s, 1H); 8.04 (d, 1H); 7.92 (d, 1H); 7.52 (d, 1H); 7.0–7.37 (3m, 10H); 4.80–5.01 (m, 4H); 4.02 (s, 1H); 3.57–3.83 (m, 7H); 3.05 (m, 2H).

UV (methanol) 1 263 e 15100

Example 40
Table 120 compound 5

The method of example 27 was applied to 400 mg of diol (Table 101, compound 28) using 2-chloromethylpyridine hydrochloride as the alkylating agent to afford the bis ether (Table 120, compound 5)(412 mg) as a crisp foam. $^1$H-NMR (CDCL$_3$) d 8.55 (d, 1H); 7.76 (m, 1H); 7.73 (m, 1H); 7.05–7.28 (m, 6H); 5 5.12 (d, 1H); 4.68 (d, 1H); 4.33 (s, 1H); 4.19 (d, 1H); 3.52 (m, 1H); 2.96 (m 2H); 1.33 (s, 3H).

Example 41
Table 120 compound 6 and Table 120 compound 7

The method of example 37 was applied to 400 mg of sulfide (Table 120, compound 5). Chromatography with ethyl acetate afforded sulfone (Table 120, compound 6)(186 mg). $^1$H-NMR (CDCL$_3$) d 8.58 (d, 1H); 7.76–7.83 (m, 2H); 7.12–7.33 (m, 6H); 5.17 (d, 1H); 4.78 (d, 1H); 4.20 (s, 1H); 4.11 (s, 1H); 3.63 (m, 3H); 3.22 (m, 1H); 1.33 (s, 1H).

Further elution with ethyl acetate/methanol (4:1) afforded the mono-N-oxide (Table 120, compound 7). $^1$H-NMR (CDCL$_3$) d 8.58 (d, 1H); 8.25 (d, 1H); 7.12–7.93 (m, 16H); 5.37 (d, 1H); 5.17 (d, 1H); 4.79 (d, 2H); 4.22 (d, 2H); 4.06 (m, 2H); 3.67 (m, 4H); 3.19 (m, 2H); 1.34 (s, 6H).

Example 42
Table 120 compound 8

The method of example 38 was applied to acetonide (Table 120, compound 6)(180 mg) to afford diol (Table 120, compound 8)(107 mg) as a solid after chromatography using ethyl acetate/methanol (9:1). $^1$H-NMR (CDCL$_3$) d 8.49 (d, 1H); 7.76 (t, 1H); 7.44 (d, 1H); 7.14–7.26 (m, 6H); 5.16 (d, 1H); 4.91 (d, 1H); 4.14 (s, 1H); 3.64–3.80 (m, 3H); 3.15 (t, 1H).

UV (methanol) 1 262 e 7560

Example 43
Table 120 compound 9

The method of example 38 was applied to acetonide (Table 120, compound 7)(216 mg) to afford the diol (Table 120, compound 9)(177 mg) as a solid after chromatography using ethyl acetate/methanol (4:1). $^1$H-NMR (CDCL$_3$) d 8.49 (d, 1H); 8.26 (d, 1H); 7.85 (d, 1H); 7.77 (t, 1H); 7.44 (t, 1H); 7.10–7.26 (m, 14H); 5.27 (m, 2H); 4.87 (m, 2H); 4.18(d, 2H); 3.45–3.80 (m, 6H); 3.18 (m, 2H).

UV (methanol) 1 262 e 10300

Example 44
Table 120 compound 17

The method of example 27 was applied to 400 mg of diol (Table 101, compound 28) using 4-chloromethylpyridine hydrochloride as the alkylating agent to afford bis ether (Table 120, compound 17)(142 mg). $^1$H-NMR (CDCL$_3$) d 8.65 (d, 2H); 7.00–7.38 (3m, 7H); 5.00 (d, 1H); 4.50 (d, 1H); 4.25 (s,1H);
4.09 (d, 1H); 3.45 (m, 1H); 2.97 (d, 2H); 1.34 (s, 3H)

Example 45
Table 120 compound 18

A solution of sulfide (Table 120, compound 17)(90 mg) in acetone/water (10 mL, 1:1) was added a solution of Oxone (150 mg) in water (2.5 mL). The mixture was stirred for 0.5 h and another portion of Oxone (150 mg) in water (2.5 mL) was added. The mixture was stirred for 0.5 h then sodium thiosulfate (0.5 g) was added. The solution was evaporated to one 25 half volume under reduced pressure, and the remaining solution was extracted with ethyl acetate. The extracts were evaporated to afford sulfone (Table 120, compound 18)(101 mg) as a solid. $^1$H-NMR (CDCL$_3$) d 8.68 (dd, 2H); 7.40 (d, 2H); 7.34 (m, 3H); 7.30 (dd, 2H); 5.03 (d, 1H); 4.74 (d, 1H); 4.12 (s, 1H); 4.02 (s, 1H); 3.60 (m, 2H); 3.20 (m, 1H); 1.35 (s, 3H).

Example 46
Table 120 compound 19

A suspension of acetonide (Table 120, compound 18)(90 mg) in 1.1 mL methanol/water (10:1) was treated with 2 mL trifluoroacetic acid. The solution was warmed to 600, allowed to stir at room temperature for 15 min., then evaporated. The residue was redissolved in 5 mL water/methanol (2:1), and the pH was adjusted to 8 with solid sodium bicarbonate. The mixture was evaporated, and the residue was triturated with 5 mL water. The ppt was collected by filtration to afford diol sulfone (Table 120, compound 19)(76 mg) as a solid. $^1$H-NMR (CDCL$_3$) d 8.49 (d, 2H); 7.37 (d, 2H); 7.30 (m, 3H); 7.11 (m, 2H); 4.96 (s, 2H); 4.04 (s, 1H); 3.76 (m, 2H); 3.12 (m, 1H).

Example 47
Table 120 compound 20

The method of example 27 was applied to 150 mg of diol (Table 101, compound 28) using 2-methyl-4-chloromethylthiazole hydrochloride as the alkylating agent to afford bis ether (Table 120, compound 20)(73 mg). $^1$H-NMR (CDCL$_3$) d 7.05–7.28 (m, 6H); 5.04 (d, 1H); 4.65 (d, 1H); 4.31 (s, 1H); 4.15 (d, 1H); 3.44 (m, 1H); 2.83 (d, 2H); 2.89 (s, 3H); 1.35 (s, 3H)

Example 48
Table 120 compound 22

The method of example 45 was applied to sulfide (Table 120, compound 20)(70 mg) to yield sulfone (Table 120, compound 21)(59 mg) as a foam after chromatography using methylene chloride/acetone (9:1). A portion (56 mg) of this foam was treated by the method of example 38 to afford diol (Table 120, compound 22)(44 mg) as a crisp foam after chromatography using methylene chloride/methanol (19:1). $^1$H-NMR (CDCL$_3$) d 7.61 (s, 2H); 7.11–7.32 (m, 4H); 5.29 (s, 1H); 5.06 (d, 1H); 4.91 (d, 1H); 4.09 (s, 1H); 3.60 (m, 2H); 3.09 (m, 1H); 2.72 (s, 3H). UV (methanol) 1 243 e 5090

Example 49
Table 120 compound 23

The method of example 27 was applied to 620 mg of diol (Table 101, compound 28) using 5-chloromethylthiazole hydrochloride as the alkylating agent to afford bis ether (Table 120, compound 23)(414 mg). $^1$H-NMR (CDCL$_3$) d 8.84 (s, 1H); 7.86 (s, 1H); 7.22 (m, 3H); 6.99 (d, 2H); 5.12 (d, 1H); 4.73 (d, 1H); 4.27 (s, 1H); 4.11 (d, 1H); 3.37 (m, 1H); 2.82 (d, 2H); 1.41 (s, 3H).

Example 50

Table 120 compound 24

The method of example 45 was applied to sulfide (Table 120, compound 23)(160 mg) to afford sulfone (Table 120, compound 24)(38 mg) as an oil after chromatography using ethyl acetate. $^1$H-NMR (CDCL$_3$) d 8.89 (s, 1H); 7.84 (s, 1H); 7.30 (m, 3H); 6.96 (d, 2H); 5.11 (d, 1H); 5.03 (d, 1H); 4.12 (s, 1H); 4.01 (s, 1H); 3.54 (m, 2H); 2.94 (t, 1H); 1.36 (s, 3H).

Example 51

Table 120 compound 25

The method of example 38 was applied to sulfone (Table 120, compound 24)(36 mg) to afford diol (Table 120, compound 25)(22 mg) as a crisp foam after chromatography using ethyl acetate/methanol (9:1). $^1$H-NMR (CDCL$_3$) d 8.85 (s, 1H); 7.83 (s, 1H); 7.35 (m, 3H); 6.99 (d, 2H); 5.26 (d, 1H); 5.01 (d, 1H); 4.00 (s, 1H); 3.73 (m, 2H); 3.00 (m, 1H).

UV (methanol) 1 240 e 8330 crystals from benzene m.p. 96°–98° C

Example 52

Table 120 compound 31

Sodium Hydride (160 mg, 4 mmol, 60% in oil) was washed 3× with hexane (5 mL). Then a solution of diol (Table 101, compound 28)(193 mg, 0.5 mmol) in THF (7 mL) and DMSO (0.25 mL) was added slowly. After 5 minutes, alpha-bromo-m-xylene (202 uL, 1.5 mmol) was added. An additional 4 mmol of NaH was then added. The reaction stirred overnight. After quenching with 5% citric acid solution, THF was removed under vacuum and the residue extracted between water and methylene chloride. After concentration, the organic layer was chromatographed on silica gel with 100% methylene chloride to afford the diether sulfide (Table 120, compound 29)(175 mg, 57%)

To a solution of sulfide (Table 120, compound 29 )(175 mg) in acetone (17 mL) and water (6 mL) was added solid sodium bicarbonate (483 mg) followed by OXONE (354 mg). After stirring overnight at ambient temperature, excess OXONE was quenched with sodium thiosulfate. After concentration under vacuum, the residue was extracted between ethyl acetate and water. The organic layer was dried over sodium sulfate and concentrated to afford sulfone acetonide (181 mg, Table 120, compound 30). The crude acetonide was dissolved in methanol (4 mL) and water (0.5 mL) followed by trifluoroacetic acid (11 mL). After stirring for 3 hrs, solvents were removed under vacuum and the residue chromatographed on silica with 2% ethyl acetate in methylene chloride to afford sulfone diol (Table 120, compound 31) (89 mg, 53%) as a white solid mp 157°–159° C.

$^1$H NMR 300 MHz (CDCl$_3$) d 7.32–7.15 (m, 14H), 6.99 (d, J=7.5 Hz, 4H), 5.02 (d, J=11.4 Hz, 2H), 4.74 (d, J=11.4, 2H), 3.95 (s, 2H), 3.78 (dd, J=11.7, 2.4 Hz, 2H), 3.49 (dd, J=14.1, 3 Hz, 2H), 3.55 (br s, 2H), 3.01 (dd, J=13.5, 12.3 Hz, 2H), 2.38 (s, 6H)

$^{13}$C NMR 75 MHz (CDCl$_3$) d 138.39, 137.90, 136.98, 129.59, 129.15, 129.09, 128.97, 128.71, 127.22, 125.50, 77.63, 77.00, 76.23, 75.07, 67.06, 31.86, 21.61

UV (methanol) Imax 265 e 800

Example 53

Table 120 compound 34

By the method of example 52, diol (Table 101, compound 28)(52.7 mg) was alkylated with 3-methoxybenzylchloride (40 uL, 3 eq) to afford sulfide diether (Table 120, compound 32)(41.8 mg, 52%). This material was treated with OXONE (80 mg) in acetone (4 mL) water (1.5 mL) and sodium bicarbonate (109 mg) for one hour. Excess OXONE was quenched with sodium thiosulfate. After concentration under vacuum, the residue was extracted between ethyl acetate and water. The organic layer was dried over sodium sulfate and concentrated to afford crude sulfone acetonide (Table 120, compound 33) which was dissolved in methanol (1.5 mL) and water (0.2 mL) followed by trifluoroacetic acid (2.5 mL). After stirring for 1 h, solvents were removed under vacuum and the residue chromatographed on silica with 5% ethyl acetate in methylene chloride to afford sulfone diol (Table 120, compound 34)(30 mg, 73%) as an oil which recrystallized from methanol as a white solid. mp 153°–154° C.

$^1$H NMR 300 MHz (CDCl$_3$) d 7.32–7.20 (m, 8H), 7.09 (br s, 2H), 7.04–6.95 (m, 6H), 6.88 (dd, J=8.1, 1.8 Hz, 2H), 4.98 (d, J=11.7 Hz, 2H), 4.80 (d, J=11.7, 2H), 3.96 (s, 2H), 3.82 (s, 6H), 3.78 (dd, J=11.7, 2.7 Hz, 2H), 3.62 (dd, J=14.4, 3 Hz, 2H), 3.59 (s, 2H), 3.03 (dd, J=13.8, 12.3 Hz, 2H)

13C NMR (CDCl$_3$)(75 MHz) 160.28, 139.91, 137.10, 129.92, 129.83, 129.35, 127.47, 120.34, 114.27, 113.49, 77.84, 77.42, 77.13, 75.27, 67.36, 55.72, 32.12

UV (methanol) Imax 273.8 e 3600

Example 54

Table 120 compound 26

Sodium Hydride (360 mg, 60% in oil) was washed 3× with hexane (10 mL) and suspended in THF (3 mL) and DMSO (0.5 mL). Then a solution of diol (Table 101, compound 28)(204 mg, 0.51 mmol) in THF (2 mL) was added slowly. After 10 minutes, 2-fluoropyridine (202 mg, 2 mmol) in THF (2 mL) was added. The reaction stirred overnight. Upon quenching into water (100 mL) with vigorous stirring, a precipitate formed which was collected by filtration. The solid was extracted with methylene chloride, dried over magnesium sulfate and concentrated to an oil (147 mg). Trituration with methanol gave sulfide diether (Table 120, compound 26)( 108 mg) as a solid. mp. 193°–199° C.

Example 55

Table 120 compound 27

Sulfide (Table 120, compound 26)(108 mg) in acetone (20 mL) and methylene chloride (1 mL) was treated with solid sodium bicarbonate (328 mg) followed by a solution of Oxone (241 mg) in water (4 mL). When the reaction was complete (TLC) the excess Oxone was quenched with sodium thiosulfate solution. Acetone was removed under vacuum and the residue extracted between ethyl acetate and water. Trituration of the residue with methanol gave sulfone acetonide (Table 120, compound 27)(97 mg).

$^1$H NMR 500 MHz (CDCl$_3$) d 8.25 (dm, J=5 Hz, 2H), 7.66 (td, J=10.5, 2 Hz, 2H), 7.4–7.35 (m, 8 H), 7.29 (m, 2 H), 6.97 (ddd, J=6.5, 6.0, 1Hz, 2 H), 6.91 (d, J=7.5 Hz, 4H), 6.35 (s, 2H), 4.20 (s, 2H), 3.82 (dd, J=11.5, 2 Hz, 2H), 3.60 (dd, J=14, 2.5 Hz, 14, 2.5 Hz, 2H), 3.03 (dd, J=14, 11Hz, 2H), 1.06 (s, 6H)

HMQC/HMBC8 NMR 125 MHz (CDCl$_3$) d 163.13, 146.90, 139.46, 137.08, 130.16, 129.96, 129.36, 118.45, 111.63, 109.55, 78.50, 72.85, 66.30, 31.46, 26.18,

Example 56

Table 120 compound 28

Sulfone acetonide (Table 120, compound 27)(93 mg) was suspended in methanol (4 mL) and water (1 mL). Complete solution occurred upon addition of TFA (7 mL). The reaction was heated at 75° for 6 h then concentrated to remove reagents and retreated with methanol (2 mL), water (1 mL) and TFA (7 mL) for 4 hrs at 750. After removal of reagents under vacuum, the residue was extracted between ethyl acetate and sodium bicarbonate solution, dried over magnesium sulfate and concentrated to give sulfone diol (Table 120, compound 28)(73 mg)

$^1$H NMR 500 MHz (CDCl$_3$) d 8.17 (dm, J=5 Hz, 2H), 7.75 (td, J=9, 2 Hz, 2H), 7.33–7.21 (m, 10 H), 7.06 (m, 4 H), 5.69 (s, 2H), 4.10 (br s, 2H), 3.90 (dd, J=11, 3 Hz, 2H), 3.79 (s, 2H), 3.60 (dd, J=14, 3 Hz, 2H), 3.07 (dd, J=14, 11.5 Hz, 2H)

**HMQC/HMBC8 NMR 125 MHz (CDCl$_3$) d 163.13*, 146.54, 140.41, 137.46*, 137.08*, 129.8, 129.35, 127.56, 118.91, 112.62, 75.03, 73.88, 68.67, 31.48

Example 57
3-benzyloxybenzylbromide

A solution of 3-benzyloxybenzyl alcohol (9.54 g) in methylene chloride (40 ml) with TMSBr (2.5 eq, 13 mL) was heated at reflux for 1 hr. After cooling, the reaction was concentrated and then reconcentrated 2 × with methylene chloride (40 ml). The residue was chromatographed on silica gel eluting first with hexane followed by 10% methylene chloride in hexane to afford 3-benzyloxybenzyl bromide which solidifies on cooling . 5.75 g m.p. 38°–40°.

$^1$H NMR 500 MHz (CDCl$_3$) d 7.43–7.3 (m, 5H), 7.22 (t, J=8.1Hz, 1H), 7.0–6.9 (m, 2H), 6.88 (ddd, J=8.1, 2.4, 0.6 Hz), 5.021 (s, 2H), 4.417 (s, 2H)

Example 58
Table 120 compound 38

Sodium Hydride (120 mg, 60% in oil) was added to a solution of diol (Table 101, compound 28)(200 mg, 0.5 mmol) in THF (4 mL) and DMSO (1 mL). After gas evolution stopped, 3-benzyloxybenzyl bromide (414 mg) in THF (2 mL) was added. The reaction was stirred for 72 h, then quenched with 5% citric acid and extracted with methylene chloride. Chromatography on silica gel with 50% hexane/methylene chloride followed by 100% methylene chloride afforded (Table 120, compound 38)( 252 mg) as an oil.

$^1$H NMR 500 MHz (CDCl$_3$) d 7.44 (d, J=7.5 Hz, 4H), 7.36 (dd, J=8, 6.5 Hz, 4H), 7.33–7.25 (m, 4H), 7.2–7.1 (m, 6H), 7.04 (br s, 2H), 6.97 (d, J=7.5 Hz, 2H), 6.96–6.90 (m, 4H), 5.09 (s, 4H), 4.93 (d, J=11.5 Hz, 2H), 4.49 (d, J=12 Hz, 2H), 4.26 (s, 2H), 4.04 (d, J=3 Hz, 2H), 3.43 (td, J=8, 2.5 Hz, 2H), 2.83 (d, J=7.5 Hz, 2H), 1.37 (s, 6H)

HMQC/HMBC8 (500 MHz) 159.34, 140.92, 139.70, 137.29, 129.67, 129.36, 128.81, 128.57, 128.18, 127.71, 126.61, 120.40, 114.42, 114.18, 109.0, 79.40, 75.41, 74.08, 70.10, 47.49, 41.03, 26.96

Example 59
Table 120 compound 39

To a solution of sulfide (Table 120, compound 38)(252 mg) in acetone (25 mL) was added sodium bicarbonate (534 mg) followed by a solution of Oxone (391 mg) in water (9 mL). After stirring overnight, sodium thiosulfate (80 mg) was added. Acetone was removed under vacuum. The residue was extracted between ethyl acetate and water, dried over magnesium sulfate and concentrated to give sulfone acetonide (Table 120, compound 39)(269 mg).

$^1$H NMR 500 MHz (CDCl$_3$) d 7.42 (d, J=7.5 Hz, 4 H), 7.34–7.22 (m, 8 H), 7.15 (m, 8 H), 6.99 ( d, J=7.0 Hz, 2 H), 6.95 (dd, J=8, 2 Hz, 2H), 6.84 (m 4H), 5.09 (s, 2H), 4.91 ( d, J=13 Hz, 2H), 4.70 ( d, J=12.5 Hz, 2H), 4.06 (s, 2 H), 4.01 (s, 2H), 3.51 (dd, J=14, 2.5 Hz, 2H), 3.47 (dd, J=11.5, 2.5 Hz, 2H), 2.98 (dd, J=14, 11.5 Hz, 2H), 1.31 (s, 6H)

HMQC/HMBC8 NMR 125 MHz (CDCl$_3$) d 1159.32, 139.47, 137.2, 137.08, 129.98, 129.89, 129.17, 128.81, 128.27, 127.73, 127.28, 120.52, 115.11, 114.21, 108.50, 79.97, 74.05, 71.58, 70.87, 70.25, 31.72, 26.83

Example 60
Table 120 compound 40

Acetonide (Table 120, compound 39)(269 mg) was dissolved in a minimum amount of methylene chloride (1 mL) then diluted in methanol (10 mL) and water (1.3 mL) followed by TFA (13 mL). A portion was chromatographed on silica gel (3% ethyl acetate in methylene chloride) to afford diol sulfone (Table 120, compound 40)(47 mg) as an oil. UV (methanol) Imax 273.8 e 3600

$^1$H NMR 300 MHz (CDCl$_3$) d 7.45–6.9 (m, 28 H), 5.10 (s, 4H) 4.99 (d, J=11.7 Hz, 2H), 4.78 ( d, J=11.7 Hz, 2H), 3.95 (s, 2H), 3.78 (dd, J=12,3.3 Hz, 3.63 (dd, J=14.1, 3 Hz, 2H), 3.55 (s, 2 H), 3.03 (dd, J=14.1, 11.7 Hz, 2H)

Example 61
Table 120 compound 41

Diol sulfone ((Table 120, compound 40)(37 mg) in THF (3 mL) was diluted with methanol (10 mL) and hydrochloric acid (1 N, 1 mL). Catalyst (10% Pd/C, 20 mg) was added. The reaction flask was evacuated and filled 3× with hydrogen gas at balloon pressure and then stirred for 1 h. After filtering through celite, the mixture was chromatographed on silica gel eluting with 5% methanol in methylene chloride to afford the bis phenol (Table 120, compound 41)(26.8 mg) as an oil.

UV (methanol) Imax 276.8 e 2600

$^1$H NMR 500 MHz (CDCl$_3$) d 7.3–7.2 (m, 10 H), 6.97 ( d, J=7.5 Hz, 2 H), 6.82 (dd, J=8.5, 2 Hz, 2H), 4.92 ( d, J=11Hz, 2H), 4.82 ( d, J=11Hz, 2H), 3.97 (s, 2H), 3.59 (s, 2 H), 3.80 (dd, J=12, 3 Hz, 2H), 3.42 (dd, J=14, 2 Hz, 2H), 2.91 (dd, J=13.5, 11.5 Hz, 2H)

HMQC/HMBC8 NMR 125 MHz (CDCl$_3$) d 157.51, 139.93, 137.09, 129.39, 129.50, 128.99, 127.05, 119.70, 115.51, 114.80, 76.62, 76.40, 74.24, 67.30, 31.60

Example 62
Table 120 compound 42

Sodium hydride (1.16 g, 60% in oil) was added to a solution of diol (Table 101, compound 28)(1.Olg) in THF (20 mL) and DMSO (5 mL). After 30 min, a solution of m-nitrobenzyl bromide (1.626 g ) in THF (5 mL) was added and allowed to stir for 60 h. The reaction was carefully quenched into 5% citric acid, concentrated to remove THF and extracted with methylene chloride. Chromatography on silica with methylene chloride gave diether (Table 120, compound 42)(1.18 g ) as a foam.

$^1$H NMR 300 MHz (CDCl$_3$) d 8.26 (s, 2H), 8.19 (d, J=8.1Hz, 2H), 7.70 (d, J=7.5 Hz, 2H), 7.56 (t, J=7.8 Hz, 2H), 7.29–7.20 (m, 6H), 7.03 (d, J=6.6 Hz, 4H), 5.05 (d, J=12.6 Hz, 2H), 4.57 (d, J=12.9, 2H), 4.30 (s, 2H), 4.13 ( d, J=3 Hz, 2H), 3.49 (ddd, J=9.6, 7.2, 3 Hz, 2H), 3.01–2.85 (m, 4H), 1.35 (s, 6H)

Example 63
Table 120 compounds 44 and 45

By the method of example 59, sulfide (Table 120, compound 42)(1.18g) was oxidized with Oxone (2.16 g) to afford sulfone (Table 120, compound 43) (1.2g) which was directly treated with TFA/water/methanol to afford, after chromatography on silica gel with 5% ethyl acetate/ methylene chloride, sulfone diol (Table 120, compound 45)(0.795 g) as a solid. mp 213–213.4°. $^1$H NMR 500 MHz (CDCl$_3$) d 8.313 (s, 2H), 8.21 (d, J=8.5 Hz, 2H), 7.88 (d, J=7

Hz, 2H), 7.61 (t, J=8 Hz, 2H), 7.31–7.22 (m, 6H), 7.09 (d, J=7 Hz, 4H), 5.07 (d, J=12.5 Hz, 2H), 5.01 (d, J=12.5, 2H), 4.01 (s, 2H), 3.79 (dd, J=12, 3 Hz, 2H), 3.67 (dd, J=14.5,3 Hz, 2H), 3.65 (s, 2H), 3.04 (dd, J=14.5, 12 Hz, 2H), 2.62 (s, 2H)

HMQC (CDCl$_3$) 133.71, 129.76, 129.51, 129.27, 127.48, 122.91,122.59, 77.85, 76.11, 74.12, 67.41, 32.12

UV (methanol) lambda 262.6 epsilon 15400

Further elution with 1% methanol, 10% ethyl acetate/ methylene chloride, gave the corresponding sulfoxide (Table 120, compound 44)(0.11 g)

$^1$H NMR 500 MHz (CDCl$_3$) d 8.30 (s, 1H), 8.18 (d, J=7.5 Hz, 1H), 8.15 (d, J=9 Hz, 1H), 8.06 (s, 1H), 7.86 (d, J=8 Hz, 1H), 7.54 (t, J=8 Hz, 1H), 7.50 (t, J=7 Hz, 2H), 7.32–7.20 (m, 6H), 7.19 (d, J=7.5 Hz, 2H), 7.06 (d, J=7.5 Hz, 2H), 5.23 (d, J=11 Hz, 1H), 4.94 (d, J=12, 1H), 4.84 (d, J=12.5 Hz, 1H), 4.66 (d, J=12.5 Hz, 1H), 4.29 (s, 1H), 4.07 (s, 1H), 3.85 (dd, J=11.5, 3.5 Hz, 1H), 3.74–3.67 (m, 2H), 3.63 (dd, J=14.5, 7 Hz, 1H), 3.62 (dd, J=13, 3 Hz, 1H), 3.41 (dd, J=8.5, 7.5 Hz, 1H), 3.15 (dd, J=14, 8 Hz, 1H), 2.93 (dd, J=13, 12 Hz, 1H), 2.86 (d, J=2.5 Hz, 1H), 2.73 (d, J=5 Hz, 1H)

HMQC/HMBC (CDCl$_3$) 148.39, 140.60, 137.63, 134.09, 133.41, 129.77, 129.45, 129.42. 129.27, 127.50, 127.41, 123.05, 122.64, 122.50, 83.5, 78.83, 77.25, 74.02, 73.90, 65.27, 59.56, 37.06, 36.83

Example 64

Table 120 compound 46

Sulfone (Table 120, compound 45)(0.795 g) in THF (9 mL), methanol (73 mL) and 1N HCl (4.5 mL) with 10% Pd/C (110 mg) was stirred under H2 at atmospheric pressure for 6 h with periodic replacement of the H2 atmosphere. After filtration through celite, the solvents were removed under vacuum and the residue extracted between NaHCO$_3$ solution and ethyl acetate to afford bis aniline sulfone (Table 120, compound 46)(0.692 g) as a foam.

Example 65

Table 120 compound 47

To the free base (Table 120, compound 46) in ethyl acetate (15 mL) was added slowly with swirling a solution of methanesulfonic acid (0.22g, 2 eq) in ethyl acetate (10 mL). The thick precipitate was broken up with more ethyl acetate and then collected by filtration. The hygroscopic solid was dissolved in deionized water and lyophilized to afford the bis methanesulfonate salt tetrahydrate (Table 120, compound 47) as a fluffy solid (0.7685)

$^1$H NMR 500 MHz (DMSO) d 7.52 (t, J=7.5 Hz, 2H), 7.44 (d, J=8 Hz, 2H), 7.35–7.2 (m, 12H), 7.11 (d, J=7.5 Hz, 2H). 4.93 (d, J=12.3 Hz, 2H), 4.88 (d, J=12.2, 2H), 3.67 (dd, J=11.2, 3.4 Hz, 2H), 3.39 (dd, J=13.6, 2.9 Hz, 2H), 2.99 (dd, J=13.7, 11.8 Hz, 2H), 2.35 (s, 6H)

Example 66

Table 120 compound 35

By the method of example 62, diol (Table 101, compound 28)(0.206 g) was alkylated with 3-bromobenzyl bromide (0.38g) to afford after chromatography on silica gel eluting with 50% hexane/methylene chloride the sulfide ((Table 120, compound 35)(0.262 g) as an oil.

$^1$H NMR 500 MHz (CDCl$_3$) d 7.546 (s, 2H), 7.45 (br d, J=8 Hz, 2 H), 7.32-7.17 (m, 10 H), 6.98 (br d, J=7.0 Hz, 4 H), 4.92 ( d, J=13 Hz, 2H), 4.48 ( d, J=12 Hz, 2H), 4.24 (s, 2 H), 4.05 (d, J=3 Hz, 2H), 3.45 (ddd, J=9.5, 7, 2.5 Hz, 2H), 2.87 (m, 4H), 1.36 (s, 6H)

HMQC NMR 125 MHz (CDCl$_3$) d 130.82, 130.66, 129.25, 128.73, 126.73, 126.19, 79.10, 75.64, 73.38, 47.16, 40.78, 27.03

Example 67

Table 120 compound 36

Oxidation of sulfide (Table 120, compound 35)(0.262 g) with Oxone (0.435 g) by the method of example 59 gave sulfone (Table 120, compound 36) (0.25 g) as a foam.

$^1$H NMR 500 MHz (CDCl$_3$) d 7.573 (s, 2H), 7.51 (br d, J=7.5 Hz, 2 H), 7.42 (br d, J=7.5 Hz, 2 H), 7.32–7.20 (m, 8 H), 6.95 (br d, J=7.0 Hz, 4 H), 4.91 ( d, J=12.5 Hz, 2H), 4.76 ( d, J=11.7 Hz, 2H), 4.08 (s, 2 H), 4.01 (s, 2H), 3.59 (dd, J=13.5, 2.5 Hz, 2H), 3.51 (dd, J=11.5, 3 Hz, 2H), 1.35 ( s, 6H)

HMQC/HMBC8 NMR 125 MHz (CDCl$_3$) d 140.15, 136.83, 131.27, 130.95, 130.45, 129.75, 129.20, 127.42, 126.60, 108.58, 79.76, 73.39, 71.22, 71.03, 31.73, 26.83,

Example 68

Table 120 compound 37

Deprotection of sulfone (Table 120, compound 36)(44.6 mg) in methanol (2 mL), water (0.2 mL) with TFA (3 mL) gave a solid which crystallized from the reaction mixture. Recrystallization from methanol afforded sulfone diol (Table 120, compound 37)(27.2 mg) m.p. 204°–206° C. UV (methanol) $^1_{max}$ 259.5 e 835

$^1$H NMR 300 MHz (CDCl$_3$) d 7.601 (s, 2H), 7.48 (br d, J=7.8 Hz, 2 H), 7.38 (br d, J=7.5 Hz, 2 H), 7.33–7.20 (m, 8 H), 7.06 (br d, J=6.6 Hz, 4 H), 5.05 ( d, J=11.7 Hz, 2H), 4.76 ( d, J=11.7 Hz, 2H), 3.96 ( s, 2 H), 3.76 (dd, J=11.7, 3 Hz, 2H), 3.66 (dd, J=14.1, 3 Hz, 2H), 3.58 ( s, 2H), 3.01 ( dd, J=13.8, 11.7 Hz, 2H), 2.45 (br s, 2H)

Example 69

Table 108 compound 16

By the methods of examples 7, and 8 using the diol (Table 101, compound 29), the sulfide diol (Table 108, compound 16) was prepared.

Example 70

Table 108 compound 17

Oxidation of sulfide diol (Table 108, compound 16) by the method of example 9 gave sulfoxide (Table 108 compound 17) after chromatography.

Example 71

Table 108 compound 18

Oxidation of sulfide diol (Table 108, compound 16) by the method of example 9 gave sulphone (Table 108 compound 18).

Example 72

Table 108 compound 21

By the methods of examples 7, 37 and 38 using the diol (Table 101, compound 30), the sulphone diol (Table 108, compound 21) was prepared.

Example 73

Table 108 compound 27

Starting from D-mannitol, by the methods of examples 1, 2, 3, 4, 5, 7, 37 and 38, the sulphone diol, (Table 108, compound 27 ) was prepared. It was identical by m.p., TLC, NMR and UV to (Table 108, compound 5).

Example 74

(Part 1)

Sodium sulfide (292 g) was dissolved in H$_2$O (250 mL) in a 2-neck 2 l round bottom flask with magnetic stirring. To this solution, ethanol (250 mL) was added and heated to reflux. 1,6 ditosyl 2,5 diacetyl 3,4 isopropylidene L-mannitol (example 1)(250 g) dissolved in THF was added slowly to the sodium sulfide solution using an addition funnel over 1 to 2 hours. After checking the reaction by tlc (ethyl acetate: methylene chloride=1:4, or methanol: methylene chloride=1:99), the reaction mixture was concentrated. The residue was taken up in 10% ethyl acetate in methylene chloride, then filtered through celite (about 1 cm) using a 600 mL sintered glass filter, and concentrated by rotary evaporation. This procedure was repeated twice to remove the white solid completely. The residue was dissolved in methylene chloride (50 - 100 mL) and chromatographed on silica gel.

Flash column chromatography ( 0.24 mol scale)

| silica gel; | 2 l loaded with $CH_2Cl_2$ | |
|---|---|---|
| fractions; | 500 ml each | |
| solvent; | 5% EtOAc in $CH_2Cl_2$, 2 l | |
| | 10% EtOAc in $CH_2Cl_2$, 4 l | F1–F8 |
| | 15% EtOAc in $CH_2Cl_2$, 2 l | F9–F12 |
| | 20% EtOAc in $CH_2Cl_2$, 6 l | F13–23 |

Thiepane diol (Table 101, compound 1) eluted as fractions 8–23, 31 g (59% yield).

Example 74
(Part 2)

Diol (Table 101, compound 1)(20 g) was dissolved in toluene (2 l) in a 2-neck or 3-neck 3 l round bottom flask with mechanical stirring and a distillation head, and heated to distill off toluene (about 50 to 100 mL)*[1]. To this hot solution was added benzaldehyde followed immediately by finely ground Al(tBuO)3 *[2]. The reaction mixture was stirred for 7 min (with toluene distilling from the reaction), then cooled in an ice bath. The reaction mixture was filtered through celite (about 1 cm) using a 600 mL sintered glass filter, and washed with methylene chloride (200 mL). The filtrate was concentrated by rotary evaporation. The crude mixture was dissolved in methylene chloride and chromatographed on silica gel.

*[1] The first 5 to 10 ml of toluene may be cloudy.
*[2] Al(tBuO)$_3$ needs to be ground into a fine powder with mortar and pestle in a glove bag with argon atmosphere.

Flash column chromatography *3 ( 130 mmol scale)

*[3] 130 mmol or less seems to be a reasonable scale for purification. Loading larger amounts makes the flow rate slow because of impurities clogging the silica gel column.

| silica gel; | 2 l (dry volume) | |
|---|---|---|
| fractions; | 500 ml each | |
| solvent; | $CH_2Cl_2$, 6 l | F1–3 |
| | 5% EtOAc in $CH_2Cl_2$, 8 l | F4–18 |
| | 20% EtOAc in $CH_2Cl_2$, 6 l | F19–29 |

Enone (Table 101, compound 13) contaminated with benzyl alcohol, eluted as fractions F9-F14 (14.2 g; including benzyl alcohol). Pure enone (Table 101, compound 13) eluted as fractions F15-F20. After concentration, the residue was recrystallized with hexane to obtain a white solid. This solid (5.84 g) and the impure fractions F9-F14 were used without further purification for the next step.

Example 74
(Part 3)

To a solution of nickel acetyl acetonate (38.6 g) in methylene chloride (200 mL) in a 3-neck 3 l round bottom flask with thermometer and mechanical stirring, was added enone (Table 101, compound 13)(23 g) dissolved in methylene chloride (100 mL). The remainder of the methylene chloride (700 mL) and ethanol*[1] (1 l) were added to the reaction mixture, then cooled to 0° C. Sodium borohydride as a solid was added to the reaction mixture in small aliquots*[2] while maintaining the temperature at 0° C. After the addition was complete, the reaction mixture was stirred for 15 min to 1 hr at 0° C. More sodium borohydride was added, if necessary, as indicated by TLC (ethyl acetate :methylene chloride=1:9). The reaction was quenched with 5% citric acid solution (500 mL) and celite (about 50 g). The reaction mixture was stirred for 10 min., then allowed to stand for 1 hr. The reaction mixture was filtered through celite (about 5 cm in a 2 l sintered glass filter funnel) to remove the black solids, and washed with water, ethyl acetate, and methylene chloride (500 mL each). The organic layers were washed with 5% citric acid solution, then water. The combined aqueous layers were back extracted with methylene chloride. The combined organic layers were dried over sodium sulfate and concentrated by rotary evaporation. The brown residue was used directly in the next step.

*[1] using ethanol already cooled to −2020 C. in freezer makes adjustment of temperature easier.
*[2] add one tenth of sodium borohydride every 5min.

Example 74
(Part 4)

Diol (Table 101, compound 14)(crude mixture) was dissolved in toluene (2 l) in a 2-neck or 3-neck 3 l round bottom flask with mechanical stirring, and heated to distill off toluene. (about 50 to 100 mL)*[1]. To this hot solution was added benzaldehyde followed immediately by finely ground Al(tBuO)3 *[2]. The reaction mixture was stirred for 7 min (with toluene distilling from the reaction), then cooled in an ice bath. The reaction mixture was filtered through celite (using 1 inch of celite in a 600 mL sintered glass filter), and the filtrate was concentrated. The crude mixture was dissolved in methylene chloride and chromatographed on silica gel.

*[1] first 5 to 10 ml toluene may be cloudy.
*[2] Al(tBuO)$_3$ needs to be ground into a fine powder with mortar and pestle.

Flash column chromatography *3

| silica gel; | 2 l, loaded with 50% hexane $CH_2Cl_2$ | |
|---|---|---|
| fractions; | 500 ml each | |
| solvent; | $CH_2Cl_2$, 6 l | F1–12 |
| | 3% EtOAc in $CH_2Cl_2$, 2 l | F13–16 |
| | 5% EtOAc in $CH_2Cl_2$, 2 l | F17–19 |
| | 7.5% EtOAc in $CH_2Cl_2$, 2 l | F20–23 |
| | 10% EtOAc in $CH_2Cl_2$, 4 l | F24–30 |

Enone (Table 101, compound 25) eluted in fractions F17–F26. After concentration of these combined fractions, the residue (6.77 g.) was recrystallized with hexane to obtain a white solid.

*[3] 110 mmol or less seems to be a reasonable scale for purification. Loading larger amounts makes the flow rate slow because of impurities clogging the silica gel column.

Example 74
(Part 5)

To nickel acetyl acetonate (27 g) dissolved in methylene chloride (100–200 ml) in a 3-neck round bottom flask with thermometer and mechanical stirring, is added enone (Table 101, compound 25)(21 g) dissolved in methylene chloride (100 mL). The remainder of the methylene chloride (700 mL) and ethanol*[1](1 L) are added to the reaction mixture, then cooled to 0° C. Sodium borohydride is added to the reaction mixture in small aliquots*[2] while maintaining the temperature at 0° C. After the addition is complete, the reaction mixture is stirred for 15 min to 1 hr at 0° C. More sodium borohydride is added as necessary as indicated by TLC (ethyl acetate:methylene chloride=1:9)*[3]. The reaction is quenched with 5% citric acid solution (500 mL) and celite (20 to 50 g). The reaction mixture is stirred for 10 min, then allowed to stand for 1 hr before being filtered through celite (300 to 400 g) using a 2 l sintered glass filter to remove the black solids, and washed with water, ethyl acetate and methylene chloride (500 mL each). The organic layers are washed with 5% citric acid solution, then water. The combined aqueous layers are back extracted with methylene chloride. The combined organic layers are dried over sodium sulfate and concentrated. The residue is a mixture of diol diastereomers separable by silica gel chromatography.

*1 using ethanol already cooled to −20° C. in freezer makes adjustment of temperature easier.
*2 add one tenth of sodium borohydride every 5 min.
*3 Rf of the intermediate reduction products (B/C), which are ketoalcohols (Table 101, compound 31) and (Table 101, compound 32), is the same as that of the starting material. The color of the stain on the tlc plate is slightly different.

Flash column chromatography (for about 0.06 mol, 20 g scale)

| silica gel; | 2 l, loaded CH$_2$Cl$_2$ | |
|---|---|---|
| fractions; | 500 ml each | |
| solvent; | 2.0% EtOAc in CH$_2$Cl$_2$, 2 l | |
| | 2.5% EtOAc in CH$_2$Cl$_2$, 2 l | F1–2 |
| | 3.0% EtOAc in CH$_2$Cl$_2$, 2 l | F3–6 |
| | 3.5% EtOAc in CH$_2$Cl$_2$, 2 l | F7–9 |
| | 4.0% EtOAc in CH$_2$Cl$_2$, 2 l | F10–13 |
| | 4.5% EtOAc in CH$_2$Cl$_2$, 2 l | F14–16 |
| | 6.0% EtOAc in CH$_2$Cl$_2$, 2 l | F17–20 |
| | 10% EtOAc in CH$_2$Cl$_2$, 2 l | F21–24 |
| | 15% EtOAc in CH$_2$Cl$_2$, 2 l | F25–28 |
| | 20% EtOAc in CH$_2$Cl$_2$, 2 l | F29–31 |
| | 20% EtOAc 2% MeOH in CH$_2$Cl$_2$, 2 l | F32–35 |
| | 20% EtOAc 4% MeOH in CH$_2$Cl$_2$, 2 l | F36– |

A: Diol (Table 101, compound 28) Rf 0.6 Fractions 12–20, ~40% B/C: ketoalcohols Rf 0.73 (Table 101, compound 31) and (Table 101, compound 32)
D: unidentified Rf 0.52, fractions 26–28
E: Diol (Table 101, compound 30) Rf 0.44, fractions 30–33, ~21%
F: Diol (Table 101, compound 29) Rf 0.31, fractions 35–37
G: unidentified Rf 0.13, fractions 40

Example 75

To a solution of diol (Table 101, compound 30)(0.2 g) in THF (10 mL)/DMSO (5 mL) is added sodium hydride (0.2g, 60% in oil). After gas evolution subsides, a solution of m-nitrobenzylbromide (0.108 g) in THF (2 mL0 is added. After 30 min, a solution of citric acid (5 mL, 5% in water) is added. After extraction with methylene chloride, the product is chromatographed on silica with methylene chloride followed by 5% ethyl acetate / methylene chloride. The monoalkylation product (121 mg)(Scheme 8, structure 40 R=m-nitrobenzyl) Rf=0.39 (5% ethyl acetate/methylene chloride) was obtained.

Part 2: The monoalcohol (Scheme 8, structure 40 R=m-nitrobenzyl)(121 mg) in acetone (15 ml) was treated with sodium bicarbonate (0.39 g) and a solution of Oxone (0.29 g) in water (2 mL). After 2 hr, a solution of sodium thiosulfate (0.1 g in 1 mL water) was added. After concentration to remove acetone, the residue was extracted into methylene chloride to afford sulfone alcohol (Scheme 8, structure 41 R=m-nitrobenzyl)(97 mg) as a white solid.

Part 3: To a solution of sulfone (Scheme 8, structure 41 R=m-nitrobenzyl)(94 mg) in methylene chloride (3 ml)/triethylamine (0.3 mL) was added a solution of methanesulfonyl chloride (38 uL) in methylene chloride (1 mL). A second portion was added after 30 min. The reaction was concentrated to remove volatiles and extracted between methylene chloride and water to afford the vinyl sulfone (Scheme 8, structure 42 R=m-nitrobenzyl)(90 mg) as an oil. Rf 0.68 (5% ethyl acetate/methylene chloride).

Part 4: To a solution of vinyl sulfone (Scheme 8, structure 42 R=m-nitrobenzyl) (89 mg) in ethanol (2 mL) was added benzyl amine (90 mg). The mixture was concentrated under vacuum and redissolved in ethanol (2 mL). After stirring for 72 h, an additional portion of benzyl amine (90 mg) was added and stirred for an additional 24 hrs. The mixture was concentrated under vacuum and chromatographed on silica gel with hexane followed by 20% ethyl acetate in hexane to provide the amine (Scheme 17, structure 205 R=m-nitrobenzyl) as an oil (69.6 mg).

$^1$H-NMR (CDCL$_3$) d 8.4–7.0 (19 H), 5.18 (d, J=12.8 Hz, 1H), 4.979 (t, J=8.8 Hz 1H), 4.54 (d, J=12.9 Hz), 4.24 (dd, J=9.1, 1.1Hz), 1H), 4.01 (dd, J=2.9, 1.1Hz, 1H), 3.76 (dd, J=13.9, 3.3 Hz, 1H), 3.68 (m, 2H), 3.53 (d, J=13.9 Hz, 1H), 3.42 (dt, J=11.7, 3.3, 3.3, 1H), 3.25 (dd, J=13.9, 10.2 Hz, 1H), 3.10 (d, J=8.4 Hz, 1H), 2.75 (dd, J=13.6, 12.4 Hz, 1H).

Part 5: The acetonide (Table 108 compound 30)(69.6 mg) in 95% TFA/water (10 mL) was heated to 85° C. Additional water (1 mL) was then added. Heating was continued for 2 hr then water (2 mL) was added. After cooling, the mixture was concentrated under vacuum to remove solvents and evaporatted twice from methanol. The residue was dissolved in methylene chloride and treated with 1N NaOH. The organic layer was dried over magnesium sulfate, filtered and concentrated to afford the diol (Table 108 compound 31)(45 mg) as an oil.

$^1$H-NMR (CDCl$_3$) d 8.4–7.0 (19 H), 5.15 (d, J=12 Hz, 1H), 4.78 (d, J=12.5 Hz), 4.012 (ddd, J=ll, 5.5,3 Hz, 1H), 3.992 (br s, 1H), 3.90 (d, J=13.5 Hz, 1H), 3.83 (t, J=9 Hz, 1H), 3.806 (dd, J=14.5, 3.1Hz, 1H), 3.64 (dd, J=14, 3.5 Hz, 1H), 3.621 (d, J=8.5 Hz, 1H), 3.48 (d, J=13.5 Hz, 1H), 3.47 (m, 1H), 3.13 (dd, J=14, 8.5 Hz, 1H), 3.056 (dd, J=15, 11Hz, 1H), 3.023 (dd, J=9,5.5 Hz, 1H).

$^{13}$C-NMR (CDCl$_3$) d 78.04, 76.64, 74.33,73.56, 66.96, 65.37, 58.90, 52.90, 31.65, 31.04.

Example 76

Table 108 compounds 32, 33, 34

To a solution of diol (Table 101 compound 30)(0.2 g) in THF (10 mL) and DMSO (1 mL) was added sodium hydride (0.2 g, 60% in oil). After 10 min, benzyl bromide ( 86 mg) was added. After 30 min, a solution of citric acid (5 mL, 5% in water) was added. After concentration to remove THF, the residue was extracted into methylene chloride. The crude product was chromatographed on silica gel with methylene chloride followed by 6% ethyl acetate in methylene chlorideto afford the desired monoalkylation product (64 mg) (Table 108 compound 32).

Part 2: The monoalcohol (Table 108 compound 32)(64 mg) in acetone (8 mL) was treated with sodium bicarbonate (0.19 g) and a solution of Oxone (0.15 g) in water (1 mL) overnight. Sodium thiosulfate (0.15 g) in water was added. After concentration to remove acetone , the residue was extracted into methylene chloride to afford sulfone alcohol (Table 108 compound 33)(63 mg).

Part 3: To a solution of the sulfone alcohol (Table 108 compound 33)(63 mg) in methylene chloride (2 mL) and triethylamine (0.2 mL) was added a solution of methanesulfonyl chloride (28 uL) in methylene chloride (0.5 mL). After 5 min, a second portion of methanesulfonyl chloride was added. After concentration to remove excess triethylamine, the residue was extracted between methylene chloride and sodium bicarbonate solution. Chromatography on silica gel with methylene chloride afforded the vinyl sulfone (Scheme 8, structure 42 R=benzyl)(54 mg) as an oil.
Part 4: Vinyl sulfone (Scheme 8, structure 42 R=benzyl)(54 mg) in methanol (2 mL) was diluted with water (1 mL) to form a cloudy suspension. Trifluoroacetic acid (TFA)(3 mL) was added. After gentle heating complete solution occured. Additional TFA (2×1 mL) was added and heating continued until starting material was not visible by TLC. After concentration, the residue was reevaporated from methanol and maintained under vacuum overnight to afford sulfone diol (Scheme 18, structure 207 R=benzyl)(53 mg).
Part 5: Benzyl amine (93 mg) was added to a solution of sulfone diol (Scheme 18, structure 207 R=benzyl)(12.6 mg) in THF (2 ml). This mixture was concentrated to remove THF and redissolved in ethanol (3 mL). The solution was heated to reflux for 24 hr, then continued at ambient temperature for 72 hr. After concentration the mixture was chromatographed on silica gel with methylene chloride followed by 3% ethyl acetate in methylene chloride to afford the amino diol (Table 108 compound 34)(10.3 mg) as an oil.

$^1$H-NMR (CDCl$_3$) d 7.6–6.9 (20 H), 5.03 (d, J=11.5 Hz, 1H), 4.771 (d, J=12 Hz) 4.186 (ddd, J=11, 6, 3 Hz, 1H), 3.969 (s, 1H), 3.968 (d, J=13.5 Hz, 1H), 3.803 (m, 1H), 3.667 (m, 1H), 3.601 (d, J=13 Hz, 1H), 3.56 (dd, J=14,3 Hz, 1H), 3.509 (d, J=8.5 Hz, 1H, 3.43 (ddd, J$_{32}$ 11, 3.5, 1 Hz, 1H), 3.09 (m, 1H), 3.08 (m, 1H), 3.07 (m, 1H). $^{13}$C-NMR (CDCl$_3$) d 129.53, 129.23, 129.14, 128.66, 128.36, 127.7, 79.56, 75.87, 75.13, 74.28, 67.09, 66.25, 58.94, 53.62, 31.70, 30.43.

Example 77
Table 108 compound 35
By the method of Example 76 part 5, sulfone diol (Scheme 18, structure 207 R=benzyl)(11.1 mg) was treated with 3-phenyl, 1-aminopropane (50 uL) for 36 h at reflux. After chromatography the amino diol (Table 108 compound 35) (8.7 mg) was obtained as a solid. $^1$H-NMR (CD30D) d 7.6–7.0 (20 H), 4.955 (d, J=ll Hz, 1H), 4.671 (d, J=11.5 Hz), 3.963 (ddd, J=8.5, 5, 3.5 Hz, 1H), 3.896 (br s, 1H), 3.75 (dd, J=9, 8.5 Hz, 1H), 3.724 (ddd, J=11.5,4, 1.5 Hz, 1H), 3.642 (dd, J=8, 1Hz, 1H), 3.415 (dd, J=14.5, 4.5 Hz, 1H), 3.398 (dd, J=14, 3.5 Hz, 1H), 3.257 (dd, J=14.5, 8 Hz, 1H), 3.019 (dd, J=14, 11.5 Hz, 1H), 2.991 (dd, J=9, 6.5 Hz, 1H), 2.607 (ddd, J=11.5, 7.5, 6.5 Hz, 1H), 2.53 (dd, J=8, 7.5 Hz, 2H), 2.392 (ddd, J=ll, 9, 7.5 Hz, 1H), 1.630 (p, J=7Hz, 2H). $^{13}$C-NMR (CD30D) d 142.15, 139.48, 138.5, 137.09, 129.32, 128.72, 128.5, 128.17, 128.12, 127.72, 126.81, 125.79, 78.15, 77.66, 75.22, 74.49, 67.16, 65.21, 59.35, 48.12, 33.23, 31.77, 31.41, 30.42.

Example 78
Table 101 compounds 40, 43, Table 108 compounds 36, 37, 38
By the method of example 74 part2, thiepane diol (Table 101, compound 1) (0.463 g) was treated with 2-fural to afford after chromatography the enone (Table 101, compound 40) as a solid (0.284 g) mp 139–140 after recrystalization from ether.

$^1$H-NMR (CDCl$_3$) d 7.944 (s, 1H), 7.613 (d, J=1.5 Hz, 1H), 7.484 (d J=3.6 Hz, 1H), 6.584 (dd, J=3.3, 1.5 Hz, 1H), 5.896 (d, J=9.3 Hz, 1H), 4.444 (m, 1H), 3.876 (dd, J=9.3, 2.1Hz, 1H), 3.216 (dd, J=15.3, 4.5 Hz, 1H), 2.895 (d, J=15.3 Hz, 1H), 2.704 (br s, 1H). $^{13}$C-NMR (CDCl$_3$) d 145.647, 130.804, 119.046, 112.956, 80.532, 77.941, 65.576, 37.163, 26.857, 26.405.
Part 2: By the method of example 74 part 3 to 5 but without purification of intermediates, enone (Table 101, compound 40)(0.28 g) was converted to the symmetrical diol (Table 101, compound 43)(83.6 mg) as an oil after chromatography.

$^1$H-NMR (CDCl$_3$) d 7.317 (d, J=1.8 Hz, 2H), 6.288 dd, J=2.7, 1.8 Hz, 2H), 6.094 (d J=3.0 Hz, 2H), 4.267 (dd, J=5.4, 3.9 Hz, 2H), 4.224 (s, 2H), 3.446 (ddd, J=9, 6.9, 3.9 Hz, 2H), 3.153 (dd, J=15, 9.3 Hz, 2H), 2.916 (dd, J=15, 6.6 Hz, 2H), 2.660 (d, J=5.4 Hz, 2H). $^{13}$C-NMR (CDCl$_3$) d 152.6, 141.495, 110.31, 107.917, 107.206, 76.529, 68.00, 43.792, 31.834, 26.798.
Part 3: By the method of example 62, diol (Table 101 compound 43)(43.6 mg) was alkylated with benzyl bromide to afford after chromatography the sulfide (Table 108 compound 36)(56.2 mg) as an oil.

$^1$H-NMR (CDCl$_3$) d 7.374 (m, 10H) 7.263 (d, J=2.1Hz, 2H), 6.220 (dd, J=3.0, 2.1 Hz, 2H), 5.793 (d J=3.0 Hz, 2H), 4.971 (d, J=11.7 Hz, 2H), 4.583 (d, J-12 Hz, 2H), 4.367 (s, 2H), 4.135 (d, J=3 Hz, 2H), 3.485 (ddd, J=9, 6.3, 3.0 Hz, 2H), 2.953 (dd, J=15, 9.3 Hz, 2H), 2.831 (dd, J=15, 6.3 Hz, 2H).

$^{13}$C-NMR (CDCl$_3$) d 153.003, 141.265, 138.616, 128.316, 127.67, 127.523, 110.15, 108.124, 106.849, 78.818, 75.533, 74.397, 44.159, 32.918, 26.850.
Part 4: The sulfide (Table 108 compound 36)(47 mg) in methanol (3 mL) was treated with a solution of Oxone (51 mg) in water (.4 mL) for 20 minutes. Then another portion of Oxone (41 mg) was added. The reaction was stirred for 4.5 hrs, quenched with sodium thiosulfate solution and extracted between water and methylene chloride. After concentration the residue was chromatographed on silica gel eluting with methylene chloride to afford the sulfone (Table 108 compound 37)( 24.7 mg) as a solid. m.p. 150°–151°.

$^1$H-NMR (CDCl$_3$) d 7.45–7.3 (m, 10H) 7.293 (d, J=1.2 Hz, 2H), 6.215 (dd, J=3.3, 1.2 Hz, 2H), 5.720 (d, J=3.3 Hz, 2H), 4.964 (d, J=12 Hz, 2H), 4.780 (d, J=12.3 Hz, 2H), 4.162 (s, 4H), 3.622 (dd, J=11.4, 3.0 Hz, 2H), 3.455 (dd, J=15, 3.0 Hz, 2H), 3.195 (dd, J=15.3, 11.7 Hz, 2H).

$^{13}$C-NMR (CDCl$_3$) d 150.013, 142.367, 137.649, 128.493, 127.879, 127.824, 110.429, 108.859, 108.831, 79.454, 74.437, 71.415, 68.453, 26.669, 24.659.
Part 5: Sulfone (Table 108 compound 37)(17.5 mg) suspended in methanol (2 mL) and water (0.5 mL). TFA (2 mL) added. As the mixture warms, the suspension dissolves. After 30 minutes, the solvents were removed under vacuum. The residue was reevaporated from methanol to afford the sulfone diol (Table 108 compound 38)(17 mg).

$^1$H-NMR (CDCl$_3$) d 7.5–7.3 (m, 10H) 7.348 (d, J=1.5 Hz, 2H), 6.297 (dd, J=2.5, 1.5 Hz, 2H), 5.948 (d, J=3 Hz, 2H), 5.035 (d, J=11.5 Hz, 2H), 4.796 (d, J=11.5 Hz, 2H), 4.064 (s, 2H), 3.898 (dd, J=12,3.5 Hz, 2H), 3.743 (s, 2H), 3.553 (dd, J=15.5, 3.5 Hz, 2H), 3.226 (dd, J=15.5, 11.5 Hz, 2H), 2.757 (br s, 2H).

Example 79
Table 125 compound 36
Sodium hydride (200 mg, 5 mmol, 60% in oil) was washed 3× with hexane (5 mL). Then a solution of diol (Table 101, compound 28)(250 mg, 0.62 mmol) in THF (8 mL) and DMSO (0.3 mL) was added slowly. After 10 min, 4 bromo-2 methyl-2-butene (216 uL, 1.67 mmol) was added via syringe. After 1 hr, 5% cirtic acid solution was added, THF was removed under vacuum and the residue extracted between water and methylene chloride. After concentration the organic layer was chromatographed on silica gel eluting with methanol to afford the diether sulfide (Table 125, compound 36)(238 mg) as an oil.

$^1$H-NMR (CDCl$_3$) d 7.4–7.0 (m, 10H), 5.383 (br t, J=6.9 Hz, 2H), 4.358 (dd, J=11.7, 6.6 Hz, 2H), 4.173 (s, 2H), 4.056 (dd, J=11.4, 7.2 Hz, 2H), 3.949 (d, J=2.7 Hz, 2H), 3.379 (ddd, J=9.0, 6.3, 2.7 Hz, 2H), 2.950 (dd, J=13.8, 9.3 Hz, 2H), 2.855 (dd, J=13.8, 6.3 Hz, 2H), 1.755 (s, 6H), 1.642 (s, 6H), 1.378 (s, 6H).

$^{13}$C-NMR (CDCl$_3$) d 139.201, 135.55, 129.05, 128.164, 126.128, 121.7, 107.553, 78.889, 74.524, 68.946, 46.727, 40.056, 26.617, 25.682, 18.016.

Example 80
Table 125 compound 19

A solution of the diol (Table 101, compound 28)(100 mg) in THF (2 mL) and t-Butanol (0.5 mL) was treated with potassium t-butoxide (200 mg) and 2-fluro-5-methylpyridine (0.4 mL). The mixture was stirred at 55° for 17 h. The mixture was partitioned between water and ethyl acetate, the organic layer was washed with brine, dried over sodium sulfate and evaporated. The residue was triturated with methanol and the precipitate was collected by filtration to afford 69 mg of solid.

Example 81
Table 125 compound 20

A solution of compound 19 (Table 125)(60 mg) in acetone (15 mL) and water (5 mL) was treated with sodium bicarbonate (200 mg) and oxone (100 mg). The mixture was stirred for 30 min and a solution of oxone (100 mg) in water (5 mL) was added. The mixure was stirred for an additional 30 min and sodium thiosulfate was added (200 mg). The mixture was diluted with water and extracted with methylene chloride. The organic extracts were washed with water, dried over magnesium sulfate and evaporated to afford 58 mg of foam.

Example 82
Table 125 compound 21

A solution of compound 20 (Table 125)(40 mg) in trifluoroacetic acid (5 mL) and water (0.1 mL) was stirred for 24 h and then evaporated. The residue was crystallized from benzene/hexane (1 mL, 1:1) to afford 18 mg of solid. $^1$H-NMR:(CDCl$_3$) d: 8.03 (s, 1H); 7.68 (dd, 1H); 7.4–7.0 (3m,6H); 5.31 (s, 1H); 3.99 (dd, 1H); 3.85 (s, 1H); 3.62 (dd, 1H); 3.07 (dd, 1H); 2.35 (s,3H).

Example 83
Table 125 compound 25

The method of example 80 was applied to the diol (Table 101, compound 28)(100 mg) using 4-nitro-3-trifluoromethylfluorobenzene (0.4 mL) as the arylating agent to obtain 66 mg of a glass after chromatography on silica gel using ethyl acetate/hexane/methylene chloride 1:1:6.

Example 84
Table 125 compound 26

The method of example 81 was applied to compound 25 (Table 125)(60 mg) to obtain 50 mg of crude material after chromatography on silica gel using ethyl acetate/hexane/methylene chloride 1:1:6.

Example 85
Table 125 compound 27

A solution of compound 26 (Table 125)(45 mg) in trifluoroacetic acid (5 mL) and water (0.1 mL) was warmed to 750 and then stirred for 1 h at rt. The mixture was then evaporated. The residue was triturated with ether to afford 8 mg of solid. $^1$H-NMR:(CDCl$_3$) d: 8.02 (d, 1H); 7.61 (d, 1H); 7.4–6.9 (3m,6H); 4.84 (s, 1H); 3.92 (s, 1H); 3.90 (dd, 1H); 3.67 (dd, 1H); 2.88 (dd, 1H).

Example 86
Table 125 compound 28

A solution of compound 27 (Table 125)(100 mg) in ethanol (5 mL) was treated with a drop of glacial acetic acid and hydrogenated over Raney nickel (0.25 cc) under a hydrogen balloon for 1 h. The catalyst was removed by filtration, the filtrates were evaporated and the residue chromatographed on silica gel using ethyl acetate to afford 88 mg of a crisp foam. $^1$H-NMR:(CDCl$_3$) d: 7.4–6.8 (8m,6H); 4.49 (s, 1H); 4.1 (bs,2h); 3.8 (dd, H); 3.76 (s, 1H); 3.6 (dd, 1h); 2.93 (dd, 1H); 2.53 (bs, 1H).

Example 87
Table 125 compound 15

The method of example 80 was applied to the diol (Table 101, compound 28)(50 mg) using 4-nitrofluorobenzene (0.2 mL) as the arylating agent to obtain 34 mg of a crisp foam after chromatography on silica gel using ethyl acetate/hexane/methylene chloride 1:1:6.

Example 88
Table 125 compound 16

The methods of example 81 and 82 were applied to compound 15 (Table 125)(30 mg) to obtain 21 mg of material after crystallization from ether. $^1$H-NMR:(CDCl$_3$) d: 8.28 (dd, 1H); 7.4–6.9 (8m,8H); 4.87 (s, 1H); 3.95 (s, 1H); 3.91 (dd, 1H); 3.66 (dd, 1h); 2.89 (dd, 1H).

Example 89
4-(chloromethyl)-2-bromothiazole

A suspension of 4-(chloromethyl)-2-aminothiazole hydrochloride (4.0 g) in aqueous hydrobromic acid (48%, 50 mL) was chilled in an ice-salt bath and a solution of sodium nitrite (2.0 g) in water (20 mL) was added with stirring over a 10 min period. The mixture was stirred for 1 h, then the ice bath was removed and the mixture was stirred for an additional 3 h. The pH was adjusted to 5 with solid sodium bicarbonate and extracted with methylene chloride. The organic extracts were evaporated and the residue was chromatographed on silica gel using methylene chloride/hexane 1:1. The elution was followed by TLC using the same solvent system and fractions containing the product with Rf=0.4 were evaporated to yield 320 mg of the product. $^1$H-NMR:(CDCl$_3$) d: 8.78 (s,1H); 4.70 (s,2H).

Example 90
Table 125 compound 11

To a solution of the diol (Table 101, compound 28) in THF (2 mL) and DMSO (0.2 mL) was added 60% sodium hydride oil dispersion (50 mg). After stirring for 5 min, 4-(chloromethyl)-2-bromothiazole (200 mg) was added. The mixture was stirred at 550 for 6 h. The mixture was partioned between ethyl acetate and water, the organic layer was evaporated and the residue chromatographed on silica gel using ethyl acetate/cyclohexane 1:2 to afford 150 mg of an oil.

Example 91
Table 125 compound 12

In a solution of dimethylamine in THF (2M) was dissolved compound 11 (Table 125)(50 mg) and the mixture was heated at 2000 at 175 psi in a steel bomb for 3 h. The mixture was evaporated and the residue chromatographed on silica gel using ethyl acetate/hexane 1:1. The fractions containing the product with Rf=0.25 were evaporated to yield 23 mg of product.

Example 92
Table 125 compound 13

To a solution of compound 12 (Table 125) in acetone (10 mL) and water (7 mL) was added, with stirring three portions of oxone (150 mg each) every 30 min. The mixture was stirred an additional 30 min after the last addition and sodium thiosulfate was added (100 mg). The mixture was evaporated and the residue was partiotioned between methylene chloride and water. the organic layer was dried over sodium sulfate and evaporated to afford 18 mg of product.

Example 93
Table 125 compound 14

A solution of compound 13 (Table 125) in trifluoroacetic acid (1.5 mL), methanol (0.5 mL) and water (0.1 mL) was heated at 500 for 30 min. The mixture was evaporated, the residue was treated with two drops of concentrated ammonium hydroxide and evaporated. This residue was chromatographed on silica gel using ethyl acetate/methanol 9:1 to afford 9.7 mg of material. $^1$H-NMR:(CDCl$_3$) d: 7.4–7.2 (m,5H); 6.51 (s,1H); 4.94 and 4.65 (2d,2H); 4.08 (s,1H); 3.8–3.6 (2dd,2H); 3.57 (s,1H); 3.1 (m,7H).

Example 94
Table 125 compound 7

To a solution of the diol (Table 101, compound 28)(300 mg) in THF (3 mL) and DMSO (0.3 mL) was added 60% sodium hydride oil dispersion (150 mg). After stirring for 5 min, 5-(chloromethyl)-2-chlorothiazole (378 mg) was added. The mixture was stirred at 550 for 24 h. The mixture was partioned between ethyl acetate and water, the organic layer was evaporated and the residue chromatographed on silica gel using ethyl acetate/cyclohexane 1:2 to affor 193 mg of an oil.

Example 95
Table 125 compound 8

In a solution of dimethylamine in THF (2M) was dissolved compound 7 (Table 125)(50 mg) and the mixture was heated at 135° at 100 psi in a steel bomb for 12 h. The mixture was evaporated and the residue chromatographed on silica gel using ethyl acetate to yield 23 mg of product.

Example 96
Table 125 compound 9

The method of example 92 was applied to compound 8 (Table 125)(30 mg) to afford 19 mg of material.

Example 97
Table 125 compound 10

The method of example 93 was applied to compound 9 (Table 125)(15 mg) to afford 9.2 mg of material. $^1$H-NMR:(CDCl$_3$) d: 7.25–6.98 (m,6H); 6.51 (s,1H); 4.96 and 4.67 (2d,2H); 3.92 (s,1H); 3.7–3.5 (2dd,2H); 3.47 (s, 1H); 3.05 9m, 7H).

Example 98
Table 125 compound 18

The method of example 86 was applied to compound 17 (Table 125)(10 mg) to afford 7.5 mg of material. $^1$H-NMR:(CDCl$_3$) d:7.3–6.7 (m,9H); 4.56 (s, 1H); 3.93 (dd, 1H); 3.80 (s, 1H); 3.63 (dd, 1H); 3.05 (dd, 1H).

Example 99
Table 125 compound 37

A solution of compound 36 (Table 125)(45 mg) in ethanol (2 mL) was treated with 10% palladium on carbon (100 mg) and was stirred under 500 psi of hydrogen pressure for 14 h. The catalyst was removed by filtration and the filtrates were evaporated to yield 42 mg of material.

Example 100
Table 125 compound 37

The method of example 81 was applied to compound 37 (Table 125) (40 mg) to afford 32 mg of material.

Example 101
Table 125 compound 38

The method of example 85 was applied to compound 37 (Table 125)(30 mg) to afford 12.5 mg of material after chromatography on silica gel using ethyl acetate/heaxane 1:5. $^1$H-NMR:(CDCl$_3$) d: 7.4–7.2 (m,5H); 4.05 (dd, 1H); 3.81 (s, 1H); 3.8–3.6 (m,3H); 3.46 (s, 1H); 3.09 (dd, 1H); 1.75 (sep, H); 1.48 (m,2H); 0.94 (2d,6H).

Example 102
Table 125 compound 32

A solution of compound 47 (Table 120)(50 mg) in pyridine (2 mL) was treated with trimethylchlorosilane (0.25 mL). The mixture was stirred for 1 h and methanesulfonyl chloride (0.1 mL) was added. The mixture was stirred for 3 hours and concentrated ammonium hydroxide (2 mL) was added. The mixture was stirred for 1 h and evaporated. The residue was partitioned between ethyl acetate and water and the organic layer was washed with water and brine, evaporated, and the residue was chromatographed on silica gel using ethyl acetate/hexane 1:1 to afford 48 mg of material. $^1$H-NMR:(DMSO-d$_6$) d: 9.80 (s, 1H); 7.4–7.0 (m,8H); 4.85 (2d,2H); 3.84 (s, 1H); 3.66 (dd, H); 3.45 (s, 1H); 3.01 (s,3H); 2.95 (dd, 1H).

Example 103
Table 125 compound 24

The methods of example 80,81,83 were applied to the diol (Table 101, compound 28)(100 mg) to yield 33 mg of material. $^1$H-NMR:(CDCl$_3$) d: 7.99 (dd, 1H); 7.55 (d, 1H); 7.4–7.2 (3m,5H); 6.95 (dd, 1H); 5.84 (s, 1H); 3.94 (dd, 1H); 3.78 (s, 1H); 3.59 (dd, 1H); 3.03 (dd, 1H); 2.42 (s,3H).

Example 104
Table 125 compound 31

The methods of example 80,81,83 were applied to the diol (Table 101, compound 28)(100 mg) to yield 17 mg of material. $^1$H-NMR:(CDCl$_3$) d: 7.62 (dd, 1H); 7.4–7.2 (3m, 6H); 6.87 (dd, 1H); 5.62 (s, 1H); 3.88 (dd, 1H); 3.76 (s, 1H); 3.58 (dd, 1H); 3.09 (dd, 1H); 2.46 (s,3H).

Example 105
Table 125 compound 35

The methods of example 80,81,83 were applied to the diol (Table 101, compound 28)(100 mg) to yield 21 mg of material. $^1$H-NMR:(CDCl$_3$) d: 8.04 (dd, 1H); 7.4–7.2 (3m, 6H); 6.90 (bs, 1H); 5.48 (s, 1H); 3.93 (dd, 1H); 3.80 (s, 1H); 3.61 (dd, 1H); 3.07 (dd, 1H); 2.42 (s,3H).

TABLE 25

| Table/Compound | Apparent Enzyme IC50 | Cell Culture IC50 |
|---|---|---|
| 107/2 | + | N/T |
| 107/3 | ++ | N/T |
| 107/4 | ++ | + |
| 107/5 | +++ | + |
| 107/8 | + | N/T |
| 107/10 | ++ | N/T |
| 107/12 | ++ | N/T |
| 107/13 | + | N/T |
| 107/15 | ++ | N/T |
| 108/3 | ++ | ++ |
| 108/4 | +++ | +++ |
| 108/5 | +++ | +++ |
| 108/17 | N/T | ++ |

TABLE 25-continued

| Table/Compound | Apparent Enzyme IC50 | Cell Culture IC50 |
|---|---|---|
| 108/17 | ++ | N/T |
| 108/18 | +++ | + |
| 108/21 | +++ | +++ |
| 108/27 | + | + |
| 108/31 | +++ | ++ |
| 108/34 | +++ | ++ |
| 108/35 | +++ | ++ |
| 120/2 | +++ | + |
| 120/3 | +++ | + |
| 102/4 | +++ | +++ |
| 120/8 | +++ | ++ |
| 120/9 | +++ | ++ |
| 120/15 | +++ | +++ |
| 120/16 | +++ | +++ |
| 120/19 | +++ | N/T |
| 120/22 | +++ | + |
| 120/25 | +++ | +++ |
| 120/28 | +++ | N/T |
| 120/31 | +++ | +++ |
| 120/34 | +++ | +++ |
| 120/37 | +++ | N/T |
| 120/40 | +++ | N/T |
| 120/41 | +++ | N/T |
| 120/44 | +++ | +++ |
| 120/45 | +++ | +++ |
| 120/46 | +++ | +++ |
| 125/14 | +++ | N/T |
| 125/17 | +++ | +++ |
| 125/21 | ++ | N/T |
| 125/27 | +++ | N/T |
| 125/28 | +++ | +++ |
| 128/31 | + | N/T |
| 128/35 | + | N/T |

What is claimed is:

1. A composition comprising a compound of the formula:

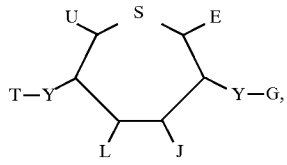

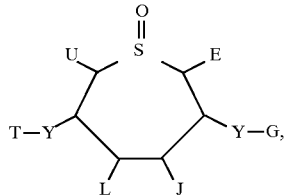

or

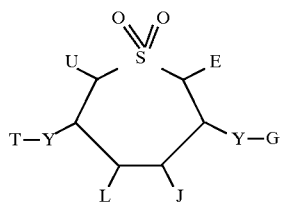

wherein:

each Y is independently $-N(R_1)-$, $-N(R_1)-SO_2-$ or $-N(R_1)-CO-$;

E and U are independently H, or $-(CR_1R_1)_{m1}-W_1$, with the proviso that at least one of E and U is $-(CR_1R_1)_{m1}-W_1$;

G and T are independently $-(CR_1R_1)_{m1}-W_1$, or $-(CR_1R_1)_{m1}-C(R_1)(W_1)(W_2)$, with the provisos that:

when E is $-(CR_1R_1)_{m1}-W_1$, then G is $-(CR_1R_1)_{m1}-W_1$;

when U is $-(CR_1R_1)_{m1}-W_1$, then T is $-(CR_1R_1)_{m1}-W_1$; and G and T may be the same or different;

J and L are independently H, $N_3$, $-OR_2$, $-N(R_2)(R_2)$, or $-N(R_2)(R_3)$, wherein $R_2$ is H, or PRT, with the proviso that at least one of J and L is $-OR_2$, or J and L are taken together to form an epoxide, or a cyclic protecting group;

$W_1$ is $W_2$ or $W_3$;

$W_2$ is carbocycle, with the proviso that each $W_2$ is independently substituted with 0 to 3 $R_5$ groups;

$W_3$ is alkyl, alkenyl, or alkynyl, with the proviso that each $W_3$ is independently substituted with 0 to 3 $R_6$ groups;

$R_1$ is $R_3$ or $R_6$;

$R_3$ is H or $R_4$;

$R_4$ is alkyl;

$R_5$ is $R_6$, or $R_7$, with the proviso that each $R_7$ is independently substituted with 0 to 3 $R_6$ groups;

$R_6$ is $-O-$(label), $-N(R_3)-$(label), $-C(O)O-$(label), $-C(O)N(R_3)-$(label), $-S-$(label), $-S-S-$(label), F, Cl, Br, I, $-CN$, $N_3$, $-NO_2$, $-OR_3$, $-OPRT$, $-O-C(O)R_4$, $=O$, $-N(R_3)(R_3)$, $-N(R_3)(PRT)$, $-N(PRT)_2$, $-N(R_3)-C(O)R_4$, $=N(R_3)$, $=N(PRT)$, $-N(OR_3)(R_3)$, $-N(OPRT)(R_3)$, $-N(OR_3)(PRT)$, $-N(OPRT)(R_3)$, $-N(N(R_3)(R_3))(R_3)$, $-N(N(PRT)(R_3))(R_3)$, $-N(N(R_3)(R_3))(PRT)$, $-N(N(PRT)(PRT))(R_3)$, $-N(N(PRT)(R_3))(PRT)$, $-N(N(PRT)(PRT))(PRT)$, $-N(R_3)-C(N(R_3))(N(R_3)_2)$, $-N(PRT)-C(N(R_3))(N(R_3)_2)$, $-N(R_3)-C(N(PRT))(N(R_3)_2)$, $-N(R_3)-C(N(R_3))(N(R_3)(PRT))$, $-N(PRT)-C(N(PRT))(N(R_3)_2)$, $-N(PRT)-C(N(R_3))(N(R_3)(PRT))$, $-N(R_3)-C(N(PRT))(N(R_3)(PRT))$, $-N(R_3)-C(N(R_3))(N(R_3)(PRT))$, $-N(R_3)-C(N(R_3))(N(PRT)_2)$, $-N(PRT)-C(N(PRT))(N(R_3)(PRT))$, $-N(PRT)-C(N(R_3))(N(R_3)(PRT))$, $-N(R_3)-C(N(PRT))(N(PRT)_2)$, $-N(R_3)-C(N(PRT))(N(PRT)_2)$, $-N(PRT)-C(N(PRT))(N(PRT)_2)$, $-C(NR_3)(N(R_3)_2)$, $-C(N(R_3))(N(R_3)(PRT))$, $-C(NPRT)(N(R_3)_2)$, $-C(N(PRT))(N(R_3)(PRT))$, $-C(N(R_3))(N(PRT)_2)$, $-C(N(PRT))(N(PRT)_2)$, $-SR_3$, $-S(PRT)$, $=S$, $-S(O)-R_3$, $-S(O)-OR_3$, $-S(O)-OPRT$, $-O-S(O)-R_3$, $-S(O)_2-R_3$, $-S(O)_2-OR_3$, $-S(O)_2-OPRT$, $-O-S(O)_2-R_3$, $-C(O)OR_3$, $-C(O)OPRT$, $-C(O)N(R_3)_2$, $-C(O)N(R_3)(PRT)$, $-C(O)N(PRT)_2$, $-C(S)N(R_3)_2$, $-C(S)N(R_3)(PRT)$, $-C(S)N(PRT)_2$, $-N(R_3)-S(O)_2-R_3$, $-N(PRT)-S(O)_2-R_3$, $-S(O)_2-N(R_3)-R_3$, $-S(O)_2-N(PRT)-R_3$, carbocycle, or heterocycle;

$R_7$ is alkyl, alkenyl;

each m1 is independently an integer from 0 to 3; and with the proviso that the compound, taken as a whole, contains 0 to 16 $R_6$ groups, and that each E, G, T, and U, taken individually, contain 0 to 8 $R_6$ groups.

2. The composition of claim 1 wherein each Y is $-N(R_1)-$.

3. The composition of claim 1 wherein G and T independently are $-(CR_1R_1)_{m1}-W_2$.

4. The composition of claim 1 wherein G and T independently are $-(CR_3R_3)_{m1}-W_2$.

5. The composition of claim 1 wherein E and U independently are $-(CR_1R_1)_{m1}-W_2$.

6. The composition of claim 1 wherein E and U independently are $-(CR_3R_3)_{m1}-W_2$.

7. The composition of claim 1 wherein E and U independently are —(CR$_1$R$_1$)$_{m1}$—W$_1$; and T and G independently are —(CR$_1$R$_1$)$_{m1}$—W$_1$.

8. The composition of claim 1 wherein E and U independently are —(CR$_3$R$_3$)$_{m1}$—W$_1$; and T and G independently are —(CR$_3$R$_3$)$_{m1}$—W$_1$.

9. The composition of claim 1 wherein E and U independently are —(CR$_1$R$_1$)$_{m1}$—W$_2$; and T and G independently are —(CR$_1$R$_1$)$_{m1}$—W$_2$.

10. The composition of claim 1 wherein E and U independently are —(CR$_3$R$_3$)$_{m1}$—W$_2$; and T and G independently are —(CR$_3$R$_3$)$_{m1}$—W$_2$.

11. The composition of claim 1 wherein one of E and U is H and the other is —(CR$_1$R$_1$)$_{m1}$—W$_1$; and T and G independently are —(CR$_1$R$_1$)$_{m1}$—W$_1$.

12. The composition of claim 1 wherein one of E and U is H and the other is —(CR$_3$R$_3$)$_{m1}$—W$_1$; and T and G independently are —(CR$_3$R$_3$)$_{m1}$—W$_1$.

13. The composition of claim 1 wherein one of E and U is H and the other is —(CR$_1$R$_1$)$_{m1}$—W$_2$; and T and G independently are —(CR$_1$R$_1$)$_{m1}$—W$_2$.

14. The composition of claim 1 wherein one of E and U is H and the other is —(CR$_3$R$_3$)$_{m1}$—W$_2$; and T and G independently are —(CR$_3$R$_3$)$_{m1}$—W$_2$.

15. The composition of claim 1 wherein one of E and U is H and the other is —(CR$_1$R$_1$)$_{m1}$—W$_1$; and with the proviso that:

when E is H, G is —(CR$_1$R$_1$)$_{m1}$—C(R$_1$)(W$_1$)(W$_2$), when E is —(CR$_1$R$_1$)$_{m1}$—W$_1$, G is —(CR$_1$R$_1$)$_{m1}$—W$_1$, when U is H, T is —(CR$_1$R$_1$)$_{m1}$—C(R$_1$)W$_1$)(W$_2$), and when U is —(CR$_1$R$_1$)$_{m1}$—W$_1$, T is —(CR$_1$R$_1$)$_{m1}$—W$_1$.

16. The composition of claim 1 wherein one of E and U is H and the other is —(CR$_3$R$_3$)$_{m1}$—W$_1$; and with the proviso that:

when E is H, G is —(CR$_1$R$_1$)$_{m1}$—C(R$_1$)(W$_1$)(W$_2$), when E is —(CR$_3$R$_3$)$_{m1}$—W$_1$, G is —(CR$_1$R$_1$)$_{m1}$—W$_1$, when U is H, T is —(CR$_1$R$_1$)$_{m1}$—C(R$_1$)(W$_1$)(W$_2$), and when U is —(CR$_3$R$_3$)$_{m1}$—W$_1$, T is —(CR$_1$R$_1$)$_{m1}$—W$_1$.

17. The composition of claim 1 wherein one of E and U is H and the other is —(CR$_1$R$_1$)$_{m1}$—W$_2$; and with the proviso that:

when E is H, G is —(CR$_1$R$_1$)$_{m1}$—C(R$_1$)(W$_1$)(W$_2$), when E is —(CR$_1$R$_1$)$_{m1}$—W$_2$, G is —(CR$_1$R$_1$)$_{m1}$—W$_1$, when U is H, T is —(CR$_1$R$_1$)$_{m1}$—C(R$_1$)(W$_1$)(W$_2$), and when U is —(CR$_1$R$_1$)$_{m1}$—W$_2$, T is —(CR$_1$R$_1$)$_{m1}$—W$_1$.

18. The composition of claim 1 wherein one of E and U is H and the other is —(CR$_3$R$_3$)$_{m1}$—W$_2$; and with the proviso that:

when E is H, G is —(CR$_1$R$_1$)$_{m1}$—C(R$_1$)(W$_1$)(W$_2$), when E is —(CR$_3$R$_3$)$_{m1}$—W$_2$, G is —(CR$_1$R$_1$)$_{m1}$—W$_1$, when U is H, T is —(CR$_1$R$_1$)$_{m1}$—C(R$_1$)(W$_1$)(W$_2$), and when U is —(CR$_3$R$_3$)$_{m1}$—W$_2$, T is —(CR$_1$R$_1$)$_{m1}$—W$_1$.

19. The composition of claim 1 wherein the compound is of the formula:

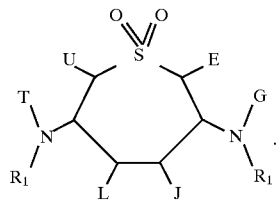

20. The composition of claim 1 wherein J and L are —OH.

21. The composition of claim 1 wherein one of J and L is —OH and the other is H.

22. The composition of claim 1 wherein one of J and L is —OH and the other is —NH$_2$.

23. The composition of claim 1 wherein J and L are taken together to form

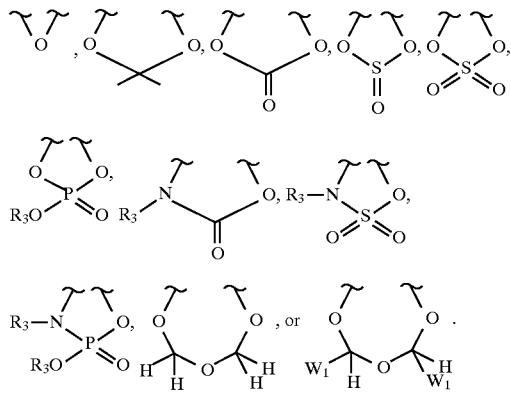

24. A composition comprising a compound of the formula:

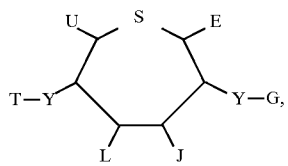

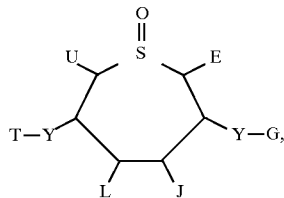

or

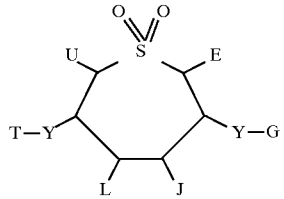

wherein:

Y is independently —O—, —S—, —SO—, —SO$_2$—, —N(R$_1$)—, —N(R$_1$)—SO$_2$—, —N(R$_1$)—CO—, or —O—SO$_2$—;

E and U are independently H, or —$(CR_1R_1)_{m1}$—$W_1$, with the proviso that at least one of E and U is —$(CR_1R_1)_{m1}$—$W_1$;

G and T are independently —$(CR_1R_1)_{m1}$—$W_1$, or —$(CR_1R_1)_{m1}$—$C(R_1)W_1)(W_2)$, with the provisos that:

when E is —$(CR_1R_1)_{m1}$—$W_1$, then G is —$(CR_1R_1)_{m1}$—$W_1$;

when U is —$(CR_1R_1)_{m1}$—$W_1$, then T is —$(CR_1R_1)_{m1}$—$W_1$; and G and T may be the same or different;

J and L are independently H, $N_3$, —$OR_2$, —$N(R_2)(R_2)$, or —$N(R_2)(R_3)$, wherein $R_2$ is H, or PRT, with the proviso that at least one of J and L is —$OR_2$, or J and L are taken together to form an epoxide, or a cyclic protecting group;

$W_1$ is $W_2$ or $W_3$;

$W_2$ is carbocycle, with the proviso that each $W_2$ is independently substituted with 0 to $_3$ $R_5$ groups;

$W_3$ is alkyl, alkenyl, or alkynyl, with the proviso that each $W_3$ is independently substituted with 0 to $_3$ $R_6$ groups;

$R_1$ is $R_3$ or $R_6$;

$R_3$ is H or $R_4$;

$R_4$ is alkyl;

$R_5$ is $R_6$, or $R_7$, with the proviso that each $R_7$ is independently substituted with 0 to 3 $R_6$ groups;

$R_6$ is —O—(label), —$N(R_3)$—(label), —C(O)O—(label), —$C(O)N(R_3)$—(label), —S—(label), —S—S—(label), F, Cl, Br, I, —CN, $N_3$, —$NO_2$, —$OR_3$, —OPRT, —O—$C(O)R_4$, =O, —$N(R_3)(R_3)$, —$N(R_3)(PRT)$, —$N(PRT)_2$, —$N(R_3)$—$C(O)R_4$, =$N(R_3)$, =$N(PRT)$, —$N(OR_3)(R_3)$, —$N(OPRT)(R_3)$, —$N(OR_3)(PRT)$, —$N(OPRT)(R_3)$, —$N(N(R_3)(R_3))(R_3)$, —$N(N(PRT)(R_3))(R_3)$, —$N(N(R_3)(R_3))(PRT)$, —$N(N(PRT)(PRT))(R_3)$, —$N(N(PRT)(R_3))(PRT)$, —$N(N(PRT)(PRT))(PRT)$, —$N(R_3)$—$C(N(R_3))(N(R_3)_2)$, —$N(PRT)$—$C(N(R_3))(N(R_3)_2)$, —$N(R_3)$—$C(N(PRT))(N(R_3)_2)$, —$N(R_3)$—$C(N(R_3))(N(R_3)(PRT))$, —$N(PRT)$—$C(N(PRT))(N(R_3)_2)$, —$N(PRT)$—$C(N(R_3))(N(R_3)(PRT))$, —$N(R_3)$—$C(N(PRT))(N(R_3)(PRT))$, —$N(R_3)$—$C(N(R_3))(N(PRT)_2)$, —$N(PRT)$—$C(N(PRT))(N(R_3)(PRT))$, —$N(PRT)$—$C(N(R_3))(N(PRT)_2)$, —$N(R_3)$—$C(N(PRT))(N(PRT)_2)$, —$C(NR_3)(N(R_3)_2)$, —$C(N(R_3))(N(R_3)(PRT))$, —$C(NPRT)(N(R_3)_2)$, —$C(N(PRT))(N(R_3)(PRT))$, —$C(N(R_3))(N(PRT)_2)$, —$C(N(PRT))(N(PRT)_2)$, —$SR_3$, —$S(PRT)$, =S, —$S(O)$—$R_3$, —$S(O)$—$OR_3$, —$S(O)$—OPRT, —O—$S(O)$—$R_3$, —$S(O)_2$—$R_3$, —$S(O)_2$—$OR_3$, —$S(O)_2$—OPRT, —O—$S(O)_2$—$R_3$, —$C(O)OR_3$, —$C(O)OPRT$, —$C(O)N(R_3)_2$, —$C(O)N(R_3)(PRT)$, —$C(O)N(PRT)_2$, —$C(S)N(R_3)_2$, —$C(S)N(R_3)(PRT)$, —$C(S)N(PRT)_2$, —$N(R_3)$—$S(O)_2$—$R_3$, —$N(PRT)$—$S(O)_2$—$R_3$, —$S(O)_2$—$N(R_3)$—$R_3$, —$S(O)_2$—$N(PRT)$—$R_3$, carbocycle;

$R_7$ is alkyl, alkenyl, or alkynyl;

each m1 is independently an integer from 0 to 3; and with the proviso that the compound, taken as a whole, contains 1 to 16 $R_6$ groups, and that each E, G, T, and U, taken individually, contain 0 to 8 $R_6$ groups, and that one or more $R_6$ groups is selected from the group consisting of —O—(label), —$N(R_3)$—(label), —C(O)O—(label), —$C(O)N(R_3)$—(label), —S—(label), —S—S—(label), =O, =$N(R_3)$, =$N(PRT)$, —$N(OR_3)(R_3)$, —$N(OPRT)(R_3)$, —$N(OR_3)(PRT)$, —$N(OPRT)(R_3)$, —$N(N(R_3)(R_3))(R_3)$, —$N(N(PRT)(R_3))(R_3)$, —$N(N(R_3)(R_3))(PRT)$, —$N(N(PRT)(PRT))(R_3)$, —$N(N(PRT)(R_3))(PRT)$, —$N(N(PRT)(PRT))(PRT)$, =S, —$S(O)$—$R_3$, —$S(O)$—$OR_3$, —$S(O)$—OPRT, —O—$S(O)$—$R_3$, —$S(O)_2$—$R_3$, —$S(O)_2$—$OR_3$, —$S(O)_2$—OPRT, —O—$S(O)_2$—$R_3$, —$C(S)N(R_3)_2$, —$C(S)N(R_3)(PRT)$, —$C(S)N(PRT)_2$, —$N(R_3)$—$S(O)_2$—$R_3$, —$N(PRT)$—$S(O)_2$—$R_3$, —$S(O)_2$—$N(R_3)$—$R_3$, —$S(O)_2$—$N(PRT)$—$R_3$.

25. The composition of claim 24 wherein one or more $R_6$ groups is selected from the group consisting of —O—(label), —$N(R_3)$—(label), —C(O)O—(label), —$C(O)N(R_3)$—(label), —S—(label) and —S—S—(label).

26. The composition of claim 24 wherein one or more $R_6$ groups is selected from the group consisting of —$N(OR_3)(R_3)$, —$N(OPRT)(R_3)$, —$N(OR_3)(PRT)$, —$N(OPRT)(R_3)$, —$N(N(R_3)(R_3))(R_3)$, —$N(N(PRT)(R_3))(R_3)$, —$N(N(R_3)(R_3))(PRT)$, —$N(N(PRT)(PRT))(R_3)$, —$N(N(PRT)(R_3))(PRT)$ and —$N(N(PRT)(PRT))(PRT)$.

27. The composition of claim 24 wherein one or more $R_6$ groups is selected from the group consisting of —$S(O)$—$R_3$, —$S(O)$—$OR_3$, —$S(O)$—OPRT, —O—$S(O)$—$R_3$, —$S(O)_2$—$R_3$, —$S(O)_2$—$OR_3$, —$S(O)_2$—OPRT and —O—$S(O)_2$—$R_3$.

28. The composition of claim 24 wherein one or more $R_6$ groups is selected from the group consisting of —$C(S)N(R_3)_2$, —$C(S)N(R_3)(PRT)$, —$C(S)N(PRT)_2$, —$N(R_3)$—$S(O)_2$—$R_3$, —$N(PRT)$—$S(O)_2$—$R_3$, —$S(O)_2$—$N(R_3)$—$R_3$ and —$S(O)_2$—$N(PRT)$—$R_3$.

29. The composition of claim 24 wherein one or more $R_6$ groups is a heterocycle.

* * * * *